US006569663B1

(12) United States Patent
Rubingh et al.

(10) Patent No.: US 6,569,663 B1
(45) Date of Patent: May 27, 2003

(54) SERINE PROTEASE VARIANTS HAVING AMINO ACID SUBSTITUTIONS

(75) Inventors: Donn Nelton Rubingh, Cincinnati, OH (US); Elizabeth Ellen Sikorski, Fairfield, OH (US); Paul Elliott Correa, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/646,982

(22) PCT Filed: Mar. 25, 1999

(86) PCT No.: PCT/IB99/00518

§ 371 (c)(1),
(2), (4) Date: Sep. 25, 2000

(87) PCT Pub. No.: WO99/49056

PCT Pub. Date: Sep. 30, 1999

Related U.S. Application Data
(60) Provisional application No. 60/079,397, filed on Mar. 26, 1998.

(51) Int. Cl.[7] ............................ C12N 9/54; C12N 9/55; C12N 15/57; C12N 15/74; C11D 3/386

(52) U.S. Cl. ...................... 435/221; 435/69.1; 435/222; 435/252.3; 435/320.1; 435/471; 510/350; 524/267; 536/232

(58) Field of Search .............................. 435/221, 222, 435/69.1, 471, 252.33, 320.1; 510/305; 536/23.2

(56) References Cited

U.S. PATENT DOCUMENTS

| 4,179,337 A |   | 12/1979 | Davis et al. ................. 435/181 |
| 4,248,786 A |   | 2/1981  | Batz et al. .................. 260/326 |
| 4,266,031 A |   | 5/1981  | Tang et al. .................. 435/188 |
| 4,556,554 A |   | 12/1985 | Calvo ........................... 424/70 |
| 4,732,863 A |   | 3/1988  | Tomasi et al. ............... 436/547 |
| 4,760,025 A |   | 7/1988  | Estell et al. ................. 435/222 |
| 4,914,031 A | * | 4/1990  | Zukowski et al. ........... 435/222 |
| 4,980,288 A |   | 12/1990 | Bryan et al. ................. 435/222 |
| 4,990,452 A | * | 2/1991  | Bryan et al. ................. 435/222 |
| 5,122,614 A |   | 6/1992  | Zalipsky ...................... 548/520 |
| 5,133,968 A |   | 7/1992  | Nakayama et al. .......... 424/401 |
| 5,208,158 A |   | 5/1993  | Bech et al. .................. 435/219 |
| 5,230,891 A |   | 7/1993  | Nakayama et al. .......... 424/401 |
| 5,324,844 A |   | 6/1994  | Zalipsky ...................... 548/520 |
| 5,397,705 A | * | 3/1995  | Zukowski et al. ........... 435/222 |
| 5,414,135 A |   | 5/1995  | Snow et al. ................... 568/29 |
| 5,446,090 A |   | 8/1995  | Harris .......................... 525/54 |
| 5,543,302 A |   | 8/1996  | Boguslawski et al. |
| 5,631,322 A |   | 5/1997  | Veronesa et al. ........... 525/54.1 |
| 5,658,871 A |   | 8/1997  | Batenburg et al. ...... 252/174.12 |
| 5,679,630 A | * | 10/1997 | Baeck et al. ................. 510/305 |
| 5,856,451 A |   | 1/1999  | Olsen et al. ................. 530/402 |
| 5,972,682 A | * | 10/1999 | Bott et al. .................... 435/221 |

FOREIGN PATENT DOCUMENTS

| DE | 2 206 826      | 8/1973  |                |
| EP | 0 215662       | 3/1987  | .......... A61K/37/54 |
| EP | 0 398539       | 11/1990 | ............ C12N/9/54 |
| EP | 0 405 901      | 1/1991  | .......... C11D/3/386 |
| EP | 0 471 125 A1   | 12/1992 |                |
| EP | 0 516200       | 12/1992 | .......... C11D/3/386 |
| EP | 0 584876       | 3/1994  | .......... A61K/47/48 |
| EP | 0 251446 B1    | 12/1994 |                |
| EP | 0 816381       | 1/1998  | .......... C07K/17/08 |
| WO | WO 87/04461 A1 | 7/1987  |                |
| WO | WO 87/05050    | 8/1987  | ............ C12Q/1/68 |
| WO | WO 88/08028    | 10/1988 | .......... C12N/15/00 |
| WO | WO 88/08033 A1 | 10/1988 |                |
| WO | WO 88/08165 A1 | 10/1988 |                |
| WO | WO 92/10755    | 6/1992  | .......... G01N/33/53 |
| WO | WO 93/15189    | 8/1993  | ............ C12N/9/96 |
| WO | WO 93/19731    | 10/1993 | ............ A61K/7/48 |
| WO | WO 93/19732    | 10/1993 | ............ A61K/7/48 |
| WO | WO 94/04193    | 3/1994  | .......... A61K/47/48 |
| WO | WO 94/06905    | 3/1994  | ............ C12N/9/54 |
| WO | WO 95/07991    | 3/1995  | .......... C12N/15/57 |
| WO | WO 95/10615    | 4/1995  | .......... C12N/15/57 |
| WO | WO 95/29979    | 11/1995 | .......... C11D/3/386 |
| WO | WO 95/30010    | 11/1995 | .......... C12N/15/57 |
| WO | WO 96/09396    | 3/1996  | .......... C12N/15/57 |
| WO | WO 96/16177    | 5/1996  | .......... C12N/15/62 |
| WO | WO 96/17929    | 6/1996  | ............ C12N/9/96 |
| WO | WO 96/40791    | 12/1996 | .......... C07K/17/08 |
| WO | WO 96/40792    | 12/1996 | .......... C07K/17/08 |
| WO | WO 97/07770    | 3/1997  | ............ A61K/7/48 |
| WO | WO 97/24421    | 7/1997  |                |
| WO | WO 97/24427    | 7/1997  | .......... C11D/3/386 |
| WO | WO 97/30148    | 8/1997  | ............ C12N/9/96 |
| WO | WO 97/37007    | 10/1997 | ............ C12N/9/96 |
| WO | WO 98/23732 A2 | 6/1998  |                |
| WO | WO 98/30682    | 7/1998  | ............ C12N/9/96 |
| WO | WO 98/35026    | 8/1998  | ............ C12N/9/96 |
| WO | WO 99/00489    | 1/1999  | ............ C12N/9/96 |

(List continued on next page.)

OTHER PUBLICATIONS

Gundlach, B.R., et al., "Determination of T Cell Epitopes with Random Peptide Libraries", Journal of Immunological Methods, vol. 192, pp. 149–155 (1996).

(List continued on next page.)

Primary Examiner—Ponnathapu Achutamurthy
Assistant Examiner—William W Moore
(74) Attorney, Agent, or Firm—Dara M. Kendall; Brent M. Peebles

(57) ABSTRACT

The present invention relates to variants of serine proteases having decreased immunogenicity relative to their corresponding wild-type proteases. More particularly, the present invention relates to variants having a modified amino acid sequence of a wild-type amino acid sequence, wherein the modified amino acid sequence comprises a substitution of one or more specifically identified positions corresponding to subtilisin BPN'. The invention further relates to mutant genes encoding such variants and cleaning and personal care compositions comprising such variants.

11 Claims, No Drawings

FOREIGN PATENT DOCUMENTS

| WO | WO 99/37324 A1 | 7/1999 |
|---|---|---|
| WO | WO 99/48918 A1 | 9/1999 |
| WO | WO 99/49056 A1 | 9/1999 |
| WO | WO 00/28007 A2 | 5/2000 |
| WO | WO 00/37658 A2 | 6/2000 |

OTHER PUBLICATIONS

Siezen, R.J., et al., "Subtilases: The Superfamily of Subtilisin–like Serine Proteases", Protein Science, vol. 6, No. 3, pp 501–523 (1997).

Yang, M–L., et al., "Chemical Modification of Cobrotoxin with Bifunctional Reagent, 1,5–Difluoro–2,4–Dinitrobenzene", Kaohsiung J. Med. Sci., vol. 4, pp 503–513 (1988).

Arlian, L.G. et al., "Antigenic and Allergenic Characteristics of the Enzymes Alcalase and Savinase by Crossed Immunoelectrophoresis and Crossed Radioimmunoelectrophoresis", Int. Arch. Allergy, Appl. Immunol., vol. 91, pp. 278–284 (1990).

Abuchowski, A. et al., "Cancer Therapy with Chemically Modified Enzymes. I. Antitumor Properties of Polyethylene Glycol–Asparaginase Conjugates", Cancer Biochem. Biophys., vol. 7, pp. 175–186 (1984).

Abuchowski, A. et al., "Soluble Polymer–Enzyme Adducts", Rutgers University, New Brunswick, NJ, Chapter 13, pp. 367–383.

Bungy Poor Fard, G.A. et al., "T Cell Epitopes of the Major Fraction of Rye Grass Lolium Perenne (loi p l) Defined Using Overlapping Peptides in Vitro and In Vivo. I. Isoallergen Clone 1A", Clin. Exp. Immunol., vol. 94, pp. 111–116 (1993).

Caliceti, P. et al., "Active Site Protection of Proteolytic Enzymes by Poly(ethylene glycol) Surface Modification" Journal of Bioactive and Compatible Polymers, vol. 8, pp. 41–50 (Jan. 1993).

Cunningham, B. C. et al., "Improvement in the alkaline stability of subtilisin using an efficient Random Mutagenesis and Screening Procedure", Protein Engineering, vol. 1, No. 4, pp. 319–325 (Aug./Sep. 1987).

Davis, F.F. et al., "Reduction of Immunogenicity and Extension of Circulating Half–Life of Peptides and Proteins", Peptide and Protein Drug Delivery, Chpt. 21, pp. 831–857, Lee, V.(ED), University of California School of Pharmacy, Los Angeles, CA.

Delgado, C. et al., "The Uses and Properties of PEG–Linked Proteins", Critical Reviews In Therapeutic Drug Carrier Systems, vol. 9, No. ¾, pp. 249–304 (1992).

Favre, C. et al., "Epitope Mapping of Recombinant Human Gamma Interferon Using Monoclonal Antibodies", Molecular Immunology, vol. 26, No. 1, pp. 17–25 (1989).

Francis, G.E. et al., "PEG–Modified Proteins", Stability of Protein Pharmaceuticals, Part B: In Vivo Pathways of Degradation and Strategies for Protein Stabilization, edited by Ahem, T.J. and Mannin, M.C., Plenum Press, pp. 235–263 (1992).

Hopp, T.P. et al., "Prediction of Protein Antigenic Determinants from Amino Acid Sequences", Proc. Natl. Acad. Sci., vol. 78, No. 6, pp. 3824–3828 (1981).

Katre, N.V., "The Conjugation of Proteins with Polyethylene Glycol and Other Polymers", Advanced Drug Delivery Reviews, vol. 10, pp. 91–114 (1993).

Khan, S.A. et al., "Polyethylene Glycol–modified Subtilisin Forms Microparticulate Suspensions in Organic Solvents", Enzyme Microb. Technology, vol. 14, pp. 96–100 (Feb. 1992).

Masunaga, T. et al., "The Protease as a Cleasing Agent and Its Stabilization by Chemical Modification", IFSCC, pp. 483–501, Yokohama.

Mitchinson, C., et al., "Protein Engineering of Disulfide Bonds in Subtilisin BPN", Biochemistry, vol. 28, No. 11, pp. 4807–4815 (1989).

Monfardini, C. et al., "A Branched Monoethoxy Poly(ethylene glycol) for Protein Modification", Biconjugate Chemistry, vol. 6, No. 1, pp. 62–69 (1995).

Nishimura, H. et al., "Improved Modification of Yeast Uricase with Polyethylene Glycol, Accompanied with Non––immunoreactivity Towards Anti–Uricase Serum and High Enzymic Activity", Enzyme, vol. 26, pp. 49–53 (1981).

Nucci, M. L, et al., "Immunogenicity of Polyethylene Glycol–Modified Superoxide Dismutase and Catalase", J. Free Radicals in Biology & Medicine, vol. 2, pp. 321–325 (1986).

Nucci, M.L. et al., "The Therapeutic Value of Poly(etheylene glycol)–modified Proteins", Advanced Drug Delivery Reviews, vol. 6, pp. 133–149 (1991).

Ohta, M. et al., "Preparation of a Dextran–Protease Conjugate and Its Application to Cosmetic Use", Kanebo, Ltd., Cosmetics & Toiletries® Magazine, vol. 111 (1996).

Reay, P.A. et al., "Use of Global Amino Acid Replacements to Define the Requirements for MHC Binding and T Cell Recognition of Moth Cytochrome c (93–103)", Journal of Immunology, vol. 152, No. 8, pp. 3946–3957 (1994).

Ritz, H.L. et al., "Respiratory and Immunological Responses of Guinea Pigs to Enzyme–Containing Detergents: A Comparison of Intratracheal and Inhalation Modes of Exposure", Fundamental and Applied Toxicology, vol. 21, pp. 31–37 (1993).

Robinson, M.K. et al., "Specific Antibody Responses to Subtilisin Carlsberg (Alcalase) in Mice: Development of an Intranasal Exposure Model", Fundamental and Applied Toxicology, vol. 34, pp. 15–24 (1996).

Savoca, K.V. et al., "Preparation of a Non–immunogenic Agrinase by the Covalent Attachment of Polyethylene Glycol", Biochemica Et Biophysica Acta, vol. 578, pp. 47–53 (1979).

Siezen, R.J. et al., "Homology Modelling and Protein Engineering Strategy of Subtilases, the Family of Subtilisin–Like Serine Proteases", Protein Engineering, vol. 4, No. 7, pp. 719–737 (1991).

Walsh, B.J. and M.E.H. Howden, "A Method for the Detection of IgE Binding Sequences of Allergens Based on a Modification of Epitope Mapping", Journal of Immunological Methods, vol. 121, pp. 275–280 (1989).

Wells, J.A., et al., "Recruitmant of Substrate–Specificity Properties From One Enzyme into a Related One by Protein Engineering", Proc. Natl. Acad. Sci. USA, vol. 84, pp. 5167–5171 (Aug. 1987).

* cited by examiner

SEQUENCE LISTING

<160> NUMBER OF SEQ ID NOS: 1

<210> SEQ ID NO 1
<211> LENGTH: 275
<212> TYPE: PRT
<213> ORGANISM: Bacillus amyloliquefaciens

<400> SEQUENCE: 1

```
Ala Gln Ser Val Pro Tyr Gly Val Ser Gln Ile Lys Ala Pro Ala Leu
 1               5                  10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160
```

-continued

```
Ser Ser Ser Thr Val Gly Tyr Pro Gly Lys Tyr Pro Ser Val Ile Ala
            165             170             175

Val Gly Ala Val Asp Ser Ser Asn Gln Arg Ala Ser Phe Ser Ser Val
            180             185             190

Gly Pro Glu Leu Asp Val Met Ala Pro Gly Val Ser Ile Gln Ser Thr
        195             200             205

Leu Pro Gly Asn Lys Tyr Gly Ala Tyr Asn Gly Thr Ser Met Ala Ser
    210             215             220

Pro His Val Ala Gly Ala Ala Ala Leu Ile Leu Ser Lys His Pro Asn
225             230             235             240

Trp Thr Asn Thr Gln Val Arg Ser Ser Leu Glu Asn Thr Thr Thr Lys
            245             250             255

Leu Gly Asp Ser Phe Tyr Tyr Gly Lys Gly Leu Ile Asn Val Gln Ala
            260             265             270

Ala Ala Gln
        275
```

SERINE PROTEASE VARIANTS HAVING AMINO ACID SUBSTITUTIONS

This application claims the benefit of provisional application No. 60/079,397, filed Mar. 26, 1998.

FIELD OF THE INVENTION

The present invention relates to serine protease variants and compositions comprising the variants which have decreased immunogenicity relative to their corresponding wild-type serine proteases.

BACKGROUND OF THE INVENTION

Enzymes make up the largest class of naturally occurring proteins. One class of enzyme includes proteases which catalyze the hydrolysis of other proteins. This ability to hydrolyze proteins has been exploited by incorporating naturally occurring and protein engineered proteases into cleaning compositions, particularly those relevant to laundry applications.

In the cleaning arts, the mostly widely utilized of these proteases are the serine proteases. Most of these serine proteases are produced by bacterial organisms while some are produced by other organisms, such as fungi. See Siezen, Roland J. et al., "Homology Modelling and Protein Engineering Strategy of Subtilases, the Family of Subtilisin-Like Serine Proteases", *Protein Engineering*, Vol. 4, No. 7, pp. 719–737 (1991). Unfortunately, the efficacy of the wild-type proteases in their natural environment frequently does not translate into the unnatural cleaning composition environment. Specifically, protease characteristics such as, for example, thermal stability, pH stability, oxidative stability and substrate specificity are not necessarily optimized for utilization outside the natural environment of the enzyme.

Several approaches have been employed to alter the wild-type amino acid sequence of serine proteases with the goal of increasing the efficacy of the protease in the unnatural wash environment. These approaches include the genetic redesign of proteases to enhance thermal stability and to improve oxidation stability under quite diverse conditions.

However, because such genetically engineered proteases are foreign to mammals, they are potential antigens. As antigens, these proteases cause immunological and allergic responses (herein collectively described as immunological responses) in mammals. In fact, sensitization to serine proteases has been observed in environments wherein humans are regularly exposed to the proteases. Such environments include manufacturing facilities, where employees are exposed to the proteases through such vehicles as uncontrolled dust or aerosolization. Aerosolization can result by the introduction of the protease into the lung, which is the route of protease exposure which causes the most dangerous response. Protease sensitization can also occur in the marketplace, where consumers' repeated use of products containing proteases may cause an allergic reaction.

Furthermore, while genetic engineering has been prominent in the continuing search for more highly effective proteases for use in laundry applications, genetically engineered proteases have been minimally utilized in personal care compositions and light duty detergents. A primary reason for the absence of engineered proteases in products such as, for example, soaps, gels, body washes, and shampoos, is due to the aforementioned problem of human sensitization leading to undesirable immunological responses. It would therefore be highly advantageous to provide a personal care composition which provides the cleansing properties of engineered proteases with minimized provocation of immunological responses.

One approach toward alleviating the immunological activity of a protease is through the redesign of one or more epitopes of the protease. Epitopes are those amino acid regions of an antigen which evoke an immunological response through the binding of antibodies or the presentation of processed antigens to T cells via a major histocompatibility complex protein (MHC). Changes in the epitopes can affect their efficiency as an antigen. See Walsh, B. J. and M. E. H. Howden, "A Method for the Detection of IgE Binding Sequences of Allergens Based on a Modification of Epitope Mapping", *Journal of Immunological Methods*, Vol. 121, pp. 275–280 (1989).

The present inventors have discovered that those serine proteases commonly known as subtilisins, including subtilisin BPN', have a prominent epitope region at amino acid positions 70–84 corresponding to BPN'. The present inventors have herein genetically redesigned such subtilisins to alleviate the immunogenic properties attributed to this epitope region. In so doing, the present inventors have discovered subtilisins which evoke a decreased immunological response yet maintain their activity as an efficient cleansing protease. Accordingly, the present proteases are suitable for use in several types of compositions including, but not limited to, laundry, dish, hard surface, skin care, hair care, beauty care, oral, and contact lens compositions.

SUMMARY OF THE INVENTION

The present invention relates to variants of serine proteases having decreased immunogenicity relative to their corresponding wild-type proteases. More particularly, the present invention relates to variants having a modified amino acid sequence of a wild-type amino acid sequence, wherein the modified amino acid sequence comprises a substitution of one or more of positions 70–84 corresponding to subtilisin BPN'. The invention further relates to mutant genes encoding such variants and cleaning and personal care compositions comprising such variants.

DETAILED DESCRIPTION OF THE INVENTION

The essential components of the present invention are herein described below. Also included are non-limiting descriptions of various optional and preferred components useful in embodiments of the present invention.

The present invention can comprise, consist of, or consist essentially of any of the required or optional components and/or limitations described herein.

All percentages and ratios are calculated by weight unless otherwise indicated.

All percentages are calculated based on the total composition unless otherwise indicated.

All component or composition levels are in reference to the active level of that component or composition, and are exclusive of impurities, for example, residual solvents or by-products, that may be present in commercially available sources.

All documents referred to herein, including all patents, patent applications, and printed publications, are hereby incorporated by reference in their entirety.

As used herein, abbreviations will be used to describe amino acids. Table I provides a list of abbreviations used herein:

TABLE I

| Amino Acid | Three-letter Abbreviation | One-letter Abbreviation |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Definitions

As used herein, the term "mutation" refers to alterations in gene sequences and amino acid sequences produced by those gene sequences. Mutations may be deletions, substitutions, or additions of amino acid residues to the wild-type protein sequence.

As used herein, the term "wild-type" refers to a protein, herein specifically a protease, produced by unmutated organisms.

As used herein, the term "variant" means a protein, herein specifically a protease, having an amino acid sequence which differs from that of the wild-type protease.

As referred to herein, while the variants of the present invention are not limited to those of subtilisin BPN', all amino acid numbering is with reference to the amino acid sequence for subtilisin BPN' E. J. which is represented by SEQ ID NO:1. The amino acid sequence for subtilisin BPN' is further described by Wells, J. A., E. Ferrari, D. J. Henner, D. A. Estell, and E. J. Chen, *Nucleic Acids Research*, Vol. II, 7911–7925 (1983), incorporated herein by reference.

Variants of the Present Invention

The present inventors have discovered an epitope region in serine proteases which corresponds to positions 70–84 of subtilisin BPN'. The present inventors have further discovered that one or more amino acid substitutions in the amino acid sequence of a wild-type serine protease provides variants which evoke a deceased allergenic and/or immune response relative to the corresponding wild-type serine protease.

As used herein, a variant may be designated by referring to the substituted amino acid positions which characterize the variant. Substitutions are herein indicated by providing the wild-type amino acid residue, followed by the position number, followed by the substituted amino acid residue to be substituted. Wherein the substituted amino acid residue may be any natural amino acid allowed at that particular position, the symbol "*" is provided. Multiple substitutions comprising a variant are separated by the symbol "+". To illustrate, a substitution of valine for glycine at position 70 is designated either Gly70Val or G70V. An example of a variant having a substitution at both positions 70 and 72 may be designated as Gly70Val+Val72Ala or G70V+V72A.

The variants of the present invention are variants of serine proteases. As used herein, the term "serine protease" means a protease which has at least 50%, and preferably 80%, amino acid sequence identity with the sequences for one or more of a subtilisin-like serine protease. A discussion relating to subtilisin-like serine proteases and their homologies may be found in Siezen et al., "Homology Modelling and Protein Engineering Strategy of Subtilases, the Family of Subtilisin-Like Serine Proteases", *Protein Engineering*, Vol. 4, No. 7, pp. 719–737 (1991). Preferred serine proteases for mutation include subtilisin BPN', subtilisin Carlsberg, subtilisin DY, subtilisin 309, proteinase K, and thermitase. The most preferred serine protease for mutation is subtilisin BPN'.

The variants of the present invention are variants of serine proteases having a modified amino acid sequence of a wild-type amino acid sequence, wherein the modified amino acid sequence comprises a substitution of one or more of positions 70, 71, 72, 73, 74, 75, 76, 77, 78, 79, 80, 81, 82, 83, and 84 (70–84) corresponding to BPN'. More preferably, the modified amino acid sequence comprises a substitution of two or more of these positions. Substitutions at these positions are made by replacing the wild-type amino acid residue with another natural amino acid residue such as one given in Table I.

More specifically, wherein the variant has a modified amino acid sequence of a wild-type amino acid sequence comprising a substitution at one position corresponding to positions 70–84 of BPN':

(a) when the substitution occurs at position 70, the substituting amino acid is selected from the group consisting of Ala, Arg, Asn, Asp, Cys, Glu, Phe, His, Ile, Lys, Leu, Met, Pro, Gln, Ser, Thr, Trp, Tyr, and Val;

(b) when the substitution occurs at position 71, the substituting amino acid is selected from the group consisting of Ala, Arg, Asn, Cys, Gly, Phe, His, Ile, Lys, Leu, Met, Pro, Gln, Ser, Trp, Tyr, and Val;

(c) when the substitution occurs at position 72, the substituting amino acid is selected from the group consisting of Ala, Arg, Asn, Asp, Cys, Glu, Gly, Phe, His, Ile, Lys, Leu, Met, Pro, Gln, Ser, Thr, Trp, and Tyr;

(d) when the substitution occurs at position 73, the substituting amino acid is selected from the group consisting of Arg, Asn, Asp, Cys, Glu, Gly, Phe, His, Ile, Lys, Met, Pro, Ser, Thr, Trp, Tyr, and Val;

(e) when the substitution occurs at position 74, the substituting amino acid is selected from the group consisting of Arg, Asn, Asp, Cys, Glu, Gly, Phe, His, Ile, Lys, Leu, Met, Gln, Ser, Thr, Trp, Tyr, and Val;

(f) when the substitution occurs at position 75, the substituting amino acid is selected from the group consisting of Ala, Arg, Asn, Asp, Cys, Glu, Gly, Phe, His, Ile, Lys, Met, Gln, Ser, Thr, Trp, Tyr, and Val;

(g) when the substitution occurs at position 76, the substituting amino acid is selected from the group consisting of Ala, Arg, Cys, Ile, Leu, Met, Gln, Ser, Thr, Trp, Tyr, and Val;

(h) when the substitution occurs at position 77, the substituting amino acid is selected from the group consisting of Ala, Arg, Cys, Glu, Gly, Phe, His, Ile, Lys, Leu, Met, Pro, Gin, Ser, Thr, Trp, Tyr, and Val;

(i) when the substitution occurs at position 78, the substituting amino acid is selected from the group consisting of Ala, Arg, Asn, Cys, Glu, Gly, Phe, His, Ile, Lys, Leu, Met, Pro, Gin, Thr, Trp, Tyr, and Val;

(j) when the substitution occurs at position 79, the substituting amino acid is selected from the group consisting of Ala, Arg, Asn, Cys, Gly, Phe, His, Lys, Leu, Met, Pro, Gln, Ser, Thr, Trp, Tyr, and Val;

(k) when the substitution occurs at position 80, the substituting amino acid is selected from the group consisting of Ala, Arg, Asn, Asp, Cys, Glu, Phe, His, Lys, Leu, Met, Pro, Gln, Ser, Thr, Trp, Tyr, and Val;

(l) when the substitution occurs at position 81, the substituting amino acid is selected from the group consisting of Ala, Arg, Asn, Asp, Cys, Glu, Gly, Phe, His, Ile, Lys, Leu, Met, Pro, Gln, Ser, Thr, Trp, and Tyr;

(m) when the substitution occurs at position 82, the substituting amino acid is selected from the group consisting of Ala, Arg, Asn, Asp, Cys, Glu, Gly, Phe, His, Ile, Lys, Met, Pro, Gln, Ser, Thr, Trp, Tyr, and Val;

(n) when the substitution occurs at position 83, the substituting amino acid is selected from the group consisting of Ala, Arg, Asn, Asp, Cys, Glu, Phe, His, Ile, Lys, Leu, Met, Pro, Gln, Ser, Thr, Trp, Tyr, and Val; and (o) when the substitution occurs at position 84, the substituting amino acid is selected from the group consisting of Ala, Arg, Asn, Asp, Cys, Glu, Gly, Phe, His, Ile, Lys, Leu, Met, Pro, Gln, Ser, Thr, Trp, and Tyr.

Wherein the variant has a modified amino acid sequence of a wild-type amino acid sequence comprising a substitution at two or more positions corresponding to positions 70–84 of BPN':

(a) when a substitution occurs at position 70, the substituting amino acid is selected from the group consisting of Ala, Arg, Asn, Asp, Cys, Gln, Glu, Phe, His, Ile, Lys, Leu, Met, Pro, Ser, Thr, Trp, Tyr, and Val;

(b) when a substitution occurs at position 71, the substituting amino acid is selected from the group consisting of Ala, Arg, Asn, Asp, Cys, Gln, Glu, Gly, Phe, His, Ile, Lys, Leu, Met, Pro, Ser, Trp, Tyr, and Val;

(c) when a substitution occurs at position 72, the substituting amino acid is selected from the group consisting of Ala, Arg, Asn, Asp, Cys, Gln, Glu, Gly, Phe, His, Ile, Lys, Leu, Met, Pro, Ser, Thr, Trp, and Tyr;

(d) when a substitution occurs at position 73, the substituting amino acid is selected from the group consisting of Arg, Asn, Asp, Cys, Gln Glu, Gly, Phe, His, Ile, Lys, Leu, Met, Pro, Ser, Thr, Trp, Tyr, and Val;

(e) when a substitution occurs at position 74, the substituting amino acid is selected from the group consisting of Arg, Asn, Asp, Cys, Gln Glu, Gly, Phe, His, Ile, Lys, Leu, Met, Pro, Ser, Thr, Trp, Tyr, and Val;

(f) when a substitution occurs at position 75, the substituting amino acid is selected from the group consisting of Ala, Arg, Asn, Asp, Cys, Gln Glu, Gly, Phe, His, Ile, Lys, Met, Pro, Ser, Thr, Trp, Tyr, and Val;

(g) when a substitution occurs at position 76, the substituting amino acid is selected from the group consisting of Ala, Arg, Asp, Cys, Gln Glu, Gly, Phe, His, Ile, Lys, Leu, Met, Pro, Ser, Thr, Trp, Tyr, and Val;

(h) when a substitution occurs at position 77, the substituting amino acid is selected from the group consisting of Ala, Arg, Asp, Cys, Gln Glu, Gly, Phe, His, Ile, Lys, Leu, Met, Pro, Ser, Thr, Trp, Tyr, and Val;

(i) when a substitution occurs at position 78, the substituting amino acid is selected from the group consisting of Ala, Arg, Asn, Asp, Cys, Gln Glu, Gly, Phe, His, Ile, Lys, Leu, Met, Pro, Thr, Trp, Tyr, and Val;

(j) when a substitution occurs at position 79, the substituting amino acid is selected from the group consisting of Ala, Arg, Asn, Asp, Cys, Gln Glu, Gly, Phe, His, Lys, Leu, Met, Pro, Ser, Thr, Trp, Tyr, and Val;

(k) when a substitution occurs at position 80, the substituting amino acid is selected from the group consisting of Ala, Arg, Asn, Asp, Cys, Gln Glu, Phe, His, Ile, Lys, Leu, Met, Pro, Ser, Thr, Trp, Tyr, and Val;

(l) when a substitution occurs at position 81, the substituting amino acid is selected from the group consisting of Ala, Arg, Asn, Asp, Cys, Gln Glu, Gly, Phe, His, Ile, Lys, Leu, Met, Pro, Ser, Thr, Trp, and Tyr;

(m) when a substitution occurs at position 82, the substituting amino acid is selected from the group consisting of Ala, Arg, Asn, Asp, Cys, Gln Glu, Gly, Phe, His, Ile, Lys, Met, Pro, Ser, Thr, Trp, Tyr, and Val;

(n) when a substitution occurs at position 83, the substituting amino acid is selected from the group consisting of Ala, Arg, Asn, Asp, Cys, Gln Glu, Phe, His, Ile, Lys, Leu, Met, Pro, Ser, Thr, Trp, Tyr, and Val; and (o) when a substitution occurs at position 84, the substituting amino acid is selected from the group consisting of Ala, Arg, Asn, Asp, Cys, Gln Glu, Gly, Phe, His, Ile, Lys, Leu, Met, Pro, Ser, Thr, Trp, and Tyr;

wherein the variant is not Asn76Asp+Asn77Asp; Asn76Asp+Ile79Glu; or Asn76Asp+Ser78Asp.

Even more preferably, the variants of the present invention comprise a deletion of one or more of positions 73, 74, 75, 76, 77, 78, 79, 80, 81, 82, 83 (73–83), even more preferably one or more of 75, 76, 77, 78, 79, 80, 81, 82 (75–82).

Tables 2–7 below exemplify non-limiting preferred variants of the present invention. With respect to these tables, in describing the specific substitutions, the wild-type amino acid residue is given first, the corresponding position number is given second, and the substituting amino acid is given third. Tables 3–7 delineate preferred variants having two or more substitutions. To illustrate, the first example of Table 3 reads "VAL 81 THR LEU 82 PHE". This example is meant to exemplify the variant Val81Thr+Leu82Phe.

Using similar notation, Tables 8–13 exemplify even more preferred variants of the present invention.

TABLE 2

| Single Substitution Variants |
| --- |
| GLY 83 VAL |
| LEU 82 PHE |
| LEU 82 HIS |
| LEU 82 TYR |
| LEU 82 ALA |
| VAL 81 THR |
| VAL 81 ALA |
| GLY 80 VAL |
| ILE 79 LEU |
| ILE 79 MET |
| ILE 79 THR |
| ILE 79 VAL |
| ILE 79 ALA |
| SER 78 ASN |
| SER 78 THR |
| SER 78 ARG |
| SER 78 GLN |
| SER 78 HIS |
| SER 78 LYS |
| SER 78 TYR |
| SER 78 ALA |
| ASN 77 ALA |
| ASN 76 ALA |

TABLE 2-continued

| Single Substitution Variants |
|---|
| LEU 75 ILE |
| LEU 75 MET |
| LEU 75 VAL |
| LEU 75 ALA |
| ALA 74 VAL |
| ALA 73 VAL |
| VAL 72 ALA |
| THR 71 ALA |
| GLY 70 VAL |

TABLE 3

| Double Substitution Variants |
|---|
| VAL 81 THR LEU 82 PHE |
| VAL 81 THR LEU 82 HIS |
| VAL 81 THR LEU 82 TYR |
| ILE 79 LEU LEU 82 PHE |
| ILE 79 LEU LEU 82 HIS |
| ILE 79 LEU LEU 82 TYR |
| ILE 79 MET LEU 82 PHE |
| ILE 79 MET LEU 82 HIS |
| ILE 79 MET LEU 82 TYR |
| ILE 79 THR LEU 82 PHE |
| ILE 79 THR LEU 82 HIS |
| ILE 79 THR LEU 82 TYR |
| ILE 79 VAL LEU 82 PHE |
| ILE 79 VAL LEU 82 HIS |
| ILE 79 VAL LEU 82 TYR |
| ILE 79 LEU VAL 81 THR |
| ILE 79 MET VAL 81 THR |
| ILE 79 THR VAL 81 THR |
| ILE 79 VAL VAL 81 THR |
| SER 78 ASN LEU 82 PHE |
| SER 78 ASN LEU 82 HIS |
| SER 78 ASN LEU 82 TYR |
| SER 78 THR LEU 82 PHE |
| SER 78 THR LEU 82 HIS |
| SER 78 THR LEU 82 TYR |
| SER 78 ARG LEU 82 PHE |
| SER 78 ARG LEU 82 HIS |
| SER 78 ARG LEU 82 TYR |
| SER 78 ASP LEU 82 PHE |
| SER 78 ASP LEU 82 HIS |
| SER 78 ASP LEU 82 TYR |
| SER 78 GLN LEU 82 PHE |
| SER 78 GLN LEU 82 HIS |
| SER 78 GLN LEU 82 TYR |
| SER 78 HIS LEU 82 PHE |
| SER 78 HIS LEU 82 HIS |
| SER 78 HIS LEU 82 TYR |
| SER 78 LYS LEU 82 PHE |
| SER 78 LYS LEU 82 HIS |
| SER 78 LYS LEU 82 TYR |
| SER 78 TYR LEU 82 PHE |
| SER 78 TYR LEU 82 HIS |
| SER 78 TYR LEU 82 TYR |
| SER 78 ASN VAL 81 THR |
| SER 78 THR VAL 81 THR |
| SER 78 ARG VAL 81 THR |
| SER 78 ASP VAL 81 THR |
| SER 78 GLN VAL 81 THR |
| SER 78 HIS VAL 81 THR |
| SER 78 LYS VAL 81 THR |
| SER 78 TYR VAL 81 THR |
| SER 78 ASN ILE 79 LEU |
| SER 78 ASN ILE 79 MET |
| SER 78 ASN ILE 79 THR |
| SER 78 ASN ILE 79 VAL |
| SER 78 THR ILE 79 LEU |
| SER 78 THR ILE 79 MET |
| SER 78 THR ILE 79 THR |
| SER 78 THR ILE 79 VAL |
| SER 78 ARG ILE 79 LEU |

TABLE 3-continued

| Double Substitution Variants |
|---|
| SER 78 ARG ILE 79 MET |
| SER 78 ARG ILE 79 THR |
| SER 78 ARG ILE 79 VAL |
| SER 78 ASP ILE 79 LEU |
| SER 78 ASP ILE 79 MET |
| SER 78 ASP ILE 79 THR |
| SER 78 ASP ILE 79 VAL |
| SER 78 GLN ILE 79 LEU |
| SER 78 GLN ILE 79 MET |
| SER 78 GLN ILE 79 THR |
| SER 78 GLN ILE 79 VAL |
| SER 78 HIS ILE 79 LEU |
| SER 78 HIS ILE 79 MET |
| SER 78 HIS ILE 79 THR |
| SER 78 HIS ILE 79 VAL |
| SER 78 LYS ILE 79 LEU |
| SER 78 LYS ILE 79 MET |
| SER 78 LYS ILE 79 THR |
| SER 78 LYS ILE 79 VAL |
| SER 78 TYR ILE 79 LEU |
| SER 78 TYR ILE 79 MET |
| SER 78 TYR ILE 79 THR |
| SER 78 TYR ILE 79 VAL |
| ASN 76 HIS LEU 82 PHE |
| ASN 76 HIS LEU 82 HIS |
| ASN 76 HIS LEU 82 TYR |
| ASN 76 HIS VAL 81 THR |
| ASN 76 HIS ILE 79 LEU |
| ASN 76 HIS ILE 79 MET |
| ASN 76 HIS ILE 79 THR |
| ASN 76 HIS ILE 79 VAL |
| ASN 76 HIS SER 78 ASN |
| ASN 76 HIS SER 78 THR |
| ASN 76 HIS SER 78 ARG |
| ASN 76 HIS SER 78 ASP |
| ASN 76 HIS SER 78 GLN |
| ASN 76 HIS SER 78 HIS |
| ASN 76 HIS SER 78 LYS |
| ASN 76 HIS SER 78 TYR |
| LEU 75 ILE LEU 82 PHE |
| LEU 75 ILE LEU 82 HIS |
| LEU 75 ILE LEU 82 TYR |
| LEU 75 MET LEU 82 PHE |
| LEU 75 MET LEU 82 HIS |
| LEU 75 MET LEU 82 TYR |
| LEU 75 VAL LEU 82 PHE |
| LEU 75 VAL LEU 82 HIS |
| LEU 75 VAL LEU 82 TYR |
| LEU 75 ILE VAL 81 THR |
| LEU 75 MET VAL 81 THR |
| LEU 75 VAL VAL 81 THR |
| LEU 75 ILE ILE 79 LEU |
| LEU 75 ILE ILE 79 MET |
| LEU 75 ILE ILE 79 THR |
| LEU 75 ILE ILE 79 VAL |
| LEU 75 MET ILE 79 LEU |
| LEU 75 MET ILE 79 MET |
| LEU 75 MET ILE 79 THR |
| LEU 75 MET ILE 79 VAL |
| LEU 75 VAL ILE 79 LEU |
| LEU 75 VAL ILE 79 MET |
| LEU 75 VAL ILE 79 THR |
| LEU 75 VAL ILE 79 VAL |
| LEU 75 ILE SER 78 ASN |
| LEU 75 ILE SER 78 THR |
| LEU 75 ILE SER 78 ARG |
| LEU 75 ILE SER 78 ASP |
| LEU 75 ILE SER 78 GLN |
| LEU 75 ILE SER 78 HIS |
| LEU 75 ILE SER 78 LYS |
| LEU 75 ILE SER 78 TYR |
| LEU 75 MET SER 78 ASN |
| LEU 75 MET SER 78 THR |
| LEU 75 MET SER 78 ARG |
| LEU 75 MET SER 78 ASP |
| LEU 75 MET SER 78 GLN |
| LEU 75 MET SER 78 HIS |

TABLE 3-continued

Double Substitution Variants

LEU 75 MET SER 78 LYS
LEU 75 MET SER 78 TYR
LEU 75 VAL SER 78 ASN
LEU 75 VAL SER 78 THR
LEU 75 VAL SER 78 ARG
LEU 75 VAL SER 78 ASP
LEU 75 VAL SER 78 GLN
LEU 75 VAL SER 78 HIS
LEU 75 VAL SER 78 LYS
LEU 75 VAL SER 78 TYR
LEU 75 ILE ASN 76 HIS
LEU 75 MET ASN 76 HIS
LEU 75 VAL ASN 76 HIS

TABLE 4

Triple Substitution Variants

| | | | | |
|---|---|---|---|---|
| ILE | 79 LEU VAL | 81 THR LEU | 82 PHE | |
| ILE | 79 LEU VAL | 81 THR LEU | 82 HIS | |
| ILE | 79 LEU VAL | 81 THR LEU | 82 TYR | |
| ILE | 79 MET VAL | 81 THR LEU | 82 PHE | |
| ILE | 79 MET VAL | 81 THR LEU | 82 HIS | |
| ILE | 79 MET VAL | 81 THR LEU | 82 TYR | |
| ILE | 79 THR VAL | 81 THR LEU | 82 PHE | |
| ILE | 79 THR VAL | 81 THR LEU | 82 HIS | |
| ILE | 79 THR VAL | 81 THR LEU | 82 TYR | |
| ILE | 79 VAL VAL | 81 THR LEU | 82 PHE | |
| ILE | 79 VAL VAL | 81 THR LEU | 82 HIS | |
| ILE | 79 VAL VAL | 81 THR LEU | 82 TYR | |
| SER | 78 ASN VAL | 81 THR LEU | 82 PHE | |
| SER | 78 ASN VAL | 81 THR LEU | 82 HIS | |
| SER | 78 ASN VAL | 81 THR LEU | 82 TYR | |
| SER | 78 THR VAL | 81 THR LEU | 82 PHE | |
| SER | 78 THR VAL | 81 THR LEU | 82 HIS | |
| SER | 78 THR VAL | 81 THR LEU | 82 TYR | |
| SER | 78 ARG VAL | 81 THR LEU | 82 PHE | |
| SER | 78 ARG VAL | 81 THR LEU | 82 HIS | |
| SER | 78 ARG VAL | 81 THR LEU | 82 TYR | |
| SER | 78 ASP VAL | 81 THR LEU | 82 PHE | |
| SER | 78 ASP VAL | 81 THR LEU | 82 HIS | |
| SER | 78 ASP VAL | 81 THR LEU | 82 TYR | |
| SER | 78 GLN VAL | 81 THR LEU | 82 PHE | |
| SER | 78 GLN VAL | 81 THR LEU | 82 HIS | |
| SER | 78 GLN VAL | 81 THR LEU | 82 TYR | |
| SER | 78 HIS VAL | 81 THR LEU | 82 PHE | |
| SER | 78 HIS VAL | 81 THR LEU | 82 HIS | |
| SER | 78 HIS VAL | 81 THR LEU | 82 TYR | |
| SER | 78 LYS VAL | 81 THR LEU | 82 PHE | |
| SER | 78 LYS VAL | 81 THR LEU | 82 HIS | |
| SER | 78 LYS VAL | 81 THR LEU | 82 TYR | |
| SER | 78 TYR VAL | 81 THR LEU | 82 PHE | |
| SER | 78 TYR VAL | 81 THR LEU | 82 HIS | |
| SER | 78 TYR VAL | 81 THR LEU | 82 TYR | |
| SER | 78 ASN ILE | 79 LEU LEU | 82 PHE | |
| SER | 78 ASN ILE | 79 LEU LEU | 82 HIS | |
| SER | 78 ASN ILE | 79 LEU LEU | 82 TYR | |
| SER | 78 ASN ILE | 79 MET LEU | 82 PHE | |
| SER | 78 ASN ILE | 79 MET LEU | 82 HIS | |
| SER | 78 ASN ILE | 79 MET LEU | 82 TYR | |
| SER | 78 ASN ILE | 79 THR LEU | 82 PHE | |
| SER | 78 ASN ILE | 79 THR LEU | 82 HIS | |
| SER | 78 ASN ILE | 79 THR LEU | 82 TYR | |
| SER | 78 ASN ILE | 79 VAL LEU | 82 PHE | |
| SER | 78 ASN ILE | 79 VAL LEU | 82 HIS | |
| SER | 78 ASN ILE | 79 VAL LEU | 82 TYR | |
| SER | 78 THR ILE | 79 LEU LEU | 82 PHE | |
| SER | 78 THR ILE | 79 LEU LEU | 82 HIS | |
| SER | 78 THR ILE | 79 LEU LEU | 82 TYR | |
| SER | 78 THR ILE | 79 MET LEU | 82 PHE | |
| SER | 78 THR ILE | 79 MET LEU | 82 HIS | |
| SER | 78 THR ILE | 79 MET LEU | 82 TYR | |
| SER | 78 THR ILE | 79 THR LEU | 82 PHE | |
| SER | 78 THR ILE | 79 THR LEU | 82 HIS | |

TABLE 4-continued

Triple Substitution Variants

| | | | | |
|---|---|---|---|---|
| SER | 78 THR ILE | 79 THR LEU | 82 TYR | |
| SER | 78 THR ILE | 79 VAL LEU | 82 PHE | |
| SER | 78 THR ILE | 79 VAL LEU | 82 HIS | |
| SER | 78 THR ILE | 79 VAL LEU | 82 TYR | |
| SER | 78 ARG ILE | 79 LEU LEU | 82 PHE | |
| SER | 78 ARG ILE | 79 LEU LEU | 82 HIS | |
| SER | 78 ARG ILE | 79 LEU LEU | 82 TYR | |
| SER | 78 ARG ILE | 79 MET LEU | 82 PHE | |
| SER | 78 ARG ILE | 79 MET LEU | 82 HIS | |
| SER | 78 ARG ILE | 79 MET LEU | 82 TYR | |
| SER | 78 ARG ILE | 79 THR LEU | 82 PHE | |
| SER | 78 ARG ILE | 79 THR LEU | 82 HIS | |
| SER | 78 ARG ILE | 79 THR LEU | 82 TYR | |
| SER | 78 ARG ILE | 79 VAL LEU | 82 PHE | |
| SER | 78 ARG ILE | 79 VAL LEU | 82 HIS | |
| SER | 78 ARG ILE | 79 VAL LEU | 82 TYR | |
| SER | 78 ASP ILE | 79 LEU LEU | 82 PHE | |
| SER | 78 ASP ILE | 79 LEU LEU | 82 HIS | |
| SER | 78 ASP ILE | 79 LEU LEU | 82 TYR | |
| SER | 78 ASP ILE | 79 MET LEU | 82 PHE | |
| SER | 78 ASP ILE | 79 MET LEU | 82 HIS | |
| SER | 78 ASP ILE | 79 MET LEU | 82 TYR | |
| SER | 78 ASP ILE | 79 THR LEU | 82 PHE | |
| SER | 78 ASP ILE | 79 THR LEU | 82 HIS | |
| SER | 78 ASP ILE | 79 THR LEU | 82 TYR | |
| SER | 78 ASP ILE | 79 VAL LEU | 82 PHE | |
| SER | 78 ASP ILE | 79 VAL LEU | 82 HIS | |
| SER | 78 ASP ILE | 79 VAL LEU | 82 TYR | |
| SER | 78 GLN ILE | 79 LEU LEU | 82 PHE | |
| SER | 78 GLN ILE | 79 LEU LEU | 82 HIS | |
| SER | 78 GLN ILE | 79 LEU LEU | 82 TYR | |
| SER | 78 GLN ILE | 79 MET LEU | 82 PRE | |
| SER | 78 GLN ILE | 79 MET LEU | 82 HIS | |
| SER | 78 GLN ILE | 79 MET LEU | 82 TYR | |
| SER | 78 GLN ILE | 79 THR LEU | 82 PHE | |
| SER | 78 GLN ILE | 79 THR LEU | 82 HIS | |
| SER | 78 GLN ILE | 79 THR LEU | 82 TYR | |
| SER | 78 GLN ILE | 79 VAL LEU | 82 PHE | |
| SER | 78 GLN ILE | 79 VAL LEU | 82 HIS | |
| SER | 78 GLN ILE | 79 VAL LEU | 82 TYR | |
| SER | 78 HIS ILE | 79 LEU LEU | 82 PHE | |
| SER | 78 HIS ILE | 79 LEU LEU | 82 HIS | |
| SER | 78 HIS ILE | 79 LEU LEU | 82 TYR | |
| SER | 78 HIS ILE | 79 MET LEU | 82 PHE | |
| SER | 78 HIS ILE | 79 MET LEU | 82 HIS | |
| SER | 78 HIS ILE | 79 MET LEU | 82 TYR | |
| SER | 78 HIS ILE | 79 THR LEU | 82 PHE | |
| SER | 78 HIS ILE | 79 THR LEU | 82 HIS | |
| SER | 78 HIS ILE | 79 THR LEU | 82 TYR | |
| SER | 78 HIS ILE | 79 VAL LEU | 82 PHE | |
| SER | 78 HIS ILE | 79 VAL LEU | 82 HIS | |
| SER | 78 HIS ILE | 79 VAL LEU | 82 TYR | |
| SER | 78 LYS ILE | 79 LEU LEU | 82 PHE | |
| SER | 78 LYS ILE | 79 LEU LEU | 82 HIS | |
| SER | 78 LYS ILE | 79 LEU LEU | 82 TYR | |
| SER | 78 LYS ILE | 79 MET LEU | 82 PHE | |
| SER | 78 LYS ILE | 79 MET LEU | 82 HIS | |
| SER | 78 LYS ILE | 79 MET LEU | 82 TYR | |
| SER | 78 LYS ILE | 79 THR LEU | 82 PHE | |
| SER | 78 LYS ILE | 79 THR LEU | 82 HIS | |
| SER | 78 LYS ILE | 79 THR LEU | 82 TYR | |
| SER | 78 LYS ILE | 79 VAL LEU | 82 PRE | |
| SER | 78 LYS ILE | 79 VAL LEU | 82 HIS | |
| SER | 78 LYS ILE | 79 VAL LEU | 82 TYR | |
| SER | 78 TYR ILE | 79 LEU LEU | 82 PRE | |
| SER | 78 TYR ILE | 79 LEU LEU | 82 HIS | |
| SER | 78 TYR ILE | 79 LEU LEU | 82 TYR | |
| SER | 78 TYR ILE | 79 MET LEU | 82 PHE | |
| SER | 78 TYR ILE | 79 MET LEU | 82 HIS | |
| SER | 78 TYR ILE | 79 MET LEU | 82 TYR | |
| SER | 78 TYR ILE | 79 THR LEU | 82 PHE | |
| SER | 78 TYR ILE | 79 THR LEU | 82 HIS | |
| SER | 78 TYR ILE | 79 THR LEU | 82 TYR | |
| SER | 78 TYR ILE | 79 VAL LEU | 82 PRE | |
| SER | 78 TYR ILE | 79 VAL LEU | 82 HIS | |
| SER | 78 TYR ILE | 79 VAL LEU | 82 TYR | |
| SER | 78 ASN ILE | 79 LEU VAL | 81 THR | |

TABLE 4-continued

| Triple Substitution Variants | | | |
|---|---|---|---|
| SER | 78 ASN ILE | 79 MET VAL | 81 THR |
| SER | 78 ASN ILE | 79 THR VAL | 81 THR |
| SER | 78 ASN ILE | 79 VAL VAL | 81 THR |
| SER | 78 THR ILE | 79 LEU VAL | 81 THR |
| SER | 78 THR ILE | 79 MET VAL | 81 THR |
| SER | 78 THR ILE | 79 THR VAL | 81 THR |
| SER | 78 THR ILE | 79 VAL VAL | 81 THR |
| SER | 78 GLN ILE | 79 LEU LEU | 82 PHE |
| SER | 78 GLN ILE | 79 LEU LEU | 82 HIS |
| SER | 78 GLN ILE | 79 LEU LEU | 82 TYR |
| SER | 78 GLN ILE | 79 MET LEU | 82 PRE |
| SER | 78 GLN ILE | 79 MET LEU | 82 HIS |
| SER | 78 GLN ILE | 79 MET LEU | 82 TYR |
| SER | 78 GLN ILE | 79 THR LEU | 82 PHE |
| SER | 78 GLN ILE | 79 THR LEU | 82 HIS |
| SER | 78 GLN ILE | 79 THR LEU | 82 TYR |
| SER | 78 GLN ILE | 79 VAL LEU | 82 PHE |
| SER | 78 GLN ILE | 79 VAL LEU | 82 HIS |
| SER | 78 GLN ILE | 79 VAL LEU | 82 TYR |
| SER | 78 HIS ILE | 79 LEU LEU | 82 PHE |
| SER | 78 HIS ILE | 79 LEU LEU | 82 HIS |
| SER | 78 HIS ILE | 79 LEU LEU | 82 TYR |
| SER | 78 HIS ILE | 79 MET LEU | 82 PHE |
| SER | 78 HIS ILE | 79 MET LEU | 82 HIS |
| SER | 78 HIS ILE | 79 MET LEU | 82 TYR |
| SER | 78 HIS ILE | 79 THR LEU | 82 PHE |
| SER | 78 HIS ILE | 79 THR LEU | 82 HIS |
| SER | 78 HIS ILE | 79 THR LEU | 82 TYR |
| SER | 78 HIS ILE | 79 VAL LEU | 82 PHE |
| SER | 78 HIS ILE | 79 VAL LEU | 82 HIS |
| SER | 78 HIS ILE | 79 VAL LEU | 82 TYR |
| SER | 78 LYS ILE | 79 LEU LEU | 82 PHE |
| SER | 78 LYS ILE | 79 LEU LEU | 82 HIS |
| SER | 78 LYS ILE | 79 LEU LEU | 82 TYR |
| SER | 78 LYS ILE | 79 MET LEU | 82 PHE |
| SER | 78 LYS ILE | 79 MET LEU | 82 HIS |
| SER | 78 LYS ILE | 79 MET LEU | 82 TYR |
| SER | 78 LYS ILE | 79 THR LEU | 82 PHE |
| SER | 78 LYS ILE | 79 THR LEU | 82 HIS |
| SER | 78 LYS ILE | 79 THR LEU | 82 TYR |
| SER | 78 LYS ILE | 79 VAL LEU | 82 PRE |
| SER | 78 LYS ILE | 79 VAL LEU | 82 HIS |
| SER | 78 LYS ILE | 79 VAL LEU | 82 TYR |
| SER | 78 TYR ILE | 79 LEU LEU | 82 PRE |
| SER | 78 TYR ILE | 79 LEU LEU | 82 HIS |
| SER | 78 TYR ILE | 79 LEU LEU | 82 TYR |
| SER | 78 TYR ILE | 79 MET LEU | 82 PHE |
| SER | 78 TYR ILE | 79 MET LEU | 82 HIS |
| SER | 78 TYR ILE | 79 MET LEU | 82 TYR |
| SER | 78 TYR ILE | 79 THR LEU | 82 PHE |
| SER | 78 TYR ILE | 79 THR LEU | 82 HIS |
| SER | 78 TYR ILE | 79 THR LEU | 82 TYR |
| SER | 78 TYR ILE | 79 VAL LEU | 82 PRE |
| SER | 78 TYR ILE | 79 VAL LEU | 82 HIS |
| SER | 78 TYR ILE | 79 VAL LEU | 82 TYR |
| SER | 78 ASN ILE | 79 LEU VAL | 81 THR |
| SER | 78 ASN ILE | 79 MET VAL | 81 THR |
| SER | 78 ASN ILE | 79 THR VAL | 81 THR |
| SER | 78 ASN ILE | 79 VAL VAL | 81 THR |
| SER | 78 THR ILE | 79 LEU VAL | 81 THR |
| SER | 78 THR ILE | 79 MET VAL | 81 THR |
| SER | 78 THR ILE | 79 THR VAL | 81 THR |
| SER | 78 THR ILE | 79 VAL VAL | 81 THR |
| SER | 78 ARG ILE | 79 LEU VAL | 81 THR |
| SER | 78 ARG ILE | 79 MET VAL | 81 THR |
| SER | 78 ARG ILE | 79 THR VAL | 81 THR |
| SER | 78 ARG ILE | 79 VAL VAL | 81 THR |
| SER | 78 ASP ILE | 79 LEU VAL | 81 THR |
| SER | 78 ASP ILE | 79 MET VAL | 81 THR |
| SER | 78 ASP ILE | 79 THR VAL | 81 THR |
| SER | 78 ASP ILE | 79 VAL VAL | 81 THR |
| SER | 78 GLN ILE | 79 LEU VAL | 81 THR |
| SER | 78 GLN ILE | 79 MET VAL | 81 THR |
| SER | 78 GLN ILE | 79 THR VAL | 81 THR |
| SER | 78 GLN ILE | 79 VAL VAL | 81 THR |
| SER | 78 HIS ILE | 79 LEU VAL | 81 THR |
| SER | 78 HIS ILE | 79 MET VAL | 81 THR |

TABLE 4-continued

| Triple Substitution Variants | | | |
|---|---|---|---|
| SER | 78 HIS ILE | 79 THR VAL | 81 THR |
| SER | 78 HIS ILE | 79 VAL VAL | 81 THR |
| SER | 78 LYS ILE | 79 LEU VAL | 81 THR |
| SER | 78 LYS ILE | 79 MET VAL | 81 THR |
| SER | 78 LYS ILE | 79 THR VAL | 81 THR |
| SER | 78 LYS ILE | 79 VAL VAL | 81 THR |
| SER | 78 TYR ILE | 79 LEU VAL | 81 THR |
| SER | 78 TYR ILE | 79 MET VAL | 81 THR |
| SER | 78 TYR ILE | 79 THR VAL | 81 THR |
| SER | 78 TYR ILE | 79 VAL VAL | 81 THR |
| ASN | 76 HIS VAL | 81 THR LEU | 82 PHE |
| ASN | 76 HIS VAL | 81 THR LEU | 82 HIS |
| ASN | 76 HIS VAL | 81 THR LEU | 82 TYR |
| ASN | 76 HIS ILE | 79 LEU LEU | 82 PHE |
| ASN | 76 HIS ILE | 79 LEU LEU | 82 HIS |
| ASN | 76 HIS ILE | 79 LEU LEU | 82 TYR |
| ASN | 76 HIS ILE | 79 MET LEU | 82 PHE |
| ASN | 76 HIS ILE | 79 MET LEU | 82 HIS |
| ASN | 76 HIS ILE | 79 MET LEU | 82 TYR |
| ASN | 76 HIS ILE | 79 THR LEU | 82 PHE |
| ASN | 76 HIS ILE | 79 THR LEU | 82 HIS |
| ASN | 76 HIS ILE | 79 THR LEU | 82 TYR |
| ASN | 76 HIS ILE | 79 VAL LEU | 82 PHE |
| ASN | 76 HIS ILE | 79 VAL LEU | 82 HIS |
| ASN | 76 HIS ILE | 79 VAL LEU | 82 TYR |
| ASN | 76 HIS ILE | 79 LEU VAL | 81 THR |
| ASN | 76 HIS ILE | 79 MET VAL | 81 THR |
| ASN | 76 HIS ILE | 79 THR VAL | 81 THR |
| ASN | 76 HIS ILE | 79 VAL VAL | 81 THR |
| ASN | 76 HIS SER | 78 ASN LEU | 82 PHE |
| ASN | 76 HIS SER | 78 ASN LEU | 82 HIS |
| ASN | 76 HIS SER | 78 ASN LEU | 82 TYR |
| ASN | 76 HIS SER | 78 THR LEU | 82 PHE |
| ASN | 76 HIS SER | 78 THR LEU | 82 HIS |
| ASN | 76 HIS SER | 78 THR LEU | 82 TYR |
| ASN | 76 HIS SER | 78 ARG LEU | 82 PHE |
| ASN | 76 HIS SER | 78 ARG LEU | 82 HIS |
| ASN | 76 HIS SER | 78 ARG LEU | 82 TYR |
| ASN | 76 HIS SER | 78 ASP LEU | 82 PHE |
| ASN | 76 HIS SER | 78 ASP LEU | 82 HIS |
| ASN | 76 HIS SER | 78 ASP LEU | 82 TYR |
| ASN | 76 HIS SER | 78 GLN LEU | 82 PHE |
| ASN | 76 HIS SER | 78 GLN LEU | 82 HIS |
| ASN | 76 HIS SER | 78 GLN LEU | 82 TYR |
| ASN | 76 HIS SER | 78 HIS LEU | 82 PHE |
| ASN | 76 HIS SER | 78 HIS LEU | 82 HIS |
| ASN | 76 HIS SER | 78 HIS LEU | 82 TYR |
| ASN | 76 HIS SER | 78 LYS LEU | 82 PHE |
| ASN | 76 HIS SER | 78 LYS LEU | 82 HIS |
| ASN | 76 HIS SER | 78 LYS LEU | 82 TYR |
| ASN | 76 HIS SER | 78 TYR LEU | 82 PHE |
| ASN | 76 HIS SER | 78 TYR LEU | 82 HIS |
| ASN | 76 HIS SER | 78 TYR LEU | 82 TYR |
| ASN | 76 HIS SER | 78 ASN VAL | 81 THR |
| ASN | 76 HIS SER | 78 THR VAL | 81 THR |
| ASN | 76 HIS SER | 78 ARG VAL | 81 THR |
| ASN | 76 HIS SER | 78 ASP VAL | 81 THR |
| ASN | 76 HIS SER | 78 GLN VAL | 81 THR |
| ASN | 76 HIS SER | 78 HIS VAL | 81 THR |
| ASN | 76 HIS SER | 78 LYS VAL | 81 THR |
| ASN | 76 HIS SER | 78 TYR VAL | 81 THR |
| ASN | 76 HIS SER | 78 ASN ILE | 79 LEU |
| ASN | 76 HIS SER | 78 ASN ILE | 79 MET |
| ASN | 76 HIS SER | 78 ASN ILE | 79 THR |
| ASN | 76 HIS SER | 78 ASN ILE | 79 VAL |
| ASN | 76 HIS SER | 78 THR ILE | 79 LEU |
| ASN | 76 HIS SER | 78 THR ILE | 79 MET |
| ASN | 76 HIS SER | 78 THR ILE | 79 THR |
| ASN | 76 HIS SER | 78 THR ILE | 79 VAL |
| ASN | 76 HIS SER | 78 ARG ILE | 79 LEU |
| ASN | 76 HIS SER | 78 ARG ILE | 79 MET |
| ASN | 76 HIS SER | 78 ARG ILE | 79 THR |
| ASN | 76 HIS SER | 78 ARG ILE | 79 VAL |
| ASN | 76 HIS SER | 78 ASP ILE | 79 LEU |
| ASN | 76 HIS SER | 78 ASP ILE | 79 MET |
| ASN | 76 HIS SER | 78 ASP ILE | 79 THR |
| ASN | 76 HIS SER | 78 ASP ILE | 79 VAL |

TABLE 4-continued

Triple Substitution Variants

| | | | | | | | | |
|---|---|---|---|---|---|---|---|---|
| ASN | 76 HIS SER | 78 GLN ILE | 79 LEU | | LEU | 75 ILE SER | 78 THR LEU | 82 HIS |
| ASN | 76 HIS SER | 78 GLN ILE | 79 MET | | LEU | 75 ILE SER | 78 THR LEU | 82 TYR |
| ASN | 76 HIS SER | 78 GLN ILE | 79 THR | | LEU | 75 ILE SER | 78 ARG LEU | 82 PHE |
| ASN | 76 HIS SER | 78 GLN ILE | 79 VAL | | LEU | 75 ILE SER | 78 ARG LEU | 82 HIS |
| ASN | 76 HIS SER | 78 HIS ILE | 79 LEU | | LEU | 75 ILE SER | 78 ARG LEU | 82 TYR |
| ASN | 76 HIS SER | 78 HIS ILE | 79 MET | | LEU | 75 ILE SER | 78 ASP LEU | 82 PHE |
| ASN | 76 HIS SER | 78 HIS ILE | 79 THR | | LEU | 75 ILE SER | 78 ASP LEU | 82 HIS |
| ASN | 76 HIS SER | 78 HIS ILE | 79 VAL | | LEU | 75 ILE SER | 78 ASP LEU | 82 TYR |
| ASN | 76 HIS SER | 78 LYS ILE | 79 LEU | | LEU | 75 ILE SER | 78 GLN LEU | 82 PHE |
| ASN | 76 HIS SER | 78 LYS ILE | 79 MET | | LEU | 75 ILE SER | 78 GLN LEU | 82 HIS |
| ASN | 76 HIS SER | 78 LYS ILE | 79 THR | | LEU | 75 ILE SER | 78 GLN LEU | 82 TYR |
| ASN | 76 HIS SER | 78 LYS ILE | 79 VAL | | LEU | 75 ILE SER | 78 HIS LEU | 82 PHE |
| ASN | 76 HIS SER | 78 TYR ILE | 79 LEU | | LEU | 75 ILE SER | 78 HIS LEU | 82 HIS |
| ASN | 76 HIS SER | 78 TYR ILE | 79 MET | | LEU | 75 ILE SER | 78 HIS LEU | 82 TYR |
| ASN | 76 HIS SER | 78 TYR ILE | 79 THR | | LEU | 75 ILE SER | 78 LYS LEU | 82 PHE |
| ASN | 76 HIS SER | 78 TYR ILE | 79 VAL | | LEU | 75 ILE SER | 78 LYS LEU | 82 HIS |
| LEU | 75 ILE VAL | 81 THR LEU | 82 PHE | | LEU | 75 ILE SER | 78 LYS LEU | 82 TYR |
| LEU | 75 ILE VAL | 81 THR LEU | 82 HIS | | LEU | 75 ILE SER | 78 TYR LEU | 82 PHE |
| LEU | 75 ILE VAL | 81 THR LEU | 82 TYR | | LEU | 75 ILE SER | 78 TYR LEU | 82 HIS |
| LEU | 75 MET VAL | 81 THR LEU | 82 PHE | | LEU | 75 ILE SER | 78 TYR LEU | 82 TYR |
| LEU | 75 MET VAL | 81 THR LEU | 82 HIS | | LEU | 75 MET SER | 78 ASN LEU | 82 PHE |
| LEU | 75 MET VAL | 81 THR LEU | 82 TYR | | LEU | 75 MET SER | 78 ASN LEU | 82 HIS |
| LEU | 75 VAL VAL | 81 THR LEU | 82 PHE | | LEU | 75 MET SER | 78 ASN LEU | 82 TYR |
| LEU | 75 VAL VAL | 81 THR LEU | 82 HIS | | LEU | 75 MET SER | 78 THR LEU | 82 PHE |
| LEU | 75 VAL VAL | 81 THR LEU | 82 TYR | | LEU | 75 MET SER | 78 THR LEU | 82 HIS |
| LEU | 75 ILE ILE | 79 LEU LEU | 82 PHE | | LEU | 75 MET SER | 78 THR LEU | 82 TYR |
| LEU | 75 ILE ILE | 79 LEU LEU | 82 HIS | | LEU | 75 MET SER | 78 ARG LEU | 82 PHE |
| LEU | 75 ILE ILE | 79 LEU LEU | 82 TYR | | LEU | 75 MET SER | 78 ARG LEU | 82 HIS |
| LEU | 75 ILE ILE | 79 MET LEU | 82 PHE | | LEU | 75 MET SER | 78 ARG LEU | 82 TYR |
| LEU | 75 ILE ILE | 79 MET LEU | 82 HIS | | LEU | 75 MET SER | 78 ASP LEU | 82 PHE |
| LEU | 75 ILE ILE | 79 MET LEU | 82 TYR | | LEU | 75 MET SER | 78 ASP LEU | 82 HIS |
| LEU | 75 ILE ILE | 79 THR LEU | 82 PHE | | LEU | 75 MET SER | 78 ASP LEU | 82 TYR |
| LEU | 75 ILE ILE | 79 THR LEU | 82 HIS | | LEU | 75 MET SER | 78 GLN LEU | 82 PHE |
| LEU | 75 ILE ILE | 79 THR LEU | 82 TYR | | LEU | 75 MET SER | 78 GLN LEU | 82 HIS |
| LEU | 75 ILE ILE | 79 VAL LEU | 82 PHE | | LEU | 75 MET SER | 78 GLN LEU | 82 TYR |
| LEU | 75 ILE ILE | 79 VAL LEU | 82 HIS | | LEU | 75 MET SER | 78 HIS LEU | 82 PHE |
| LEU | 75 ILE ILE | 79 VAL LEU | 82 TYR | | LEU | 75 MET SER | 78 HIS LEU | 82 HIS |
| LEU | 75 MET ILE | 79 LEU LEU | 82 PHE | | LEU | 75 MET SER | 78 HIS LEU | 82 TYR |
| LEU | 75 MET ILE | 79 LEU LEU | 82 HIS | | LEU | 75 MET SER | 78 LYS LEU | 82 PHE |
| LEU | 75 MET ILE | 79 LEU LEU | 82 TYR | | LEU | 75 MET SER | 78 LYS LEU | 82 HIS |
| LEU | 75 MET ILE | 79 MET LEU | 82 PHE | | LEU | 75 MET SER | 78 LYS LEU | 82 TYR |
| LEU | 75 MET ILE | 79 MET LEU | 82 HIS | | LEU | 75 MET SER | 78 TYR LEU | 82 PHE |
| LEU | 75 MET ILE | 79 MET LEU | 82 TYR | | LEU | 75 MET SER | 78 TYR LEU | 82 HIS |
| LEU | 75 MET ILE | 79 THR LEU | 82 PHE | | LEU | 75 MET SER | 78 TYR LEU | 82 TYR |
| LEU | 75 MET ILE | 79 THR LEU | 82 HIS | | LEU | 75 VAL SER | 78 ASN LEU | 82 PHE |
| LEU | 75 MET ILE | 79 THR LEU | 82 TYR | | LEU | 75 VAL SER | 78 ASN LEU | 82 HIS |
| LEU | 75 MET ILE | 79 VAL LEU | 82 PHE | | LEU | 75 VAL SER | 78 ASN LEU | 82 TYR |
| LEU | 75 MET ILE | 79 VAL LEU | 82 HIS | | LEU | 75 VAL SER | 78 THR LEU | 82 PHE |
| LEU | 75 MET ILE | 79 VAL LEU | 82 TYR | | LEU | 75 VAL SER | 78 THR LEU | 82 HIS |
| LEU | 75 VAL ILE | 79 LEU LEU | 82 PHE | | LEU | 75 VAL SER | 78 THR LEU | 82 TYR |
| LEU | 75 VAL ILE | 79 LEU LEU | 82 HIS | | LEU | 75 VAL SER | 78 ARG LEU | 82 PHE |
| LEU | 75 VAL ILE | 79 LEU LEU | 82 TYR | | LEU | 75 VAL SER | 78 ARG LEU | 82 HIS |
| LEU | 75 VAL ILE | 79 MET LEU | 82 PHE | | LEU | 75 VAL SER | 78 ARG LEU | 82 TYR |
| LEU | 75 VAL ILE | 79 MET LEU | 82 HIS | | LEU | 75 VAL SER | 78 ASP LEU | 82 PHE |
| LEU | 75 VAL ILE | 79 MET LEU | 82 TYR | | LEU | 75 VAL SER | 78 ASP LEU | 82 HIS |
| LEU | 75 VAL ILE | 79 THR LEU | 82 PHE | | LEU | 75 VAL SER | 78 ASP LEU | 82 TYR |
| LEU | 75 VAL ILE | 79 THR LEU | 82 HIS | | LEU | 75 VAL SER | 78 GLN LEU | 82 PHE |
| LEU | 75 VAL ILE | 79 THR LEU | 82 TYR | | LEU | 75 VAL SER | 78 GLN LEU | 82 HIS |
| LEU | 75 VAL ILE | 79 VAL LEU | 82 PHE | | LEU | 75 VAL SER | 78 GLN LEU | 82 TYR |
| LEU | 75 VAL ILE | 79 VAL LEU | 82 HIS | | LEU | 75 VAL SER | 78 HIS LEU | 82 PHE |
| LEU | 75 VAL ILE | 79 VAL LEU | 82 TYR | | LEU | 75 VAL SER | 78 HIS LEU | 82 HIS |
| LEU | 75 ILE ILE | 79 LEU VAL | 81 THR | | LEU | 75 VAL SER | 78 HIS LEU | 82 TYR |
| LEU | 75 ILE ILE | 79 MET VAL | 81 THR | | LEU | 75 VAL SER | 78 LYS LEU | 82 PHE |
| LEU | 75 ILE ILE | 79 THR VAL | 81 THR | | LEU | 75 VAL SER | 78 LYS LEU | 82 HIS |
| LEU | 75 ILE ILE | 79 VAL VAL | 81 THR | | LEU | 75 VAL SER | 78 LYS LEU | 82 TYR |
| LEU | 75 MET ILE | 79 LEU VAL | 81 THR | | LEU | 75 VAL SER | 78 TYR LEU | 82 PHE |
| LEU | 75 MET ILE | 79 MET VAL | 81 THR | | LEU | 75 VAL SER | 78 TYR LEU | 82 HIS |
| LEU | 75 MET ILE | 79 THR VAL | 81 THR | | LEU | 75 VAL SER | 78 TYR LEU | 82 TYR |
| LEU | 75 MET ILE | 79 VAL VAL | 81 THR | | LEU | 75 ILE SER | 78 ASN VAL | 81 THR |
| LEU | 75 VAL ILE | 79 LEU VAL | 81 THR | | LEU | 75 ILE SER | 78 THR VAL | 81 THR |
| LEU | 75 VAL ILE | 79 MET VAL | 81 THR | | LEU | 75 ILE SER | 78 ARG VAL | 81 THR |
| LEU | 75 VAL ILE | 79 THR VAL | 81 THR | | LEU | 75 ILE SER | 78 ASP VAL | 81 THR |
| LEU | 75 VAL ILE | 79 VAL VAL | 81 THR | | LEU | 75 ILE SER | 78 GLN VAL | 81 THR |
| LEU | 75 ILE SER | 78 ASN LEU | 82 PHE | | LEU | 75 ILE SER | 78 HIS VAL | 81 THR |
| LEU | 75 ILE SER | 78 ASN LEU | 82 HIS | | LEU | 75 ILE SER | 78 LYS VAL | 81 THR |
| LEU | 75 ILE SER | 78 ASN LEU | 82 TYR | | LEU | 75 ILE SER | 78 TYR VAL | 81 THR |
| LEU | 75 ILE SER | 78 THR LEU | 82 PHE | | LEU | 75 MET SER | 78 ASN VAL | 81 THR |

TABLE 4-continued

Triple Substitution Variants

| | | | |
|---|---|---|---|
| LEU | 75 MET SER | 78 THR VAL | 81 THR |
| LEU | 75 MET SER | 78 ARG VAL | 81 THR |
| LEU | 75 MET SER | 78 ASP VAL | 81 THR |
| LEU | 75 MET SER | 78 GLN VAL | 81 THR |
| LEU | 75 MET SER | 78 HIS VAL | 81 THR |
| LEU | 75 MET SER | 78 LYS VAL | 81 THR |
| LEU | 75 MET SER | 78 TYR VAL | 81 THR |
| LEU | 75 VAL SER | 78 ASN VAL | 81 THR |
| LEU | 75 VAL SER | 78 THR VAL | 81 THR |
| LEU | 75 VAL SER | 78 ARG VAL | 81 THR |
| LEU | 75 VAL SER | 78 ASP VAL | 81 THR |
| LEU | 75 VAL SER | 78 GLN VAL | 81 THR |
| LEU | 75 VAL SER | 78 HIS VAL | 81 THR |
| LEU | 75 VAL SER | 78 LYS VAL | 81 THR |
| LEU | 75 VAL SER | 78 TYR VAL | 81 THR |
| LEU | 75 ILE SER | 78 ASN ILE | 79 LEU |
| LEU | 75 ILE SER | 78 ASN ILE | 79 MET |
| LEU | 75 ILE SER | 78 ASN ILE | 79 THR |
| LEU | 75 ILE SER | 78 ASN ILE | 79 VAL |
| LEU | 75 ILE SER | 78 THR ILE | 79 LEU |
| LEU | 75 ILE SER | 78 THR ILE | 79 MET |
| LEU | 75 ILE SER | 78 THR ILE | 79 THR |
| LEU | 75 ILE SER | 78 THR ILE | 79 VAL |
| LEU | 75 ILE SER | 78 ARG ILE | 79 LEU |
| LEU | 75 ILE SER | 78 ARG ILE | 79 MET |
| LEU | 75 ILE SER | 78 ARG ILE | 79 THR |
| LEU | 75 ILE SER | 78 ARG ILE | 79 VAL |
| LEU | 75 ILE SER | 78 ASP ILE | 79 LEU |
| LEU | 75 ILE SER | 78 ASP ILE | 79 MET |
| LEU | 75 ILE SER | 78 ASP ILE | 79 THR |
| LEU | 75 ILE SER | 78 ASP ILE | 79 VAL |
| LEU | 75 ILE SER | 78 GLN ILE | 79 LEU |
| LEU | 75 ILE SER | 78 GLN ILE | 79 MET |
| LEU | 75 ILE SER | 78 GLN ILE | 79 THR |
| LEU | 75 ILE SER | 78 GLN ILE | 79 VAL |
| LEU | 75 ILE SER | 78 HIS ILE | 79 LEU |
| LEU | 75 ILE SER | 78 HIS ILE | 79 MET |
| LEU | 75 ILE SER | 78 HIS ILE | 79 THR |
| LEU | 75 ILE SER | 78 HIS ILE | 79 VAL |
| LEU | 75 ILE SER | 78 LYS ILE | 79 LEU |
| LEU | 75 ILE SER | 78 LYS ILE | 79 MET |
| LEU | 75 ILE SER | 78 LYS ILE | 79 THR |
| LEU | 75 ILE SER | 78 LYS ILE | 79 VAL |
| LEU | 75 ILE SER | 78 TYR ILE | 79 LEU |
| LEU | 75 ILE SER | 78 TYR ILE | 79 MET |
| LEU | 75 ILE SER | 78 TYR ILE | 79 THR |
| LEU | 75 ILE SER | 78 TYR ILE | 79 VAL |
| LEU | 75 MET SER | 78 ASN ILE | 79 LEU |
| LEU | 75 MET SER | 78 ASN ILE | 79 MET |
| LEU | 75 MET SER | 78 ASN ILE | 79 THR |
| LEU | 75 MET SER | 78 ASN ILE | 79 VAL |
| LEU | 75 MET SER | 78 THR ILE | 79 LEU |
| LEU | 75 MET SER | 78 THR ILE | 79 MET |
| LEU | 75 MET SER | 78 THR ILE | 79 THR |
| LEU | 75 MET SER | 78 THR ILE | 79 VAL |
| LEU | 75 MET SER | 78 ARG ILE | 79 LEU |
| LEU | 75 MET SER | 78 ARG ILE | 79 MET |
| LEU | 75 MET SER | 78 ARG ILE | 79 THR |
| LEU | 75 MET SER | 78 ARG ILE | 79 VAL |
| LEU | 75 MET SER | 78 ASP ILE | 79 LEU |
| LEU | 75 MET SER | 78 ASP ILE | 79 MET |
| LEU | 75 MET SER | 78 ASP ILE | 79 THR |
| LEU | 75 MET SER | 78 ASP ILE | 79 VAL |
| LEU | 75 MET SER | 78 GLN ILE | 79 LEU |
| LEU | 75 MET SER | 78 GLN ILE | 79 MET |
| LEU | 75 MET SER | 78 GLN ILE | 79 THR |
| LEU | 75 MET SER | 78 GLN ILE | 79 VAL |
| LEU | 75 MET SER | 78 HIS ILE | 79 LEU |
| LEU | 75 MET SER | 78 HIS ILE | 79 MET |
| LEU | 75 MET SER | 78 HIS ILE | 79 THR |
| LEU | 75 MET SER | 78 HIS ILE | 79 VAL |
| LEU | 75 MET SER | 78 LYS ILE | 79 LEU |
| LEU | 75 MET SER | 78 LYS ILE | 79 MET |
| LEU | 75 MET SER | 78 LYS ILE | 79 THR |
| LEU | 75 MET SER | 78 LYS ILE | 79 VAL |
| LEU | 75 MET SER | 78 TYR ILE | 79 LEU |
| LEU | 75 MET SER | 78 TYR ILE | 79 MET |
| LEU | 75 MET SER | 78 TYR ILE | 79 THR |
| LEU | 75 MET SER | 78 TYR ILE | 79 VAL |
| LEU | 75 VAL SER | 78 ASN ILE | 79 LEU |
| LEU | 75 VAL SER | 78 ASN ILE | 79 MET |
| LEU | 75 VAL SER | 78 ASN ILE | 79 THR |
| LEU | 75 VAL SER | 78 ASN ILE | 79 VAL |
| LEU | 75 VAL SER | 78 THR ILE | 79 LEU |
| LEU | 75 VAL SER | 78 THR ILE | 79 MET |
| LEU | 75 VAL SER | 78 THR ILE | 79 THR |
| LEU | 75 VAL SER | 78 THR ILE | 79 VAL |
| LEU | 75 VAL SER | 78 ARG ILE | 79 LEU |
| LEU | 75 VAL SER | 78 ARG ILE | 79 MET |
| LEU | 75 VAL SER | 78 ARG ILE | 79 THR |
| LEU | 75 VAL SER | 78 ARG ILE | 79 VAL |
| LEU | 75 VAL SER | 78 ASP ILE | 79 LEU |
| LEU | 75 VAL SER | 78 ASP ILE | 79 MET |
| LEU | 75 VAL SER | 78 ASP ILE | 79 THR |
| LEU | 75 VAL SER | 78 ASP ILE | 79 VAL |
| LEU | 75 VAL SER | 78 GLN ILE | 79 LEU |
| LEU | 75 VAL SER | 78 GLN ILE | 79 MET |
| LEU | 75 VAL SER | 78 GLN ILE | 79 THR |
| LEU | 75 VAL SER | 78 GLN ILE | 79 VAL |
| LEU | 75 VAL SER | 78 HIS ILE | 79 LEU |
| LEU | 75 VAL SER | 78 HIS ILE | 79 MET |
| LEU | 75 VAL SER | 78 HIS ILE | 79 THR |
| LEU | 75 VAL SER | 78 HIS ILE | 79 VAL |
| LEU | 75 VAL SER | 78 LYS ILE | 79 LEU |
| LEU | 75 VAL SER | 78 LYS ILE | 79 MET |
| LEU | 75 VAL SER | 78 LYS ILE | 79 THR |
| LEU | 75 VAL SER | 78 LYS ILE | 79 VAL |
| LEU | 75 VAL SER | 78 TYR ILE | 79 LEU |
| LEU | 75 VAL SER | 78 TYR ILE | 79 MET |
| LEU | 75 VAL SER | 78 TYR ILE | 79 THR |
| LEU | 75 VAL SER | 78 TYR ILE | 79 VAL |
| LEU | 75 ILE ASN | 76 HIS LEU | 82 PHE |
| LEU | 75 ILE ASN | 76 HIS LEU | 82 HIS |
| LEU | 75 ILE ASN | 76 HIS LEU | 82 TYR |
| LEU | 75 MET ASN | 76 HIS LEU | 82 PHE |
| LEU | 75 MET ASN | 76 HIS LEU | 82 HIS |
| LEU | 75 MET ASN | 76 HIS LEU | 82 TYR |
| LEU | 75 VAL ASN | 76 HIS LEU | 82 PHE |
| LEU | 75 VAL ASN | 76 HIS LEU | 82 HIS |
| LEU | 75 VAL ASN | 76 HIS LEU | 82 TYR |
| LEU | 75 ILE ASN | 76 HIS VAL | 81 THR |
| LEU | 75 MET ASN | 76 HIS VAL | 81 THR |
| LEU | 75 VAL ASN | 76 HIS VAL | 81 THR |
| LEU | 75 ILE ASN | 76 HIS ILE | 79 LEU |
| LEU | 75 ILE ASN | 76 HIS ILE | 79 MET |
| LEU | 75 ILE ASN | 76 HIS ILE | 79 THR |
| LEU | 75 ILE ASN | 76 HIS ILE | 79 VAL |
| LEU | 75 MET ASN | 76 HIS ILE | 79 LEU |
| LEU | 75 MET ASN | 76 HIS ILE | 79 MET |
| LEU | 75 MET ASN | 76 HIS ILE | 79 THR |
| LEU | 75 MET ASN | 76 HIS ILE | 79 VAL |
| LEU | 75 VAL ASN | 76 HIS ILE | 79 LEU |
| LEU | 75 VAL ASN | 76 HIS ILE | 79 MET |
| LEU | 75 VAL ASN | 76 HIS ILE | 79 THR |
| LEU | 75 VAL ASN | 76 HIS ILE | 79 VAL |
| LEU | 75 ILE ASN | 76 HIS SER | 78 ASN |
| LEU | 75 ILE ASN | 76 HIS SER | 78 THR |
| LEU | 75 ILE ASN | 76 HIS SER | 78 ARG |
| LEU | 75 ILE ASN | 76 HIS SER | 78 ASP |
| LEU | 75 ILE ASN | 76 HIS SER | 78 GLN |
| LEU | 75 ILE ASN | 76 HIS SER | 78 HIS |
| LEU | 75 ILE ASN | 76 HIS SER | 78 LYS |
| LEU | 75 ILE ASN | 76 HIS SER | 78 TYR |
| LEU | 75 MET ASN | 76 HIS SER | 78 ASN |
| LEU | 75 MET ASN | 76 HIS SER | 78 THR |
| LEU | 75 MET ASN | 76 HIS SER | 78 ARG |
| LEU | 75 MET ASN | 76 HIS SER | 78 ASP |
| LEU | 75 MET ASN | 76 HIS SER | 78 GLN |
| LEU | 75 MET ASN | 76 HIS SER | 78 HIS |
| LEU | 75 MET ASN | 76 HIS SER | 78 LYS |
| LEU | 75 MET ASN | 76 HIS SER | 78 TYR |
| LEU | 75 VAL ASN | 76 HIS SER | 78 ASN |
| LEU | 75 VAL ASN | 76 HIS SER | 78 THR |
| LEU | 75 VAL ASN | 76 HIS SER | 78 ARG |

TABLE 4-continued

Triple Substitution Variants

| | | | |
|---|---|---|---|
| LEU | 75 VAL ASN | 76 HIS SER | 78 ASP |
| LEU | 75 VAL ASN | 76 HIS SER | 78 GLN |
| LEU | 75 VAL ASN | 76 HIS SER | 78 HIS |
| LEU | 75 VAL ASN | 76 HIS SER | 78 LYS |
| LEU | 75 VAL ASN | 76 HIS SER | 78 TYR |

TABLE 5

Quadruple Substitution Variants

| | | | | |
|---|---|---|---|---|
| SER | 78 ASN ILE | 79 LEU VAL | 81 THR LEU | 82 PHE |
| SER | 78 ASN ILE | 79 LEU VAL | 81 THR LEU | 82 HIS |
| SER | 78 ASN ILE | 79 LEU VAL | 81 THR LEU | 82 TYR |
| SER | 78 ASN ILE | 79 MET VAL | 81 THR LEU | 82 PHE |
| SER | 78 ASN ILE | 79 MET VAL | 81 THR LEU | 82 HIS |
| SER | 78 ASN ILE | 79 MET VAL | 81 THR LEU | 82 TYR |
| SER | 78 ASN ILE | 79 THR VAL | 81 THR LEU | 82 PHE |
| SER | 78 ASN ILE | 79 THR VAL | 81 THR LEU | 82 HIS |
| SER | 78 ASN ILE | 79 THR VAL | 81 THR LEU | 82 TYR |
| SER | 78 ASN ILE | 79 VAL VAL | 81 THR LEU | 82 PHE |
| SER | 78 ASN ILE | 79 VAL VAL | 81 THR LEU | 82 HIS |
| SER | 78 ASN ILE | 79 VAL VAL | 81 THR LEU | 82 TYR |
| SER | 78 THR ILE | 79 LEU VAL | 81 THR LEU | 82 PHE |
| SER | 78 THR ILE | 79 LEU VAL | 81 THR LEU | 82 HIS |
| SER | 78 THR ILE | 79 LEU VAL | 81 THR LEU | 82 TYR |
| SER | 78 THR ILE | 79 MET VAL | 81 THR LEU | 82 PHE |
| SER | 78 THR ILE | 79 MET VAL | 81 THR LEU | 82 HIS |
| SER | 78 THR ILE | 79 MET VAL | 81 THR LEU | 82 TYR |
| SER | 78 THR ILE | 79 THR VAL | 81 THR LEU | 82 PHE |
| SER | 78 THR ILE | 79 THR VAL | 81 THR LEU | 82 HIS |
| SER | 78 THR ILE | 79 THR VAL | 81 THR LEU | 82 TYR |
| SER | 78 THR ILE | 79 VAL VAL | 81 THR LEU | 82 PHE |
| SER | 78 THR ILE | 79 VAL VAL | 81 THR LEU | 82 HIS |
| SER | 78 THR ILE | 79 VAL VAL | 81 THR LEU | 82 TYR |
| SER | 78 ARG ILE | 79 LEU VAL | 81 THR LEU | 82 PHE |
| SER | 78 ARG ILE | 79 LEU VAL | 81 THR LEU | 82 HIS |
| SER | 78 ARG ILE | 79 LEU VAL | 81 THR LEU | 82 TYR |
| SER | 78 ARG ILE | 79 MET VAL | 81 THR LEU | 82 PHE |
| SER | 78 ARG ILE | 79 MET VAL | 81 THR LEU | 82 HIS |
| SER | 78 ARG ILE | 79 MET VAL | 81 THR LEU | 82 TYR |
| SER | 78 ARG ILE | 79 THR VAL | 81 THR LEU | 82 PHE |
| SER | 78 ARG ILE | 79 THR VAL | 81 THR LEU | 82 HIS |
| SER | 78 ARG ILE | 79 THR VAL | 81 THR LEU | 82 TYR |
| SER | 78 ARG ILE | 79 VAL VAL | 81 THR LEU | 82 PHE |
| SER | 78 ARG ILE | 79 VAL VAL | 81 THR LEU | 82 HIS |
| SER | 78 ARG ILE | 79 VAL VAL | 81 THR LEU | 82 TYR |
| SER | 78 ASP ILE | 79 LEU VAL | 81 THR LEU | 82 PHE |
| SER | 78 ASP ILE | 79 LEU VAL | 81 THR LEU | 82 HIS |
| SER | 78 ASP ILE | 79 LEU VAL | 81 THR LEU | 82 TYR |
| SER | 78 ASP ILE | 79 MET VAL | 81 THR LEU | 82 PHE |
| SER | 78 ASP ILE | 79 MET VAL | 81 THR LEU | 82 HIS |
| SER | 78 ASP ILE | 79 MET VAL | 81 THR LEU | 82 TYR |
| SER | 78 ASP ILE | 79 THR VAL | 81 THR LEU | 82 PHE |
| SER | 78 ASP ILE | 79 THR VAL | 81 THR LEU | 82 HIS |
| SER | 78 ASP ILE | 79 THR VAL | 81 THR LEU | 82 TYR |
| SER | 78 ASP ILE | 79 VAL VAL | 81 THR LEU | 82 PHE |
| SER | 78 ASP ILE | 79 VAL VAL | 81 THR LEU | 82 HIS |
| SER | 78 ASP ILE | 79 VAL VAL | 81 THR LEU | 82 TYR |
| SER | 78 GLN ILE | 79 LEU VAL | 81 THR LEU | 82 PHE |
| SER | 78 GLN ILE | 79 LEU VAL | 81 THR LEU | 82 HIS |
| SER | 78 GLN ILE | 79 LEU VAL | 81 THR LEU | 82 TYR |
| SER | 78 GLN ILE | 79 MET VAL | 81 THR LEU | 82 PHE |
| SER | 78 GLN ILE | 79 MET VAL | 81 THR LEU | 82 HIS |
| SER | 78 GLN ILE | 79 MET VAL | 81 THR LEU | 82 TYR |
| SER | 78 GLN ILE | 79 THR VAL | 81 THR LEU | 82 PHE |
| SER | 78 GLN ILE | 79 THR VAL | 81 THR LEU | 82 HIS |
| SER | 78 GLN ILE | 79 THR VAL | 81 THR LEU | 82 TYR |
| SER | 78 GLN ILE | 79 VAL VAL | 81 THR LEU | 82 PHE |
| SER | 78 GLN ILE | 79 VAL VAL | 81 THR LEU | 82 HIS |
| SER | 78 GLN ILE | 79 VAL VAL | 81 THR LEU | 82 TYR |
| SER | 78 HIS ILE | 79 LEU VAL | 81 THR LEU | 82 PHE |
| SER | 78 HIS ILE | 79 LEU VAL | 81 THR LEU | 82 HIS |
| SER | 78 HIS ILE | 79 LEU VAL | 81 THR LEU | 82 TYR |
| SER | 78 HIS ILE | 79 MET VAL | 81 THR LEU | 82 PHE |

TABLE 5-continued

Quadruple Substitution Variants

| | | | | |
|---|---|---|---|---|
| SER | 78 HIS ILE | 79 MET VAL | 81 THR LEU | 82 HIS |
| SER | 78 HIS ILE | 79 MET VAL | 81 THR LEU | 82 TYR |
| SER | 78 HIS ILE | 79 THR VAL | 81 THR LEU | 82 PHE |
| SER | 78 HIS ILE | 79 THR VAL | 81 THR LEU | 82 HIS |
| SER | 78 HIS ILE | 79 THR VAL | 81 THR LEU | 82 TYR |
| SER | 78 HIS ILE | 79 VAL VAL | 81 THR LEU | 82 PHE |
| SER | 78 HIS ILE | 79 VAL VAL | 81 THR LEU | 82 HIS |
| SER | 78 HIS ILE | 79 VAL VAL | 81 THR LEU | 82 TYR |
| SER | 78 LYS ILE | 79 LEU VAL | 81 THR LEU | 82 PHE |
| SER | 78 LYS ILE | 79 LEU VAL | 81 THR LEU | 82 HIS |
| SER | 78 LYS ILE | 79 LEU VAL | 81 THR LEU | 82 TYR |
| SER | 78 LYS ILE | 79 MET VAL | 81 THR LEU | 82 PHE |
| SER | 78 LYS ILE | 79 MET VAL | 81 THR LEU | 82 HIS |
| SER | 78 LYS ILE | 79 MET VAL | 81 THR LEU | 82 TYR |
| SER | 78 LYS ILE | 79 THR VAL | 81 THR LEU | 82 PHE |
| SER | 78 LYS ILE | 79 THR VAL | 81 THR LEU | 82 HIS |
| SER | 78 LYS ILE | 79 THR VAL | 81 THR LEU | 82 TYR |
| SER | 78 LYS ILE | 79 VAL VAL | 81 THR LEU | 82 PHE |
| SER | 78 LYS ILE | 79 VAL VAL | 81 THR LEU | 82 HIS |
| SER | 78 LYS ILE | 79 VAL VAL | 81 THR LEU | 82 TYR |
| SER | 78 TYR ILE | 79 LEU VAL | 81 THR LEU | 82 PHE |
| SER | 78 TYR ILE | 79 LEU VAL | 81 THR LEU | 82 HIS |
| SER | 78 TYR ILE | 79 LEU VAL | 81 THR LEU | 82 TYR |
| SER | 78 TYR ILE | 79 MET VAL | 81 THR LEU | 82 PHE |
| SER | 78 TYR ILE | 79 MET VAL | 81 THR LEU | 82 HIS |
| SER | 78 TYR ILE | 79 MET VAL | 81 THR LEU | 82 TYR |
| SER | 78 TYR ILE | 79 THR VAL | 81 THR LEU | 82 PHE |
| SER | 78 TYR ILE | 79 THR VAL | 81 THR LEU | 82 HIS |
| SER | 78 TYR ILE | 79 THR VAL | 81 THR LEU | 82 TYR |
| SER | 78 TYR ILE | 79 VAL VAL | 81 THR LEU | 82 PHE |
| SER | 78 TYR ILE | 79 VAL VAL | 81 THR LEU | 82 HIS |
| SER | 78 TYR ILE | 79 VAL VAL | 81 THR LEU | 82 TYR |
| ASN | 76 HIS ILE | 79 LEU VAL | 81 THR LEU | 82 PHE |
| ASN | 76 HIS ILE | 79 LEU VAL | 81 THR LEU | 82 HIS |
| ASN | 76 HIS ILE | 79 LEU VAL | 81 THR LEU | 82 TYR |
| ASN | 76 HIS ILE | 79 MET VAL | 81 THR LEU | 82 PHE |
| ASN | 76 HIS ILE | 79 MET VAL | 81 THR LEU | 82 HIS |
| ASN | 76 HIS ILE | 79 MET VAL | 81 THR LEU | 82 TYR |
| ASN | 76 HIS ILE | 79 THR VAL | 81 THR LEU | 82 PHE |
| ASN | 76 HIS ILE | 79 THR VAL | 81 THR LEU | 82 HIS |
| ASN | 76 HIS ILE | 79 THR VAL | 81 THR LEU | 82 TYR |
| ASN | 76 HIS ILE | 79 VAL VAL | 81 THR LEU | 82 PHE |
| ASN | 76 HIS ILE | 79 VAL VAL | 81 THR LEU | 82 HIS |
| ASN | 76 HIS ILE | 79 VAL VAL | 81 THR LEU | 82 TYR |
| ASN | 76 HIS SER | 78 ASN VAL | 81 THR LEU | 82 PHE |
| ASN | 76 HIS SER | 78 ASN VAL | 81 THR LEU | 82 HIS |
| ASN | 76 HIS SER | 78 ASN VAL | 81 THR LEU | 82 TYR |
| ASN | 76 HIS SER | 78 THR VAL | 81 THR LEU | 82 PHE |
| ASN | 76 HIS SER | 78 THR VAL | 81 THR LEU | 82 HIS |
| ASN | 76 HIS SER | 78 THR VAL | 81 THR LEU | 82 TYR |
| ASN | 76 HIS SER | 78 ARG VAL | 81 THR LEU | 82 PHE |
| ASN | 76 HIS SER | 78 ARG VAL | 81 THR LEU | 82 HIS |
| ASN | 76 HIS SER | 78 ARG VAL | 81 THR LEU | 82 TYR |
| ASN | 76 HIS SER | 78 ASP VAL | 81 THR LEU | 82 PHE |
| ASN | 76 HIS SER | 78 ASP VAL | 81 THR LEU | 82 HIS |
| ASN | 76 HIS SER | 78 ASP VAL | 81 THR LEU | 82 TYR |
| ASN | 76 HIS SER | 78 GLN VAL | 81 THR LEU | 82 PHE |
| ASN | 76 HIS SER | 78 GLN VAL | 81 THR LEU | 82 HIS |
| ASN | 76 HIS SER | 78 GLN VAL | 81 THR LEU | 82 TYR |
| ASN | 76 HIS SER | 78 HIS VAL | 81 THR LEU | 82 PHE |
| ASN | 76 HIS SER | 78 HIS VAL | 81 THR LEU | 82 HIS |
| ASN | 76 HIS SER | 78 HIS VAL | 81 THR LEU | 82 TYR |
| ASN | 76 HIS SER | 78 LYS VAL | 81 THR LEU | 82 PHE |
| ASN | 76 HIS SER | 78 LYS VAL | 81 THR LEU | 82 HIS |
| ASN | 76 HIS SER | 78 LYS VAL | 81 THR LEU | 82 TYR |
| ASN | 76 HIS SER | 78 TYR VAL | 81 THR LEU | 82 PHE |
| ASN | 76 HIS SER | 78 TYR VAL | 81 THR LEU | 82 HIS |
| ASN | 76 HIS SER | 78 TYR VAL | 81 THR LEU | 82 TYR |
| ASN | 76 HIS SER | 78 ASN ILE | 79 LEU LEU | 82 PHE |
| ASN | 76 HIS SER | 78 ASN ILE | 79 LEU LEU | 82 HIS |
| ASN | 76 HIS SER | 78 ASN ILE | 79 LEU LEU | 82 TYR |
| ASN | 76 HIS SER | 78 ASN ILE | 79 MET LEU | 82 PHE |
| ASN | 76 HIS SER | 78 ASN ILE | 79 MET LEU | 82 HIS |
| ASN | 76 HIS SER | 78 ASN ILE | 79 MET LEU | 82 TYR |
| ASN | 76 HIS SER | 78 ASN ILE | 79 THR LEU | 82 PHE |
| ASN | 76 HIS SER | 78 ASN ILE | 79 THR LEU | 82 HIS |
| ASN | 76 HIS SER | 78 ASN ILE | 79 THR LEU | 82 TYR |

TABLE 5-continued

Quadruple Substitution Variants

| | | | | | | | | | |
|---|---|---|---|---|---|---|---|---|---|
| ASN | 76 HIS SER | 78 ASN ILE | 79 VAL LEU | 82 PHE | ASN | 76 HIS SER | 78 TYR ILE | 79 LEU LEU | 82 TYR |
| ASN | 76 HIS SER | 78 ASN ILE | 79 VAL LEU | 82 HIS | ASN | 76 HIS SER | 78 TYR ILE | 79 MET LEU | 82 PHE |
| ASN | 76 HIS SER | 78 ASN ILE | 79 VAL LEU | 82 TYR | ASN | 76 HIS SER | 78 TYR ILE | 79 MET LEU | 82 HIS |
| ASN | 76 HIS SER | 78 THR ILE | 79 LEU LEU | 82 PHE | ASN | 76 HIS SER | 78 TYR ILE | 79 MET LEU | 82 TYR |
| ASN | 76 HIS SER | 78 THR ILE | 79 LEU LEU | 82 HIS | ASN | 76 HIS SER | 78 TYR ILE | 79 THR LEU | 82 PHE |
| ASN | 76 HIS SER | 78 THR ILE | 79 LEU LEU | 82 TYR | ASN | 76 HIS SER | 78 TYR ILE | 79 THR LEU | 82 HIS |
| ASN | 76 HIS SER | 78 THR ILE | 79 MET LEU | 82 PHE | ASN | 76 HIS SER | 78 TYR ILE | 79 THR LEU | 82 TYR |
| ASN | 76 HIS SER | 78 THR ILE | 79 MET LEU | 82 HIS | ASN | 76 HIS SER | 78 TYR ILE | 79 VAL LEU | 82 PHE |
| ASN | 76 HIS SER | 78 THR ILE | 79 MET LEU | 82 TYR | ASN | 76 HIS SER | 78 TYR ILE | 79 VAL LEU | 82 HIS |
| ASN | 76 HIS SER | 78 THR ILE | 79 THR LEU | 82 PHE | ASN | 76 HIS SER | 78 TYR ILE | 79 VAL LEU | 82 TYR |
| ASN | 76 HIS SER | 78 THR ILE | 79 THR LEU | 82 HIS | ASN | 76 HIS SER | 78 ASN ILE | 79 LEU VAL | 81 THR |
| ASN | 76 HIS SER | 78 THR ILE | 79 THR LEU | 82 TYR | ASN | 76 HIS SER | 78 ASN ILE | 79 MET VAL | 81 THR |
| ASN | 76 HIS SER | 78 THR ILE | 79 VAL LEU | 82 PHE | ASN | 76 HIS SER | 78 ASN ILE | 79 THR VAL | 81 THR |
| ASN | 76 HIS SER | 78 THR ILE | 79 VAL LEU | 82 HIS | ASN | 76 HIS SER | 78 ASN ILE | 79 VAL VAL | 81 THR |
| ASN | 76 HIS SER | 78 THR ILE | 79 VAL LEU | 82 TYR | ASN | 76 HIS SER | 78 THR ILE | 79 LEU VAL | 81 THR |
| ASN | 76 HIS SER | 78 ARG ILE | 79 LEU LEU | 82 PHE | ASN | 76 HIS SER | 78 THR ILE | 79 MET VAL | 81 THR |
| ASN | 76 HIS SER | 78 ARG ILE | 79 LEU LEU | 82 HIS | ASN | 76 HIS SER | 78 THR ILE | 79 THR VAL | 81 THR |
| ASN | 76 HIS SER | 78 ARG ILE | 79 LEU LEU | 82 TYR | ASN | 76 HIS SER | 78 THR ILE | 79 VAL VAL | 81 THR |
| ASN | 76 HIS SER | 78 ARG ILE | 79 MET LEU | 82 PHE | ASN | 76 HIS SER | 78 ARG ILE | 79 LEU VAL | 81 THR |
| ASN | 76 HIS SER | 78 ARG ILE | 79 MET LEU | 82 HIS | ASN | 76 HIS SER | 78 ARG ILE | 79 MET VAL | 81 THR |
| ASN | 76 HIS SER | 78 ARG ILE | 79 MET LEU | 82 TYR | ASN | 76 HIS SER | 78 ARG ILE | 79 THR VAL | 81 THR |
| ASN | 76 HIS SER | 78 ARG ILE | 79 THR LEU | 82 PHE | ASN | 76 HIS SER | 78 ARG ILE | 79 VAL VAL | 81 THR |
| ASN | 76 HIS SER | 78 ARG ILE | 79 THR LEU | 82 HIS | ASN | 76 HIS SER | 78 ASP ILE | 79 LEU VAL | 81 THR |
| ASN | 76 HIS SER | 78 ARG ILE | 79 THR LEU | 82 TYR | ASN | 76 HIS SER | 78 ASP ILE | 79 MET VAL | 81 THR |
| ASN | 76 HIS SER | 78 ARG ILE | 79 VAL LEU | 82 PHE | ASN | 76 HIS SER | 78 ASP ILE | 79 THR VAL | 81 THR |
| ASN | 76 HIS SER | 78 ARG ILE | 79 VAL LEU | 82 HIS | ASN | 76 HIS SER | 78 ASP ILE | 79 VAL VAL | 81 THR |
| ASN | 76 HIS SER | 78 ARG ILE | 79 VAL LEU | 82 TYR | ASN | 76 HIS SER | 78 GLN ILE | 79 LEU VAL | 81 THR |
| ASN | 76 HIS SER | 78 ASP ILE | 79 LEU LEU | 82 PHE | ASN | 76 HIS SER | 78 GLN ILE | 79 MET VAL | 81 THR |
| ASN | 76 HIS SER | 78 ASP ILE | 79 LEU LEU | 82 HIS | ASN | 76 HIS SER | 78 GLN ILE | 79 THR VAL | 81 THR |
| ASN | 76 HIS SER | 78 ASP ILE | 79 LEU LEU | 82 TYR | ASN | 76 HIS SER | 78 GLN ILE | 79 VAL VAL | 81 THR |
| ASN | 76 HIS SER | 78 ASP ILE | 79 MET LEU | 82 PHE | ASN | 76 HIS SER | 78 HIS ILE | 79 LEU VAL | 81 THR |
| ASN | 76 HIS SER | 78 ASP ILE | 79 MET LEU | 82 HIS | ASN | 76 HIS SER | 78 HIS ILE | 79 MET VAL | 81 THR |
| ASN | 76 HIS SER | 78 ASP ILE | 79 MET LEU | 82 TYR | ASN | 76 HIS SER | 78 HIS ILE | 79 THR VAL | 81 THR |
| ASN | 76 HIS SER | 78 ASP ILE | 79 THR LEU | 82 PHE | ASN | 76 HIS SER | 78 HIS ILE | 79 VAL VAL | 81 THR |
| ASN | 76 HIS SER | 78 ASP ILE | 79 THR LEU | 82 HIS | ASN | 76 HIS SER | 78 LYS ILE | 79 LEU VAL | 81 THR |
| ASN | 76 HIS SER | 78 ASP ILE | 79 THR LEU | 82 TYR | ASN | 76 HIS SER | 78 LYS ILE | 79 MET VAL | 81 THR |
| ASN | 76 HIS SER | 78 ASP ILE | 79 VAL LEU | 82 PHE | ASN | 76 HIS SER | 78 LYS ILE | 79 THR VAL | 81 THR |
| ASN | 76 HIS SER | 78 ASP ILE | 79 VAL LEU | 82 HIS | ASN | 76 HIS SER | 78 LYS ILE | 79 VAL VAL | 81 THR |
| ASN | 76 HIS SER | 78 ASP ILE | 79 VAL LEU | 82 TYR | ASN | 76 HIS SER | 78 TYR ILE | 79 LEU VAL | 81 THR |
| ASN | 76 HIS SER | 78 GLN ILE | 79 LEU LEU | 82 PHE | ASN | 76 HIS SER | 78 TYR ILE | 79 MET VAL | 81 THR |
| ASN | 76 HIS SER | 78 GLN ILE | 79 LEU LEU | 82 HIS | ASN | 76 HIS SER | 78 TYR ILE | 79 THR VAL | 81 THR |
| ASN | 76 HIS SER | 78 GLN ILE | 79 LEU LEU | 82 TYR | ASN | 76 HIS SER | 78 TYR ILE | 79 VAL VAL | 81 THR |
| ASN | 76 HIS SER | 78 GLN ILE | 79 MET LEU | 82 PHE | LEU | 75 ILE ILE | 79 LEU VAL | 81 THR LEU | 82 PHE |
| ASN | 76 HIS SER | 78 GLN ILE | 79 MET LEU | 82 HIS | LEU | 75 ILE ILE | 79 LEU VAL | 81 THR LEU | 82 HIS |
| ASN | 76 HIS SER | 78 GLN ILE | 79 MET LEU | 82 TYR | LEU | 75 ILE ILE | 79 LEU VAL | 81 THR LEU | 82 TYR |
| ASN | 76 HIS SER | 78 GLN ILE | 79 THR LEU | 82 PHE | LEU | 75 ILE ILE | 79 MET VAL | 81 THR LEU | 82 PHE |
| ASN | 76 HIS SER | 78 GLN ILE | 79 THR LEU | 82 HIS | LEU | 75 ILE ILE | 79 MET VAL | 81 THR LEU | 82 HIS |
| ASN | 76 HIS SER | 78 GLN ILE | 79 THR LEU | 82 TYR | LEU | 75 ILE ILE | 79 MET VAL | 81 THR LEU | 82 TYR |
| ASN | 76 HIS SER | 78 GLN ILE | 79 VAL LEU | 82 PHE | LEU | 75 ILE ILE | 79 THR VAL | 81 THR LEU | 82 PHE |
| ASN | 76 HIS SER | 78 GLN ILE | 79 VAL LEU | 82 HIS | LEU | 75 ILE ILE | 79 THR VAL | 81 THR LEU | 82 HIS |
| ASN | 76 HIS SER | 78 GLN ILE | 79 VAL LEU | 82 TYR | LEU | 75 ILE ILE | 79 THR VAL | 81 THR LEU | 82 TYR |
| ASN | 76 HIS SER | 78 HIS ILE | 79 LEU LEU | 82 PHE | LEU | 75 ILE ILE | 79 VAL VAL | 81 THR LEU | 82 PHE |
| ASN | 76 HIS SER | 78 HIS ILE | 79 LEU LEU | 82 HIS | LEU | 75 ILE ILE | 79 VAL VAL | 81 THR LEU | 82 HIS |
| ASN | 76 HIS SER | 78 HIS ILE | 79 LEU LEU | 82 TYR | LEU | 75 ILE ILE | 79 VAL VAL | 81 THR LEU | 82 TYR |
| ASN | 76 HIS SER | 78 HIS ILE | 79 MET LEU | 82 PHE | LEU | 75 MET ILE | 79 LEU VAL | 81 THR LEU | 82 PHE |
| ASN | 76 HIS SER | 78 HIS ILE | 79 MET LEU | 82 HIS | LEU | 75 MET ILE | 79 LEU VAL | 81 THR LEU | 82 HIS |
| ASN | 76 HIS SER | 78 HIS ILE | 79 MET LEU | 82 TYR | LEU | 75 MET ILE | 79 LEU VAL | 81 THR LEU | 82 TYR |
| ASN | 76 HIS SER | 78 HIS ILE | 79 THR LEU | 82 PHE | LEU | 75 MET ILE | 79 MET VAL | 81 THR LEU | 82 PHE |
| ASN | 76 HIS SER | 78 HIS ILE | 79 THR LEU | 82 HIS | LEU | 75 MET ILE | 79 MET VAL | 81 THR LEU | 82 HIS |
| ASN | 76 HIS SER | 78 HIS ILE | 79 THR LEU | 82 TYR | LEU | 75 MET ILE | 79 MET VAL | 81 THR LEU | 82 TYR |
| ASN | 76 HIS SER | 78 HIS ILE | 79 VAL LEU | 82 PHE | LEU | 75 MET ILE | 79 THR VAL | 81 THR LEU | 82 PHE |
| ASN | 76 HIS SER | 78 HIS ILE | 79 VAL LEU | 82 HIS | LEU | 75 MET ILE | 79 THR VAL | 81 THR LEU | 82 HIS |
| ASN | 76 HIS SER | 78 HIS ILE | 79 VAL LEU | 82 TYR | LEU | 75 MET ILE | 79 THR VAL | 81 THR LEU | 82 TYR |
| ASN | 76 HIS SER | 78 LYS ILE | 79 LEU LEU | 82 PHE | LEU | 75 MET ILE | 79 VAL VAL | 81 THR LEU | 82 PHE |
| ASN | 76 HIS SER | 78 LYS ILE | 79 LEU LEU | 82 HIS | LEU | 75 MET ILE | 79 VAL VAL | 81 THR LEU | 82 HIS |
| ASN | 76 HIS SER | 78 LYS ILE | 79 LEU LEU | 82 TYR | LEU | 75 MET ILE | 79 VAL VAL | 81 THR LEU | 82 TYR |
| ASN | 76 HIS SER | 78 LYS ILE | 79 MET LEU | 82 PHE | LEU | 75 VAL ILE | 79 LEU VAL | 81 THR LEU | 82 PHE |
| ASN | 76 HIS SER | 78 LYS ILE | 79 MET LEU | 82 HIS | LEU | 75 VAL ILE | 79 LEU VAL | 81 THR LEU | 82 HIS |
| ASN | 76 HIS SER | 78 LYS ILE | 79 MET LEU | 82 TYR | LEU | 75 VAL ILE | 79 LEU VAL | 81 THR LEU | 82 TYR |
| ASN | 76 HIS SER | 78 LYS ILE | 79 THR LEU | 82 PHE | LEU | 75 VAL ILE | 79 MET VAL | 81 THR LEU | 82 PHE |
| ASN | 76 HIS SER | 78 LYS ILE | 79 THR LEU | 82 HIS | LEU | 75 VAL ILE | 79 MET VAL | 81 THR LEU | 82 HIS |
| ASN | 76 HIS SER | 78 LYS ILE | 79 THR LEU | 82 TYR | LEU | 75 VAL ILE | 79 MET VAL | 81 THR LEU | 82 TYR |
| ASN | 76 HIS SER | 78 LYS ILE | 79 VAL LEU | 82 PHE | LEU | 75 VAL ILE | 79 THR VAL | 81 THR LEU | 82 PHE |
| ASN | 76 HIS SER | 78 LYS ILE | 79 VAL LEU | 82 HIS | LEU | 75 VAL ILE | 79 THR VAL | 81 THR LEU | 82 HIS |
| ASN | 76 HIS SER | 78 LYS ILE | 79 VAL LEU | 82 TYR | LEU | 75 VAL ILE | 79 THR VAL | 81 THR LEU | 82 TYR |
| ASN | 76 HIS SER | 78 TYR ILE | 79 LEU LEU | 82 PHE | LEU | 75 VAL ILE | 79 VAL VAL | 81 THR LEU | 82 PHE |
| ASN | 76 HIS SER | 78 TYR ILE | 79 LEU LEU | 82 HIS | LEU | 75 VAL ILE | 79 VAL VAL | 81 THR LEU | 82 HIS |

TABLE 5-continued

Quadruple Substitution Variants

| | | | | |
|---|---|---|---|---|
| LEU 75 VAL ILE | 79 VAL VAL | 81 THR LEU | 82 TYR | |
| LEU 75 ILE SER | 78 ASN VAL | 81 THR LEU | 82 PHE | |
| LEU 75 ILE SER | 78 ASN VAL | 81 THR LEU | 82 HIS | |
| LEU 75 ILE SER | 78 ASN VAL | 81 THR LEU | 82 TYR | |
| LEU 75 ILE SER | 78 THR VAL | 81 THR LEU | 82 PHE | |
| LEU 75 ILE SER | 78 THR VAL | 81 THR LEU | 82 HIS | |
| LEU 75 ILE SER | 78 THR VAL | 81 THR LEU | 82 TYR | |
| LEU 75 ILE SER | 78 ARG VAL | 81 THR LEU | 82 PHE | |
| LEU 75 ILE SER | 78 ARG VAL | 81 THR LEU | 82 HIS | |
| LEU 75 ILE SER | 78 ARG VAL | 81 THR LEU | 82 TYR | |
| LEU 75 ILE SER | 78 ASP VAL | 81 THR LEU | 82 PHE | |
| LEU 75 ILE SER | 78 ASP VAL | 81 THR LEU | 82 HIS | |
| LEU 75 ILE SER | 78 ASP VAL | 81 THR LEU | 82 TYR | |
| LEU 75 ILE SER | 78 GLN VAL | 81 THR LEU | 82 PHE | |
| LEU 75 ILE SER | 78 GLN VAL | 81 THR LEU | 82 HIS | |
| LEU 75 ILE SER | 78 GLN VAL | 81 THR LEU | 82 TYR | |
| LEU 75 ILE SER | 78 HIS VAL | 81 THR LEU | 82 PHE | |
| LEU 75 ILE SER | 78 HIS VAL | 81 THR LEU | 82 HIS | |
| LEU 75 ILE SER | 78 HIS VAL | 81 THR LEU | 82 TYR | |
| LEU 75 ILE SER | 78 LYS VAL | 81 THR LEU | 82 PHE | |
| LEU 75 ILE SER | 78 LYS VAL | 81 THR LEU | 82 HIS | |
| LEU 75 ILE SER | 78 LYS VAL | 81 THR LEU | 82 TYR | |
| LEU 75 ILE SER | 78 TYR VAL | 81 THR LEU | 82 PHE | |
| LEU 75 ILE SER | 78 TYR VAL | 81 THR LEU | 82 HIS | |
| LEU 75 ILE SER | 78 TYR VAL | 81 THR LEU | 82 TYR | |
| LEU 75 MET SER | 78 ASN VAL | 81 THR LEU | 82 PHE | |
| LEU 75 MET SER | 78 ASN VAL | 81 THR LEU | 82 HIS | |
| LEU 75 MET SER | 78 ASN VAL | 81 THR LEU | 82 TYR | |
| LEU 75 MET SER | 78 THR VAL | 81 THR LEU | 82 PHE | |
| LEU 75 MET SER | 78 THR VAL | 81 THR LEU | 82 HIS | |
| LEU 75 MET SER | 78 THR VAL | 81 THR LEU | 82 TYR | |
| LEU 75 MET SER | 78 ARG VAL | 81 THR LEU | 82 PHE | |
| LEU 75 MET SER | 78 ARG VAL | 81 THR LEU | 82 HIS | |
| LEU 75 MET SER | 78 ARG VAL | 81 THR LEU | 82 TYR | |
| LEU 75 MET SER | 78 ASP VAL | 81 THR LEU | 82 PHE | |
| LEU 75 MET SER | 78 ASP VAL | 81 THR LEU | 82 HIS | |
| LEU 75 MET SER | 78 ASP VAL | 81 THR LEU | 82 TYR | |
| LEU 75 MET SER | 78 GLN VAL | 81 THR LEU | 82 PHE | |
| LEU 75 MET SER | 78 GLN VAL | 81 THR LEU | 82 HIS | |
| LEU 75 MET SER | 78 GLN VAL | 81 THR LEU | 82 TYR | |
| LEU 75 MET SER | 78 HIS VAL | 81 THR LEU | 82 PHE | |
| LEU 75 MET SER | 78 HIS VAL | 81 THR LEU | 82 HIS | |
| LEU 75 MET SER | 78 HIS VAL | 81 THR LEU | 82 TYR | |
| LEU 75 MET SER | 78 LYS VAL | 81 THR LEU | 82 PHE | |
| LEU 75 MET SER | 78 LYS VAL | 81 THR LEU | 82 HIS | |
| LEU 75 MET SER | 78 LYS VAL | 81 THR LEU | 82 TYR | |
| LEU 75 MET SER | 78 TYR VAL | 81 THR LEU | 82 PHE | |
| LEU 75 MET SER | 78 TYR VAL | 81 THR LEU | 82 HIS | |
| LEU 75 MET SER | 78 TYR VAL | 81 THR LEU | 82 TYR | |
| LEU 75 VAL SER | 78 ASN VAL | 81 THR LEU | 82 PHE | |
| LEU 75 VAL SER | 78 ASN VAL | 81 THR LEU | 82 HIS | |
| LEU 75 VAL SER | 78 ASN VAL | 81 THR LEU | 82 TYR | |
| LEU 75 VAL SER | 78 THR VAL | 81 THR LEU | 82 PHE | |
| LEU 75 VAL SER | 78 THR VAL | 81 THR LEU | 82 HIS | |
| LEU 75 VAL SER | 78 THR VAL | 81 THR LEU | 82 TYR | |
| LEU 75 VAL SER | 78 ARG VAL | 81 THR LEU | 82 PHE | |
| LEU 75 VAL SER | 78 ARG VAL | 81 THR LEU | 82 HIS | |
| LEU 75 VAL SER | 78 ARG VAL | 81 THR LEU | 82 TYR | |
| LEU 75 VAL SER | 78 ASP VAL | 81 THR LEU | 82 PHE | |
| LEU 75 VAL SER | 78 ASP VAL | 81 THR LEU | 82 HIS | |
| LEU 75 VAL SER | 78 ASP VAL | 81 THR LEU | 82 TYR | |
| LEU 75 VAL SER | 78 GLN VAL | 81 THR LEU | 82 PHE | |
| LEU 75 VAL SER | 78 GLN VAL | 81 THR LEU | 82 HIS | |
| LEU 75 VAL SER | 78 GLN VAL | 81 THR LEU | 82 TYR | |
| LEU 75 VAL SER | 78 HIS VAL | 81 THR LEU | 82 PHE | |
| LEU 75 VAL SER | 78 HIS VAL | 81 THR LEU | 82 HIS | |
| LEU 75 VAL SER | 78 HIS VAL | 81 THR LEU | 82 TYR | |
| LEU 75 VAL SER | 78 LYS VAL | 81 THR LEU | 82 PHE | |
| LEU 75 VAL SER | 78 LYS VAL | 81 THR LEU | 82 HIS | |
| LEU 75 VAL SER | 78 LYS VAL | 81 THR LEU | 82 TYR | |
| LEU 75 VAL SER | 78 TYR VAL | 81 THR LEU | 82 PHE | |
| LEU 75 VAL SER | 78 TYR VAL | 81 THR LEU | 82 HIS | |
| LEU 75 VAL SER | 78 TYR VAL | 81 THR LEU | 82 TYR | |
| LEU 75 ILE SER | 78 ASN ILE | 79 LEU LEU | 82 PHE | |
| LEU 75 ILE SER | 78 ASN ILE | 79 LEU LEU | 82 HIS | |
| LEU 75 ILE SER | 78 ASN ILE | 79 LEU LEU | 82 TYR | |
| LEU 75 ILE SER | 78 ASN ILE | 79 MET LEU | 82 PHE | |
| LEU 75 ILE SER | 78 ASN ILE | 79 MET LEU | 82 HIS | |
| LEU 75 ILE SER | 78 ASN ILE | 79 MET LEU | 82 TYR | |
| LEU 75 ILE SER | 78 ASN ILE | 79 THR LEU | 82 PHE | |
| LEU 75 ILE SER | 78 ASN ILE | 79 THR LEU | 82 HIS | |
| LEU 75 ILE SER | 78 ASN ILE | 79 THR LEU | 82 TYR | |
| LEU 75 ILE SER | 78 ASN ILE | 79 VAL LEU | 82 PHE | |
| LEU 75 ILE SER | 78 ASN ILE | 79 VAL LEU | 82 HIS | |
| LEU 75 ILE SER | 78 ASN ILE | 79 VAL LEU | 82 TYR | |
| LEU 75 ILE SER | 78 THR ILE | 79 LEU LEU | 82 PHE | |
| LEU 75 ILE SER | 78 THR ILE | 79 LEU LEU | 82 HIS | |
| LEU 75 ILE SER | 78 THR ILE | 79 LEU LEU | 82 TYR | |
| LEU 75 ILE SER | 78 THR ILE | 79 MET LEU | 82 PHE | |
| LEU 75 ILE SER | 78 THR ILE | 79 MET LEU | 82 HIS | |
| LEU 75 ILE SER | 78 THR ILE | 79 MET LEU | 82 TYR | |
| LEU 75 ILE SER | 78 THR ILE | 79 THR LEU | 82 PHE | |
| LEU 75 ILE SER | 78 THR ILE | 79 THR LEU | 82 HIS | |
| LEU 75 ILE SER | 78 THR ILE | 79 THR LEU | 82 TYR | |
| LEU 75 ILE SER | 78 THR ILE | 79 VAL LEU | 82 PHE | |
| LEU 75 ILE SER | 78 THR ILE | 79 VAL LEU | 82 HIS | |
| LEU 75 ILE SER | 78 THR ILE | 79 VAL LEU | 82 TYR | |
| LEU 75 ILE SER | 78 ARG ILE | 79 LEU LEU | 82 PHE | |
| LEU 75 ILE SER | 78 ARG ILE | 79 LEU LEU | 82 HIS | |
| LEU 75 ILE SER | 78 ARG ILE | 79 LEU LEU | 82 TYR | |
| LEU 75 ILE SER | 78 ARG ILE | 79 MET LEU | 82 PHE | |
| LEU 75 ILE SER | 78 ARG ILE | 79 MET LEU | 82 HIS | |
| LEU 75 ILE SER | 78 ARG ILE | 79 MET LEU | 82 TYR | |
| LEU 75 ILE SER | 78 ARG ILE | 79 THR LEU | 82 PHE | |
| LEU 75 ILE SER | 78 ARG ILE | 79 THR LEU | 82 HIS | |
| LEU 75 ILE SER | 78 ARG ILE | 79 THR LEU | 82 TYR | |
| LEU 75 ILE SER | 78 ARG ILE | 79 VAL LEU | 82 PHE | |
| LEU 75 ILE SER | 78 ARG ILE | 79 VAL LEU | 82 HIS | |
| LEU 75 ILE SER | 78 ARG ILE | 79 VAL LEU | 82 TYR | |
| LEU 75 ILE SER | 78 ASP ILE | 79 LEU LEU | 82 PHE | |
| LEU 75 ILE SER | 78 ASP ILE | 79 LEU LEU | 82 HIS | |
| LEU 75 ILE SER | 78 ASP ILE | 79 LEU LEU | 82 TYR | |
| LEU 75 ILE SER | 78 ASP ILE | 79 MET LEU | 82 PHE | |
| LEU 75 ILE SER | 78 ASP ILE | 79 MET LEU | 82 HIS | |
| LEU 75 ILE SER | 78 ASP ILE | 79 MET LEU | 82 TYR | |
| LEU 75 ILE SER | 78 ASP ILE | 79 THR LEU | 82 PHE | |
| LEU 75 ILE SER | 78 ASP ILE | 79 THR LEU | 82 HIS | |
| LEU 75 ILE SER | 78 ASP ILE | 79 THR LEU | 82 TYR | |
| LEU 75 ILE SER | 78 ASP ILE | 79 VAL LEU | 82 PHE | |
| LEU 75 ILE SER | 78 ASP ILE | 79 VAL LEU | 82 HIS | |
| LEU 75 ILE SER | 78 ASP ILE | 79 VAL LEU | 82 TYR | |
| LEU 75 ILE SER | 78 GLN ILE | 79 LEU LEU | 82 PHE | |
| LEU 75 ILE SER | 78 GLN ILE | 79 LEU LEU | 82 HIS | |
| LEU 75 ILE SER | 78 GLN ILE | 79 LEU LEU | 82 TYR | |
| LEU 75 ILE SER | 78 GLN ILE | 79 MET LEU | 82 PHE | |
| LEU 75 ILE SER | 78 GLN ILE | 79 MET LEU | 82 HIS | |
| LEU 75 ILE SER | 78 GLN ILE | 79 MET LEU | 82 TYR | |
| LEU 75 ILE SER | 78 GLN ILE | 79 THR LEU | 82 PHE | |
| LEU 75 ILE SER | 78 GLN ILE | 79 THR LEU | 82 HIS | |
| LEU 75 ILE SER | 78 GLN ILE | 79 THR LEU | 82 TYR | |
| LEU 75 ILE SER | 78 GLN ILE | 79 VAL LEU | 82 PHE | |
| LEU 75 ILE SER | 78 GLN ILE | 79 VAL LEU | 82 HIS | |
| LEU 75 ILE SER | 78 GLN ILE | 79 VAL LEU | 82 TYR | |
| LEU 75 ILE SER | 78 HIS ILE | 79 LEU LEU | 82 PHE | |
| LEU 75 ILE SER | 78 HIS ILE | 79 LEU LEU | 82 HIS | |
| LEU 75 ILE SER | 78 HIS ILE | 79 LEU LEU | 82 TYR | |
| LEU 75 ILE SER | 78 HIS ILE | 79 MET LEU | 82 PHE | |
| LEU 75 ILE SER | 78 HIS ILE | 79 MET LEU | 82 HIS | |
| LEU 75 ILE SER | 78 HIS ILE | 79 MET LEU | 82 TYR | |
| LEU 75 ILE SER | 78 HIS ILE | 79 THR LEU | 82 PHE | |
| LEU 75 ILE SER | 78 HIS ILE | 79 THR LEU | 82 HIS | |
| LEU 75 ILE SER | 78 HIS ILE | 79 THR LEU | 82 TYR | |
| LEU 75 ILE SER | 78 HIS ILE | 79 VAL LEU | 82 PHE | |
| LEU 75 ILE SER | 78 HIS ILE | 79 VAL LEU | 82 HIS | |
| LEU 75 ILE SER | 78 HIS ILE | 79 VAL LEU | 82 TYR | |
| LEU 75 ILE SER | 78 LYS ILE | 79 LEU LEU | 82 PHE | |
| LEU 75 ILE SER | 78 LYS ILE | 79 LEU LEU | 82 HIS | |
| LEU 75 ILE SER | 78 LYS ILE | 79 LEU LEU | 82 TYR | |
| LEU 75 ILE SER | 78 LYS ILE | 79 MET LEU | 82 PHE | |
| LEU 75 ILE SER | 78 LYS ILE | 79 MET LEU | 82 HIS | |
| LEU 75 ILE SER | 78 LYS ILE | 79 MET LEU | 82 TYR | |
| LEU 75 ILE SER | 78 LYS ILE | 79 THR LEU | 82 PHE | |
| LEU 75 ILE SER | 78 LYS ILE | 79 THR LEU | 82 HIS | |
| LEU 75 ILE SER | 78 LYS ILE | 79 THR LEU | 82 TYR | |

TABLE 5-continued

| Quadruple Substitution Variants | | | | |
|---|---|---|---|---|
| LEU | 75 ILE SER | 78 LYS ILE | 79 VAL LEU | 82 PHE |
| LEU | 75 ILE SER | 78 LYS ILE | 79 VAL LEU | 82 HIS |
| LEU | 75 ILE SER | 78 LYS ILE | 79 VAL LEU | 82 TYR |
| LEU | 75 ILE SER | 78 TYR ILE | 79 LEU LEU | 82 PHE |
| LEU | 75 ILE SER | 78 TYR ILE | 79 LEU LEU | 82 HIS |
| LEU | 75 ILE SER | 78 TYR ILE | 79 LEU LEU | 82 TYR |
| LEU | 75 ILE SER | 78 TYR ILE | 79 MET LEU | 82 PHE |
| LEU | 75 ILE SER | 78 TYR ILE | 79 MET LEU | 82 HIS |
| LEU | 75 ILE SER | 78 TYR ILE | 79 MET LEU | 82 TYR |
| LEU | 75 ILE SER | 78 TYR ILE | 79 THR LEU | 82 PHE |
| LEU | 75 ILE SER | 78 TYR ILE | 79 THR LEU | 82 HIS |
| LEU | 75 ILE SER | 78 TYR ILE | 79 THR LEU | 82 TYR |
| LEU | 75 ILE SER | 78 TYR ILE | 79 VAL LEU | 82 PHE |
| LEU | 75 ILE SER | 78 TYR ILE | 79 VAL LEU | 82 HIS |
| LEU | 75 ILE SER | 78 TYR ILE | 79 VAL LEU | 82 TYR |
| LEU | 75 MET SER | 78 ASN ILE | 79 LEU LEU | 82 PHE |
| LEU | 75 MET SER | 78 ASN ILE | 79 LEU LEU | 82 HIS |
| LEU | 75 MET SER | 78 ASN ILE | 79 LEU LEU | 82 TYR |
| LEU | 75 MET SER | 78 ASN ILE | 79 MET LEU | 82 PHE |
| LEU | 75 MET SER | 78 ASN ILE | 79 MET LEU | 82 HIS |
| LEU | 75 MET SER | 78 ASN ILE | 79 MET LEU | 82 TYR |
| LEU | 75 MET SER | 78 ASN ILE | 79 THR LEU | 82 PHE |
| LEU | 75 MET SER | 78 ASN ILE | 79 THR LEU | 82 HIS |
| LEU | 75 MET SER | 78 ASN ILE | 79 THR LEU | 82 TYR |
| LEU | 75 MET SER | 78 ASN ILE | 79 VAL LEU | 82 PHE |
| LEU | 75 MET SER | 78 ASN ILE | 79 VAL LEU | 82 HIS |
| LEU | 75 MET SER | 78 ASN ILE | 79 VAL LEU | 82 TYR |
| LEU | 75 MET SER | 78 THR ILE | 79 LEU LEU | 82 PHE |
| LEU | 75 MET SER | 78 THR ILE | 79 LEU LEU | 82 HIS |
| LEU | 75 MET SER | 78 THR ILE | 79 LEU LEU | 82 TYR |
| LEU | 75 MET SER | 78 THR ILE | 79 MET LEU | 82 PHE |
| LEU | 75 MET SER | 78 THR ILE | 79 MET LEU | 82 HIS |
| LEU | 75 MET SER | 78 THR ILE | 79 MET LEU | 82 TYR |
| LEU | 75 MET SER | 78 THR ILE | 79 THR LEU | 82 PHE |
| LEU | 75 MET SER | 78 THR ILE | 79 THR LEU | 82 HIS |
| LEU | 75 MET SER | 78 THR ILE | 79 THR LEU | 82 TYR |
| LEU | 75 MET SER | 78 THR ILE | 79 VAL LEU | 82 PHE |
| LEU | 75 MET SER | 78 THR ILE | 79 VAL LEU | 82 HIS |
| LEU | 75 MET SER | 78 THR ILE | 79 VAL LEU | 82 TYR |
| LEU | 75 MET SER | 78 ARG ILE | 79 LEU LEU | 82 PHE |
| LEU | 75 MET SER | 78 ARG ILE | 79 LEU LEU | 82 HIS |
| LEU | 75 MET SER | 78 ARG ILE | 79 LEU LEU | 82 TYR |
| LEU | 75 MET SER | 78 ARG ILE | 79 MET LEU | 82 PHE |
| LEU | 75 MET SER | 78 ARG ILE | 79 MET LEU | 82 HIS |
| LEU | 75 MET SER | 78 ARG ILE | 79 MET LEU | 82 TYR |
| LEU | 75 MET SER | 78 ARG ILE | 79 THR LEU | 82 PHE |
| LEU | 75 MET SER | 78 ARG ILE | 79 THR LEU | 82 HIS |
| LEU | 75 MET SER | 78 ARG ILE | 79 THR LEU | 82 TYR |
| LEU | 75 MET SER | 78 ARG ILE | 79 VAL LEU | 82 PHE |
| LEU | 75 MET SER | 78 ARG ILE | 79 VAL LEU | 82 HIS |
| LEU | 75 MET SER | 78 ARG ILE | 79 VAL LEU | 82 TYR |
| LEU | 75 MET SER | 78 ASP ILE | 79 LEU LEU | 82 PHE |
| LEU | 75 MET SER | 78 ASP ILE | 79 LEU LEU | 82 HIS |
| LEU | 75 MET SER | 78 ASP ILE | 79 LEU LEU | 82 TYR |
| LEU | 75 MET SER | 78 ASP ILE | 79 MET LEU | 82 PHE |
| LEU | 75 MET SER | 78 ASP ILE | 79 MET LEU | 82 HIS |
| LEU | 75 MET SER | 78 ASP ILE | 79 MET LEU | 82 TYR |
| LEU | 75 MET SER | 78 ASP ILE | 79 THR LEU | 82 PHE |
| LEU | 75 MET SER | 78 ASP ILE | 79 THR LEU | 82 HIS |
| LEU | 75 MET SER | 78 ASP ILE | 79 THR LEU | 82 TYR |
| LEU | 75 MET SER | 78 ASP ILE | 79 VAL LEU | 82 PHE |
| LEU | 75 MET SER | 78 ASP ILE | 79 VAL LEU | 82 HIS |
| LEU | 75 MET SER | 78 ASP ILE | 79 VAL LEU | 82 TYR |
| LEU | 75 MET SER | 78 GLN ILE | 79 LEU LEU | 82 PHE |
| LEU | 75 MET SER | 78 GLN ILE | 79 LEU LEU | 82 HIS |
| LEU | 75 MET SER | 78 GLN ILE | 79 LEU LEU | 82 TYR |
| LEU | 75 MET SER | 78 GLN ILE | 79 MET LEU | 82 PHE |
| LEU | 75 MET SER | 78 GLN ILE | 79 MET LEU | 82 HIS |
| LEU | 75 MET SER | 78 GLN ILE | 79 MET LEU | 82 TYR |
| LEU | 75 MET SER | 78 GLN ILE | 79 THR LEU | 82 PHE |
| LEU | 75 MET SER | 78 GLN ILE | 79 THR LEU | 82 HIS |
| LEU | 75 MET SER | 78 GLN ILE | 79 THR LEU | 82 TYR |
| LEU | 75 MET SER | 78 GLN ILE | 79 VAL LEU | 82 PHE |
| LEU | 75 MET SER | 78 GLN ILE | 79 VAL LEU | 82 HIS |
| LEU | 75 MET SER | 78 GLN ILE | 79 VAL LEU | 82 TYR |
| LEU | 75 MET SER | 78 HIS ILE | 79 LEU LEU | 82 PHE |
| LEU | 75 MET SER | 78 HIS ILE | 79 LEU LEU | 82 HIS |

TABLE 5-continued

| Quadruple Substitution Variants | | | | |
|---|---|---|---|---|
| LEU | 75 MET SER | 78 HIS ILE | 79 LEU LEU | 82 TYR |
| LEU | 75 MET SER | 78 HIS ILE | 79 MET LEU | 82 PHE |
| LEU | 75 MET SER | 78 HIS ILE | 79 MET LEU | 82 HIS |
| LEU | 75 MET SER | 78 HIS ILE | 79 MET LEU | 82 TYR |
| LEU | 75 MET SER | 78 HIS ILE | 79 THR LEU | 82 PHE |
| LEU | 75 MET SER | 78 HIS ILE | 79 THR LEU | 82 HIS |
| LEU | 75 MET SER | 78 HIS ILE | 79 THR LEU | 82 TYR |
| LEU | 75 MET SER | 78 HIS ILE | 79 VAL LEU | 82 PHE |
| LEU | 75 MET SER | 78 HIS ILE | 79 VAL LEU | 82 HIS |
| LEU | 75 MET SER | 78 HIS ILE | 79 VAL LEU | 82 TYR |
| LEU | 75 MET SER | 78 LYS ILE | 79 LEU LEU | 82 PHE |
| LEU | 75 MET SER | 78 LYS ILE | 79 LEU LEU | 82 HIS |
| LEU | 75 MET SER | 78 LYS ILE | 79 LEU LEU | 82 TYR |
| LEU | 75 MET SER | 78 LYS ILE | 79 MET LEU | 82 PHE |
| LEU | 75 MET SER | 78 LYS ILE | 79 MET LEU | 82 HIS |
| LEU | 75 MET SER | 78 LYS ILE | 79 MET LEU | 82 TYR |
| LEU | 75 MET SER | 78 LYS ILE | 79 THR LEU | 82 PHE |
| LEU | 75 MET SER | 78 LYS ILE | 79 THR LEU | 82 HIS |
| LEU | 75 MET SER | 78 LYS ILE | 79 THR LEU | 82 TYR |
| LEU | 75 MET SER | 78 LYS ILE | 79 VAL LEU | 82 PHE |
| LEU | 75 MET SER | 78 LYS ILE | 79 VAL LEU | 82 HIS |
| LEU | 75 MET SER | 78 LYS ILE | 79 VAL LEU | 82 TYR |
| LEU | 75 MET SER | 78 TYR ILE | 79 LEU LEU | 82 PHE |
| LEU | 75 MET SER | 78 TYR ILE | 79 LEU LEU | 82 HIS |
| LEU | 75 MET SER | 78 TYR ILE | 79 LEU LEU | 82 TYR |
| LEU | 75 MET SER | 78 TYR ILE | 79 MET LEU | 82 PHE |
| LEU | 75 MET SER | 78 TYR ILE | 79 MET LEU | 82 HIS |
| LEU | 75 MET SER | 78 TYR ILE | 79 MET LEU | 82 TYR |
| LEU | 75 MET SER | 78 TYR ILE | 79 THR LEU | 82 PHE |
| LEU | 75 MET SER | 78 TYR ILE | 79 THR LEU | 82 HIS |
| LEU | 75 MET SER | 78 TYR ILE | 79 THR LEU | 82 TYR |
| LEU | 75 MET SER | 78 TYR ILE | 79 VAL LEU | 82 PHE |
| LEU | 75 MET SER | 78 TYR ILE | 79 VAL LEU | 82 HIS |
| LEU | 75 MET SER | 78 TYR ILE | 79 VAL LEU | 82 TYR |
| LEU | 75 VAL SER | 78 ASN ILE | 79 LEU LEU | 82 PHE |
| LEU | 75 VAL SER | 78 ASN ILE | 79 LEU LEU | 82 HIS |
| LEU | 75 VAL SER | 78 ASN ILE | 79 LEU LEU | 82 TYR |
| LEU | 75 VAL SER | 78 ASN ILE | 79 MET LEU | 82 PHE |
| LEU | 75 VAL SER | 78 ASN ILE | 79 MET LEU | 82 HIS |
| LEU | 75 VAL SER | 78 ASN ILE | 79 MET LEU | 82 TYR |
| LEU | 75 VAL SER | 78 ASN ILE | 79 THR LEU | 82 PHE |
| LEU | 75 VAL SER | 78 ASN ILE | 79 THR LEU | 82 HIS |
| LEU | 75 VAL SER | 78 ASN ILE | 79 THR LEU | 82 TYR |
| LEU | 75 VAL SER | 78 ASN ILE | 79 VAL LEU | 82 PHE |
| LEU | 75 VAL SER | 78 ASN ILE | 79 VAL LEU | 82 HIS |
| LEU | 75 VAL SER | 78 ASN ILE | 79 VAL LEU | 82 TYR |
| LEU | 75 VAL SER | 78 THR ILE | 79 LEU LEU | 82 PHE |
| LEU | 75 VAL SER | 78 THR ILE | 79 LEU LEU | 82 HIS |
| LEU | 75 VAL SER | 78 THR ILE | 79 LEU LEU | 82 TYR |
| LEU | 75 VAL SER | 78 THR ILE | 79 MET LEU | 82 PHE |
| LEU | 75 VAL SER | 78 THR ILE | 79 MET LEU | 82 HIS |
| LEU | 75 VAL SER | 78 THR ILE | 79 MET LEU | 82 TYR |
| LEU | 75 VAL SER | 78 THR ILE | 79 THR LEU | 82 PHE |
| LEU | 75 VAL SER | 78 THR ILE | 79 THR LEU | 82 HIS |
| LEU | 75 VAL SER | 78 THR ILE | 79 THR LEU | 82 TYR |
| LEU | 75 VAL SER | 78 THR ILE | 79 VAL LEU | 82 PHE |
| LEU | 75 VAL SER | 78 THR ILE | 79 VAL LEU | 82 HIS |
| LEU | 75 VAL SER | 78 THR ILE | 79 VAL LEU | 82 TYR |
| LEU | 75 VAL SER | 78 ARG ILE | 79 LEU LEU | 82 PHE |
| LEU | 75 VAL SER | 78 ARG ILE | 79 LEU LEU | 82 HIS |
| LEU | 75 VAL SER | 78 ARG ILE | 79 LEU LEU | 82 TYR |
| LEU | 75 VAL SER | 78 ARG ILE | 79 MET LEU | 82 PHE |
| LEU | 75 VAL SER | 78 ARG ILE | 79 MET LEU | 82 HIS |
| LEU | 75 VAL SER | 78 ARG ILE | 79 MET LEU | 82 TYR |
| LEU | 75 VAL SER | 78 ARG ILE | 79 THR LEU | 82 PHE |
| LEU | 75 VAL SER | 78 ARG ILE | 79 THR LEU | 82 HIS |
| LEU | 75 VAL SER | 78 ARG ILE | 79 THR LEU | 82 TYR |
| LEU | 75 VAL SER | 78 ARG ILE | 79 VAL LEU | 82 PHE |
| LEU | 75 VAL SER | 78 ARG ILE | 79 VAL LEU | 82 HIS |
| LEU | 75 VAL SER | 78 ARG ILE | 79 VAL LEU | 82 TYR |
| LEU | 75 VAL SER | 78 ASP ILE | 79 LEU LEU | 82 PHE |
| LEU | 75 VAL SER | 78 ASP ILE | 79 LEU LEU | 82 HIS |
| LEU | 75 VAL SER | 78 ASP ILE | 79 LEU LEU | 82 TYR |
| LEU | 75 VAL SER | 78 ASP ILE | 79 MET LEU | 82 PHE |
| LEU | 75 VAL SER | 78 ASP ILE | 79 MET LEU | 82 HIS |
| LEU | 75 VAL SER | 78 ASP ILE | 79 MET LEU | 82 TYR |
| LEU | 75 VAL SER | 78 ASP ILE | 79 THR LEU | 82 PHE |

TABLE 5-continued

Quadruple Substitution Variants

| | | | | |
|---|---|---|---|---|
| LEU 75 VAL SER | 78 ASP ILE | 79 THR LEU | 82 HIS | |
| LEU 75 VAL SER | 78 ASP ILE | 79 THR LEU | 82 TYR | |
| LEU 75 VAL SER | 78 ASP ILE | 79 VAL LEU | 82 PHE | |
| LEU 75 VAL SER | 78 ASP ILE | 79 VAL LEU | 82 HIS | |
| LEU 75 VAL SER | 78 ASP ILE | 79 VAL LEU | 82 TYR | |
| LEU 75 VAL SER | 78 GLN ILE | 79 LEU LEU | 82 PHE | |
| LEU 75 VAL SER | 78 GLN ILE | 79 LEU LEU | 82 HIS | |
| LEU 75 VAL SER | 78 GLN ILE | 79 LEU LEU | 82 TYR | |
| LEU 75 VAL SER | 78 GLN ILE | 79 MET LEU | 82 PHE | |
| LEU 75 VAL SER | 78 GLN ILE | 79 MET LEU | 82 HIS | |
| LEU 75 VAL SER | 78 GLN ILE | 79 MET LEU | 82 TYR | |
| LEU 75 VAL SER | 78 GLN ILE | 79 THR LEU | 82 PHE | |
| LEU 75 VAL SER | 78 GLN ILE | 79 THR LEU | 82 HIS | |
| LEU 75 VAL SER | 78 GLN ILE | 79 THR LEU | 82 TYR | |
| LEU 75 VAL SER | 78 GLN ILE | 79 VAL LEU | 82 PHE | |
| LEU 75 VAL SER | 78 GLN ILE | 79 VAL LEU | 82 HIS | |
| LEU 75 VAL SER | 78 GLN ILE | 79 VAL LEU | 82 TYR | |
| LEU 75 VAL SER | 78 HIS ILE | 79 LEU LEU | 82 PHE | |
| LEU 75 VAL SER | 78 HIS ILE | 79 LEU LEU | 82 HIS | |
| LEU 75 VAL SER | 78 HIS ILE | 79 LEU LEU | 82 TYR | |
| LEU 75 VAL SER | 78 HIS ILE | 79 MET LEU | 82 PHE | |
| LEU 75 VAL SER | 78 HIS ILE | 79 MET LEU | 82 HIS | |
| LEU 75 VAL SER | 78 HIS ILE | 79 MET LEU | 82 TYR | |
| LEU 75 VAL SER | 78 HIS ILE | 79 THR LEU | 82 PHE | |
| LEU 75 VAL SER | 78 HIS ILE | 79 THR LEU | 82 HIS | |
| LEU 75 VAL SER | 78 HIS ILE | 79 THR LEU | 82 TYR | |
| LEU 75 VAL SER | 78 HIS ILE | 79 VAL LEU | 82 PHE | |
| LEU 75 VAL SER | 78 HIS ILE | 79 VAL LEU | 82 HIS | |
| LEU 75 VAL SER | 78 HIS ILE | 79 VAL LEU | 82 TYR | |
| LEU 75 VAL SER | 78 LYS ILE | 79 LEU LEU | 82 PHE | |
| LEU 75 VAL SER | 78 LYS ILE | 79 LEU LEU | 82 HIS | |
| LEU 75 VAL SER | 78 LYS ILE | 79 LEU LEU | 82 TYR | |
| LEU 75 VAL SER | 78 LYS ILE | 79 MET LEU | 82 PHE | |
| LEU 75 VAL SER | 78 LYS ILE | 79 MET LEU | 82 HIS | |
| LEU 75 VAL SER | 78 LYS ILE | 79 MET LEU | 82 TYR | |
| LEU 75 VAL SER | 78 LYS ILE | 79 THR LEU | 82 PHE | |
| LEU 75 VAL SER | 78 LYS ILE | 79 THR LEU | 82 HIS | |
| LEU 75 VAL SER | 78 LYS ILE | 79 THR LEU | 82 TYR | |
| LEU 75 VAL SER | 78 LYS ILE | 79 VAL LEU | 82 PHE | |
| LEU 75 VAL SER | 78 LYS ILE | 79 VAL LEU | 82 HIS | |
| LEU 75 VAL SER | 78 LYS ILE | 79 VAL LEU | 82 TYR | |
| LEU 75 VAL SER | 78 TYR ILE | 79 LEU LEU | 82 PHE | |
| LEU 75 VAL SER | 78 TYR ILE | 79 LEU LEU | 82 HIS | |
| LEU 75 VAL SER | 78 TYR ILE | 79 LEU LEU | 82 TYR | |
| LEU 75 VAL SER | 78 TYR ILE | 79 MET LEU | 82 PHE | |
| LEU 75 VAL SER | 78 TYR ILE | 79 MET LEU | 82 HIS | |
| LEU 75 VAL SER | 78 TYR ILE | 79 MET LEU | 82 TYR | |
| LEU 75 VAL SER | 78 TYR ILE | 79 THR LEU | 82 PHE | |
| LEU 75 VAL SER | 78 TYR ILE | 79 THR LEU | 82 HIS | |
| LEU 75 VAL SER | 78 TYR ILE | 79 THR LEU | 82 TYR | |
| LEU 75 VAL SER | 78 TYR ILE | 79 VAL LEU | 82 PHE | |
| LEU 75 VAL SER | 78 TYR ILE | 79 VAL LEU | 82 HIS | |
| LEU 75 VAL SER | 78 TYR ILE | 79 VAL LEU | 82 TYR | |
| LEU 75 ILE SER | 78 ASN ILE | 79 LEU VAL | 81 THR | |
| LEU 75 ILE SER | 78 ASN ILE | 79 MET VAL | 81 THR | |
| LEU 75 ILE SER | 78 ASN ILE | 79 THR VAL | 81 THR | |
| LEU 75 ILE SER | 78 ASN ILE | 79 VAL VAL | 81 THR | |
| LEU 75 ILE SER | 78 THR ILE | 79 LEU VAL | 81 THR | |
| LEU 75 ILE SER | 78 THR ILE | 79 MET VAL | 81 THR | |
| LEU 75 ILE SER | 78 THR ILE | 79 THR VAL | 81 THR | |
| LEU 75 ILE SER | 78 THR ILE | 79 VAL VAL | 81 THR | |
| LEU 75 ILE SER | 78 ARG ILE | 79 LEU VAL | 81 THR | |
| LEU 75 ILE SER | 78 ARG ILE | 79 MET VAL | 81 THR | |
| LEU 75 ILE SER | 78 ARG ILE | 79 THR VAL | 81 THR | |
| LEU 75 ILE SER | 78 ARG ILE | 79 VAL VAL | 81 THR | |
| LEU 75 ILE SER | 78 ASP ILE | 79 LEU VAL | 81 THR | |
| LEU 75 ILE SER | 78 ASP ILE | 79 MET VAL | 81 THR | |
| LEU 75 ILE SER | 78 ASP ILE | 79 THR VAL | 81 THR | |
| LEU 75 ILE SER | 78 ASP ILE | 79 VAL VAL | 81 THR | |
| LEU 75 ILE SER | 78 GLN ILE | 79 LEU VAL | 81 THR | |
| LEU 75 ILE SER | 78 GLN ILE | 79 MET VAL | 81 THR | |
| LEU 75 ILE SER | 78 GLN ILE | 79 THR VAL | 81 THR | |
| LEU 75 ILE SER | 78 GLN ILE | 79 VAL VAL | 81 THR | |
| LEU 75 ILE SER | 78 HIS ILE | 79 LEU VAL | 81 THR | |
| LEU 75 ILE SER | 78 HIS ILE | 79 MET VAL | 81 THR | |
| LEU 75 ILE SER | 78 HIS ILE | 79 THR VAL | 81 THR | |
| LEU 75 ILE SER | 78 HIS ILE | 79 VAL VAL | 81 THR | |
| LEU 75 ILE SER | 78 LYS ILE | 79 LEU VAL | 81 THR | |
| LEU 75 ILE SER | 78 LYS ILE | 79 MET VAL | 81 THR | |
| LEU 75 ILE SER | 78 LYS ILE | 79 THR VAL | 81 THR | |
| LEU 75 ILE SER | 78 LYS ILE | 79 VAL VAL | 81 THR | |
| LEU 75 ILE SER | 78 TYR ILE | 79 LEU VAL | 81 THR | |
| LEU 75 ILE SER | 78 TYR ILE | 79 MET VAL | 81 THR | |
| LEU 75 ILE SER | 78 TYR ILE | 79 THR VAL | 81 THR | |
| LEU 75 ILE SER | 78 TYR ILE | 79 VAL VAL | 81 THR | |
| LEU 75 MET SER | 78 ASN ILE | 79 LEU VAL | 81 THR | |
| LEU 75 MET SER | 78 ASN ILE | 79 MET VAL | 81 THR | |
| LEU 75 MET SER | 78 ASN ILE | 79 THR VAL | 81 THR | |
| LEU 75 MET SER | 78 ASN ILE | 79 VAL VAL | 81 THR | |
| LEU 75 MET SER | 78 THR ILE | 79 LEU VAL | 81 THR | |
| LEU 75 MET SER | 78 THR ILE | 79 MET VAL | 81 THR | |
| LEU 75 MET SER | 78 THR ILE | 79 THR VAL | 81 THR | |
| LEU 75 MET SER | 78 THR ILE | 79 VAL VAL | 81 THR | |
| LEU 75 MET SER | 78 ARG ILE | 79 LEU VAL | 81 THR | |
| LEU 75 MET SER | 78 ARG ILE | 79 MET VAL | 81 THR | |
| LEU 75 MET SER | 78 ARG ILE | 79 THR VAL | 81 THR | |
| LEU 75 MET SER | 78 ARG ILE | 79 VAL VAL | 81 THR | |
| LEU 75 MET SER | 78 ASP ILE | 79 LEU VAL | 81 THR | |
| LEU 75 MET SER | 78 ASP ILE | 79 MET VAL | 81 THR | |
| LEU 75 MET SER | 78 ASP ILE | 79 THR VAL | 81 THR | |
| LEU 75 MET SER | 78 ASP ILE | 79 VAL VAL | 81 THR | |
| LEU 75 MET SER | 78 GLN ILE | 79 LEU VAL | 81 THR | |
| LEU 75 MET SER | 78 GLN ILE | 79 MET VAL | 81 THR | |
| LEU 75 MET SER | 78 GLN ILE | 79 THR VAL | 81 THR | |
| LEU 75 MET SER | 78 GLN ILE | 79 VAL VAL | 81 THR | |
| LEU 75 MET SER | 78 HIS ILE | 79 LEU VAL | 81 THR | |
| LEU 75 MET SER | 78 HIS ILE | 79 MET VAL | 81 THR | |
| LEU 75 MET SER | 78 HIS ILE | 79 THR VAL | 81 THR | |
| LEU 75 MET SER | 78 HIS ILE | 79 VAL VAL | 81 THR | |
| LEU 75 MET SER | 78 LYS ILE | 79 LEU VAL | 81 THR | |
| LEU 75 MET SER | 78 LYS ILE | 79 MET VAL | 81 THR | |
| LEU 75 MET SER | 78 LYS ILE | 79 THR VAL | 81 THR | |
| LEU 75 MET SER | 78 LYS ILE | 79 VAL VAL | 81 THR | |
| LEU 75 MET SER | 78 TYR ILE | 79 LEU VAL | 81 THR | |
| LEU 75 MET SER | 78 TYR ILE | 79 MET VAL | 81 THR | |
| LEU 75 MET SER | 78 TYR ILE | 79 THR VAL | 81 THR | |
| LEU 75 MET SER | 78 TYR ILE | 79 VAL VAL | 81 THR | |
| LEU 75 VAL SER | 78 ASN ILE | 79 LEU VAL | 81 THR | |
| LEU 75 VAL SER | 78 ASN ILE | 79 MET VAL | 81 THR | |
| LEU 75 VAL SER | 78 ASN ILE | 79 THR VAL | 81 THR | |
| LEU 75 VAL SER | 78 ASN ILE | 79 VAL VAL | 81 THR | |
| LEU 75 VAL SER | 78 THR ILE | 79 LEU VAL | 81 THR | |
| LEU 75 VAL SER | 78 THR ILE | 79 MET VAL | 81 THR | |
| LEU 75 VAL SER | 78 THR ILE | 79 THR VAL | 81 THR | |
| LEU 75 VAL SER | 78 THR ILE | 79 VAL VAL | 81 THR | |
| LEU 75 VAL SER | 78 ARG ILE | 79 LEU VAL | 81 THR | |
| LEU 75 VAL SER | 78 ARG ILE | 79 MET VAL | 81 THR | |
| LEU 75 VAL SER | 78 ARG ILE | 79 THR VAL | 81 THR | |
| LEU 75 VAL SER | 78 ARG ILE | 79 VAL VAL | 81 THR | |
| LEU 75 VAL SER | 78 ASP ILE | 79 LEU VAL | 81 THR | |
| LEU 75 VAL SER | 78 ASP ILE | 79 MET VAL | 81 THR | |
| LEU 75 VAL SER | 78 ASP ILE | 79 THR VAL | 81 THR | |
| LEU 75 VAL SER | 78 ASP ILE | 79 VAL VAL | 81 THR | |
| LEU 75 VAL SER | 78 GLN ILE | 79 LEU VAL | 81 THR | |
| LEU 75 VAL SER | 78 GLN ILE | 79 MET VAL | 81 THR | |
| LEU 75 VAL SER | 78 GLN ILE | 79 THR VAL | 81 THR | |
| LEU 75 VAL SER | 78 GLN ILE | 79 VAL VAL | 81 THR | |
| LEU 75 VAL SER | 78 HIS ILE | 79 LEU VAL | 81 THR | |
| LEU 75 VAL SER | 78 HIS ILE | 79 MET VAL | 81 THR | |
| LEU 75 VAL SER | 78 HIS ILE | 79 THR VAL | 81 THR | |
| LEU 75 VAL SER | 78 HIS ILE | 79 VAL VAL | 81 THR | |
| LEU 75 VAL SER | 78 LYS ILE | 79 LEU VAL | 81 THR | |
| LEU 75 VAL SER | 78 LYS ILE | 79 MET VAL | 81 THR | |
| LEU 75 VAL SER | 78 LYS ILE | 79 THR VAL | 81 THR | |
| LEU 75 VAL SER | 78 LYS ILE | 79 VAL VAL | 81 THR | |
| LEU 75 VAL SER | 78 TYR ILE | 79 LEU VAL | 81 THR | |
| LEU 75 VAL SER | 78 TYR ILE | 79 MET VAL | 81 THR | |
| LEU 75 VAL SER | 78 TYR ILE | 79 THR VAL | 81 THR | |
| LEU 75 VAL SER | 78 TYR ILE | 79 VAL VAL | 81 THR | |
| LEU 75 ILE ASN | 76 HIS VAL | 81 THR LEU | 82 PHE | |
| LEU 75 ILE ASN | 76 HIS VAL | 81 THR LEU | 82 HIS | |
| LEU 75 ILE ASN | 76 HIS VAL | 81 THR LEU | 82 TYR | |
| LEU 75 MET ASN | 76 HIS VAL | 81 THR LEU | 82 PHE | |
| LEU 75 MET ASN | 76 HIS VAL | 81 THR LEU | 82 HIS | |

TABLE 5-continued

Quadruple Substitution Variants

| | | | | | |
|---|---|---|---|---|---|
| LEU | 75 MET ASN | 76 HIS VAL | 81 THR LEU | 82 TYR | |
| LEU | 75 VAL ASN | 76 HIS VAL | 81 THR LEU | 82 PHE | |
| LEU | 75 VAL ASN | 76 HIS VAL | 81 THR LEU | 82 HIS | |
| LEU | 75 VAL ASN | 76 HIS VAL | 81 THR LEU | 82 TYR | |
| LEU | 75 ILE ASN | 76 HIS ILE | 79 LEU LEU | 82 PHE | |
| LEU | 75 ILE ASN | 76 HIS ILE | 79 LEU LEU | 82 HIS | |
| LEU | 75 ILE ASN | 76 HIS ILE | 79 LEU LEU | 82 TYR | |
| LEU | 75 ILE ASN | 76 HIS ILE | 79 MET LEU | 82 PHE | |
| LEU | 75 ILE ASN | 76 HIS ILE | 79 MET LEU | 82 HIS | |
| LEU | 75 ILE ASN | 76 HIS ILE | 79 MET LEU | 82 TYR | |
| LEU | 75 ILE ASN | 76 HIS ILE | 79 THR LEU | 82 PHE | |
| LEU | 75 ILE ASN | 76 HIS ILE | 79 THR LEU | 82 HIS | |
| LEU | 75 ILE ASN | 76 HIS ILE | 79 THR LEU | 82 TYR | |
| LEU | 75 ILE ASN | 76 HIS ILE | 79 VAL LEU | 82 PHE | |
| LEU | 75 ILE ASN | 76 HIS ILE | 79 VAL LEU | 82 HIS | |
| LEU | 75 ILE ASN | 76 HIS ILE | 79 VAL LEU | 82 TYR | |
| LEU | 75 MET ASN | 76 HIS ILE | 79 LEU LEU | 82 PHE | |
| LEU | 75 MET ASN | 76 HIS ILE | 79 LEU LEU | 82 HIS | |
| LEU | 75 MET ASN | 76 HIS ILE | 79 LEU LEU | 82 TYR | |
| LEU | 75 MET ASN | 76 HIS ILE | 79 MET LEU | 82 PHE | |
| LEU | 75 MET ASN | 76 HIS ILE | 79 MET LEU | 82 HIS | |
| LEU | 75 MET ASN | 76 HIS ILE | 79 MET LEU | 82 TYR | |
| LEU | 75 MET ASN | 76 HIS ILE | 79 THR LEU | 82 PHE | |
| LEU | 75 MET ASN | 76 HIS ILE | 79 THR LEU | 82 HIS | |
| LEU | 75 MET ASN | 76 HIS ILE | 79 THR LEU | 82 TYR | |
| LEU | 75 MET ASN | 76 HIS ILE | 79 VAL LEU | 82 PHE | |
| LEU | 75 MET ASN | 76 HIS ILE | 79 VAL LEU | 82 HIS | |
| LEU | 75 MET ASN | 76 HIS ILE | 79 VAL LEU | 82 TYR | |
| LEU | 75 VAL ASN | 76 HIS ILE | 79 LEU LEU | 82 PHE | |
| LEU | 75 VAL ASN | 76 HIS ILE | 79 LEU LEU | 82 HIS | |
| LEU | 75 VAL ASN | 76 HIS ILE | 79 LEU LEU | 82 TYR | |
| LEU | 75 VAL ASN | 76 HIS ILE | 79 MET LEU | 82 PHE | |
| LEU | 75 VAL ASN | 76 HIS ILE | 79 MET LEU | 82 HIS | |
| LEU | 75 VAL ASN | 76 HIS ILE | 79 MET LEU | 82 TYR | |
| LEU | 75 VAL ASN | 76 HIS ILE | 79 THR LEU | 82 PHE | |
| LEU | 75 VAL ASN | 76 HIS ILE | 79 THR LEU | 82 HIS | |
| LEU | 75 VAL ASN | 76 HIS ILE | 79 THR LEU | 82 TYR | |
| LEU | 75 VAL ASN | 76 HIS ILE | 79 VAL LEU | 82 PHE | |
| LEU | 75 VAL ASN | 76 HIS ILE | 79 VAL LEU | 82 HIS | |
| LEU | 75 VAL ASN | 76 HIS ILE | 79 VAL LEU | 82 TYR | |
| LEU | 75 ILE ASN | 76 HIS ILE | 79 LEU VAL | 81 THR | |
| LEU | 75 ILE ASN | 76 HIS ILE | 79 MET VAL | 81 THR | |
| LEU | 75 ILE ASN | 76 HIS ILE | 79 THR VAL | 81 THR | |
| LEU | 75 ILE ASN | 76 HIS ILE | 79 VAL VAL | 81 THR | |
| LEU | 75 MET ASN | 76 HIS ILE | 79 LEU VAL | 81 THR | |
| LEU | 75 MET ASN | 76 HIS ILE | 79 MET VAL | 81 THR | |
| LEU | 75 MET ASN | 76 HIS ILE | 79 THR VAL | 81 THR | |
| LEU | 75 MET ASN | 76 HIS ILE | 79 VAL VAL | 81 THR | |
| LEU | 75 VAL ASN | 76 HIS ILE | 79 LEU VAL | 81 THR | |
| LEU | 75 VAL ASN | 76 HIS ILE | 79 MET VAL | 81 THR | |
| LEU | 75 VAL ASN | 76 HIS ILE | 79 THR VAL | 81 THR | |
| LEU | 75 VAL ASN | 76 HIS ILE | 79 VAL VAL | 81 THR | |
| LEU | 75 ILE ASN | 76 HIS SER | 78 ASN LEU | 82 PHE | |
| LEU | 75 ILE ASN | 76 HIS SER | 78 ASN LEU | 82 HIS | |
| LEU | 75 ILE ASN | 76 HIS SER | 78 ASN LEU | 82 TYR | |
| LEU | 75 ILE ASN | 76 HIS SER | 78 THR LEU | 82 PHE | |
| LEU | 75 ILE ASN | 76 HIS SER | 78 THR LEU | 82 HIS | |
| LEU | 75 ILE ASN | 76 HIS SER | 78 THR LEU | 82 TYR | |
| LEU | 75 ILE ASN | 76 HIS SER | 78 ARG LEU | 82 PHE | |
| LEU | 75 ILE ASN | 76 HIS SER | 78 ARG LEU | 82 HIS | |
| LEU | 75 ILE ASN | 76 HIS SER | 78 ARG LEU | 82 TYR | |
| LEU | 75 ILE ASN | 76 HIS SER | 78 ASP LEU | 82 PHE | |
| LEU | 75 ILE ASN | 76 HIS SER | 78 ASP LEU | 82 HIS | |
| LEU | 75 ILE ASN | 76 HIS SER | 78 ASP LEU | 82 TYR | |
| LEU | 75 ILE ASN | 76 HIS SER | 78 GLN LEU | 82 PHE | |
| LEU | 75 ILE ASN | 76 HIS SER | 78 GLN LEU | 82 HIS | |
| LEU | 75 ILE ASN | 76 HIS SER | 78 GLN LEU | 82 TYR | |
| LEU | 75 ILE ASN | 76 HIS SER | 78 HIS LEU | 82 PHE | |
| LEU | 75 ILE ASN | 76 HIS SER | 78 HIS LEU | 82 HIS | |
| LEU | 75 ILE ASN | 76 HIS SER | 78 HIS LEU | 82 TYR | |
| LEU | 75 ILE ASN | 76 HIS SER | 78 LYS LEU | 82 PHE | |
| LEU | 75 ILE ASN | 76 HIS SER | 78 LYS LEU | 82 HIS | |
| LEU | 75 ILE ASN | 76 HIS SER | 78 LYS LEU | 82 TYR | |
| LEU | 75 ILE ASN | 76 HIS SER | 78 TYR LEU | 82 PHE | |
| LEU | 75 ILE ASN | 76 HIS SER | 78 TYR LEU | 82 HIS | |
| LEU | 75 ILE ASN | 76 HIS SER | 78 TYR LEU | 82 TYR | |
| LEU | 75 MET ASN | 76 HIS SER | 78 ASN LEU | 82 PHE | |
| LEU | 75 MET ASN | 76 HIS SER | 78 ASN LEU | 82 HIS | |
| LEU | 75 MET ASN | 76 HIS SER | 78 ASN LEU | 82 TYR | |
| LEU | 75 MET ASN | 76 HIS SER | 78 THR LEU | 82 PHE | |
| LEU | 75 MET ASN | 76 HIS SER | 78 THR LEU | 82 HIS | |
| LEU | 75 MET ASN | 76 HIS SER | 78 THR LEU | 82 TYR | |
| LEU | 75 MET ASN | 76 HIS SER | 78 ARG LEU | 82 PHE | |
| LEU | 75 MET ASN | 76 HIS SER | 78 ARG LEU | 82 HIS | |
| LEU | 75 MET ASN | 76 HIS SER | 78 ARG LEU | 82 TYR | |
| LEU | 75 MET ASN | 76 HIS SER | 78 ASP LEU | 82 PHE | |
| LEU | 75 MET ASN | 76 HIS SER | 78 ASP LEU | 82 HIS | |
| LEU | 75 MET ASN | 76 HIS SER | 78 ASP LEU | 82 TYR | |
| LEU | 75 MET ASN | 76 HIS SER | 78 GLN LEU | 82 PHE | |
| LEU | 75 MET ASN | 76 HIS SER | 78 GLN LEU | 82 HIS | |
| LEU | 75 MET ASN | 76 HIS SER | 78 GLN LEU | 82 TYR | |
| LEU | 75 MET ASN | 76 HIS SER | 78 HIS LEU | 82 PHE | |
| LEU | 75 MET ASN | 76 HIS SER | 78 HIS LEU | 82 HIS | |
| LEU | 75 MET ASN | 76 HIS SER | 78 HIS LEU | 82 TYR | |
| LEU | 75 MET ASN | 76 HIS SER | 78 LYS LEU | 82 PHE | |
| LEU | 75 MET ASN | 76 HIS SER | 78 LYS LEU | 82 HIS | |
| LEU | 75 MET ASN | 76 HIS SER | 78 LYS LEU | 82 TYR | |
| LEU | 75 MET ASN | 76 HIS SER | 78 TYR LEU | 82 PHE | |
| LEU | 75 MET ASN | 76 HIS SER | 78 TYR LEU | 82 HIS | |
| LEU | 75 MET ASN | 76 HIS SER | 78 TYR LEU | 82 TYR | |
| LEU | 75 VAL ASN | 76 HIS SER | 78 ASN LEU | 82 PHE | |
| LEU | 75 VAL ASN | 76 HIS SER | 78 ASN LEU | 82 HIS | |
| LEU | 75 VAL ASN | 76 HIS SER | 78 ASN LEU | 82 TYR | |
| LEU | 75 VAL ASN | 76 HIS SER | 78 THR LEU | 82 PHE | |
| LEU | 75 VAL ASN | 76 HIS SER | 78 THR LEU | 82 HIS | |
| LEU | 75 VAL ASN | 76 HIS SER | 78 THR LEU | 82 TYR | |
| LEU | 75 VAL ASN | 76 HIS SER | 78 ARG LEU | 82 PHE | |
| LEU | 75 VAL ASN | 76 HIS SER | 78 ARG LEU | 82 HIS | |
| LEU | 75 VAL ASN | 76 HIS SER | 78 ARG LEU | 82 TYR | |
| LEU | 75 VAL ASN | 76 HIS SER | 78 ASP LEU | 82 PHE | |
| LEU | 75 VAL ASN | 76 HIS SER | 78 ASP LEU | 82 HIS | |
| LEU | 75 VAL ASN | 76 HIS SER | 78 ASP LEU | 82 TYR | |
| LEU | 75 VAL ASN | 76 HIS SER | 78 GLN LEU | 82 PHE | |
| LEU | 75 VAL ASN | 76 HIS SER | 78 GLN LEU | 82 HIS | |
| LEU | 75 VAL ASN | 76 HIS SER | 78 GLN LEU | 82 TYR | |
| LEU | 75 VAL ASN | 76 HIS SER | 78 HIS LEU | 82 PHE | |
| LEU | 75 VAL ASN | 76 HIS SER | 78 HIS LEU | 82 HIS | |
| LEU | 75 VAL ASN | 76 HIS SER | 78 HIS LEU | 82 TYR | |
| LEU | 75 VAL ASN | 76 HIS SER | 78 LYS LEU | 82 PHE | |
| LEU | 75 VAL ASN | 76 HIS SER | 78 LYS LEU | 82 HIS | |
| LEU | 75 VAL ASN | 76 HIS SER | 78 LYS LEU | 82 TYR | |
| LEU | 75 VAL ASN | 76 HIS SER | 78 TYR LEU | 82 PHE | |
| LEU | 75 VAL ASN | 76 HIS SER | 78 TYR LEU | 82 HIS | |
| LEU | 75 VAL ASN | 76 HIS SER | 78 TYR LEU | 82 TYR | |
| LEU | 75 ILE ASN | 76 HIS SER | 78 ASN VAL | 81 THR | |
| LEU | 75 ILE ASN | 76 HIS SER | 78 THR VAL | 81 THR | |
| LEU | 75 ILE ASN | 76 HIS SER | 78 ARG VAL | 81 THR | |
| LEU | 75 ILE ASN | 76 HIS SER | 78 ASP VAL | 81 THR | |
| LEU | 75 ILE ASN | 76 HIS SER | 78 GLN VAL | 81 THR | |
| LEU | 75 ILE ASN | 76 HIS SER | 78 HIS VAL | 81 THR | |
| LEU | 75 ILE ASN | 76 HIS SER | 78 LYS VAL | 81 THR | |
| LEU | 75 ILE ASN | 76 HIS SER | 78 TYR VAL | 81 THR | |
| LEU | 75 MET ASN | 76 HIS SER | 78 ASN VAL | 81 THR | |
| LEU | 75 MET ASN | 76 HIS SER | 78 THR VAL | 81 THR | |
| LEU | 75 MET ASN | 76 HIS SER | 78 ARG VAL | 81 THR | |
| LEU | 75 MET ASN | 76 HIS SER | 78 ASP VAL | 81 THR | |
| LEU | 75 MET ASN | 76 HIS SER | 78 GLN VAL | 81 THR | |
| LEU | 75 MET ASN | 76 HIS SER | 78 HIS VAL | 81 THR | |
| LEU | 75 MET ASN | 76 HIS SER | 78 LYS VAL | 81 THR | |
| LEU | 75 MET ASN | 76 HIS SER | 78 TYR VAL | 81 THR | |
| LEU | 75 VAL ASN | 76 HIS SER | 78 ASN VAL | 81 THR | |
| LEU | 75 VAL ASN | 76 HIS SER | 78 THR VAL | 81 THR | |
| LEU | 75 VAL ASN | 76 HIS SER | 78 ARG VAL | 81 THR | |
| LEU | 75 VAL ASN | 76 HIS SER | 78 ASP VAL | 81 THR | |
| LEU | 75 VAL ASN | 76 HIS SER | 78 GLN VAL | 81 THR | |
| LEU | 75 VAL ASN | 76 HIS SER | 78 HIS VAL | 81 THR | |
| LEU | 75 VAL ASN | 76 HIS SER | 78 LYS VAL | 81 THR | |
| LEU | 75 VAL ASN | 76 HIS SER | 78 TYR VAL | 81 THR | |
| LEU | 75 ILE ASN | 76 HIS SER | 78 ASN ILE | 79 LEU | |
| LEU | 75 ILE ASN | 76 HIS SER | 78 ASN ILE | 79 MET | |
| LEU | 75 ILE ASN | 76 HIS SER | 78 ASN ILE | 79 THR | |
| LEU | 75 ILE ASN | 76 HIS SER | 78 ASN ILE | 79 VAL | |
| LEU | 75 ILE ASN | 76 HIS SER | 78 THR ILE | 79 LEU | |
| LEU | 75 ILE ASN | 76 HIS SER | 78 THR ILE | 79 MET | |

TABLE 5-continued

| Quadruple Substitution Variants | | | | |
|---|---|---|---|---|
| LEU | 75 ILE ASN | 76 HIS SER | 78 THR ILE | 79 THR |
| LEU | 75 ILE ASN | 76 HIS SER | 78 THR ILE | 79 VAL |
| LEU | 75 ILE ASN | 76 HIS SER | 78 ARG ILE | 79 LEU |
| LEU | 75 ILE ASN | 76 HIS SER | 78 ARG ILE | 79 MET |
| LEU | 75 ILE ASN | 76 HIS SER | 78 ARG ILE | 79 THR |
| LEU | 75 ILE ASN | 76 HIS SER | 78 ARG ILE | 79 VAL |
| LEU | 75 ILE ASN | 76 HIS SER | 78 ASP ILE | 79 LEU |
| LEU | 75 ILE ASN | 76 HIS SER | 78 ASP ILE | 79 MET |
| LEU | 75 ILE ASN | 76 HIS SER | 78 ASP ILE | 79 THR |
| LEU | 75 ILE ASN | 76 HIS SER | 78 ASP ILE | 79 VAL |
| LEU | 75 ILE ASN | 76 HIS SER | 78 GLN ILE | 79 LEU |
| LEU | 75 ILE ASN | 76 HIS SER | 78 GLN ILE | 79 MET |
| LEU | 75 ILE ASN | 76 HIS SER | 78 GLN ILE | 79 THR |
| LEU | 75 ILE ASN | 76 HIS SER | 78 GLN ILE | 79 VAL |
| LEU | 75 ILE ASN | 76 HIS SER | 78 HIS ILE | 79 LEU |
| LEU | 75 ILE ASN | 76 HIS SER | 78 HIS ILE | 79 MET |
| LEU | 75 ILE ASN | 76 HIS SER | 78 HIS ILE | 79 THR |
| LEU | 75 ILE ASN | 76 HIS SER | 78 HIS ILE | 79 VAL |
| LEU | 75 ILE ASN | 76 HIS SER | 78 LYS ILE | 79 LEU |
| LEU | 75 ILE ASN | 76 HIS SER | 78 LYS ILE | 79 MET |
| LEU | 75 ILE ASN | 76 HIS SER | 78 LYS ILE | 79 THR |
| LEU | 75 ILE ASN | 76 HIS SER | 78 LYS ILE | 79 VAL |
| LEU | 75 ILE ASN | 76 HIS SER | 78 TYR ILE | 79 LEU |
| LEU | 75 ILE ASN | 76 HIS SER | 78 TYR ILE | 79 MET |
| LEU | 75 ILE ASN | 76 HIS SER | 78 TYR ILE | 79 THR |
| LEU | 75 ILE ASN | 76 HIS SER | 78 TYR ILE | 79 VAL |
| LEU | 75 MET ASN | 76 HIS SER | 78 ASN ILE | 79 LEU |
| LEU | 75 MET ASN | 76 HIS SER | 78 ASN ILE | 79 MET |
| LEU | 75 MET ASN | 76 HIS SER | 78 ASN ILE | 79 THR |
| LEU | 75 MET ASN | 76 HIS SER | 78 ASN ILE | 79 VAL |
| LEU | 75 MET ASN | 76 HIS SER | 78 THR ILE | 79 LEU |
| LEU | 75 MET ASN | 76 HIS SER | 78 THR ILE | 79 MET |
| LEU | 75 MET ASN | 76 HIS SER | 78 THR ILE | 79 THR |
| LEU | 75 MET ASN | 76 HIS SER | 78 THR ILE | 79 VAL |
| LEU | 75 MET ASN | 76 HIS SER | 78 ARG ILE | 79 LEU |
| LEU | 75 MET ASN | 76 HIS SER | 78 ARG ILE | 79 MET |
| LEU | 75 MET ASN | 76 HIS SER | 78 ARG ILE | 79 THR |
| LEU | 75 MET ASN | 76 HIS SER | 78 ARG ILE | 79 VAL |
| LEU | 75 MET ASN | 76 HIS SER | 78 ASP ILE | 79 LEU |
| LEU | 75 MET ASN | 76 HIS SER | 78 ASP ILE | 79 MET |
| LEU | 75 MET ASN | 76 HIS SER | 78 ASP ILE | 79 THR |
| LEU | 75 MET ASN | 76 HIS SER | 78 ASP ILE | 79 VAL |
| LEU | 75 MET ASN | 76 HIS SER | 78 GLN ILE | 79 LEU |
| LEU | 75 MET ASN | 76 HIS SER | 78 GLN ILE | 79 MET |
| LEU | 75 MET ASN | 76 HIS SER | 78 GLN ILE | 79 THR |
| LEU | 75 MET ASN | 76 HIS SER | 78 GLN ILE | 79 VAL |
| LEU | 75 MET ASN | 76 HIS SER | 78 HIS ILE | 79 LEU |
| LEU | 75 MET ASN | 76 HIS SER | 78 HIS ILE | 79 MET |
| LEU | 75 MET ASN | 76 HIS SER | 78 HIS ILE | 79 THR |
| LEU | 75 MET ASN | 76 HIS SER | 78 HIS ILE | 79 VAL |
| LEU | 75 MET ASN | 76 HIS SER | 78 LYS ILE | 79 LEU |

TABLE 5-continued

| Quadruple Substitution Variants | | | | |
|---|---|---|---|---|
| LEU | 75 MET ASN | 76 HIS SER | 78 LYS ILE | 79 MET |
| LEU | 75 MET ASN | 76 HIS SER | 78 LYS ILE | 79 THR |
| LEU | 75 MET ASN | 76 HIS SER | 78 LYS ILE | 79 VAL |
| LEU | 75 MET ASN | 76 HIS SER | 78 TYR ILE | 79 LEU |
| LEU | 75 MET ASN | 76 HIS SER | 78 TYR ILE | 79 MET |
| LEU | 75 MET ASN | 76 HIS SER | 78 TYR ILE | 79 THR |
| LEU | 75 MET ASN | 76 HIS SER | 78 TYR ILE | 79 VAL |
| LEU | 75 VAL ASN | 76 HIS SER | 78 ASN ILE | 79 LEU |
| LEU | 75 VAL ASN | 76 HIS SER | 78 ASN ILE | 79 MET |
| LEU | 75 VAL ASN | 76 HIS SER | 78 ASN ILE | 79 THR |
| LEU | 75 VAL ASN | 76 HIS SER | 78 ASN ILE | 79 VAL |
| LEU | 75 VAL ASN | 76 HIS SER | 78 THR ILE | 79 LEU |
| LEU | 75 VAL ASN | 76 HIS SER | 78 THR ILE | 79 MET |
| LEU | 75 VAL ASN | 76 HIS SER | 78 THR ILE | 79 THR |
| LEU | 75 VAL ASN | 76 HIS SER | 78 THR ILE | 79 VAL |
| LEU | 75 VAL ASN | 76 HIS SER | 78 ARG ILE | 79 LEU |
| LEU | 75 VAL ASN | 76 HIS SER | 78 ARG ILE | 79 MET |
| LEU | 75 VAL ASN | 76 HIS SER | 78 ARG ILE | 79 THR |
| LEU | 75 VAL ASN | 76 HIS SER | 78 ARG ILE | 79 VAL |
| LEU | 75 VAL ASN | 76 HIS SER | 78 ASP ILE | 79 LEU |
| LEU | 75 VAL ASN | 76 HIS SER | 78 ASP ILE | 79 MET |
| LEU | 75 VAL ASN | 76 HIS SER | 78 ASP ILE | 79 THR |
| LEU | 75 VAL ASN | 76 HIS SER | 78 ASP ILE | 79 VAL |
| LEU | 75 VAL ASN | 76 HIS SER | 78 GLN ILE | 79 LEU |
| LEU | 75 VAL ASN | 76 HIS SER | 78 GLN ILE | 79 MET |
| LEU | 75 VAL ASN | 76 HIS SER | 78 GLN ILE | 79 THR |
| LEU | 75 VAL ASN | 76 HIS SER | 78 GLN ILE | 79 VAL |
| LEU | 75 VAL ASN | 76 HIS SER | 78 HIS ILE | 79 LEU |
| LEU | 75 VAL ASN | 76 HIS SER | 78 HIS ILE | 79 MET |
| LEU | 75 VAL ASN | 76 HIS SER | 78 HIS ILE | 79 THR |
| LEU | 75 VAL ASN | 76 HIS SER | 78 HIS ILE | 79 VAL |
| LEU | 75 VAL ASN | 76 HIS SER | 78 LYS ILE | 79 LEU |
| LEU | 75 VAL ASN | 76 HIS SER | 78 LYS ILE | 79 MET |
| LEU | 75 VAL ASN | 76 HIS SER | 78 LYS ILE | 79 THR |
| LEU | 75 VAL ASN | 76 HIS SER | 78 LYS ILE | 79 VAL |
| LEU | 75 VAL ASN | 76 HIS SER | 78 TYR ILE | 79 LEU |
| LEU | 75 VAL ASN | 76 HIS SER | 78 TYR ILE | 79 MET |
| LEU | 75 VAL ASN | 76 HIS SER | 78 TYR ILE | 79 THR |
| LEU | 75 VAL ASN | 76 HIS SER | 78 TYR ILE | 79 VAL |

TABLE 6

| Quintuple Substitution Variants | | | | | |
|---|---|---|---|---|---|
| ASN | 76 HIS SER | 78 ASN ILE | 79 LEU VAL | 81 THR LEU | 82 PHE |
| ASN | 76 HIS SER | 78 ASN ILE | 79 LEU VAL | 81 THR LEU | 82 HIS |
| ASN | 76 HIS SER | 78 ASN ILE | 79 LEU VAL | 81 THR LEU | 82 TYR |
| ASN | 76 HIS SER | 78 ASN ILE | 79 MET VAL | 81 THR LEU | 82 PHE |
| ASN | 76 HIS SER | 78 ASN ILE | 79 MET VAL | 81 THR LEU | 82 HIS |
| ASN | 76 HIS SER | 78 ASN ILE | 79 MET VAL | 81 THR LEU | 82 TYR |
| ASN | 76 HIS SER | 78 ASN ILE | 79 THR VAL | 81 THR LEU | 82 PHE |
| ASN | 76 HIS SER | 78 ASN ILE | 79 THR VAL | 81 THR LEU | 82 HIS |
| ASN | 76 HIS SER | 78 ASN ILE | 79 THR VAL | 81 THR LEU | 82 TYR |
| ASN | 76 HIS SER | 78 ASN ILE | 79 VAL VAL | 81 THR LEU | 82 PHE |
| ASN | 76 HIS SER | 78 ASN ILE | 79 VAL VAL | 81 THR LEU | 82 HIS |
| ASN | 76 HIS SER | 78 ASN ILE | 79 VAL VAL | 81 THR LEU | 82 TYR |
| ASN | 76 HIS SER | 78 THR ILE | 79 LEU VAL | 81 THR LEU | 82 PHE |
| ASN | 76 HIS SER | 78 THR ILE | 79 LEU VAL | 81 THR LEU | 82 HIS |
| ASN | 76 HIS SER | 78 THR ILE | 79 LEU VAL | 81 THR LEU | 82 TYR |
| ASN | 76 HIS SER | 78 THR ILE | 79 MET VAL | 81 THR LEU | 82 PHE |
| ASN | 76 HIS SER | 78 THR ILE | 79 MET VAL | 81 THR LEU | 82 HIS |
| ASN | 76 HIS SER | 78 THR ILE | 79 MET VAL | 81 THR LEU | 82 TYR |

TABLE 6-continued

| Quintuple Substitution Variants | | | | | |
|---|---|---|---|---|---|
| ASN | 76 HIS SER | 78 THR ILE | 79 THR VAL | 81 THR LEU | 82 PHE |
| ASN | 76 HIS SER | 78 THR ILE | 79 THR VAL | 81 THR LEU | 82 HIS |
| ASN | 76 HIS SER | 78 THR ILE | 79 THR VAL | 81 THR LEU | 82 TYR |
| ASN | 76 HIS SER | 78 THR ILE | 79 VAL VAL | 81 THR LEU | 82 PHE |
| ASN | 76 HIS SER | 78 THR ILE | 79 VAL VAL | 81 THR LEU | 82 HIS |
| ASN | 76 HIS SER | 78 THR ILE | 79 VAL VAL | 81 THR LEU | 82 TYR |
| ASN | 76 HIS SER | 78 ARG ILE | 79 LEU VAL | 81 THR LEU | 82 PHE |
| ASN | 76 HIS SER | 78 ARG ILE | 79 LEU VAL | 81 THR LEU | 82 HIS |
| ASN | 76 HIS SER | 78 ARG ILE | 79 LEU VAL | 81 THR LEU | 82 TYR |
| ASN | 76 HIS SER | 78 ARG ILE | 79 MET VAL | 81 THR LEU | 82 PHE |
| ASN | 76 HIS SER | 78 ARG ILE | 79 MET VAL | 81 THR LEU | 82 HIS |
| ASN | 76 HIS SER | 78 ARG ILE | 79 MET VAL | 81 THR LEU | 82 TYR |
| ASN | 76 HIS SER | 78 ARG ILE | 79 THR VAL | 81 THR LEU | 82 PHE |
| ASN | 76 HIS SER | 78 ARG ILE | 79 THR VAL | 81 THR LEU | 82 HIS |
| ASN | 76 HIS SER | 78 ARG ILE | 79 THR VAL | 81 THR LEU | 82 TYR |
| ASN | 76 HIS SER | 78 ARG ILE | 79 VAL VAL | 81 THR LEU | 82 PHE |
| ASN | 76 HIS SER | 78 ARG ILE | 79 VAL VAL | 81 THR LEU | 82 HIS |
| ASN | 76 HIS SER | 78 ARG ILE | 79 VAL VAL | 81 THR LEU | 82 TYR |
| ASN | 76 HIS SER | 78 ASP ILE | 79 LEU VAL | 81 THR LEU | 82 PHE |
| ASN | 76 HIS SER | 78 ASP ILE | 79 LEU VAL | 81 THR LEU | 82 HIS |
| ASN | 76 HIS SER | 78 ASP ILE | 79 LEU VAL | 81 THR LEU | 82 TYR |
| ASN | 76 HIS SER | 78 ASP ILE | 79 MET VAL | 81 THR LEU | 82 PHE |
| ASN | 76 HIS SER | 78 ASP ILE | 79 MET VAL | 81 THR LEU | 82 HIS |
| ASN | 76 HIS SER | 78 ASP ILE | 79 MET VAL | 81 THR LEU | 82 TYR |
| ASN | 76 HIS SER | 78 ASP ILE | 79 THR VAL | 81 THR LEU | 82 PHE |
| ASN | 76 HIS SER | 78 ASP ILE | 79 THR VAL | 81 THR LEU | 82 HIS |
| ASN | 76 HIS SER | 78 ASP ILE | 79 THR VAL | 81 THR LEU | 82 TYR |
| ASN | 76 HIS SER | 78 ASP ILE | 79 VAL VAL | 81 THR LEU | 82 PHE |
| ASN | 76 HIS SER | 78 ASP ILE | 79 VAL VAL | 81 THR LEU | 82 HIS |
| ASN | 76 HIS SER | 78 ASP ILE | 79 VAL VAL | 81 THR LEU | 82 TYR |
| ASN | 76 HIS SER | 78 GLN ILE | 79 LEU VAL | 81 THR LEU | 82 PHE |
| ASN | 76 HIS SER | 78 GLN ILE | 79 LEU VAL | 81 THR LEU | 82 HIS |
| ASN | 76 HIS SER | 78 GLN ILE | 79 LEU VAL | 81 THR LEU | 82 TYR |
| ASN | 76 HIS SER | 78 GLN ILE | 79 MET VAL | 81 THR LEU | 82 PHE |
| ASN | 76 HIS SER | 78 GLN ILE | 79 MET VAL | 81 THR LEU | 82 HIS |
| ASN | 76 HIS SER | 78 GLN ILE | 79 MET VAL | 81 THR LEU | 82 TYR |
| ASN | 76 HIS SER | 78 GLN ILE | 79 THR VAL | 81 THR LEU | 82 PHE |
| ASN | 76 HIS SER | 78 GLN ILE | 79 THR VAL | 81 THR LEU | 82 HIS |
| ASN | 76 HIS SER | 78 GLN ILE | 79 THR VAL | 81 THR LEU | 82 TYR |
| ASN | 76 HIS SER | 78 GLN ILE | 79 VAL VAL | 81 THR LEU | 82 PHE |
| ASN | 76 HIS SER | 78 GLN ILE | 79 VAL VAL | 81 THR LEU | 82 HIS |
| ASN | 76 HIS SER | 78 GLN ILE | 79 VAL VAL | 81 THR LEU | 82 TYR |
| ASN | 76 HIS SER | 78 HIS ILE | 79 LEU VAL | 81 THR LEU | 82 PHE |
| ASN | 76 HIS SER | 78 HIS ILE | 79 LEU VAL | 81 THR LEU | 82 HIS |
| ASN | 76 HIS SER | 78 HIS ILE | 79 LEU VAL | 81 THR LEU | 82 TYR |
| ASN | 76 HIS SER | 78 HIS ILE | 79 MET VAL | 81 THR LEU | 82 PHE |
| ASN | 76 HIS SER | 78 HIS ILE | 79 MET VAL | 81 THR LEU | 82 HIS |
| ASN | 76 HIS SER | 78 HIS ILE | 79 MET VAL | 81 THR LEU | 82 TYR |
| ASN | 76 HIS SER | 78 HIS ILE | 79 THR VAL | 81 THR LEU | 82 PHE |
| ASN | 76 HIS SER | 78 HIS ILE | 79 THR VAL | 81 THR LEU | 82 HIS |
| ASN | 76 HIS SER | 78 HIS ILE | 79 THR VAL | 81 THR LEU | 82 TYR |
| ASN | 76 HIS SER | 78 HIS ILE | 79 VAL VAL | 81 THR LEU | 82 PHE |
| ASN | 76 HIS SER | 78 HIS ILE | 79 VAL VAL | 81 THR LEU | 82 HIS |
| ASN | 76 HIS SER | 78 HIS ILE | 79 VAL VAL | 81 THR LEU | 82 TYR |
| ASN | 76 HIS SER | 78 LYS ILE | 79 LEU VAL | 81 THR LEU | 82 PHE |
| ASN | 76 HIS SER | 78 LYS ILE | 79 LEU VAL | 81 THR LEU | 82 HIS |
| ASN | 76 HIS SER | 78 LYS ILE | 79 LEU VAL | 81 THR LEU | 82 TYR |
| ASN | 76 HIS SER | 78 LYS ILE | 79 MET VAL | 81 THR LEU | 82 PHE |
| ASN | 76 HIS SER | 78 LYS ILE | 79 MET VAL | 81 THR LEU | 82 HIS |
| ASN | 76 HIS SER | 78 LYS ILE | 79 MET VAL | 81 THR LEU | 82 TYR |
| ASN | 76 HIS SER | 78 LYS ILE | 79 THR VAL | 81 THR LEU | 82 PHE |
| ASN | 76 HIS SER | 78 LYS ILE | 79 THR VAL | 81 THR LEU | 82 HIS |
| ASN | 76 HIS SER | 78 LYS ILE | 79 THR VAL | 81 THR LEU | 82 TYR |
| ASN | 76 HIS SER | 78 LYS ILE | 79 VAL VAL | 81 THR LEU | 82 PHE |
| ASN | 76 HIS SER | 78 LYS ILE | 79 VAL VAL | 81 THR LEU | 82 HIS |
| ASN | 76 HIS SER | 78 LYS ILE | 79 VAL VAL | 81 THR LEU | 82 TYR |
| ASN | 76 HIS SER | 78 TYR ILE | 79 LEU VAL | 81 THR LEU | 82 PHE |
| ASN | 76 HIS SER | 78 TYR ILE | 79 LEU VAL | 81 THR LEU | 82 HIS |
| ASN | 76 HIS SER | 78 TYR ILE | 79 LEU VAL | 81 THR LEU | 82 TYR |
| ASN | 76 HIS SER | 78 TYR ILE | 79 MET VAL | 81 THR LEU | 82 PHE |
| ASN | 76 HIS SER | 78 TYR ILE | 79 MET VAL | 81 THR LEU | 82 HIS |
| ASN | 76 HIS SER | 78 TYR ILE | 79 MET VAL | 81 THR LEU | 82 TYR |
| ASN | 76 HIS SER | 78 TYR ILE | 79 THR VAL | 81 THR LEU | 82 PHE |
| ASN | 76 HIS SER | 78 TYR ILE | 79 THR VAL | 81 THR LEU | 82 HIS |
| ASN | 76 HIS SER | 78 TYR ILE | 79 THR VAL | 81 THR LEU | 82 TYR |
| ASN | 76 HIS SER | 78 TYR ILE | 79 VAL VAL | 81 THR LEU | 82 PHE |
| ASN | 76 HIS SER | 78 TYR ILE | 79 VAL VAL | 81 THR LEU | 82 HIS |

TABLE 6-continued

| Quintuple Substitution Variants | | | | | |
|---|---|---|---|---|---|
| ASN | 76 HIS SER | 78 TYR ILE | 79 VAL VAL | 81 THR LEU | 82 TYR |
| LEU | 75 ILE SER | 78 ASN ILE | 79 LEU VAL | 81 THR LEU | 82 PHE |
| LEU | 75 ILE SER | 78 ASN ILE | 79 LEU VAL | 81 THR LEU | 82 HIS |
| LEU | 75 ILE SER | 78 ASN ILE | 79 LEU VAL | 81 THR LEU | 82 TYR |
| LEU | 75 ILE SER | 78 ASN ILE | 79 MET VAL | 81 THR LEU | 82 PHE |
| LEU | 75 ILE SER | 78 ASN ILE | 79 MET VAL | 81 THR LEU | 82 HIS |
| LEU | 75 ILE SER | 78 ASN ILE | 79 MET VAL | 81 THR LEU | 82 TYR |
| LEU | 75 ILE SER | 78 ASN ILE | 79 THR VAL | 81 THR LEU | 82 PHE |
| LEU | 75 ILE SER | 78 ASN ILE | 79 THR VAL | 81 THR LEU | 82 HIS |
| LEU | 75 ILE SER | 78 ASN ILE | 79 THR VAL | 81 THR LEU | 82 TYR |
| LEU | 75 ILE SER | 78 ASN ILE | 79 VAL VAL | 81 THR LEU | 82 PHE |
| LEU | 75 ILE SER | 78 ASN ILE | 79 VAL VAL | 81 THR LEU | 82 HIS |
| LEU | 75 ILE SER | 78 ASN ILE | 79 VAL VAL | 81 THR LEU | 82 TYR |
| LEU | 75 ILE SER | 78 THR ILE | 79 LEU VAL | 81 THR LEU | 82 PHE |
| LEU | 75 ILE SER | 78 THR ILE | 79 LEU VAL | 81 THR LEU | 82 HIS |
| LEU | 75 ILE SER | 78 THR ILE | 79 LEU VAL | 81 THR LEU | 82 TYR |
| LEU | 75 ILE SER | 78 THR ILE | 79 MET VAL | 81 THR LEU | 82 PHE |
| LEU | 75 ILE SER | 78 THR ILE | 79 MET VAL | 81 THR LEU | 82 HIS |
| LEU | 75 ILE SER | 78 THR ILE | 79 MET VAL | 81 THR LEU | 82 TYR |
| LEU | 75 ILE SER | 78 THR ILE | 79 THR VAL | 81 THR LEU | 82 PHE |
| LEU | 75 ILE SER | 78 THR ILE | 79 THR VAL | 81 THR LEU | 82 HIS |
| LEU | 75 ILE SER | 78 THR ILE | 79 THR VAL | 81 THR LEU | 82 TYR |
| LEU | 75 ILE SER | 78 THR ILE | 79 VAL VAL | 81 THR LEU | 82 PHE |
| LEU | 75 ILE SER | 78 THR ILE | 79 VAL VAL | 81 THR LEU | 82 HIS |
| LEU | 75 ILE SER | 78 THR ILE | 79 VAL VAL | 81 THR LEU | 82 TYR |
| LEU | 75 ILE SER | 78 ARG ILE | 79 LEU VAL | 81 THR LEU | 82 PHE |
| LEU | 75 ILE SER | 78 ARG ILE | 79 LEU VAL | 81 THR LEU | 82 HIS |
| LEU | 75 ILE SER | 78 ARG ILE | 79 LEU VAL | 81 THR LEU | 82 TYR |
| LEU | 75 ILE SER | 78 ARG ILE | 79 MET VAL | 81 THR LEU | 82 PHE |
| LEU | 75 ILE SER | 78 ARG ILE | 79 MET VAL | 81 THR LEU | 82 HIS |
| LEU | 75 ILE SER | 78 ARG ILE | 79 MET VAL | 81 THR LEU | 82 TYR |
| LEU | 75 ILE SER | 78 ARG ILE | 79 THR VAL | 81 THR LEU | 82 PHE |
| LEU | 75 ILE SER | 78 ARG ILE | 79 THR VAL | 81 THR LEU | 82 HIS |
| LEU | 75 ILE SER | 78 ARG ILE | 79 THR VAL | 81 THR LEU | 82 TYR |
| LEU | 75 ILE SER | 78 ARG ILE | 79 VAL VAL | 81 THR LEU | 82 PHE |
| LEU | 75 ILE SER | 78 ARG ILE | 79 VAL VAL | 81 THR LEU | 82 HIS |
| LEU | 75 ILE SER | 78 ARG ILE | 79 VAL VAL | 81 THR LEU | 82 TYR |
| LEU | 75 ILE SER | 78 ASP ILE | 79 LEU VAL | 81 THR LEU | 82 PHE |
| LEU | 75 ILE SER | 78 ASP ILE | 79 LEU VAL | 81 THR LEU | 82 HIS |
| LEU | 75 ILE SER | 78 ASP ILE | 79 LEU VAL | 81 THR LEU | 82 TYR |
| LEU | 75 ILE SER | 78 ASP ILE | 79 MET VAL | 81 THR LEU | 82 PHE |
| LEU | 75 ILE SER | 78 ASP ILE | 79 MET VAL | 81 THR LEU | 82 HIS |
| LEU | 75 ILE SER | 78 ASP ILE | 79 MET VAL | 81 THR LEU | 82 TYR |
| LEU | 75 ILE SER | 78 ASP ILE | 79 THR VAL | 81 THR LEU | 82 PHE |
| LEU | 75 ILE SER | 78 ASP ILE | 79 THR VAL | 81 THR LEU | 82 HIS |
| LEU | 75 ILE SER | 78 ASP ILE | 79 THR VAL | 81 THR LEU | 82 TYR |
| LEU | 75 ILE SER | 78 ASP ILE | 79 VAL VAL | 81 THR LEU | 82 PHE |
| LEU | 75 ILE SER | 78 ASP ILE | 79 VAL VAL | 81 THR LEU | 82 HIS |
| LEU | 75 ILE SER | 78 ASP ILE | 79 VAL VAL | 81 THR LEU | 82 TYR |
| LEU | 75 ILE SER | 78 GLN ILE | 79 LEU VAL | 81 THR LEU | 82 PHE |
| LEU | 75 ILE SER | 78 GLN ILE | 79 LEU VAL | 81 THR LEU | 82 HIS |
| LEU | 75 ILE SER | 78 GLN ILE | 79 LEU VAL | 81 THR LEU | 82 TYR |
| LEU | 75 ILE SER | 78 GLN ILE | 79 MET VAL | 81 THR LEU | 82 PHE |
| LEU | 75 ILE SER | 78 GLN ILE | 79 MET VAL | 81 THR LEU | 82 HIS |
| LEU | 75 ILE SER | 78 GLN ILE | 79 MET VAL | 81 THR LEU | 82 TYR |
| LEU | 75 ILE SER | 78 GLN ILE | 79 THR VAL | 81 THR LEU | 82 PHE |
| LEU | 75 ILE SER | 78 GLN ILE | 79 THR VAL | 81 THR LEU | 82 HIS |
| LEU | 75 ILE SER | 78 GLN ILE | 79 THR VAL | 81 THR LEU | 82 TYR |
| LEU | 75 ILE SER | 78 GLN ILE | 79 VAL VAL | 81 THR LEU | 82 PHE |
| LEU | 75 ILE SER | 78 GLN ILE | 79 VAL VAL | 81 THR LEU | 82 HIS |
| LEU | 75 ILE SER | 78 GLN ILE | 79 VAL VAL | 81 THR LEU | 82 TYR |
| LEU | 75 ILE SER | 78 HIS ILE | 79 LEU VAL | 81 THR LEU | 82 PHE |
| LEU | 75 ILE SER | 78 HIS ILE | 79 LEU VAL | 81 THR LEU | 82 HIS |
| LEU | 75 ILE SER | 78 HIS ILE | 79 LEU VAL | 81 THR LEU | 82 TYR |
| LEU | 75 ILE SER | 78 HIS ILE | 79 MET VAL | 81 THR LEU | 82 PHE |
| LEU | 75 ILE SER | 78 HIS ILE | 79 MET VAL | 81 THR LEU | 82 HIS |
| LEU | 75 ILE SER | 78 HIS ILE | 79 MET VAL | 81 THR LEU | 82 TYR |
| LEU | 75 ILE SER | 78 HIS ILE | 79 THR VAL | 81 THR LEU | 82 PHE |
| LEU | 75 ILE SER | 78 HIS ILE | 79 THR VAL | 81 THR LEU | 82 HIS |
| LEU | 75 ILE SER | 78 HIS ILE | 79 THR VAL | 81 THR LEU | 82 TYR |
| LEU | 75 ILE SER | 78 HIS ILE | 79 VAL VAL | 81 THR LEU | 82 PHE |
| LEU | 75 ILE SER | 78 HIS ILE | 79 VAL VAL | 81 THR LEU | 82 HIS |
| LEU | 75 ILE SER | 78 HIS ILE | 79 VAL VAL | 81 THR LEU | 82 TYR |
| LEU | 75 ILE SER | 78 LYS ILE | 79 LEU VAL | 81 THR LEU | 82 PHE |
| LEU | 75 ILE SER | 78 LYS ILE | 79 LEU VAL | 81 THR LEU | 82 HIS |
| LEU | 75 ILE SER | 78 LYS ILE | 79 LEU VAL | 81 THR LEU | 82 TYR |
| LEU | 75 ILE SER | 78 LYS ILE | 79 MET VAL | 81 THR LEU | 82 PHE |

TABLE 6-continued

Quintuple Substitution Variants

| | | | | | |
|---|---|---|---|---|---|
| LEU | 75 ILE SER | 78 LYS ILE | 79 MET VAL | 81 THR LEU | 82 HIS |
| LEU | 75 ILE SER | 78 LYS ILE | 79 MET VAL | 81 THR LEU | 82 TYR |
| LEU | 75 ILE SER | 78 LYS ILE | 79 THR VAL | 81 THR LEU | 82 PHE |
| LEU | 75 ILE SER | 78 LYS ILE | 79 THR VAL | 81 THR LEU | 82 HIS |
| LEU | 75 ILE SER | 78 LYS ILE | 79 THR VAL | 81 THR LEU | 82 TYR |
| LEU | 75 ILE SER | 78 LYS ILE | 79 VAL VAL | 81 THR LEU | 82 PHE |
| LEU | 75 ILE SER | 78 LYS ILE | 79 VAL VAL | 81 THR LEU | 82 HIS |
| LEU | 75 ILE SER | 78 LYS ILE | 79 VAL VAL | 81 THR LEU | 82 TYR |
| LEU | 75 ILE SER | 78 TYR ILE | 79 LEU VAL | 81 THR LEU | 82 PHE |
| LEU | 75 ILE SER | 78 TYR ILE | 79 LEU VAL | 81 THR LEU | 82 HIS |
| LEU | 75 ILE SER | 78 TYR ILE | 79 LEU VAL | 81 THR LEU | 82 TYR |
| LEU | 75 ILE SER | 78 TYR ILE | 79 MET VAL | 81 THR LEU | 82 PHE |
| LEU | 75 ILE SER | 78 TYR ILE | 79 MET VAL | 81 THR LEU | 82 HIS |
| LEU | 75 ILE SER | 78 TYR ILE | 79 MET VAL | 81 THR LEU | 82 TYR |
| LEU | 75 ILE SER | 78 TYR ILE | 79 THR VAL | 81 THR LEU | 82 PHE |
| LEU | 75 ILE SER | 78 TYR ILE | 79 THR VAL | 81 THR LEU | 82 HIS |
| LEU | 75 ILE SER | 78 TYR ILE | 79 THR VAL | 81 THR LEU | 82 TYR |
| LEU | 75 ILE SER | 78 TYR ILE | 79 VAL VAL | 81 THR LEU | 82 PHE |
| LEU | 75 ILE SER | 78 TYR ILE | 79 VAL VAL | 81 THR LEU | 82 HIS |
| LEU | 75 ILE SER | 78 TYR ILE | 79 VAL VAL | 81 THR LEU | 82 TYR |
| LEU | 75 MET SER | 78 ASN ILE | 79 LEU VAL | 81 THR LEU | 82 PHE |
| LEU | 75 MET SER | 78 ASN ILE | 79 LEU VAL | 81 THR LEU | 82 HIS |
| LEU | 75 MET SER | 78 ASN ILE | 79 LEU VAL | 81 THR LEU | 82 TYR |
| LEU | 75 MET SER | 78 ASN ILE | 79 MET VAL | 81 THR LEU | 82 PHE |
| LEU | 75 MET SER | 78 ASN ILE | 79 MET VAL | 81 THR LEU | 82 HIS |
| LEU | 75 MET SER | 78 ASN ILE | 79 MET VAL | 81 THR LEU | 82 TYR |
| LEU | 75 MET SER | 78 ASN ILE | 79 THR VAL | 81 THR LEU | 82 PHE |
| LEU | 75 MET SER | 78 ASN ILE | 79 THR VAL | 81 THR LEU | 82 HIS |
| LEU | 75 MET SER | 78 ASN ILE | 79 THR VAL | 81 THR LEU | 82 TYR |
| LEU | 75 MET SER | 78 ASN ILE | 79 VAL VAL | 81 THR LEU | 82 PHE |
| LEU | 75 MET SER | 78 ASN ILE | 79 VAL VAL | 81 THR LEU | 82 HIS |
| LEU | 75 MET SER | 78 ASN ILE | 79 VAL VAL | 81 THR LEU | 82 TYR |
| LEU | 75 MET SER | 78 THR ILE | 79 LEU VAL | 81 THR LEU | 82 PHE |
| LEU | 75 MET SER | 78 THR ILE | 79 LEU VAL | 81 THR LEU | 82 HIS |
| LEU | 75 MET SER | 78 THR ILE | 79 LEU VAL | 81 THR LEU | 82 TYR |
| LEU | 75 MET SER | 78 THR ILE | 79 MET VAL | 81 THR LEU | 82 PHE |
| LEU | 75 MET SER | 78 THR ILE | 79 MET VAL | 81 THR LEU | 82 HIS |
| LEU | 75 MET SER | 78 THR ILE | 79 MET VAL | 81 THR LEU | 82 TYR |
| LEU | 75 MET SER | 78 THR ILE | 79 THR VAL | 81 THR LEU | 82 PHE |
| LEU | 75 MET SER | 78 THR ILE | 79 THR VAL | 81 THR LEU | 82 HIS |
| LEU | 75 MET SER | 78 THR ILE | 79 THR VAL | 81 THR LEU | 82 TYR |
| LEU | 75 MET SER | 78 THR ILE | 79 VAL VAL | 81 THR LEU | 82 PHE |
| LEU | 75 MET SER | 78 THR ILE | 79 VAL VAL | 81 THR LEU | 82 HIS |
| LEU | 75 MET SER | 78 THR ILE | 79 VAL VAL | 81 THR LEU | 82 TYR |
| LEU | 75 MET SER | 78 ARG ILE | 79 LEU VAL | 81 THR LEU | 82 PHE |
| LEU | 75 MET SER | 78 ARG ILE | 79 LEU VAL | 81 THR LEU | 82 HIS |
| LEU | 75 MET SER | 78 ARG ILE | 79 LEU VAL | 81 THR LEU | 82 TYR |
| LEU | 75 MET SER | 78 ARG ILE | 79 MET VAL | 81 THR LEU | 82 PHE |
| LEU | 75 MET SER | 78 ARG ILE | 79 MET VAL | 81 THR LEU | 82 HIS |
| LEU | 75 MET SER | 78 ARG ILE | 79 MET VAL | 81 THR LEU | 82 TYR |
| LEU | 75 MET SER | 78 ARG ILE | 79 THR VAL | 81 THR LEU | 82 PHE |
| LEU | 75 MET SER | 78 ARG ILE | 79 THR VAL | 81 THR LEU | 82 HIS |
| LEU | 75 MET SER | 78 ARG ILE | 79 THR VAL | 81 THR LEU | 82 TYR |
| LEU | 75 MET SER | 78 ARG ILE | 79 VAL VAL | 81 THR LEU | 82 PHE |
| LEU | 75 MET SER | 78 ARG ILE | 79 VAL VAL | 81 THR LEU | 82 HIS |
| LEU | 75 MET SER | 78 ARG ILE | 79 VAL VAL | 81 THR LEU | 82 TYR |
| LEU | 75 MET SER | 78 ASP ILE | 79 LEU VAL | 81 THR LEU | 82 PHE |
| LEU | 75 MET SER | 78 ASP ILE | 79 LEU VAL | 81 THR LEU | 82 HIS |
| LEU | 75 MET SER | 78 ASP ILE | 79 LEU VAL | 81 THR LEU | 82 TYR |
| LEU | 75 MET SER | 78 ASP ILE | 79 MET VAL | 81 THR LEU | 82 PHE |
| LEU | 75 MET SER | 78 ASP ILE | 79 MET VAL | 81 THR LEU | 82 HIS |
| LEU | 75 MET SER | 78 ASP ILE | 79 MET VAL | 81 THR LEU | 82 TYR |
| LEU | 75 MET SER | 78 ASP ILE | 79 THR VAL | 81 THR LEU | 82 PHE |
| LEU | 75 MET SER | 78 ASP ILE | 79 THR VAL | 81 THR LEU | 82 HIS |
| LEU | 75 MET SER | 78 ASP ILE | 79 THR VAL | 81 THR LEU | 82 TYR |
| LEU | 75 MET SER | 78 ASP ILE | 79 VAL VAL | 81 THR LEU | 82 PHE |
| LEU | 75 MET SER | 78 ASP ILE | 79 VAL VAL | 81 THR LEU | 82 HIS |
| LEU | 75 MET SER | 78 ASP ILE | 79 VAL VAL | 81 THR LEU | 82 TYR |
| LEU | 75 MET SER | 78 GLN ILE | 79 LEU VAL | 81 THR LEU | 82 PHE |
| LEU | 75 MET SER | 78 GLN ILE | 79 LEU VAL | 81 THR LEU | 82 HIS |
| LEU | 75 MET SER | 78 GLN ILE | 79 LEU VAL | 81 THR LEU | 82 TYR |
| LEU | 75 MET SER | 78 GLN ILE | 79 MET VAL | 81 THR LEU | 82 PHE |
| LEU | 75 MET SER | 78 GLN ILE | 79 MET VAL | 81 THR LEU | 82 HIS |
| LEU | 75 MET SER | 78 GLN ILE | 79 MET VAL | 81 THR LEU | 82 TYR |
| LEU | 75 MET SER | 78 GLN ILE | 79 THR VAL | 81 THR LEU | 82 PHE |
| LEU | 75 MET SER | 78 GLN ILE | 79 THR VAL | 81 THR LEU | 82 HIS |
| LEU | 75 MET SER | 78 GLN ILE | 79 THR VAL | 81 THR LEU | 82 TYR |

TABLE 6-continued

Quintuple Substitution Variants

| | | | | | |
|---|---|---|---|---|---|
| LEU 75 MET SER | 78 GLN ILE | 79 VAL VAL | 81 THR LEU | 82 PHE |
| LEU 75 MET SER | 78 GLN ILE | 79 VAL VAL | 81 THR LEU | 82 HIS |
| LEU 75 MET SER | 78 GLN ILE | 79 VAL VAL | 81 THR LEU | 82 TYR |
| LEU 75 MET SER | 78 HIS ILE | 79 LEU VAL | 81 THR LEU | 82 PHE |
| LEU 75 MET SER | 78 HIS ILE | 79 LEU VAL | 81 THR LEU | 82 HIS |
| LEU 75 MET SER | 78 HIS ILE | 79 LEU VAL | 81 THR LEU | 82 TYR |
| LEU 75 MET SER | 78 HIS ILE | 79 MET VAL | 81 THR LEU | 82 PHE |
| LEU 75 MET SER | 78 HIS ILE | 79 MET VAL | 81 THR LEU | 82 HIS |
| LEU 75 MET SER | 78 HIS ILE | 79 MET VAL | 81 THR LEU | 82 TYR |
| LEU 75 MET SER | 78 HIS ILE | 79 THR VAL | 81 THR LEU | 82 PHE |
| LEU 75 MET SER | 78 HIS ILE | 79 THR VAL | 81 THR LEU | 82 HIS |
| LEU 75 MET SER | 78 HIS ILE | 79 THR VAL | 81 THR LEU | 82 TYR |
| LEU 75 MET SER | 78 HIS ILE | 79 VAL VAL | 81 THR LEU | 82 PHE |
| LEU 75 MET SER | 78 HIS ILE | 79 VAL VAL | 81 THR LEU | 82 HIS |
| LEU 75 MET SER | 78 HIS ILE | 79 VAL VAL | 81 THR LEU | 82 TYR |
| LEU 75 MET SER | 78 LYS ILE | 79 LEU VAL | 81 THR LEU | 82 PHE |
| LEU 75 MET SER | 78 LYS ILE | 79 LEU VAL | 81 THR LEU | 82 HIS |
| LEU 75 MET SER | 78 LYS ILE | 79 LEU VAL | 81 THR LEU | 82 TYR |
| LEU 75 MET SER | 78 LYS ILE | 79 MET VAL | 81 THR LEU | 82 PHE |
| LEU 75 MET SER | 78 LYS ILE | 79 MET VAL | 81 THR LEU | 82 HIS |
| LEU 75 MET SER | 78 LYS ILE | 79 MET VAL | 81 THR LEU | 82 TYR |
| LEU 75 MET SER | 78 LYS ILE | 79 THR VAL | 81 THR LEU | 82 PHE |
| LEU 75 MET SER | 78 LYS ILE | 79 THR VAL | 81 THR LEU | 82 HIS |
| LEU 75 MET SER | 78 LYS ILE | 79 THR VAL | 81 THR LEU | 82 TYR |
| LEU 75 MET SER | 78 LYS ILE | 79 VAL VAL | 81 THR LEU | 82 PHE |
| LEU 75 MET SER | 78 LYS ILE | 79 VAL VAL | 81 THR LEU | 82 HIS |
| LEU 75 MET SER | 78 LYS ILE | 79 VAL VAL | 81 THR LEU | 82 TYR |
| LEU 75 MET SER | 78 TYR ILE | 79 LEU VAL | 81 THR LEU | 82 PHE |
| LEU 75 MET SER | 78 TYR ILE | 79 LEU VAL | 81 THR LEU | 82 HIS |
| LEU 75 MET SER | 78 TYR ILE | 79 LEU VAL | 81 THR LEU | 82 TYR |
| LEU 75 MET SER | 78 TYR ILE | 79 MET VAL | 81 THR LEU | 82 PHE |
| LEU 75 MET SER | 78 TYR ILE | 79 MET VAL | 81 THR LEU | 82 HIS |
| LEU 75 MET SER | 78 TYR ILE | 79 MET VAL | 81 THR LEU | 82 TYR |
| LEU 75 MET SER | 78 TYR ILE | 79 THR VAL | 81 THR LEU | 82 PHE |
| LEU 75 MET SER | 78 TYR ILE | 79 THR VAL | 81 THR LEU | 82 HIS |
| LEU 75 MET SER | 78 TYR ILE | 79 THR VAL | 81 THR LEU | 82 TYR |
| LEU 75 MET SER | 78 TYR ILE | 79 VAL VAL | 81 THR LEU | 82 PHE |
| LEU 75 MET SER | 78 TYR ILE | 79 VAL VAL | 81 THR LEU | 82 HIS |
| LEU 75 MET SER | 78 TYR ILE | 79 VAL VAL | 81 THR LEU | 82 TYR |
| LEU 75 VAL SER | 78 ASN ILE | 79 LEU VAL | 81 THR LEU | 82 PHE |
| LEU 75 VAL SER | 78 ASN ILE | 79 LEU VAL | 81 THR LEU | 82 HIS |
| LEU 75 VAL SER | 78 ASN ILE | 79 LEU VAL | 81 THR LEU | 82 TYR |
| LEU 75 VAL SER | 78 ASN ILE | 79 MET VAL | 81 THR LEU | 82 PHE |
| LEU 75 VAL SER | 78 ASN ILE | 79 MET VAL | 81 THR LEU | 82 HIS |
| LEU 75 VAL SER | 78 ASN ILE | 79 MET VAL | 81 THR LEU | 82 TYR |
| LEU 75 VAL SER | 78 ASN ILE | 79 THR VAL | 81 THR LEU | 82 PHE |
| LEU 75 VAL SER | 78 ASN ILE | 79 THR VAL | 81 THR LEU | 82 HIS |
| LEU 75 VAL SER | 78 ASN ILE | 79 THR VAL | 81 THR LEU | 82 TYR |
| LEU 75 VAL SER | 78 ASN ILE | 79 VAL VAL | 81 THR LEU | 82 PHE |
| LEU 75 VAL SER | 78 ASN ILE | 79 VAL VAL | 81 THR LEU | 82 HIS |
| LEU 75 VAL SER | 78 ASN ILE | 79 VAL VAL | 81 THR LEU | 82 TYR |
| LEU 75 VAL SER | 78 THR ILE | 79 LEU VAL | 81 THR LEU | 82 PHE |
| LEU 75 VAL SER | 78 THR ILE | 79 LEU VAL | 81 THR LEU | 82 HIS |
| LEU 75 VAL SER | 78 THR ILE | 79 LEU VAL | 81 THR LEU | 82 TYR |
| LEU 75 VAL SER | 78 THR ILE | 79 MET VAL | 81 THR LEU | 82 PHE |
| LEU 75 VAL SER | 78 THR ILE | 79 MET VAL | 81 THR LEU | 82 HIS |
| LEU 75 VAL SER | 78 THR ILE | 79 MET VAL | 81 THR LEU | 82 TYR |
| LEU 75 VAL SER | 78 THR ILE | 79 THR VAL | 81 THR LEU | 82 PHE |
| LEU 75 VAL SER | 78 THR ILE | 79 THR VAL | 81 THR LEU | 82 HIS |
| LEU 75 VAL SER | 78 THR ILE | 79 THR VAL | 81 THR LEU | 82 TYR |
| LEU 75 VAL SER | 78 THR ILE | 79 VAL VAL | 81 THR LEU | 82 PHE |
| LEU 75 VAL SER | 78 THR ILE | 79 VAL VAL | 81 THR LEU | 82 HIS |
| LEU 75 VAL SER | 78 THR ILE | 79 VAL VAL | 81 THR LEU | 82 TYR |
| LEU 75 VAL SER | 78 ARG ILE | 79 LEU VAL | 81 THR LEU | 82 PHE |
| LEU 75 VAL SER | 78 ARG ILE | 79 LEU VAL | 81 THR LEU | 82 HIS |
| LEU 75 VAL SER | 78 ARG ILE | 79 LEU VAL | 81 THR LEU | 82 TYR |
| LEU 75 VAL SER | 78 ARG ILE | 79 MET VAL | 81 THR LEU | 82 PHE |
| LEU 75 VAL SER | 78 ARG ILE | 79 MET VAL | 81 THR LEU | 82 HIS |
| LEU 75 VAL SER | 78 ARG ILE | 79 MET VAL | 81 THR LEU | 82 TYR |
| LEU 75 VAL SER | 78 ARG ILE | 79 THR VAL | 81 THR LEU | 82 PHE |
| LEU 75 VAL SER | 78 ARG ILE | 79 THR VAL | 81 THR LEU | 82 HIS |
| LEU 75 VAL SER | 78 ARG ILE | 79 THR VAL | 81 THR LEU | 82 TYR |
| LEU 75 VAL SER | 78 ARG ILE | 79 VAL VAL | 81 THR LEU | 82 PHE |
| LEU 75 VAL SER | 78 ARG ILE | 79 VAL VAL | 81 THR LEU | 82 HIS |
| LEU 75 VAL SER | 78 ARG ILE | 79 VAL VAL | 81 THR LEU | 82 TYR |
| LEU 75 VAL SER | 78 ASP ILE | 79 LEU VAL | 81 THR LEU | 82 PHE |
| LEU 75 VAL SER | 78 ASP ILE | 79 LEU VAL | 81 THR LEU | 82 HIS |

TABLE 6-continued

Quintuple Substitution Variants

| | | | | | |
|---|---|---|---|---|---|
| LEU | 75 VAL SER | 78 ASP ILE | 79 LEU VAL | 81 THR LEU | 82 TYR |
| LEU | 75 VAL SER | 78 ASP ILE | 79 MET VAL | 81 THR LEU | 82 PHE |
| LEU | 75 VAL SER | 78 ASP ILE | 79 MET VAL | 81 THR LEU | 82 HIS |
| LEU | 75 VAL SER | 78 ASP ILE | 79 MET VAL | 81 THR LEU | 82 TYR |
| LEU | 75 VAL SER | 78 ASP ILE | 79 THR VAL | 81 THR LEU | 82 PHE |
| LEU | 75 VAL SER | 78 ASP ILE | 79 THR VAL | 81 THR LEU | 82 HIS |
| LEU | 75 VAL SER | 78 ASP ILE | 79 THR VAL | 81 THR LEU | 82 TYR |
| LEU | 75 VAL SER | 78 ASP ILE | 79 VAL VAL | 81 THR LEU | 82 PHE |
| LEU | 75 VAL SER | 78 ASP ILE | 79 VAL VAL | 81 THR LEU | 82 HIS |
| LEU | 75 VAL SER | 78 ASP ILE | 79 VAL VAL | 81 THR LEU | 82 TYR |
| LEU | 75 VAL SER | 78 GLN ILE | 79 LEU VAL | 81 THR LEU | 82 PHE |
| LEU | 75 VAL SER | 78 GLN ILE | 79 LEU VAL | 81 THR LEU | 82 HIS |
| LEU | 75 VAL SER | 78 GLN ILE | 79 LEU VAL | 81 THR LEU | 82 TYR |
| LEU | 75 VAL SER | 78 GLN ILE | 79 MET VAL | 81 THR LEU | 82 PHE |
| LEU | 75 VAL SER | 78 GLN ILE | 79 MET VAL | 81 THR LEU | 82 HIS |
| LEU | 75 VAL SER | 78 GLN ILE | 79 MET VAL | 81 THR LEU | 82 TYR |
| LEU | 75 VAL SER | 78 GLN ILE | 79 THR VAL | 81 THR LEU | 82 PHE |
| LEU | 75 VAL SER | 78 GLN ILE | 79 THR VAL | 81 THR LEU | 82 HIS |
| LEU | 75 VAL SER | 78 GLN ILE | 79 THR VAL | 81 THR LEU | 82 TYR |
| LEU | 75 VAL SER | 78 GLN ILE | 79 VAL VAL | 81 THR LEU | 82 PHE |
| LEU | 75 VAL SER | 78 GLN ILE | 79 VAL VAL | 81 THR LEU | 82 HIS |
| LEU | 75 VAL SER | 78 GLN ILE | 79 VAL VAL | 81 THR LEU | 82 TYR |
| LEU | 75 VAL SER | 78 HIS ILE | 79 LEU VAL | 81 THR LEU | 82 PHE |
| LEU | 75 VAL SER | 78 HIS ILE | 79 LEU VAL | 81 THR LEU | 82 HIS |
| LEU | 75 VAL SER | 78 HIS ILE | 79 LEU VAL | 81 THR LEU | 82 TYR |
| LEU | 75 VAL SER | 78 HIS ILE | 79 MET VAL | 81 THR LEU | 82 PHE |
| LEU | 75 VAL SER | 78 HIS ILE | 79 MET VAL | 81 THR LEU | 82 HIS |
| LEU | 75 VAL SER | 78 HIS ILE | 79 MET VAL | 81 THR LEU | 82 TYR |
| LEU | 75 VAL SER | 78 HIS ILE | 79 THR VAL | 81 THR LEU | 82 PHE |
| LEU | 75 VAL SER | 78 HIS ILE | 79 THR VAL | 81 THR LEU | 82 HIS |
| LEU | 75 VAL SER | 78 HIS ILE | 79 THR VAL | 81 THR LEU | 82 TYR |
| LEU | 75 VAL SER | 78 HIS ILE | 79 VAL VAL | 81 THR LEU | 82 PHE |
| LEU | 75 VAL SER | 78 HIS ILE | 79 VAL VAL | 81 THR LEU | 82 HIS |
| LEU | 75 VAL SER | 78 HIS ILE | 79 VAL VAL | 81 THR LEU | 82 TYR |
| LEU | 75 VAL SER | 78 LYS ILE | 79 LEU VAL | 81 THR LEU | 82 PHE |
| LEU | 75 VAL SER | 78 LYS ILE | 79 LEU VAL | 81 THR LEU | 82 HIS |
| LEU | 75 VAL SER | 78 LYS ILE | 79 LEU VAL | 81 THR LEU | 82 TYR |
| LEU | 75 VAL SER | 78 LYS ILE | 79 MET VAL | 81 THR LEU | 82 PHE |
| LEU | 75 VAL SER | 78 LYS ILE | 79 MET VAL | 81 THR LEU | 82 HIS |
| LEU | 75 VAL SER | 78 LYS ILE | 79 MET VAL | 81 THR LEU | 82 TYR |
| LEU | 75 VAL SER | 78 LYS ILE | 79 THR VAL | 81 THR LEU | 82 PHE |
| LEU | 75 VAL SER | 78 LYS ILE | 79 THR VAL | 81 THR LEU | 82 HIS |
| LEU | 75 VAL SER | 78 LYS ILE | 79 THR VAL | 81 THR LEU | 82 TYR |
| LEU | 75 VAL SER | 78 LYS ILE | 79 VAL VAL | 81 THR LEU | 82 PHE |
| LEU | 75 VAL SER | 78 LYS ILE | 79 VAL VAL | 81 THR LEU | 82 HIS |
| LEU | 75 VAL SER | 78 LYS ILE | 79 VAL VAL | 81 THR LEU | 82 TYR |
| LEU | 75 VAL SER | 78 TYR ILE | 79 LEU VAL | 81 THR LEU | 82 PHE |
| LEU | 75 VAL SER | 78 TYR ILE | 79 LEU VAL | 81 THR LEU | 82 HIS |
| LEU | 75 VAL SER | 78 TYR ILE | 79 LEU VAL | 81 THR LEU | 82 TYR |
| LEU | 75 VAL SER | 78 TYR ILE | 79 MET VAL | 81 THR LEU | 82 PHE |
| LEU | 75 VAL SER | 78 TYR ILE | 79 MET VAL | 81 THR LEU | 82 HIS |
| LEU | 75 VAL SER | 78 TYR ILE | 79 MET VAL | 81 THR LEU | 82 TYR |
| LEU | 75 VAL SER | 78 TYR ILE | 79 THR VAL | 81 THR LEU | 82 PHE |
| LEU | 75 VAL SER | 78 TYR ILE | 79 THR VAL | 81 THR LEU | 82 HIS |
| LEU | 75 VAL SER | 78 TYR ILE | 79 THR VAL | 81 THR LEU | 82 TYR |
| LEU | 75 VAL SER | 78 TYR ILE | 79 VAL VAL | 81 THR LEU | 82 PHE |
| LEU | 75 VAL SER | 78 TYR ILE | 79 VAL VAL | 81 THR LEU | 82 HIS |
| LEU | 75 VAL SER | 78 TYR ILE | 79 VAL VAL | 81 THR LEU | 82 TYR |
| LEU | 75 ILE ASN | 76 HIS ILE | 79 LEU VAL | 81 THR LEU | 82 PHE |
| LEU | 75 ILE ASN | 76 HIS ILE | 79 LEU VAL | 81 THR LEU | 82 HIS |
| LEU | 75 ILE ASN | 76 HIS ILE | 79 LEU VAL | 81 THR LEU | 82 TYR |
| LEU | 75 ILE ASN | 76 HIS ILE | 79 MET VAL | 81 THR LEU | 82 PHE |
| LEU | 75 ILE ASN | 76 HIS ILE | 79 MET VAL | 81 THR LEU | 82 HIS |
| LEU | 75 ILE ASN | 76 HIS ILE | 79 MET VAL | 81 THR LEU | 82 TYR |
| LEU | 75 ILE ASN | 76 HIS ILE | 79 THR VAL | 81 THR LEU | 82 PHE |
| LEU | 75 ILE ASN | 76 HIS ILE | 79 THR VAL | 81 THR LEU | 82 HIS |
| LEU | 75 ILE ASN | 76 HIS ILE | 79 THR VAL | 81 THR LEU | 82 TYR |
| LEU | 75 ILE ASN | 76 HIS ILE | 79 VAL VAL | 81 THR LEU | 82 PHE |
| LEU | 75 ILE ASN | 76 HIS ILE | 79 VAL VAL | 81 THR LEU | 82 HIS |
| LEU | 75 ILE ASN | 76 HIS ILE | 79 VAL VAL | 81 THR LEU | 82 TYR |
| LEU | 75 MET ASN | 76 HIS ILE | 79 LEU VAL | 81 THR LEU | 82 PHE |
| LEU | 75 MET ASN | 76 HIS ILE | 79 LEU VAL | 81 THR LEU | 82 HIS |
| LEU | 75 MET ASN | 76 HIS ILE | 79 LEU VAL | 81 THR LEU | 82 TYR |
| LEU | 75 MET ASN | 76 HIS ILE | 79 MET VAL | 81 THR LEU | 82 PHE |
| LEU | 75 MET ASN | 76 HIS ILE | 79 MET VAL | 81 THR LEU | 82 HIS |
| LEU | 75 MET ASN | 76 HIS ILE | 79 MET VAL | 81 THR LEU | 82 TYR |
| LEU | 75 MET ASN | 76 HIS ILE | 79 THR VAL | 81 THR LEU | 82 PHE |

TABLE 6-continued

Quintuple Substitution Variants

| | | | | | |
|---|---|---|---|---|---|
| LEU | 75 MET ASN | 76 HIS ILE | 79 THR VAL | 81 THR LEU | 82 HIS |
| LEU | 75 MET ASN | 76 HIS ILE | 79 THR VAL | 81 THR LEU | 82 TYR |
| LEU | 75 MET ASN | 76 HIS ILE | 79 VAL VAL | 81 THR LEU | 82 PHE |
| LEU | 75 MET ASN | 76 HIS ILE | 79 VAL VAL | 81 THR LEU | 82 HIS |
| LEU | 75 MET ASN | 76 HIS ILE | 79 VAL VAL | 81 THR LEU | 82 TYR |
| LEU | 75 VAL ASN | 76 HIS ILE | 79 LEU VAL | 81 THR LEU | 82 PHE |
| LEU | 75 VAL ASN | 76 HIS ILE | 79 LEU VAL | 81 THR LEU | 82 HIS |
| LEU | 75 VAL ASN | 76 HIS ILE | 79 LEU VAL | 81 THR LEU | 82 TYR |
| LEU | 75 VAL ASN | 76 HIS ILE | 79 MET VAL | 81 THR LEU | 82 PHE |
| LEU | 75 VAL ASN | 76 HIS ILE | 79 MET VAL | 81 THR LEU | 82 HIS |
| LEU | 75 VAL ASN | 76 HIS ILE | 79 MET VAL | 81 THR LEU | 82 TYR |
| LEU | 75 VAL ASN | 76 HIS ILE | 79 THR VAL | 81 THR LEU | 82 PHE |
| LEU | 75 VAL ASN | 76 HIS ILE | 79 THR VAL | 81 THR LEU | 82 HIS |
| LEU | 75 VAL ASN | 76 HIS ILE | 79 THR VAL | 81 THR LEU | 82 TYR |
| LEU | 75 VAL ASN | 76 HIS ILE | 79 VAL VAL | 81 THR LEU | 82 PHE |
| LEU | 75 VAL ASN | 76 HIS ILE | 79 VAL VAL | 81 THR LEU | 82 HIS |
| LEU | 75 VAL ASN | 76 HIS ILE | 79 VAL VAL | 81 THR LEU | 82 TYR |
| LEU | 75 ILE ASN | 76 HIS SER | 78 ASN VAL | 81 THR LEU | 82 PHE |
| LEU | 75 ILE ASN | 76 HIS SER | 78 ASN VAL | 81 THR LEU | 82 HIS |
| LEU | 75 ILE ASN | 76 HIS SER | 78 ASN VAL | 81 THR LEU | 82 TYR |
| LEU | 75 ILE ASN | 76 HIS SER | 78 THR VAL | 81 THR LEU | 82 PHE |
| LEU | 75 ILE ASN | 76 HIS SER | 78 THR VAL | 81 THR LEU | 82 HIS |
| LEU | 75 ILE ASN | 76 HIS SER | 78 THR VAL | 81 THR LEU | 82 TYR |
| LEU | 75 ILE ASN | 76 HIS SER | 78 ARG VAL | 81 THR LEU | 82 PHE |
| LEU | 75 ILE ASN | 76 HIS SER | 78 ARG VAL | 81 THR LEU | 82 HIS |
| LEU | 75 ILE ASN | 76 HIS SER | 78 ARG VAL | 81 THR LEU | 82 TYR |
| LEU | 75 ILE ASN | 76 HIS SER | 78 ASP VAL | 81 THR LEU | 82 PHE |
| LEU | 75 ILE ASN | 76 HIS SER | 78 ASP VAL | 81 THR LEU | 82 HIS |
| LEU | 75 ILE ASN | 76 HIS SER | 78 ASP VAL | 81 THR LEU | 82 TYR |
| LEU | 75 ILE ASN | 76 HIS SER | 78 GLN VAL | 81 THR LEU | 82 PHE |
| LEU | 75 ILE ASN | 76 HIS SER | 78 GLN VAL | 81 THR LEU | 82 HIS |
| LEU | 75 ILE ASN | 76 HIS SER | 78 GLN VAL | 81 THR LEU | 82 TYR |
| LEU | 75 ILE ASN | 76 HIS SER | 78 HIS VAL | 81 THR LEU | 82 PHE |
| LEU | 75 ILE ASN | 76 HIS SER | 78 HIS VAL | 81 THR LEU | 82 HIS |
| LEU | 75 ILE ASN | 76 HIS SER | 78 HIS VAL | 81 THR LEU | 82 TYR |
| LEU | 75 ILE ASN | 76 HIS SER | 78 LYS VAL | 81 THR LEU | 82 PHE |
| LEU | 75 ILE ASN | 76 HIS SER | 78 LYS VAL | 81 THR LEU | 82 HIS |
| LEU | 75 ILE ASN | 76 HIS SER | 78 LYS VAL | 81 THR LEU | 82 TYR |
| LEU | 75 ILE ASN | 76 HIS SER | 78 TYR VAL | 81 THR LEU | 82 PHE |
| LEU | 75 ILE ASN | 76 HIS SER | 78 TYR VAL | 81 THR LEU | 82 HIS |
| LEU | 75 ILE ASN | 76 HIS SER | 78 TYR VAL | 81 THR LEU | 82 TYR |
| LEU | 75 MET ASN | 76 HIS SER | 78 ASN VAL | 81 THR LEU | 82 PHE |
| LEU | 75 MET ASN | 76 HIS SER | 78 ASN VAL | 81 THR LEU | 82 HIS |
| LEU | 75 MET ASN | 76 HIS SER | 78 ASN VAL | 81 THR LEU | 82 TYR |
| LEU | 75 MET ASN | 76 HIS SER | 78 THR VAL | 81 THR LEU | 82 PHE |
| LEU | 75 MET ASN | 76 HIS SER | 78 THR VAL | 81 THR LEU | 82 HIS |
| LEU | 75 MET ASN | 76 HIS SER | 78 THR VAL | 81 THR LEU | 82 TYR |
| LEU | 75 MET ASN | 76 HIS SER | 78 ARG VAL | 81 THR LEU | 82 PHE |
| LEU | 75 MET ASN | 76 HIS SER | 78 ARG VAL | 81 THR LEU | 82 HIS |
| LEU | 75 MET ASN | 76 HIS SER | 78 ARG VAL | 81 THR LEU | 82 TYR |
| LEU | 75 MET ASN | 76 HIS SER | 78 ASP VAL | 81 THR LEU | 82 PHE |
| LEU | 75 MET ASN | 76 HIS SER | 78 ASP VAL | 81 THR LEU | 82 HIS |
| LEU | 75 MET ASN | 76 HIS SER | 78 ASP VAL | 81 THR LEU | 82 TYR |
| LEU | 75 MET ASN | 76 HIS SER | 78 GLN VAL | 81 THR LEU | 82 PHE |
| LEU | 75 MET ASN | 76 HIS SER | 78 GLN VAL | 81 THR LEU | 82 HIS |
| LEU | 75 MET ASN | 76 HIS SER | 78 GLN VAL | 81 THR LEU | 82 TYR |
| LEU | 75 MET ASN | 76 HIS SER | 78 HIS VAL | 81 THR LEU | 82 PHE |
| LEU | 75 MET ASN | 76 HIS SER | 78 HIS VAL | 81 THR LEU | 82 HIS |
| LEU | 75 MET ASN | 76 HIS SER | 78 HIS VAL | 81 THR LEU | 82 TYR |
| LEU | 75 MET ASN | 76 HIS SER | 78 LYS VAL | 81 THR LEU | 82 PHE |
| LEU | 75 MET ASN | 76 HIS SER | 78 LYS VAL | 81 THR LEU | 82 HIS |
| LEU | 75 MET ASN | 76 HIS SER | 78 LYS VAL | 81 THR LEU | 82 TYR |
| LEU | 75 MET ASN | 76 HIS SER | 78 TYR VAL | 81 THR LEU | 82 PHE |
| LEU | 75 MET ASN | 76 HIS SER | 78 TYR VAL | 81 THR LEU | 82 HIS |
| LEU | 75 MET ASN | 76 HIS SER | 78 TYR VAL | 81 THR LEU | 82 TYR |
| LEU | 75 VAL ASN | 76 HIS SER | 78 ASN VAL | 81 THR LEU | 82 PHE |
| LEU | 75 VAL ASN | 76 HIS SER | 78 ASN VAL | 81 THR LEU | 82 HIS |
| LEU | 75 VAL ASN | 76 HIS SER | 78 ASN VAL | 81 THR LEU | 82 TYR |
| LEU | 75 VAL ASN | 76 HIS SER | 78 THR VAL | 81 THR LEU | 82 PHE |
| LEU | 75 VAL ASN | 76 HIS SER | 78 THR VAL | 81 THR LEU | 82 HIS |
| LEU | 75 VAL ASN | 76 HIS SER | 78 THR VAL | 81 THR LEU | 82 TYR |
| LEU | 75 VAL ASN | 76 HIS SER | 78 ARG VAL | 81 THR LEU | 82 PHE |
| LEU | 75 VAL ASN | 76 HIS SER | 78 ARG VAL | 81 THR LEU | 82 HIS |
| LEU | 75 VAL ASN | 76 HIS SER | 78 ARG VAL | 81 THR LEU | 82 TYR |
| LEU | 75 VAL ASN | 76 HIS SER | 78 ASP VAL | 81 THR LEU | 82 PHE |
| LEU | 75 VAL ASN | 76 HIS SER | 78 ASP VAL | 81 THR LEU | 82 HIS |
| LEU | 75 VAL ASN | 76 HIS SER | 78 ASP VAL | 81 THR LEU | 82 TYR |

TABLE 6-continued

| Quintuple Substitution Variants | | | | | |
|---|---|---|---|---|---|
| LEU | 75 VAL ASN | 76 HIS SER | 78 GLN VAL | 81 THR LEU | 82 PHE |
| LEU | 75 VAL ASN | 76 HIS SER | 78 GLN VAL | 81 THR LEU | 82 HIS |
| LEU | 75 VAL ASN | 76 HIS SER | 78 GLN VAL | 81 THR LEU | 82 TYR |
| LEU | 75 VAL ASN | 76 HIS SER | 78 HIS VAL | 81 THR LEU | 82 PHE |
| LEU | 75 VAL ASN | 76 HIS SER | 78 HIS VAL | 81 THR LEU | 82 HIS |
| LEU | 75 VAL ASN | 76 HIS SER | 78 HIS VAL | 81 THR LEU | 82 TYR |
| LEU | 75 VAL ASN | 76 HIS SER | 78 LYS VAL | 81 THR LEU | 82 PHE |
| LEU | 75 VAL ASN | 76 HIS SER | 78 LYS VAL | 81 THR LEU | 82 HIS |
| LEU | 75 VAL ASN | 76 HIS SER | 78 LYS VAL | 81 THR LEU | 82 TYR |
| LEU | 75 VAL ASN | 76 HIS SER | 78 TYR VAL | 81 THR LEU | 82 PHE |
| LEU | 75 VAL ASN | 76 HIS SER | 78 TYR VAL | 81 THR LEU | 82 HIS |
| LEU | 75 VAL ASN | 76 HIS SER | 78 TYR VAL | 81 THR LEU | 82 TYR |
| LEU | 75 ILE ASN | 76 HIS SER | 78 ASN ILE | 79 LEU LEU | 82 PHE |
| LEU | 75 ILE ASN | 76 HIS SER | 78 ASN ILE | 79 LEU LEU | 82 HIS |
| LEU | 75 ILE ASN | 76 HIS SER | 78 ASN ILE | 79 LEU LEU | 82 TYR |
| LEU | 75 ILE ASN | 76 HIS SER | 78 ASN ILE | 79 MET LEU | 82 PHE |
| LEU | 75 ILE ASN | 76 HIS SER | 78 ASN ILE | 79 MET LEU | 82 HIS |
| LEU | 75 ILE ASN | 76 HIS SER | 78 ASN ILE | 79 MET LEU | 82 TYR |
| LEU | 75 ILE ASN | 76 HIS SER | 78 ASN ILE | 79 THR LEU | 82 PHE |
| LEU | 75 ILE ASN | 76 HIS SER | 78 ASN ILE | 79 THR LEU | 82 HIS |
| LEU | 75 ILE ASN | 76 HIS SER | 78 ASN ILE | 79 THR LEU | 82 TYR |
| LEU | 75 ILE ASN | 76 HIS SER | 78 ASN ILE | 79 VAL LEU | 82 PHE |
| LEU | 75 ILE ASN | 76 HIS SER | 78 ASN ILE | 79 VAL LEU | 82 HIS |
| LEU | 75 ILE ASN | 76 HIS SER | 78 ASN ILE | 79 VAL LEU | 82 TYR |
| LEU | 75 ILE ASN | 76 HIS SER | 78 THR ILE | 79 LEU LEU | 82 PHE |
| LEU | 75 ILE ASN | 76 HIS SER | 78 THR ILE | 79 LEU LEU | 82 HIS |
| LEU | 75 ILE ASN | 76 HIS SER | 78 THR ILE | 79 LEU LEU | 82 TYR |
| LEU | 75 ILE ASN | 76 HIS SER | 78 THR ILE | 79 MET LEU | 82 PHE |
| LEU | 75 ILE ASN | 76 HIS SER | 78 THR ILE | 79 MET LEU | 82 HIS |
| LEU | 75 ILE ASN | 76 HIS SER | 78 THR ILE | 79 MET LEU | 82 TYR |
| LEU | 75 ILE ASN | 76 HIS SER | 78 THR ILE | 79 THR LEU | 82 PHE |
| LEU | 75 ILE ASN | 76 HIS SER | 78 THR ILE | 79 THR LEU | 82 HIS |
| LEU | 75 ILE ASN | 76 HIS SER | 78 THR ILE | 79 THR LEU | 82 TYR |
| LEU | 75 ILE ASN | 76 HIS SER | 78 THR ILE | 79 VAL LEU | 82 PHE |
| LEU | 75 ILE ASN | 76 HIS SER | 78 THR ILE | 79 VAL LEU | 82 HIS |
| LEU | 75 ILE ASN | 76 HIS SER | 78 THR ILE | 79 VAL LEU | 82 TYR |
| LEU | 75 ILE ASN | 76 HIS SER | 78 ARG ILE | 79 LEU LEU | 82 PHE |
| LEU | 75 ILE ASN | 76 HIS SER | 78 ARG ILE | 79 LEU LEU | 82 HIS |
| LEU | 75 ILE ASN | 76 HIS SER | 78 ARG ILE | 79 LEU LEU | 82 TYR |
| LEU | 75 ILE ASN | 76 HIS SER | 78 ARG ILE | 79 MET LEU | 82 PHE |
| LEU | 75 ILE ASN | 76 HIS SER | 78 ARG ILE | 79 MET LEU | 82 HIS |
| LEU | 75 ILE ASN | 76 HIS SER | 78 ARG ILE | 79 MET LEU | 82 TYR |
| LEU | 75 ILE ASN | 76 HIS SER | 78 ARG ILE | 79 THR LEU | 82 PHE |
| LEU | 75 ILE ASN | 76 HIS SER | 78 ARG ILE | 79 THR LEU | 82 HIS |
| LEU | 75 ILE ASN | 76 HIS SER | 78 ARG ILE | 79 THR LEU | 82 TYR |
| LEU | 75 ILE ASN | 76 HIS SER | 78 ARG ILE | 79 VAL LEU | 82 PHE |
| LEU | 75 ILE ASN | 76 HIS SER | 78 ARG ILE | 79 VAL LEU | 82 HIS |
| LEU | 75 ILE ASN | 76 HIS SER | 78 ARG ILE | 79 VAL LEU | 82 TYR |
| LEU | 75 ILE ASN | 76 HIS SER | 78 ASP ILE | 79 LEU LEU | 82 PHE |
| LEU | 75 ILE ASN | 76 HIS SER | 78 ASP ILE | 79 LEU LEU | 82 HIS |
| LEU | 75 ILE ASN | 76 HIS SER | 78 ASP ILE | 79 LEU LEU | 82 TYR |
| LEU | 75 ILE ASN | 76 HIS SER | 78 ASP ILE | 79 MET LEU | 82 PHE |
| LEU | 75 ILE ASN | 76 HIS SER | 78 ASP ILE | 79 MET LEU | 82 HIS |
| LEU | 75 ILE ASN | 76 HIS SER | 78 ASP ILE | 79 MET LEU | 82 TYR |
| LEU | 75 ILE ASN | 76 HIS SER | 78 ASP ILE | 79 THR LEU | 82 PHE |
| LEU | 75 ILE ASN | 76 HIS SER | 78 ASP ILE | 79 THR LEU | 82 HIS |
| LEU | 75 ILE ASN | 76 HIS SER | 78 ASP ILE | 79 THR LEU | 82 TYR |
| LEU | 75 ILE ASN | 76 HIS SER | 78 ASP ILE | 79 VAL LEU | 82 PHE |
| LEU | 75 ILE ASN | 76 HIS SER | 78 ASP ILE | 79 VAL LEU | 82 HIS |
| LEU | 75 ILE ASN | 76 HIS SER | 78 ASP ILE | 79 VAL LEU | 82 TYR |
| LEU | 75 ILE ASN | 76 HIS SER | 78 GLN ILE | 79 LEU LEU | 82 PHE |
| LEU | 75 ILE ASN | 76 HIS SER | 78 GLN ILE | 79 LEU LEU | 82 HIS |
| LEU | 75 ILE ASN | 76 HIS SER | 78 GLN ILE | 79 LEU LEU | 82 TYR |
| LEU | 75 ILE ASN | 76 HIS SER | 78 GLN ILE | 79 MET LEU | 82 PHE |
| LEU | 75 ILE ASN | 76 HIS SER | 78 GLN ILE | 79 MET LEU | 82 HIS |
| LEU | 75 ILE ASN | 76 HIS SER | 78 GLN ILE | 79 MET LEU | 82 TYR |
| LEU | 75 ILE ASN | 76 HIS SER | 78 GLN ILE | 79 THR LEU | 82 PHE |
| LEU | 75 ILE ASN | 76 HIS SER | 78 GLN ILE | 79 THR LEU | 82 HIS |
| LEU | 75 ILE ASN | 76 HIS SER | 78 GLN ILE | 79 THR LEU | 82 TYR |
| LEU | 75 ILE ASN | 76 HIS SER | 78 GLN ILE | 79 VAL LEU | 82 PHE |
| LEU | 75 ILE ASN | 76 HIS SER | 78 GLN ILE | 79 VAL LEU | 82 HIS |
| LEU | 75 ILE ASN | 76 HIS SER | 78 GLN ILE | 79 VAL LEU | 82 TYR |
| LEU | 75 ILE ASN | 76 HIS SER | 78 HIS ILE | 79 LEU LEU | 82 PHE |
| LEU | 75 ILE ASN | 76 HIS SER | 78 HIS ILE | 79 LEU LEU | 82 HIS |
| LEU | 75 ILE ASN | 76 HIS SER | 78 HIS ILE | 79 LEU LEU | 82 TYR |
| LEU | 75 ILE ASN | 76 HIS SER | 78 HIS ILE | 79 MET LEU | 82 PHE |
| LEU | 75 ILE ASN | 76 HIS SER | 78 HIS ILE | 79 MET LEU | 82 HIS |

TABLE 6-continued

Quintuple Substitution Variants

| | | | | | |
|---|---|---|---|---|---|
| LEU | 75 ILE ASN | 76 HIS SER | 78 HIS ILE | 79 MET LEU | 82 TYR |
| LEU | 75 ILE ASN | 76 HIS SER | 78 HIS ILE | 79 THR LEU | 82 PHE |
| LEU | 75 ILE ASN | 76 HIS SER | 78 HIS ILE | 79 THR LEU | 82 HIS |
| LEU | 75 ILE ASN | 76 HIS SER | 78 HIS ILE | 79 THR LEU | 82 TYR |
| LEU | 75 ILE ASN | 76 HIS SER | 78 HIS ILE | 79 VAL LEU | 82 PHE |
| LEU | 75 ILE ASN | 76 HIS SER | 78 HIS ILE | 79 VAL LEU | 82 HIS |
| LEU | 75 ILE ASN | 76 HIS SER | 78 HIS ILE | 79 VAL LEU | 82 TYR |
| LEU | 75 ILE ASN | 76 HIS SER | 78 LYS ILE | 79 LEU LEU | 82 PHE |
| LEU | 75 ILE ASN | 76 HIS SER | 78 LYS ILE | 79 LEU LEU | 82 HIS |
| LEU | 75 ILE ASN | 76 HIS SER | 78 LYS ILE | 79 LEU LEU | 82 TYR |
| LEU | 75 ILE ASN | 76 HIS SER | 78 LYS ILE | 79 MET LEU | 82 PHE |
| LEU | 75 ILE ASN | 76 HIS SER | 78 LYS ILE | 79 MET LEU | 82 HIS |
| LEU | 75 ILE ASN | 76 HIS SER | 78 LYS ILE | 79 MET LEU | 82 TYR |
| LEU | 75 ILE ASN | 76 HIS SER | 78 LYS ILE | 79 THR LEU | 82 PHE |
| LEU | 75 ILE ASN | 76 HIS SER | 78 LYS ILE | 79 THR LEU | 82 HIS |
| LEU | 75 ILE ASN | 76 HIS SER | 78 LYS ILE | 79 THR LEU | 82 TYR |
| LEU | 75 ILE ASN | 76 HIS SER | 78 LYS ILE | 79 VAL LEU | 82 PHE |
| LEU | 75 ILE ASN | 76 HIS SER | 78 LYS ILE | 79 VAL LEU | 82 HIS |
| LEU | 75 ILE ASN | 76 HIS SER | 78 LYS ILE | 79 VAL LEU | 82 TYR |
| LEU | 75 ILE ASN | 76 HIS SER | 78 TYR ILE | 79 LEU LEU | 82 PHE |
| LEU | 75 ILE ASN | 76 HIS SER | 78 TYR ILE | 79 LEU LEU | 82 HIS |
| LEU | 75 ILE ASN | 76 HIS SER | 78 TYR ILE | 79 LEU LEU | 82 TYR |
| LEU | 75 ILE ASN | 76 HIS SER | 78 TYR ILE | 79 MET LEU | 82 PHE |
| LEU | 75 ILE ASN | 76 HIS SER | 78 TYR ILE | 79 MET LEU | 82 HIS |
| LEU | 75 ILE ASN | 76 HIS SER | 78 TYR ILE | 79 MET LEU | 82 TYR |
| LEU | 75 ILE ASN | 76 HIS SER | 78 TYR ILE | 79 THR LEU | 82 PHE |
| LEU | 75 ILE ASN | 76 HIS SER | 78 TYR ILE | 79 THR LEU | 82 HIS |
| LEU | 75 ILE ASN | 76 HIS SER | 78 TYR ILE | 79 THR LEU | 82 TYR |
| LEU | 75 ILE ASN | 76 HIS SER | 78 TYR ILE | 79 VAL LEU | 82 PHE |
| LEU | 75 ILE ASN | 76 HIS SER | 78 TYR ILE | 79 VAL LEU | 82 HIS |
| LEU | 75 ILE ASN | 76 HIS SER | 78 TYR ILE | 79 VAL LEU | 82 TYR |
| LEU | 75 MET ASN | 76 HIS SER | 78 ASN ILE | 79 LEU LEU | 82 PHE |
| LEU | 75 MET ASN | 76 HIS SER | 78 ASN ILE | 79 LEU LEU | 82 HIS |
| LEU | 75 MET ASN | 76 HIS SER | 78 ASN ILE | 79 LEU LEU | 82 TYR |
| LEU | 75 MET ASN | 76 HIS SER | 78 ASN ILE | 79 MET LEU | 82 PHE |
| LEU | 75 MET ASN | 76 HIS SER | 78 ASN ILE | 79 MET LEU | 82 HIS |
| LEU | 75 MET ASN | 76 HIS SER | 78 ASN ILE | 79 MET LEU | 82 TYR |
| LEU | 75 MET ASN | 76 HIS SER | 78 ASN ILE | 79 THR LEU | 82 PHE |
| LEU | 75 MET ASN | 76 HIS SER | 78 ASN ILE | 79 THR LEU | 82 HIS |
| LEU | 75 MET ASN | 76 HIS SER | 78 ASN ILE | 79 THR LEU | 82 TYR |
| LEU | 75 MET ASN | 76 HIS SER | 78 ASN ILE | 79 VAL LEU | 82 PHE |
| LEU | 75 MET ASN | 76 HIS SER | 78 ASN ILE | 79 VAL LEU | 82 HIS |
| LEU | 75 MET ASN | 76 HIS SER | 78 ASN ILE | 79 VAL LEU | 82 TYR |
| LEU | 75 MET ASN | 76 HIS SER | 78 THR ILE | 79 LEU LEU | 82 PHE |
| LEU | 75 MET ASN | 76 HIS SER | 78 THR ILE | 79 LEU LEU | 82 HIS |
| LEU | 75 MET ASN | 76 HIS SER | 78 THR ILE | 79 LEU LEU | 82 TYR |
| LEU | 75 MET ASN | 76 HIS SER | 78 THR ILE | 79 MET LEU | 82 PHE |
| LEU | 75 MET ASN | 76 HIS SER | 78 THR ILE | 79 MET LEU | 82 HIS |
| LEU | 75 MET ASN | 76 HIS SER | 78 THR ILE | 79 MET LEU | 82 TYR |
| LEU | 75 MET ASN | 76 HIS SER | 78 THR ILE | 79 THR LEU | 82 PHE |
| LEU | 75 MET ASN | 76 HIS SER | 78 THR ILE | 79 THR LEU | 82 HIS |
| LEU | 75 MET ASN | 76 HIS SER | 78 THR ILE | 79 THR LEU | 82 TYR |
| LEU | 75 MET ASN | 76 HIS SER | 78 THR ILE | 79 VAL LEU | 82 PHE |
| LEU | 75 MET ASN | 76 HIS SER | 78 THR ILE | 79 VAL LEU | 82 HIS |
| LEU | 75 MET ASN | 76 HIS SER | 78 THR ILE | 79 VAL LEU | 82 TYR |
| LEU | 75 MET ASN | 76 HIS SER | 78 ARG ILE | 79 LEU LEU | 82 PHE |
| LEU | 75 MET ASN | 76 HIS SER | 78 ARG ILE | 79 LEU LEU | 82 HIS |
| LEU | 75 MET ASN | 76 HIS SER | 78 ARG ILE | 79 LEU LEU | 82 TYR |
| LEU | 75 MET ASN | 76 HIS SER | 78 ARG ILE | 79 MET LEU | 82 PHE |
| LEU | 75 MET ASN | 76 HIS SER | 78 ARG ILE | 79 MET LEU | 82 HIS |
| LEU | 75 MET ASN | 76 HIS SER | 78 ARG ILE | 79 MET LEU | 82 TYR |
| LEU | 75 MET ASN | 76 HIS SER | 78 ARG ILE | 79 THR LEU | 82 PHE |
| LEU | 75 MET ASN | 76 HIS SER | 78 ARG ILE | 79 THR LEU | 82 HIS |
| LEU | 75 MET ASN | 76 HIS SER | 78 ARG ILE | 79 THR LEU | 82 TYR |
| LEU | 75 MET ASN | 76 HIS SER | 78 ARG ILE | 79 VAL LEU | 82 PHE |
| LEU | 75 MET ASN | 76 HIS SER | 78 ARG ILE | 79 VAL LEU | 82 HIS |
| LEU | 75 MET ASN | 76 HIS SER | 78 ARG ILE | 79 VAL LEU | 82 TYR |
| LEU | 75 MET ASN | 76 HIS SER | 78 ASP ILE | 79 LEU LEU | 82 PHE |
| LEU | 75 MET ASN | 76 HIS SER | 78 ASP ILE | 79 LEU LEU | 82 HIS |
| LEU | 75 MET ASN | 76 HIS SER | 78 ASP ILE | 79 LEU LEU | 82 TYR |
| LEU | 75 MET ASN | 76 HIS SER | 78 ASP ILE | 79 MET LEU | 82 PHE |
| LEU | 75 MET ASN | 76 HIS SER | 78 ASP ILE | 79 MET LEU | 82 HIS |
| LEU | 75 MET ASN | 76 HIS SER | 78 ASP ILE | 79 MET LEU | 82 TYR |
| LEU | 75 MET ASN | 76 HIS SER | 78 ASP ILE | 79 THR LEU | 82 PHE |
| LEU | 75 MET ASN | 76 HIS SER | 78 ASP ILE | 79 THR LEU | 82 HIS |
| LEU | 75 MET ASN | 76 HIS SER | 78 ASP ILE | 79 THR LEU | 82 TYR |
| LEU | 75 MET ASN | 76 HIS SER | 78 ASP ILE | 79 VAL LEU | 82 PHE |

TABLE 6-continued

Quintuple Substitution Variants

| | | | | | |
|---|---|---|---|---|---|
| LEU | 75 MET ASN | 76 HIS SER | 78 ASP ILE | 79 VAL LEU | 82 HIS |
| LEU | 75 MET ASN | 76 HIS SER | 78 ASP ILE | 79 VAL LEU | 82 TYR |
| LEU | 75 MET ASN | 76 HIS SER | 78 GLN ILE | 79 LEU LEU | 82 PHE |
| LEU | 75 MET ASN | 76 HIS SER | 78 GLN ILE | 79 LEU LEU | 82 HIS |
| LEU | 75 MET ASN | 76 HIS SER | 78 GLN ILE | 79 LEU LEU | 82 TYR |
| LEU | 75 MET ASN | 76 HIS SER | 78 GLN ILE | 79 MET LEU | 82 PHE |
| LEU | 75 MET ASN | 76 HIS SER | 78 GLN ILE | 79 MET LEU | 82 HIS |
| LEU | 75 MET ASN | 76 HIS SER | 78 GLN ILE | 79 MET LEU | 82 TYR |
| LEU | 75 MET ASN | 76 HIS SER | 78 GLN ILE | 79 THR LEU | 82 PHE |
| LEU | 75 MET ASN | 76 HIS SER | 78 GLN ILE | 79 THR LEU | 82 HIS |
| LEU | 75 MET ASN | 76 HIS SER | 78 GLN ILE | 79 THR LEU | 82 TYR |
| LEU | 75 MET ASN | 76 HIS SER | 78 GLN ILE | 79 VAL LEU | 82 PHE |
| LEU | 75 MET ASN | 76 HIS SER | 78 GLN ILE | 79 VAL LEU | 82 HIS |
| LEU | 75 MET ASN | 76 HIS SER | 78 GLN ILE | 79 VAL LEU | 82 TYR |
| LEU | 75 MET ASN | 76 HIS SER | 78 HIS ILE | 79 LEU LEU | 82 PHE |
| LEU | 75 MET ASN | 76 HIS SER | 78 HIS ILE | 79 LEU LEU | 82 HIS |
| LEU | 75 MET ASN | 76 HIS SER | 78 HIS ILE | 79 LEU LEU | 82 TYR |
| LEU | 75 MET ASN | 76 HIS SER | 78 HIS ILE | 79 MET LEU | 82 PHE |
| LEU | 75 MET ASN | 76 HIS SER | 78 HIS ILE | 79 MET LEU | 82 HIS |
| LEU | 75 MET ASN | 76 HIS SER | 78 HIS ILE | 79 MET LEU | 82 TYR |
| LEU | 75 MET ASN | 76 HIS SER | 78 HIS ILE | 79 THR LEU | 82 PHE |
| LEU | 75 MET ASN | 76 HIS SER | 78 HIS ILE | 79 THR LEU | 82 HIS |
| LEU | 75 MET ASN | 76 HIS SER | 78 HIS ILE | 79 THR LEU | 82 TYR |
| LEU | 75 MET ASN | 76 HIS SER | 78 HIS ILE | 79 VAL LEU | 82 PHE |
| LEU | 75 MET ASN | 76 HIS SER | 78 HIS ILE | 79 VAL LEU | 82 HIS |
| LEU | 75 MET ASN | 76 HIS SER | 78 HIS ILE | 79 VAL LEU | 82 TYR |
| LEU | 75 MET ASN | 76 HIS SER | 78 LYS ILE | 79 LEU LEU | 82 PHE |
| LEU | 75 MET ASN | 76 HIS SER | 78 LYS ILE | 79 LEU LEU | 82 HIS |
| LEU | 75 MET ASN | 76 HIS SER | 78 LYS ILE | 79 LEU LEU | 82 TYR |
| LEU | 75 MET ASN | 76 HIS SER | 78 LYS ILE | 79 MET LEU | 82 PHE |
| LEU | 75 MET ASN | 76 HIS SER | 78 LYS ILE | 79 MET LEU | 82 HIS |
| LEU | 75 MET ASN | 76 HIS SER | 78 LYS ILE | 79 MET LEU | 82 TYR |
| LEU | 75 MET ASN | 76 HIS SER | 78 LYS ILE | 79 THR LEU | 82 PHE |
| LEU | 75 MET ASN | 76 HIS SER | 78 LYS ILE | 79 THR LEU | 82 HIS |
| LEU | 75 MET ASN | 76 HIS SER | 78 LYS ILE | 79 THR LEU | 82 TYR |
| LEU | 75 MET ASN | 76 HIS SER | 78 LYS ILE | 79 VAL LEU | 82 PHE |
| LEU | 75 MET ASN | 76 HIS SER | 78 LYS ILE | 79 VAL LEU | 82 HIS |
| LEU | 75 MET ASN | 76 HIS SER | 78 LYS ILE | 79 VAL LEU | 82 TYR |
| LEU | 75 MET ASN | 76 HIS SER | 78 TYR ILE | 79 LEU LEU | 82 PHE |
| LEU | 75 MET ASN | 76 HIS SER | 78 TYR ILE | 79 LEU LEU | 82 HIS |
| LEU | 75 MET ASN | 76 HIS SER | 78 TYR ILE | 79 LEU LEU | 82 TYR |
| LEU | 75 MET ASN | 76 HIS SER | 78 TYR ILE | 79 MET LEU | 82 PHE |
| LEU | 75 MET ASN | 76 HIS SER | 78 TYR ILE | 79 MET LEU | 82 HIS |
| LEU | 75 MET ASN | 76 HIS SER | 78 TYR ILE | 79 MET LEU | 82 TYR |
| LEU | 75 MET ASN | 76 HIS SER | 78 TYR ILE | 79 THR LEU | 82 PHE |
| LEU | 75 MET ASN | 76 HIS SER | 78 TYR ILE | 79 THR LEU | 82 HIS |
| LEU | 75 MET ASN | 76 HIS SER | 78 TYR ILE | 79 THR LEU | 82 TYR |
| LEU | 75 MET ASN | 76 HIS SER | 78 TYR ILE | 79 VAL LEU | 82 PHE |
| LEU | 75 MET ASN | 76 HIS SER | 78 TYR ILE | 79 VAL LEU | 82 HIS |
| LEU | 75 MET ASN | 76 HIS SER | 78 TYR ILE | 79 VAL LEU | 82 TYR |
| LEU | 75 VAL ASN | 76 HIS SER | 78 ASN ILE | 79 LEU LEU | 82 PHE |
| LEU | 75 VAL ASN | 76 HIS SER | 78 ASN ILE | 79 LEU LEU | 82 HIS |
| LEU | 75 VAL ASN | 76 HIS SER | 78 ASN ILE | 79 LEU LEU | 82 TYR |
| LEU | 75 VAL ASN | 76 HIS SER | 78 ASN ILE | 79 MET LEU | 82 PHE |
| LEU | 75 VAL ASN | 76 HIS SER | 78 ASN ILE | 79 MET LEU | 82 HIS |
| LEU | 75 VAL ASN | 76 HIS SER | 78 ASN ILE | 79 MET LEU | 82 TYR |
| LEU | 75 VAL ASN | 76 HIS SER | 78 ASN ILE | 79 THR LEU | 82 PHE |
| LEU | 75 VAL ASN | 76 HIS SER | 78 ASN ILE | 79 THR LEU | 82 HIS |
| LEU | 75 VAL ASN | 76 HIS SER | 78 ASN ILE | 79 THR LEU | 82 TYR |
| LEU | 75 VAL ASN | 76 HIS SER | 78 ASN ILE | 79 VAL LEU | 82 PHE |
| LEU | 75 VAL ASN | 76 HIS SER | 78 ASN ILE | 79 VAL LEU | 82 HIS |
| LEU | 75 VAL ASN | 76 HIS SER | 78 ASN ILE | 79 VAL LEU | 82 TYR |
| LEU | 75 VAL ASN | 76 HIS SER | 78 THR ILE | 79 LEU LEU | 82 PHE |
| LEU | 75 VAL ASN | 76 HIS SER | 78 THR ILE | 79 LEU LEU | 82 HIS |
| LEU | 75 VAL ASN | 76 HIS SER | 78 THR ILE | 79 LEU LEU | 82 TYR |
| LEU | 75 VAL ASN | 76 HIS SER | 78 THR ILE | 79 MET LEU | 82 PHE |
| LEU | 75 VAL ASN | 76 HIS SER | 78 THR ILE | 79 MET LEU | 82 HIS |
| LEU | 75 VAL ASN | 76 HIS SER | 78 THR ILE | 79 MET LEU | 82 TYR |
| LEU | 75 VAL ASN | 76 HIS SER | 78 THR ILE | 79 THR LEU | 82 PHE |
| LEU | 75 VAL ASN | 76 HIS SER | 78 THR ILE | 79 THR LEU | 82 HIS |
| LEU | 75 VAL ASN | 76 HIS SER | 78 THR ILE | 79 THR LEU | 82 TYR |
| LEU | 75 VAL ASN | 76 HIS SER | 78 THR ILE | 79 VAL LEU | 82 PHE |
| LEU | 75 VAL ASN | 76 HIS SER | 78 THR ILE | 79 VAL LEU | 82 HIS |
| LEU | 75 VAL ASN | 76 HIS SER | 78 THR ILE | 79 VAL LEU | 82 TYR |
| LEU | 75 VAL ASN | 76 HIS SER | 78 ARG ILE | 79 LEU LEU | 82 PHE |
| LEU | 75 VAL ASN | 76 HIS SER | 78 ARG ILE | 79 LEU LEU | 82 HIS |
| LEU | 75 VAL ASN | 76 HIS SER | 78 ARG ILE | 79 LEU LEU | 82 TYR |

TABLE 6-continued

| Quintuple Substitution Variants | | | | | |
|---|---|---|---|---|---|
| LEU | 75 VAL ASN | 76 HIS SER | 78 ARG ILE | 79 MET LEU | 82 PHE |
| LEU | 75 VAL ASN | 76 HIS SER | 78 ARG ILE | 79 MET LEU | 82 HIS |
| LEU | 75 VAL ASN | 76 HIS SER | 78 ARG ILE | 79 MET LEU | 82 TYR |
| LEU | 75 VAL ASN | 76 HIS SER | 78 ARG ILE | 79 THR LEU | 82 PHE |
| LEU | 75 VAL ASN | 76 HIS SER | 78 ARG ILE | 79 THR LEU | 82 HIS |
| LEU | 75 VAL ASN | 76 HIS SER | 78 ARG ILE | 79 THR LEU | 82 TYR |
| LEU | 75 VAL ASN | 76 HIS SER | 78 ARG ILE | 79 VAL LEU | 82 PHE |
| LEU | 75 VAL ASN | 76 HIS SER | 78 ARG ILE | 79 VAL LEU | 82 HIS |
| LEU | 75 VAL ASN | 76 HIS SER | 78 ARG ILE | 79 VAL LEU | 82 TYR |
| LEU | 75 VAL ASN | 76 HIS SER | 78 ASP ILE | 79 LEU LEU | 82 PHE |
| LEU | 75 VAL ASN | 76 HIS SER | 78 ASP ILE | 79 LEU LEU | 82 HIS |
| LEU | 75 VAL ASN | 76 HIS SER | 78 ASP ILE | 79 LEU LEU | 82 TYR |
| LEU | 75 VAL ASN | 76 HIS SER | 78 ASP ILE | 79 MET LEU | 82 PHE |
| LEU | 75 VAL ASN | 76 HIS SER | 78 ASP ILE | 79 MET LEU | 82 HIS |
| LEU | 75 VAL ASN | 76 HIS SER | 78 ASP ILE | 79 MET LEU | 82 TYR |
| LEU | 75 VAL ASN | 76 HIS SER | 78 ASP ILE | 79 THR LEU | 82 PHE |
| LEU | 75 VAL ASN | 76 HIS SER | 78 ASP ILE | 79 THR LEU | 82 HIS |
| LEU | 75 VAL ASN | 76 HIS SER | 78 ASP ILE | 79 THR LEU | 82 TYR |
| LEU | 75 VAL ASN | 76 HIS SER | 78 ASP ILE | 79 VAL LEU | 82 PHE |
| LEU | 75 VAL ASN | 76 HIS SER | 78 ASP ILE | 79 VAL LEU | 82 HIS |
| LEU | 75 VAL ASN | 76 HIS SER | 78 ASP ILE | 79 VAL LEU | 82 TYR |
| LEU | 75 VAL ASN | 76 HIS SER | 78 GLN ILE | 79 LEU LEU | 82 PHE |
| LEU | 75 VAL ASN | 76 HIS SER | 78 GLN ILE | 79 LEU LEU | 82 HIS |
| LEU | 75 VAL ASN | 76 HIS SER | 78 GLN ILE | 79 LEU LEU | 82 TYR |
| LEU | 75 VAL ASN | 76 HIS SER | 78 GLN ILE | 79 MET LEU | 82 PHE |
| LEU | 75 VAL ASN | 76 HIS SER | 78 GLN ILE | 79 MET LEU | 82 HIS |
| LEU | 75 VAL ASN | 76 HIS SER | 78 GLN ILE | 79 MET LEU | 82 TYR |
| LEU | 75 VAL ASN | 76 HIS SER | 78 GLN ILE | 79 THR LEU | 82 PHE |
| LEU | 75 VAL ASN | 76 HIS SER | 78 GLN ILE | 79 THR LEU | 82 HIS |
| LEU | 75 VAL ASN | 76 HIS SER | 78 GLN ILE | 79 THR LEU | 82 TYR |
| LEU | 75 VAL ASN | 76 HIS SER | 78 GLN ILE | 79 VAL LEU | 82 PHE |
| LEU | 75 VAL ASN | 76 HIS SER | 78 GLN ILE | 79 VAL LEU | 82 HIS |
| LEU | 75 VAL ASN | 76 HIS SER | 78 GLN ILE | 79 VAL LEU | 82 TYR |
| LEU | 75 VAL ASN | 76 HIS SER | 78 HIS ILE | 79 LEU LEU | 82 PHE |
| LEU | 75 VAL ASN | 76 HIS SER | 78 HIS ILE | 79 LEU LEU | 82 HIS |
| LEU | 75 VAL ASN | 76 HIS SER | 78 HIS ILE | 79 LEU LEU | 82 TYR |
| LEU | 75 VAL ASN | 76 HIS SER | 78 HIS ILE | 79 MET LEU | 82 PHE |
| LEU | 75 VAL ASN | 76 HIS SER | 78 HIS ILE | 79 MET LEU | 82 HIS |
| LEU | 75 VAL ASN | 76 HIS SER | 78 HIS ILE | 79 MET LEU | 82 TYR |
| LEU | 75 VAL ASN | 76 HIS SER | 78 HIS ILE | 79 THR LEU | 82 PHE |
| LEU | 75 VAL ASN | 76 HIS SER | 78 HIS ILE | 79 THR LEU | 82 HIS |
| LEU | 75 VAL ASN | 76 HIS SER | 78 HIS ILE | 79 THR LEU | 82 TYR |
| LEU | 75 VAL ASN | 76 HIS SER | 78 HIS ILE | 79 VAL LEU | 82 PHE |
| LEU | 75 VAL ASN | 76 HIS SER | 78 HIS ILE | 79 VAL LEU | 82 HIS |
| LEU | 75 VAL ASN | 76 HIS SER | 78 HIS ILE | 79 VAL LEU | 82 TYR |
| LEU | 75 VAL ASN | 76 HIS SER | 78 LYS ILE | 79 LEU LEU | 82 PHE |
| LEU | 75 VAL ASN | 76 HIS SER | 78 LYS ILE | 79 LEU LEU | 82 HIS |
| LEU | 75 VAL ASN | 76 HIS SER | 78 LYS ILE | 79 LEU LEU | 82 TYR |
| LEU | 75 VAL ASN | 76 HIS SER | 78 LYS ILE | 79 MET LEU | 82 PHE |
| LEU | 75 VAL ASN | 76 HIS SER | 78 LYS ILE | 79 MET LEU | 82 HIS |
| LEU | 75 VAL ASN | 76 HIS SER | 78 LYS ILE | 79 MET LEU | 82 TYR |
| LEU | 75 VAL ASN | 76 HIS SER | 78 LYS ILE | 79 THR LEU | 82 PHE |
| LEU | 75 VAL ASN | 76 HIS SER | 78 LYS ILE | 79 THR LEU | 82 HIS |
| LEU | 75 VAL ASN | 76 HIS SER | 78 LYS ILE | 79 THR LEU | 82 TYR |
| LEU | 75 VAL ASN | 76 HIS SER | 78 LYS ILE | 79 VAL LEU | 82 PHE |
| LEU | 75 VAL ASN | 76 HIS SER | 78 LYS ILE | 79 VAL LEU | 82 HIS |
| LEU | 75 VAL ASN | 76 HIS SER | 78 LYS ILE | 79 VAL LEU | 82 TYR |
| LEU | 75 VAL ASN | 76 HIS SER | 78 TYR ILE | 79 LEU LEU | 82 PHE |
| LEU | 75 VAL ASN | 76 HIS SER | 78 TYR ILE | 79 LEU LEU | 82 HIS |
| LEU | 75 VAL ASN | 76 HIS SER | 78 TYR ILE | 79 LEU LEU | 82 TYR |
| LEU | 75 VAL ASN | 76 HIS SER | 78 TYR ILE | 79 MET LEU | 82 PHE |
| LEU | 75 VAL ASN | 76 HIS SER | 78 TYR ILE | 79 MET LEU | 82 HIS |
| LEU | 75 VAL ASN | 76 HIS SER | 78 TYR ILE | 79 MET LEU | 82 TYR |
| LEU | 75 VAL ASN | 76 HIS SER | 78 TYR ILE | 79 THR LEU | 82 PHE |
| LEU | 75 VAL ASN | 76 HIS SER | 78 TYR ILE | 79 THR LEU | 82 HIS |
| LEU | 75 VAL ASN | 76 HIS SER | 78 TYR ILE | 79 THR LEU | 82 TYR |
| LEU | 75 VAL ASN | 76 HIS SER | 78 TYR ILE | 79 VAL LEU | 82 PHE |
| LEU | 75 VAL ASN | 76 HIS SER | 78 TYR ILE | 79 VAL LEU | 82 HIS |
| LEU | 75 VAL ASN | 76 HIS SER | 78 TYR ILE | 79 VAL LEU | 82 TYR |
| LEU | 75 ILE ASN | 76 HIS SER | 78 ASN ILE | 79 LEU VAL | 81 THR |
| LEU | 75 ILE ASN | 76 HIS SER | 78 ASN ILE | 79 MET VAL | 81 THR |
| LEU | 75 ILE ASN | 76 HIS SER | 78 ASN ILE | 79 THR VAL | 81 THR |
| LEU | 75 ILE ASN | 76 HIS SER | 78 ASN ILE | 79 VAL VAL | 81 THR |
| LEU | 75 ILE ASN | 76 HIS SER | 78 THR ILE | 79 LEU VAL | 81 THR |
| LEU | 75 ILE ASN | 76 HIS SER | 78 THR ILE | 79 MET VAL | 81 THR |
| LEU | 75 ILE ASN | 76 HIS SER | 78 THR ILE | 79 THR VAL | 81 THR |
| LEU | 75 ILE ASN | 76 HIS SER | 78 THR ILE | 79 VAL VAL | 81 THR |

TABLE 6-continued

| Quintuple Substitution Variants | | | | | |
|---|---|---|---|---|---|
| LEU | 75 ILE ASN | 76 HIS SER | 78 ARG ILE | 79 LEU VAL | 81 THR |
| LEU | 75 ILE ASN | 76 HIS SER | 78 ARG ILE | 79 MET VAL | 81 THR |
| LEU | 75 ILE ASN | 76 HIS SER | 78 ARG ILE | 79 THR VAL | 81 THR |
| LEU | 75 ILE ASN | 76 HIS SER | 78 ARG ILE | 79 VAL VAL | 81 THR |
| LEU | 75 ILE ASN | 76 HIS SER | 78 ASP ILE | 79 LEU VAL | 81 THR |
| LEU | 75 ILE ASN | 76 HIS SER | 78 ASP ILE | 79 MET VAL | 81 THR |
| LEU | 75 ILE ASN | 76 HIS SER | 78 ASP ILE | 79 THR VAL | 81 THR |
| LEU | 75 ILE ASN | 76 HIS SER | 78 ASP ILE | 79 VAL VAL | 81 THR |
| LEU | 75 ILE ASN | 76 HIS SER | 78 GLN ILE | 79 LEU VAL | 81 THR |
| LEU | 75 ILE ASN | 76 HIS SER | 78 GLN ILE | 79 MET VAL | 81 THR |
| LEU | 75 ILE ASN | 76 HIS SER | 78 GLN ILE | 79 THR VAL | 81 THR |
| LEU | 75 ILE ASN | 76 HIS SER | 78 GLN ILE | 79 VAL VAL | 81 THR |
| LEU | 75 ILE ASN | 76 HIS SER | 78 HIS ILE | 79 LEU VAL | 81 THR |
| LEU | 75 ILE ASN | 76 HIS SER | 78 HIS ILE | 79 MET VAL | 81 THR |
| LEU | 75 ILE ASN | 76 HIS SER | 78 HIS ILE | 79 THR VAL | 81 THR |
| LEU | 75 ILE ASN | 76 HIS SER | 78 HIS ILE | 79 VAL VAL | 81 THR |
| LEU | 75 ILE ASN | 76 HIS SER | 78 LYS ILE | 79 LEU VAL | 81 THR |
| LEU | 75 ILE ASN | 76 HIS SER | 78 LYS ILE | 79 MET VAL | 81 THR |
| LEU | 75 ILE ASN | 76 HIS SER | 78 LYS ILE | 79 THR VAL | 81 THR |
| LEU | 75 ILE ASN | 76 HIS SER | 78 LYS ILE | 79 VAL VAL | 81 THR |
| LEU | 75 ILE ASN | 76 HIS SER | 78 TYR ILE | 79 LEU VAL | 81 THR |
| LEU | 75 ILE ASN | 76 HIS SER | 78 TYR ILE | 79 MET VAL | 81 THR |
| LEU | 75 ILE ASN | 76 HIS SER | 78 TYR ILE | 79 THR VAL | 81 THR |
| LEU | 75 ILE ASN | 76 HIS SER | 78 TYR ILE | 79 VAL VAL | 81 THR |
| LEU | 75 MET ASN | 76 HIS SER | 78 ASN ILE | 79 LEU VAL | 81 THR |
| LEU | 75 MET ASN | 76 HIS SER | 78 ASN ILE | 79 MET VAL | 81 THR |
| LEU | 75 MET ASN | 76 HIS SER | 78 ASN ILE | 79 THR VAL | 81 THR |
| LEU | 75 MET ASN | 76 HIS SER | 78 ASN ILE | 79 VAL VAL | 81 THR |
| LEU | 75 MET ASN | 76 HIS SER | 78 THR ILE | 79 LEU VAL | 81 THR |
| LEU | 75 MET ASN | 76 HIS SER | 78 THR ILE | 79 MET VAL | 81 THR |
| LEU | 75 MET ASN | 76 HIS SER | 78 THR ILE | 79 THR VAL | 81 THR |
| LEU | 75 MET ASN | 76 HIS SER | 78 THR ILE | 79 VAL VAL | 81 THR |
| LEU | 75 MET ASN | 76 HIS SER | 78 ARG ILE | 79 LEU VAL | 81 THR |
| LEU | 75 MET ASN | 76 HIS SER | 78 ARG ILE | 79 MET VAL | 81 THR |
| LEU | 75 MET ASN | 76 HIS SER | 78 ARG ILE | 79 THR VAL | 81 THR |
| LEU | 75 MET ASN | 76 HIS SER | 78 ARG ILE | 79 VAL VAL | 81 THR |
| LEU | 75 MET ASN | 76 HIS SER | 78 ASP ILE | 79 LEU VAL | 81 THR |
| LEU | 75 MET ASN | 76 HIS SER | 78 ASP ILE | 79 MET VAL | 81 THR |
| LEU | 75 MET ASN | 76 HIS SER | 78 ASP ILE | 79 THR VAL | 81 THR |
| LEU | 75 MET ASN | 76 HIS SER | 78 ASP ILE | 79 VAL VAL | 81 THR |
| LEU | 75 MET ASN | 76 HIS SER | 78 GLN ILE | 79 LEU VAL | 81 THR |
| LEU | 75 MET ASN | 76 HIS SER | 78 GLN ILE | 79 MET VAL | 81 THR |
| LEU | 75 MET ASN | 76 HIS SER | 78 GLN ILE | 79 THR VAL | 81 THR |
| LEU | 75 MET ASN | 76 HIS SER | 78 GLN ILE | 79 VAL VAL | 81 THR |
| LEU | 75 MET ASN | 76 HIS SER | 78 HIS ILE | 79 LEU VAL | 81 THR |
| LEU | 75 MET ASN | 76 HIS SER | 78 HIS ILE | 79 MET VAL | 81 THR |
| LEU | 75 MET ASN | 76 HIS SER | 78 HIS ILE | 79 THR VAL | 81 THR |
| LEU | 75 MET ASN | 76 HIS SER | 78 HIS ILE | 79 VAL VAL | 81 THR |
| LEU | 75 MET ASN | 76 HIS SER | 78 LYS ILE | 79 LEU VAL | 81 THR |
| LEU | 75 MET ASN | 76 HIS SER | 78 LYS ILE | 79 MET VAL | 81 THR |
| LEU | 75 MET ASN | 76 HIS SER | 78 LYS ILE | 79 THR VAL | 81 THR |
| LEU | 75 MET ASN | 76 HIS SER | 78 LYS ILE | 79 VAL VAL | 81 THR |
| LEU | 75 MET ASN | 76 HIS SER | 78 TYR ILE | 79 LEU VAL | 81 THR |
| LEU | 75 MET ASN | 76 HIS SER | 78 TYR ILE | 79 MET VAL | 81 THR |
| LEU | 75 MET ASN | 76 HIS SER | 78 TYR ILE | 79 THR VAL | 81 THR |
| LEU | 75 MET ASN | 76 HIS SER | 78 TYR ILE | 79 VAL VAL | 81 THR |
| LEU | 75 VAL ASN | 76 HIS SER | 78 ASN ILE | 79 LEU VAL | 81 THR |
| LEU | 75 VAL ASN | 76 HIS SER | 78 ASN ILE | 79 MET VAL | 81 THR |
| LEU | 75 VAL ASN | 76 HIS SER | 78 ASN ILE | 79 THR VAL | 81 THR |
| LEU | 75 VAL ASN | 76 HIS SER | 78 ASN ILE | 79 VAL VAL | 81 THR |
| LEU | 75 VAL ASN | 76 HIS SER | 78 THR ILE | 79 LEU VAL | 81 THR |
| LEU | 75 VAL ASN | 76 HIS SER | 78 THR ILE | 79 MET VAL | 81 THR |
| LEU | 75 VAL ASN | 76 HIS SER | 78 THR ILE | 79 THR VAL | 81 THR |
| LEU | 75 VAL ASN | 76 HIS SER | 78 THR ILE | 79 VAL VAL | 81 THR |
| LEU | 75 VAL ASN | 76 HIS SER | 78 ARG ILE | 79 LEU VAL | 81 THR |
| LEU | 75 VAL ASN | 76 HIS SER | 78 ARG ILE | 79 MET VAL | 81 THR |
| LEU | 75 VAL ASN | 76 HIS SER | 78 ARG ILE | 79 THR VAL | 81 THR |
| LEU | 75 VAL ASN | 76 HIS SER | 78 ARG ILE | 79 VAL VAL | 81 THR |
| LEU | 75 VAL ASN | 76 HIS SER | 78 ASP ILE | 79 LEU VAL | 81 THR |
| LEU | 75 VAL ASN | 76 HIS SER | 78 ASP ILE | 79 MET VAL | 81 THR |
| LEU | 75 VAL ASN | 76 HIS SER | 78 ASP ILE | 79 THR VAL | 81 THR |
| LEU | 75 VAL ASN | 76 HIS SER | 78 ASP ILE | 79 VAL VAL | 81 THR |
| LEU | 75 VAL ASN | 76 HIS SER | 78 GLN ILE | 79 LEU VAL | 81 THR |
| LEU | 75 VAL ASN | 76 HIS SER | 78 GLN ILE | 79 MET VAL | 81 THR |
| LEU | 75 VAL ASN | 76 HIS SER | 78 GLN ILE | 79 THR VAL | 81 THR |
| LEU | 75 VAL ASN | 76 HIS SER | 78 GLN ILE | 79 VAL VAL | 81 THR |
| LEU | 75 VAL ASN | 76 HIS SER | 78 HIS ILE | 79 LEU VAL | 81 THR |

TABLE 6-continued

Quintuple Substitution Variants

| | | | | | |
|---|---|---|---|---|---|
| LEU | 75 VAL ASN | 76 HIS SER | 78 HIS ILE | 79 MET VAL | 81 THR |
| LEU | 75 VAL ASN | 76 HIS SER | 78 HIS ILE | 79 THR VAL | 81 THR |
| LEU | 75 VAL ASN | 76 HIS SER | 78 HIS ILE | 79 VAL VAL | 81 THR |
| LEU | 75 VAL ASN | 76 HIS SER | 78 LYS ILE | 79 LEU VAL | 81 THR |
| LEU | 75 VAL ASN | 76 HIS SER | 78 LYS ILE | 79 MET VAL | 81 THR |
| LEU | 75 VAL ASN | 76 HIS SER | 78 LYS ILE | 79 THR VAL | 81 THR |
| LEU | 75 VAL ASN | 76 HIS SER | 78 LYS ILE | 79 VAL VAL | 81 THR |
| LEU | 75 VAL ASN | 76 HIS SER | 78 TYR ILE | 79 LEU VAL | 81 THR |
| LEU | 75 VAL ASN | 76 HIS SER | 78 TYR ILE | 79 MET VAL | 81 THR |
| LEU | 75 VAL ASN | 76 HIS SER | 78 TYR ILE | 79 THR VAL | 81 THR |
| LEU | 75 VAL ASN | 76 HIS SER | 78 TYR ILE | 79 VAL VAL | 81 THR |

TABLE 7

Sextuple Substitution Variants

| | | | | | | |
|---|---|---|---|---|---|---|
| LEU | 75 ILE ASN | 76 HIS SER | 78 ASN ILE | 79 LEU VAL | 81 THR LEU | 82 PHE |
| LEU | 75 ILE ASN | 76 HIS SER | 78 ASN ILE | 79 LEU VAL | 81 THR LEU | 82 HIS |
| LEU | 75 ILE ASN | 76 HIS SER | 78 ASN ILE | 79 LEU VAL | 81 THR LEU | 82 TYR |
| LEU | 75 ILE ASN | 76 HIS SER | 78 ASN ILE | 79 MET VAL | 81 THR LEU | 82 PHE |
| LEU | 75 ILE ASN | 76 HIS SER | 78 ASN ILE | 79 MET VAL | 81 THR LEU | 82 HIS |
| LEU | 75 ILE ASN | 76 HIS SER | 78 ASN ILE | 79 MET VAL | 81 THR LEU | 82 TYR |
| LEU | 75 ILE ASN | 76 HIS SER | 78 ASN ILE | 79 THR VAL | 81 THR LEU | 82 PRE |
| LEU | 75 ILE ASN | 76 HIS SER | 78 ASN ILE | 79 THR VAL | 81 THR LEU | 82 HIS |
| LEU | 75 ILE ASN | 76 HIS SER | 78 ASN ILE | 79 THR VAL | 81 THR LEU | 82 TYR |
| LEU | 75 ILE ASN | 76 HIS SER | 78 ASN ILE | 79 VAL VAL | 81 THR LEU | 82 PHE |
| LEU | 75 ILE ASN | 76 HIS SER | 78 ASN ILE | 79 VAL VAL | 81 THR LEU | 82 HIS |
| LEU | 75 ILE ASN | 76 HIS SER | 78 ASN ILE | 79 VAL VAL | 81 THR LEU | 82 TYR |
| LEU | 75 ILE ASN | 76 HIS SER | 78 THR ILE | 79 LEU VAL | 81 THR LEU | 82 PHE |
| LEU | 75 ILE ASN | 76 HIS SER | 78 THR ILE | 79 LEU VAL | 81 THR LEU | 82 HIS |
| LEU | 75 ILE ASN | 76 HIS SER | 78 THR ILE | 79 LEU VAL | 81 THR LEU | 82 TYR |
| LEU | 75 ILE ASN | 76 HIS SER | 78 THR ILE | 79 MET VAL | 81 THR LEU | 82 PHE |
| LEU | 75 ILE ASN | 76 HIS SER | 78 THR ILE | 79 MET VAL | 81 THR LEU | 82 HIS |
| LEU | 75 ILE ASN | 76 HIS SER | 78 THR ILE | 79 MET VAL | 81 THR LEU | 82 TYR |
| LEU | 75 ILE ASN | 76 HIS SER | 78 THR ILE | 79 THR VAL | 81 THR LEU | 82 PHE |
| LEU | 75 ILE ASN | 76 HIS SER | 78 THR ILE | 79 THR VAL | 81 THR LEU | 82 HIS |
| LEU | 75 ILE ASN | 76 HIS SER | 78 THR ILE | 79 THR VAL | 81 THR LEU | 82 TYR |
| LEU | 75 ILE ASN | 76 HIS SER | 78 THR ILE | 79 VAL VAL | 81 THR LEU | 82 PHE |
| LEU | 75 ILE ASN | 76 HIS SER | 78 THR ILE | 79 VAL VAL | 81 THR LEU | 82 HIS |
| LEU | 75 ILE ASN | 76 HIS SER | 78 THR ILE | 79 VAL VAL | 81 THR LEU | 82 TYR |
| LEU | 75 ILE ASN | 76 HIS SER | 78 ARG ILE | 79 LEU VAL | 81 THR LEU | 82 PHE |
| LEU | 75 ILE ASN | 76 HIS SER | 78 ARG ILE | 79 LEU VAL | 81 THR LEU | 82 HIS |
| LEU | 75 ILE ASN | 76 HIS SER | 78 ARG ILE | 79 LEU VAL | 81 THR LEU | 82 TYR |
| LEU | 75 ILE ASN | 76 HIS SER | 78 ARG ILE | 79 MET VAL | 81 THR LEU | 82 PHE |
| LEU | 75 ILE ASN | 76 HIS SER | 78 ARG ILE | 79 MET VAL | 81 THR LEU | 82 HIS |
| LEU | 75 ILE ASN | 76 HIS SER | 78 ARG ILE | 79 MET VAL | 81 THR LEU | 82 TYR |
| LEU | 75 ILE ASN | 76 HIS SER | 78 ARG ILE | 79 THR VAL | 81 THR LEU | 82 PHE |
| LEU | 75 ILE ASN | 76 HIS SER | 78 ARG ILE | 79 THR VAL | 81 THR LEU | 82 HIS |
| LEU | 75 ILE ASN | 76 HIS SER | 78 ARG ILE | 79 THR VAL | 81 THR LEU | 82 TYR |
| LEU | 75 ILE ASN | 76 HIS SER | 78 ARG ILE | 79 VAL VAL | 81 THR LEU | 82 PHE |
| LEU | 75 ILE ASN | 76 HIS SER | 78 ARG ILE | 79 VAL VAL | 81 THR LEU | 82 HIS |
| LEU | 75 ILE ASN | 76 HIS SER | 78 ARG ILE | 79 VAL VAL | 81 THR LEU | 82 TYR |
| LEU | 75 ILE ASN | 76 HIS SER | 78 ASP ILE | 79 LEU VAL | 81 THR LEU | 82 PHE |
| LEU | 75 ILE ASN | 76 HIS SER | 78 ASP ILE | 79 LEU VAL | 81 THR LEU | 82 HIS |
| LEU | 75 ILE ASN | 76 HIS SER | 78 ASP ILE | 79 LEU VAL | 81 THR LEU | 82 TYR |
| LEU | 75 ILE ASN | 76 HIS SER | 78 ASP ILE | 79 MET VAL | 81 THR LEU | 82 PHE |
| LEU | 75 ILE ASN | 76 HIS SER | 78 ASP ILE | 79 MET VAL | 81 THR LEU | 82 HIS |
| LEU | 75 ILE ASN | 76 HIS SER | 78 ASP ILE | 79 MET VAL | 81 THR LEU | 82 TYR |
| LEU | 75 ILE ASN | 76 HIS SER | 78 ASP ILE | 79 THR VAL | 81 THR LEU | 82 PHE |
| LEU | 75 ILE ASN | 76 HIS SER | 78 ASP ILE | 79 THR VAL | 81 THR LEU | 82 HIS |
| LEU | 75 ILE ASN | 76 HIS SER | 78 ASP ILE | 79 THR VAL | 81 THR LEU | 82 TYR |
| LEU | 75 ILE ASN | 76 HIS SER | 78 ASP ILE | 79 VAL VAL | 81 THR LEU | 82 PHE |
| LEU | 75 ILE ASN | 76 HIS SER | 78 ASP ILE | 79 VAL VAL | 81 THR LEU | 82 HIS |
| LEU | 75 ILE ASN | 76 HIS SER | 78 ASP ILE | 79 VAL VAL | 81 THR LEU | 82 TYR |
| LEU | 75 ILE ASN | 76 HIS SER | 78 GLN ILE | 79 LEU VAL | 81 THR LEU | 82 PHE |
| LEU | 75 ILE ASN | 76 HIS SER | 78 GLN ILE | 79 LEU VAL | 81 THR LEU | 82 HIS |
| LEU | 75 ILE ASN | 76 HIS SER | 78 GLN ILE | 79 LEU VAL | 81 THR LEU | 82 TYR |
| LEU | 75 ILE ASN | 76 HIS SER | 78 GLN ILE | 79 MET VAL | 81 THR LEU | 82 PHE |
| LEU | 75 ILE ASN | 76 HIS SER | 78 GLN ILE | 79 MET VAL | 81 THR LEU | 82 HIS |
| LEU | 75 ILE ASN | 76 HIS SER | 78 GLN ILE | 79 MET VAL | 81 THR LEU | 82 TYR |
| LEU | 75 ILE ASN | 76 HIS SER | 78 GLN ILE | 79 THR VAL | 81 THR LEU | 82 PHE |
| LEU | 75 ILE ASN | 76 HIS SER | 78 GLN ILE | 79 THR VAL | 81 THR LEU | 82 HIS |
| LEU | 75 ILE ASN | 76 HIS SER | 78 GLN ILE | 79 THR VAL | 81 THR LEU | 82 TYR |
| LEU | 75 ILE ASN | 76 HIS SER | 78 GLN ILE | 79 VAL VAL | 81 THR LEU | 82 PHE |

TABLE 7-continued

| Sextuple Substitution Variants | | | | | | |
|---|---|---|---|---|---|---|
| LEU | 75 ILE ASN | 76 HIS SER | 78 GLN ILE | 79 VAL VAL | 81 THR LEU | 82 HIS |
| LEU | 75 ILE ASN | 76 HIS SER | 78 GLN ILE | 79 VAL VAL | 81 THR LEU | 82 TYR |
| LEU | 75 ILE ASN | 76 HIS SER | 78 HIS ILE | 79 LEU VAL | 81 THR LEU | 82 PHE |
| LEU | 75 ILE ASN | 76 HIS SER | 78 HIS ILE | 79 LEU VAL | 81 THR LEU | 82 HIS |
| LEU | 75 ILE ASN | 76 HIS SER | 78 HIS ILE | 79 LEU VAL | 81 THR LEU | 82 TYR |
| LEU | 75 ILE ASN | 76 HIS SER | 78 HIS ILE | 79 MET VAL | 81 THR LEU | 82 PHE |
| LEU | 75 ILE ASN | 76 HIS SER | 78 HIS ILE | 79 MET VAL | 81 THR LEU | 82 HIS |
| LEU | 75 ILE ASN | 76 HIS SER | 78 HIS ILE | 79 MET VAL | 81 THR LEU | 82 TYR |
| LEU | 75 ILE ASN | 76 HIS SER | 78 HIS ILE | 79 THR VAL | 81 THR LEU | 82 PHE |
| LEU | 75 ILE ASN | 76 HIS SER | 78 HIS ILE | 79 THR VAL | 81 THR LEU | 82 HIS |
| LEU | 75 ILE ASN | 76 HIS SER | 78 HIS ILE | 79 THR VAL | 81 THR LEU | 82 TYR |
| LEU | 75 ILE ASN | 76 HIS SER | 78 HIS ILE | 79 VAL VAL | 81 THR LEU | 82 PHE |
| LEU | 75 ILE ASN | 76 HIS SER | 78 HIS ILE | 79 VAL VAL | 81 THR LEU | 82 HIS |
| LEU | 75 ILE ASN | 76 HIS SER | 78 HIS ILE | 79 VAL VAL | 81 THR LEU | 82 TYR |
| LEU | 75 ILE ASN | 76 HIS SER | 78 LYS ILE | 79 LEU VAL | 81 THR LEU | 82 PHE |
| LEU | 75 ILE ASN | 76 HIS SER | 78 LYS ILE | 79 LEU VAL | 81 THR LEU | 82 HIS |
| LEU | 75 ILE ASN | 76 HIS SER | 78 LYS ILE | 79 LEU VAL | 81 THR LEU | 82 TYR |
| LEU | 75 ILE ASN | 76 HIS SER | 78 LYS ILE | 79 MET VAL | 81 THR LEU | 82 PHE |
| LEU | 75 ILE ASN | 76 HIS SER | 78 LYS ILE | 79 MET VAL | 81 THR LEU | 82 HIS |
| LEU | 75 ILE ASN | 76 HIS SER | 78 LYS ILE | 79 MET VAL | 81 THR LEU | 82 TYR |
| LEU | 75 ILE ASN | 76 HIS SER | 78 LYS ILE | 79 THR VAL | 81 THR LEU | 82 PHE |
| LEU | 75 ILE ASN | 76 HIS SER | 78 LYS ILE | 79 THR VAL | 81 THR LEU | 82 HIS |
| LEU | 75 ILE ASN | 76 HIS SER | 78 LYS ILE | 79 THR VAL | 81 THR LEU | 82 TYR |
| LEU | 75 ILE ASN | 76 HIS SER | 78 LYS ILE | 79 VAL VAL | 81 THR LEU | 82 PHE |
| LEU | 75 ILE ASN | 76 HIS SER | 78 LYS ILE | 79 VAL VAL | 81 THR LEU | 82 HIS |
| LEU | 75 ILE ASN | 76 HIS SER | 78 LYS ILE | 79 VAL VAL | 81 THR LEU | 82 TYR |
| LEU | 75 ILE ASN | 76 HIS SER | 78 TYR ILE | 79 LEU VAL | 81 THR LEU | 82 PHE |
| LEU | 75 ILE ASN | 76 HIS SER | 78 TYR ILE | 79 LEU VAL | 81 THR LEU | 82 HIS |
| LEU | 75 ILE ASN | 76 HIS SER | 78 TYR ILE | 79 LEU VAL | 81 THR LEU | 82 TYR |
| LEU | 75 ILE ASN | 76 HIS SER | 78 TYR ILE | 79 MET VAL | 81 THR LEU | 82 PHE |
| LEU | 75 ILE ASN | 76 HIS SER | 78 TYR ILE | 79 MET VAL | 81 THR LEU | 82 HIS |
| LEU | 75 ILE ASN | 76 HIS SER | 78 TYR ILE | 79 MET VAL | 81 THR LEU | 82 TYR |
| LEU | 75 ILE ASN | 76 HIS SER | 78 TYR ILE | 79 THR VAL | 81 THR LEU | 82 PHE |
| LEU | 75 ILE ASN | 76 HIS SER | 78 TYR ILE | 79 THR VAL | 81 THR LEU | 82 HIS |
| LEU | 75 ILE ASN | 76 HIS SER | 78 TYR ILE | 79 THR VAL | 81 THR LEU | 82 TYR |
| LEU | 75 ILE ASN | 76 HIS SER | 78 TYR ILE | 79 VAL VAL | 81 THR LEU | 82 PHE |
| LEU | 75 ILE ASN | 76 HIS SER | 78 TYR ILE | 79 VAL VAL | 81 THR LEU | 82 HIS |
| LEU | 75 ILE ASN | 76 HIS SER | 78 TYR ILE | 79 VAL VAL | 81 THR LEU | 82 TYR |
| LEU | 75 MET ASN | 76 HIS SER | 78 ASN ILE | 79 LEU VAL | 81 THR LEU | 82 PHE |
| LEU | 75 MET ASN | 76 HIS SER | 78 ASN ILE | 79 LEU VAL | 81 THR LEU | 82 HIS |
| LEU | 75 MET ASN | 76 HIS SER | 78 ASN ILE | 79 LEU VAL | 81 THR LEU | 82 TYR |
| LEU | 75 MET ASN | 76 HIS SER | 78 ASN ILE | 79 MET VAL | 81 THR LEU | 82 PHE |
| LEU | 75 MET ASN | 76 HIS SER | 78 ASN ILE | 79 MET VAL | 81 THR LEU | 82 HIS |
| LEU | 75 MET ASN | 76 HIS SER | 78 ASN ILE | 79 MET VAL | 81 THR LEU | 82 TYR |
| LEU | 75 MET ASN | 76 HIS SER | 78 ASN ILE | 79 THR VAL | 81 THR LEU | 82 PHE |
| LEU | 75 MET ASN | 76 HIS SER | 78 ASN ILE | 79 THR VAL | 81 THR LEU | 82 HIS |
| LEU | 75 MET ASN | 76 HIS SER | 78 ASN ILE | 79 THR VAL | 81 THR LEU | 82 TYR |
| LEU | 75 MET ASN | 76 HIS SER | 78 ASN ILE | 79 VAL VAL | 81 THR LEU | 82 PHE |
| LEU | 75 MET ASN | 76 HIS SER | 78 ASN ILE | 79 VAL VAL | 81 THR LEU | 82 HIS |
| LEU | 75 MET ASN | 76 HIS SER | 78 ASN ILE | 79 VAL VAL | 81 THR LEU | 82 TYR |
| LEU | 75 MET ASN | 76 HIS SER | 78 THR ILE | 79 LEU VAL | 81 THR LEU | 82 PHE |
| LEU | 75 MET ASN | 76 HIS SER | 78 THR ILE | 79 LEU VAL | 81 THR LEU | 82 HIS |
| LEU | 75 MET ASN | 76 HIS SER | 78 THR ILE | 79 LEU VAL | 81 THR LEU | 82 TYR |
| LEU | 75 MET ASN | 76 HIS SER | 78 THR ILE | 79 MET VAL | 81 THR LEU | 82 PHE |
| LEU | 75 MET ASN | 76 HIS SER | 78 THR ILE | 79 MET VAL | 81 THR LEU | 82 HIS |
| LEU | 75 MET ASN | 76 HIS SER | 78 THR ILE | 79 MET VAL | 81 THR LEU | 82 TYR |
| LEU | 75 MET ASN | 76 HIS SER | 78 THR ILE | 79 THR VAL | 81 THR LEU | 82 PHE |
| LEU | 75 MET ASN | 76 HIS SER | 78 THR ILE | 79 THR VAL | 81 THR LEU | 82 HIS |
| LEU | 75 MET ASN | 76 HIS SER | 78 THR ILE | 79 THR VAL | 81 THR LEU | 82 TYR |
| LEU | 75 MET ASN | 76 HIS SER | 78 THR ILE | 79 VAL VAL | 81 THR LEU | 82 PHE |
| LEU | 75 MET ASN | 76 HIS SER | 78 THR ILE | 79 VAL VAL | 81 THR LEU | 82 HIS |
| LEU | 75 MET ASN | 76 HIS SER | 78 THR ILE | 79 VAL VAL | 81 THR LEU | 82 TYR |
| LEU | 75 MET ASN | 76 HIS SER | 78 ARG ILE | 79 LEU VAL | 81 THR LEU | 82 PHE |
| LEU | 75 MET ASN | 76 HIS SER | 78 ARG ILE | 79 LEU VAL | 81 THR LEU | 82 HIS |
| LEU | 75 MET ASN | 76 HIS SER | 78 ARG ILE | 79 LEU VAL | 81 THR LEU | 82 TYR |
| LEU | 75 MET ASN | 76 HIS SER | 78 ARG ILE | 79 MET VAL | 81 THR LEU | 82 PHE |
| LEU | 75 MET ASN | 76 HIS SER | 78 ARG ILE | 79 MET VAL | 81 THR LEU | 82 HIS |
| LEU | 75 MET ASN | 76 HIS SER | 78 ARG ILE | 79 MET VAL | 81 THR LEU | 82 TYR |
| LEU | 75 MET ASN | 76 HIS SER | 78 ARG ILE | 79 THR VAL | 81 THR LEU | 82 PHE |
| LEU | 75 MET ASN | 76 HIS SER | 78 ARG ILE | 79 THR VAL | 81 THR LEU | 82 HIS |
| LEU | 75 MET ASN | 76 HIS SER | 78 ARG ILE | 79 THR VAL | 81 THR LEU | 82 TYR |
| LEU | 75 MET ASN | 76 HIS SER | 78 ARG ILE | 79 VAL VAL | 81 THR LEU | 82 PHE |
| LEU | 75 MET ASN | 76 HIS SER | 78 ARG ILE | 79 VAL VAL | 81 THR LEU | 82 HIS |
| LEU | 75 MET ASN | 76 HIS SER | 78 ARG ILE | 79 VAL VAL | 81 THR LEU | 82 TYR |
| LEU | 75 MET ASN | 76 HIS SER | 78 ASP ILE | 79 LEU VAL | 81 THR LEU | 82 PHE |
| LEU | 75 MET ASN | 76 HIS SER | 78 ASP ILE | 79 LEU VAL | 81 THR LEU | 82 HIS |
| LEU | 75 MET ASN | 76 HIS SER | 78 ASP ILE | 79 LEU VAL | 81 THR LEU | 82 TYR |

TABLE 7-continued

Sextuple Substitution Variants

| | | | | | | | | | | | | |
|---|---|---|---|---|---|---|---|---|---|---|---|---|
| LEU | 75 | MET | ASN | 76 | HIS | SER | 78 | ASP ILE | 79 | MET VAL | 81 | THR LEU | 82 PHE |
| LEU | 75 | MET | ASN | 76 | HIS | SER | 78 | ASP ILE | 79 | MET VAL | 81 | THR LEU | 82 HIS |
| LEU | 75 | MET | ASN | 76 | HIS | SER | 78 | ASP ILE | 79 | MET VAL | 81 | THR LEU | 82 TYR |
| LEU | 75 | MET | ASN | 76 | HIS | SER | 78 | ASP ILE | 79 | THR VAL | 81 | THR LEU | 82 PHE |
| LEU | 75 | MET | ASN | 76 | HIS | SER | 78 | ASP ILE | 79 | THR VAL | 81 | THR LEU | 82 HIS |
| LEU | 75 | MET | ASN | 76 | HIS | SER | 78 | ASP ILE | 79 | THR VAL | 81 | THR LEU | 82 TYR |
| LEU | 75 | MET | ASN | 76 | HIS | SER | 78 | ASP ILE | 79 | VAL VAL | 81 | THR LEU | 82 PHE |
| LEU | 75 | MET | ASN | 76 | HIS | SER | 78 | ASP ILE | 79 | VAL VAL | 81 | THR LEU | 82 HIS |
| LEU | 75 | MET | ASN | 76 | HIS | SER | 78 | ASP ILE | 79 | VAL VAL | 81 | THR LEU | 82 TYR |
| LEU | 75 | MET | ASN | 76 | HIS | SER | 78 | GLN ILE | 79 | LEU VAL | 81 | THR LEU | 82 PHE |
| LEU | 75 | MET | ASN | 76 | HIS | SER | 78 | GLN ILE | 79 | LEU VAL | 81 | THR LEU | 82 HIS |
| LEU | 75 | MET | ASN | 76 | HIS | SER | 78 | GLN ILE | 79 | LEU VAL | 81 | THR LEU | 82 TYR |
| LEU | 75 | MET | ASN | 76 | HIS | SER | 78 | GLN ILE | 79 | MET VAL | 81 | THR LEU | 82 PHE |
| LEU | 75 | MET | ASN | 76 | HIS | SER | 78 | GLN ILE | 79 | MET VAL | 81 | THR LEU | 82 HIS |
| LEU | 75 | MET | ASN | 76 | HIS | SER | 78 | GLN ILE | 79 | MET VAL | 81 | THR LEU | 82 TYR |
| LEU | 75 | MET | ASN | 76 | HIS | SER | 78 | GLN ILE | 79 | THR VAL | 81 | THR LEU | 82 PHE |
| LEU | 75 | MET | ASN | 76 | HIS | SER | 78 | GLN ILE | 79 | THR VAL | 81 | THR LEU | 82 HIS |
| LEU | 75 | MET | ASN | 76 | HIS | SER | 78 | GLN ILE | 79 | THR VAL | 81 | THR LEU | 82 TYR |
| LEU | 75 | MET | ASN | 76 | HIS | SER | 78 | GLN ILE | 79 | VAL VAL | 81 | THR LEU | 82 PHE |
| LEU | 75 | MET | ASN | 76 | HIS | SER | 78 | GLN ILE | 79 | VAL VAL | 81 | THR LEU | 82 HIS |
| LEU | 75 | MET | ASN | 76 | HIS | SER | 78 | GLN ILE | 79 | VAL VAL | 81 | THR LEU | 82 TYR |
| LEU | 75 | MET | ASN | 76 | HIS | SER | 78 | HIS ILE | 79 | LEU VAL | 81 | THR LEU | 82 PHE |
| LEU | 75 | MET | ASN | 76 | HIS | SER | 78 | HIS ILE | 79 | LEU VAL | 81 | THR LEU | 82 HIS |
| LEU | 75 | MET | ASN | 76 | HIS | SER | 78 | HIS ILE | 79 | LEU VAL | 81 | THR LEU | 82 TYR |
| LEU | 75 | MET | ASN | 76 | HIS | SER | 78 | HIS ILE | 79 | MET VAL | 81 | THR LEU | 82 PHE |
| LEU | 75 | MET | ASN | 76 | HIS | SER | 78 | HIS ILE | 79 | MET VAL | 81 | THR LEU | 82 HIS |
| LEU | 75 | MET | ASN | 76 | HIS | SER | 78 | HIS ILE | 79 | MET VAL | 81 | THR LEU | 82 TYR |
| LEU | 75 | MET | ASN | 76 | HIS | SER | 78 | HIS ILE | 79 | THR VAL | 81 | THR LEU | 82 PHE |
| LEU | 75 | MET | ASN | 76 | HIS | SER | 78 | HIS ILE | 79 | THR VAL | 81 | THR LEU | 82 HIS |
| LEU | 75 | MET | ASN | 76 | HIS | SER | 78 | HIS ILE | 79 | THR VAL | 81 | THR LEU | 82 TYR |
| LEU | 75 | MET | ASN | 76 | HIS | SER | 78 | HIS ILE | 79 | VAL VAL | 81 | THR LEU | 82 PHE |
| LEU | 75 | MET | ASN | 76 | HIS | SER | 78 | HIS ILE | 79 | VAL VAL | 81 | THR LEU | 82 HIS |
| LEU | 75 | MET | ASN | 76 | HIS | SER | 78 | HIS ILE | 79 | VAL VAL | 81 | THR LEU | 82 TYR |
| LEU | 75 | MET | ASN | 76 | HIS | SER | 78 | LYS ILE | 79 | LEU VAL | 81 | THR LEU | 82 PHE |
| LEU | 75 | MET | ASN | 76 | HIS | SER | 78 | LYS ILE | 79 | LEU VAL | 81 | THR LEU | 82 HIS |
| LEU | 75 | MET | ASN | 76 | HIS | SER | 78 | LYS ILE | 79 | LEU VAL | 81 | THR LEU | 82 TYR |
| LEU | 75 | MET | ASN | 76 | HIS | SER | 78 | LYS ILE | 79 | MET VAL | 81 | THR LEU | 82 PHE |
| LEU | 75 | MET | ASN | 76 | HIS | SER | 78 | LYS ILE | 79 | MET VAL | 81 | THR LEU | 82 HIS |
| LEU | 75 | MET | ASN | 76 | HIS | SER | 78 | LYS ILE | 79 | MET VAL | 81 | THR LEU | 82 TYR |
| LEU | 75 | MET | ASN | 76 | HIS | SER | 78 | LYS ILE | 79 | THR VAL | 81 | THR LEU | 82 PHE |
| LEU | 75 | MET | ASN | 76 | HIS | SER | 78 | LYS ILE | 79 | THR VAL | 81 | THR LEU | 82 HIS |
| LEU | 75 | MET | ASN | 76 | HIS | SER | 78 | LYS ILE | 79 | THR VAL | 81 | THR LEU | 82 TYR |
| LEU | 75 | MET | ASN | 76 | HIS | SER | 78 | LYS ILE | 79 | VAL VAL | 81 | THR LEU | 82 PHE |
| LEU | 75 | MET | ASN | 76 | HIS | SER | 78 | LYS ILE | 79 | VAL VAL | 81 | THR LEU | 82 HIS |
| LEU | 75 | MET | ASN | 76 | HIS | SER | 78 | LYS ILE | 79 | VAL VAL | 81 | THR LEU | 82 TYR |
| LEU | 75 | MET | ASN | 76 | HIS | SER | 78 | TYR ILE | 79 | LEU VAL | 81 | THR LEU | 82 PHE |
| LEU | 75 | MET | ASN | 76 | HIS | SER | 78 | TYR ILE | 79 | LEU VAL | 81 | THR LEU | 82 HIS |
| LEU | 75 | MET | ASN | 76 | HIS | SER | 78 | TYR ILE | 79 | LEU VAL | 81 | THR LEU | 82 TYR |
| LEU | 75 | MET | ASN | 76 | HIS | SER | 78 | TYR ILE | 79 | MET VAL | 81 | THR LEU | 82 PHE |
| LEU | 75 | MET | ASN | 76 | HIS | SER | 78 | TYR ILE | 79 | MET VAL | 81 | THR LEU | 82 HIS |
| LEU | 75 | MET | ASN | 76 | HIS | SER | 78 | TYR ILE | 79 | MET VAL | 81 | THR LEU | 82 TYR |
| LEU | 75 | MET | ASN | 76 | HIS | SER | 78 | TYR ILE | 79 | THR VAL | 81 | THR LEU | 82 PHE |
| LEU | 75 | MET | ASN | 76 | HIS | SER | 78 | TYR ILE | 79 | THR VAL | 81 | THR LEU | 82 HIS |
| LEU | 75 | MET | ASN | 76 | HIS | SER | 78 | TYR ILE | 79 | THR VAL | 81 | THR LEU | 82 TYR |
| LEU | 75 | MET | ASN | 76 | HIS | SER | 78 | TYR ILE | 79 | VAL VAL | 81 | THR LEU | 82 PHE |
| LEU | 75 | MET | ASN | 76 | HIS | SER | 78 | TYR ILE | 79 | VAL VAL | 81 | THR LEU | 82 HIS |
| LEU | 75 | MET | ASN | 76 | HIS | SER | 78 | TYR ILE | 79 | VAL VAL | 81 | THR LEU | 82 TYR |
| LEU | 75 | VAL | ASN | 76 | HIS | SER | 78 | ASN ILE | 79 | LEU VAL | 81 | THR LEU | 82 PHE |
| LEU | 75 | VAL | ASN | 76 | HIS | SER | 78 | ASN ILE | 79 | LEU VAL | 81 | THR LEU | 82 HIS |
| LEU | 75 | VAL | ASN | 76 | HIS | SER | 78 | ASN ILE | 79 | LEU VAL | 81 | THR LEU | 82 TYR |
| LEU | 75 | VAL | ASN | 76 | HIS | SER | 78 | ASN ILE | 79 | MET VAL | 81 | THR LEU | 82 PHE |
| LEU | 75 | VAL | ASN | 76 | HIS | SER | 78 | ASN ILE | 79 | MET VAL | 81 | THR LEU | 82 HIS |
| LEU | 75 | VAL | ASN | 76 | HIS | SER | 78 | ASN ILE | 79 | MET VAL | 81 | THR LEU | 82 TYR |
| LEU | 75 | VAL | ASN | 76 | HIS | SER | 78 | ASN ILE | 79 | THR VAL | 81 | THR LEU | 82 PHE |
| LEU | 75 | VAL | ASN | 76 | HIS | SER | 78 | ASN ILE | 79 | THR VAL | 81 | THR LEU | 82 HIS |
| LEU | 75 | VAL | ASN | 76 | HIS | SER | 78 | ASN ILE | 79 | THR VAL | 81 | THR LEU | 82 TYR |
| LEU | 75 | VAL | ASN | 76 | HIS | SER | 78 | ASN ILE | 79 | VAL VAL | 81 | THR LEU | 82 PHE |
| LEU | 75 | VAL | ASN | 76 | HIS | SER | 78 | ASN ILE | 79 | VAL VAL | 81 | THR LEU | 82 HIS |
| LEU | 75 | VAL | ASN | 76 | HIS | SER | 78 | ASN ILE | 79 | VAL VAL | 81 | THR LEU | 82 TYR |
| LEU | 75 | VAL | ASN | 76 | HIS | SER | 78 | THR ILE | 79 | LEU VAL | 81 | THR LEU | 82 PHE |
| LEU | 75 | VAL | ASN | 76 | HIS | SER | 78 | THR ILE | 79 | LEU VAL | 81 | THR LEU | 82 HIS |
| LEU | 75 | VAL | ASN | 76 | HIS | SER | 78 | THR ILE | 79 | LEU VAL | 81 | THR LEU | 82 TYR |
| LEU | 75 | VAL | ASN | 76 | HIS | SER | 78 | THR ILE | 79 | MET VAL | 81 | THR LEU | 82 PHE |
| LEU | 75 | VAL | ASN | 76 | HIS | SER | 78 | THR ILE | 79 | MET VAL | 81 | THR LEU | 82 HIS |
| LEU | 75 | VAL | ASN | 76 | HIS | SER | 78 | THR ILE | 79 | MET VAL | 81 | THR LEU | 82 TYR |
| LEU | 75 | VAL | ASN | 76 | HIS | SER | 78 | THR ILE | 79 | THR VAL | 81 | THR LEU | 82 PHE |
| LEU | 75 | VAL | ASN | 76 | HIS | SER | 78 | THR ILE | 79 | THR VAL | 81 | THR LEU | 82 HIS |

TABLE 7-continued

| Sextuple Substitution Variants | | | | | | |
|---|---|---|---|---|---|---|
| LEU | 75 VAL ASN | 76 HIS SER | 78 THR ILE | 79 THR VAL | 81 THR LEU | 82 TYR |
| LEU | 75 VAL ASN | 76 HIS SER | 78 THR ILE | 79 VAL VAL | 81 THR LEU | 82 PHE |
| LEU | 75 VAL ASN | 76 HIS SER | 78 THR ILE | 79 VAL VAL | 81 THR LEU | 82 HIS |
| LEU | 75 VAL ASN | 76 HIS SER | 78 THR ILE | 79 VAL VAL | 81 THR LEU | 82 TYR |
| LEU | 75 VAL ASN | 76 HIS SER | 78 ARG ILE | 79 LEU VAL | 81 THR LEU | 82 PHE |
| LEU | 75 VAL ASN | 76 HIS SER | 78 ARG ILE | 79 LEU VAL | 81 THR LEU | 82 HIS |
| LEU | 75 VAL ASN | 76 HIS SER | 78 ARG ILE | 79 LEU VAL | 81 THR LEU | 82 TYR |
| LEU | 75 VAL ASN | 76 HIS SER | 78 ARG ILE | 79 MET VAL | 81 THR LEU | 82 PHE |
| LEU | 75 VAL ASN | 76 HIS SER | 78 ARG ILE | 79 MET VAL | 81 THR LEU | 82 HIS |
| LEU | 75 VAL ASN | 76 HIS SER | 78 ARG ILE | 79 MET VAL | 81 THR LEU | 82 TYR |
| LEU | 75 VAL ASN | 76 HIS SER | 78 ARG ILE | 79 THR VAL | 81 THR LEU | 82 PHE |
| LEU | 75 VAL ASN | 76 HIS SER | 78 ARG ILE | 79 THR VAL | 81 THR LEU | 82 HIS |
| LEU | 75 VAL ASN | 76 HIS SER | 78 ARG ILE | 79 THR VAL | 81 THR LEU | 82 TYR |
| LEU | 75 VAL ASN | 76 HIS SER | 78 ARG ILE | 79 VAL VAL | 81 THR LEU | 82 PHE |
| LEU | 75 VAL ASN | 76 HIS SER | 78 ARG ILE | 79 VAL VAL | 81 THR LEU | 82 HIS |
| LEU | 75 VAL ASN | 76 HIS SER | 78 ARG ILE | 79 VAL VAL | 81 THR LEU | 82 TYR |
| LEU | 75 VAL ASN | 76 HIS SER | 78 ASP ILE | 79 LEU VAL | 81 THR LEU | 82 PHE |
| LEU | 75 VAL ASN | 76 HIS SER | 78 ASP ILE | 79 LEU VAL | 81 THR LEU | 82 HIS |
| LEU | 75 VAL ASN | 76 HIS SER | 78 ASP ILE | 79 LEU VAL | 81 THR LEU | 82 TYR |
| LEU | 75 VAL ASN | 76 HIS SER | 78 ASP ILE | 79 MET VAL | 81 THR LEU | 82 PHE |
| LEU | 75 VAL ASN | 76 HIS SER | 78 ASP ILE | 79 MET VAL | 81 THR LEU | 82 HIS |
| LEU | 75 VAL ASN | 76 HIS SER | 78 ASP ILE | 79 MET VAL | 81 THR LEU | 82 TYR |
| LEU | 75 VAL ASN | 76 HIS SER | 78 ASP ILE | 79 THR VAL | 81 THR LEU | 82 PHE |
| LEU | 75 VAL ASN | 76 HIS SER | 78 ASP ILE | 79 THR VAL | 81 THR LEU | 82 HIS |
| LEU | 75 VAL ASN | 76 HIS SER | 78 ASP ILE | 79 THR VAL | 81 THR LEU | 82 TYR |
| LEU | 75 VAL ASN | 76 HIS SER | 78 ASP ILE | 79 VAL VAL | 81 THR LEU | 82 PHE |
| LEU | 75 VAL ASN | 76 HIS SER | 78 ASP ILE | 79 VAL VAL | 81 THR LEU | 82 HIS |
| LEU | 75 VAL ASN | 76 HIS SER | 78 ASP ILE | 79 VAL VAL | 81 THR LEU | 82 TYR |
| LEU | 75 VAL ASN | 76 HIS SER | 78 GLN ILE | 79 LEU VAL | 81 THR LEU | 82 PHE |
| LEU | 75 VAL ASN | 76 HIS SER | 78 GLN ILE | 79 LEU VAL | 81 THR LEU | 82 HIS |
| LEU | 75 VAL ASN | 76 HIS SER | 78 GLN ILE | 79 LEU VAL | 81 THR LEU | 82 TYR |
| LEU | 75 VAL ASN | 76 HIS SER | 78 GLN ILE | 79 MET VAL | 81 THR LEU | 82 PHE |
| LEU | 75 VAL ASN | 76 HIS SER | 78 GLN ILE | 79 MET VAL | 81 THR LEU | 82 HIS |
| LEU | 75 VAL ASN | 76 HIS SER | 78 GLN ILE | 79 MET VAL | 81 THR LEU | 82 TYR |
| LEU | 75 VAL ASN | 76 HIS SER | 78 GLN ILE | 79 THR VAL | 81 THR LEU | 82 PHE |
| LEU | 75 VAL ASN | 76 HIS SER | 78 GLN ILE | 79 THR VAL | 81 THR LEU | 82 HIS |
| LEU | 75 VAL ASN | 76 HIS SER | 78 GLN ILE | 79 THR VAL | 81 THR LEU | 82 TYR |
| LEU | 75 VAL ASN | 76 HIS SER | 78 GLN ILE | 79 VAL VAL | 81 THR LEU | 82 PHE |
| LEU | 75 VAL ASN | 76 HIS SER | 78 GLN ILE | 79 VAL VAL | 81 THR LEU | 82 HIS |
| LEU | 75 VAL ASN | 76 HIS SER | 78 GLN ILE | 79 VAL VAL | 81 THR LEU | 82 TYR |
| LEU | 75 VAL ASN | 76 HIS SER | 78 HIS ILE | 79 LEU VAL | 81 THR LEU | 82 PHE |
| LEU | 75 VAL ASN | 76 HIS SER | 78 HIS ILE | 79 LEU VAL | 81 THR LEU | 82 HIS |
| LEU | 75 VAL ASN | 76 HIS SER | 78 HIS ILE | 79 LEU VAL | 81 THR LEU | 82 TYR |
| LEU | 75 VAL ASN | 76 HIS SER | 78 HIS ILE | 79 MET VAL | 81 THR LEU | 82 PHE |
| LEU | 75 VAL ASN | 76 HIS SER | 78 HIS ILE | 79 MET VAL | 81 THR LEU | 82 HIS |
| LEU | 75 VAL ASN | 76 HIS SER | 78 HIS ILE | 79 MET VAL | 81 THR LEU | 82 TYR |
| LEU | 75 VAL ASN | 76 HIS SER | 78 HIS ILE | 79 THR VAL | 81 THR LEU | 82 PHE |
| LEU | 75 VAL ASN | 76 HIS SER | 78 HIS ILE | 79 THR VAL | 81 THR LEU | 82 HIS |
| LEU | 75 VAL ASN | 76 HIS SER | 78 HIS ILE | 79 THR VAL | 81 THR LEU | 82 TYR |
| LEU | 75 VAL ASN | 76 HIS SER | 78 HIS ILE | 79 VAL VAL | 81 THR LEU | 82 PHE |
| LEU | 75 VAL ASN | 76 HIS SER | 78 HIS ILE | 79 VAL VAL | 81 THR LEU | 82 HIS |
| LEU | 75 VAL ASN | 76 HIS SER | 78 HIS ILE | 79 VAL VAL | 81 THR LEU | 82 TYR |
| LEU | 75 VAL ASN | 76 HIS SER | 78 LYS ILE | 79 LEU VAL | 81 THR LEU | 82 PHE |
| LEU | 75 VAL ASN | 76 HIS SER | 78 LYS ILE | 79 LEU VAL | 81 THR LEU | 82 HIS |
| LEU | 75 VAL ASN | 76 HIS SER | 78 LYS ILE | 79 LEU VAL | 81 THR LEU | 82 TYR |
| LEU | 75 VAL ASN | 76 HIS SER | 78 LYS ILE | 79 MET VAL | 81 THR LEU | 82 PHE |
| LEU | 75 VAL ASN | 76 HIS SER | 78 LYS ILE | 79 MET VAL | 81 THR LEU | 82 HIS |
| LEU | 75 VAL ASN | 76 HIS SER | 78 LYS ILE | 79 MET VAL | 81 THR LEU | 82 TYR |
| LEU | 75 VAL ASN | 76 HIS SER | 78 LYS ILE | 79 THR VAL | 81 THR LEU | 82 PHE |
| LEU | 75 VAL ASN | 76 HIS SER | 78 LYS ILE | 79 THR VAL | 81 THR LEU | 82 HIS |
| LEU | 75 VAL ASN | 76 HIS SER | 78 LYS ILE | 79 THR VAL | 81 THR LEU | 82 TYR |
| LEU | 75 VAL ASN | 76 HIS SER | 78 LYS ILE | 79 VAL VAL | 81 THR LEU | 82 PHE |
| LEU | 75 VAL ASN | 76 HIS SER | 78 LYS ILE | 79 VAL VAL | 81 THR LEU | 82 HIS |
| LEU | 75 VAL ASN | 76 HIS SER | 78 LYS ILE | 79 VAL VAL | 81 THR LEU | 82 TYR |
| LEU | 75 VAL ASN | 76 HIS SER | 78 TYR ILE | 79 LEU VAL | 81 THR LEU | 82 PHE |
| LEU | 75 VAL ASN | 76 HIS SER | 78 TYR ILE | 79 LEU VAL | 81 THR LEU | 82 HIS |
| LEU | 75 VAL ASN | 76 HIS SER | 78 TYR ILE | 79 LEU VAL | 81 THR LEU | 82 TYR |
| LEU | 75 VAL ASN | 76 HIS SER | 78 TYR ILE | 79 MET VAL | 81 THR LEU | 82 PHE |
| LEU | 75 VAL ASN | 76 HIS SER | 78 TYR ILE | 79 MET VAL | 81 THR LEU | 82 HIS |
| LEU | 75 VAL ASN | 76 HIS SER | 73 TYR ILE | 79 MET VAL | 81 THR LEU | 82 TYR |
| LEU | 75 VAL ASN | 76 HIS SER | 78 TYR ILE | 79 THR VAL | 81 THR LEU | 82 PHE |
| LEU | 75 VAL ASN | 76 HIS SER | 78 TYR ILE | 79 THR VAL | 81 THR LEU | 82 HIS |
| LEU | 75 VAL ASN | 76 HIS SER | 78 TYR ILE | 79 THR VAL | 81 THR LEU | 82 TYR |
| LEU | 75 VAL ASN | 76 HIS SER | 78 TYR ILE | 79 VAL VAL | 81 THR LEU | 82 PHE |
| LEU | 75 VAL ASN | 76 HIS SER | 78 TYR ILE | 79 VAL VAL | 81 THR LEU | 82 HIS |

TABLE 8

Single Substitution Variants

| | | |
|---|---|---|
| LEU | 82 | PHE |
| LEU | 82 | HIS |
| VAL | 81 | THR |
| ILE | 79 | LEU |
| ILE | 79 | MET |
| ILE | 79 | THR |
| SER | 78 | ASN |
| SER | 78 | THR |
| ASN | 76 | HIS |
| LEU | 75 | ILE |
| LEU | 75 | MET |

TABLE 9

Double Substitution Variants

| | | | | |
|---|---|---|---|---|
| VAL | 81 THR | LEU | 82 | PHE |
| VAL | 81 THR | LEU | 82 | HIS |
| ILE | 79 LEU | LEU | 82 | PHE |
| ILE | 79 LEU | LEU | 82 | HIS |
| ILE | 79 MET | LEU | 82 | PHE |
| ILE | 79 MET | LEU | 82 | HIS |
| ILE | 79 THR | LEU | 82 | PHE |
| ILE | 79 THR | LEU | 82 | HIS |
| ILE | 79 LEU | VAL | 81 | THR |
| ILE | 79 MET | VAL | 81 | THR |
| ILE | 79 THR | VAL | 81 | THR |
| SER | 78 ASN | LEU | 82 | PHE |
| SER | 78 ASN | LEU | 82 | HIS |
| SER | 78 THR | LEU | 82 | PHE |
| SER | 78 THR | LEU | 82 | HIS |
| SER | 78 ASN | VAL | 81 | THR |
| SER | 78 THR | VAL | 81 | THR |
| SER | 78 ASN | ILE | 79 | LEU |
| SER | 78 ASN | ILE | 79 | MET |
| SER | 78 ASN | ILE | 79 | THR |
| SER | 78 THR | ILE | 79 | LEU |
| SER | 78 THR | ILE | 79 | MET |
| SER | 78 THR | ILE | 79 | THR |
| ASN | 76 HIS | LEU | 82 | PHE |
| ASN | 76 HIS | LEU | 82 | HIS |
| ASN | 76 HIS | VAL | 81 | THR |
| ASN | 76 HIS | ILE | 79 | LEU |
| ASN | 76 HIS | ILE | 79 | MET |
| ASN | 76 HIS | ILE | 79 | THR |
| ASN | 76 HIS | SER | 78 | ASN |
| ASN | 76 HIS | SER | 78 | THR |
| LEU | 75 ILE | LEU | 82 | PHE |
| LEU | 75 ILE | LEU | 82 | HIS |
| LEU | 75 MET | LEU | 82 | PHE |
| LEU | 75 MET | LEU | 82 | HIS |
| LEU | 75 ILE | VAL | 81 | THR |
| LEU | 75 MET | VAL | 81 | THR |
| LEU | 75 ILE | ILE | 79 | LEU |
| LEU | 75 ILE | ILE | 79 | MET |
| LEU | 75 ILE | ILE | 79 | THR |
| LEU | 75 MET | ILE | 79 | LEU |
| LEU | 75 MET | ILE | 79 | MET |
| LEU | 75 MET | ILE | 79 | THR |
| LEU | 75 ILE | SER | 78 | ASN |
| LEU | 75 ILE | SER | 78 | THR |
| LEU | 75 MET | SER | 78 | ASN |
| LEU | 75 MET | SER | 78 | THR |
| LEU | 75 ILE | ASN | 76 | HIS |
| LEU | 75 MET | ASN | 76 | HIS |

TABLE 10

Triple Substitution Variants

| | | | | | | |
|---|---|---|---|---|---|---|
| ILE | 79 LEU VAL | 81 THR LEU | 82 PHE |
| ILE | 79 LEU VAL | 81 THR LEU | 82 HIS |
| ILE | 79 MET VAL | 81 THR LEU | 82 PHE |
| ILE | 79 MET VAL | 81 THR LEU | 82 HIS |
| ILE | 79 THR VAL | 81 THR LEU | 82 PHE |
| ILE | 79 THR VAL | 81 THR LEU | 82 HIS |
| SER | 78 ASN VAL | 81 THR LEU | 82 PHE |
| SER | 78 ASN VAL | 81 THR LEU | 82 HIS |
| SER | 78 THR VAL | 81 THR LEU | 82 PHE |
| SER | 78 THR VAL | 81 THR LEU | 82 HIS |
| SER | 78 ASN ILE | 79 LEU LEU | 82 PHE |
| SER | 78 ASN ILE | 79 LEU LEU | 82 HIS |
| SER | 78 ASN ILE | 79 MET LEU | 82 PHE |
| SER | 78 ASN ILE | 79 MET LEU | 82 HIS |
| SER | 78 ASN ILE | 79 THR LEU | 82 PHE |
| SER | 78 ASN ILE | 79 THR LEU | 82 HIS |
| SER | 78 THR ILE | 79 LEU LEU | 82 PHE |
| SER | 78 THR ILE | 79 LEU LEU | 82 HIS |
| SER | 78 THR ILE | 79 MET LEU | 82 PHE |
| SER | 78 THR ILE | 79 MET LEU | 82 HIS |
| SER | 78 THR ILE | 79 THR LEU | 82 PHE |
| SER | 78 THR ILE | 79 THR LEU | 82 HIS |
| SER | 78 ASN ILE | 79 LEU VAL | 81 THR |
| SER | 78 ASN ILE | 79 MET VAL | 81 THR |
| SER | 78 ASN ILE | 79 THR VAL | 81 THR |
| SER | 78 THR ILE | 79 LEU VAL | 81 THR |
| SER | 78 THR ILE | 79 MET VAL | 81 THR |
| SER | 78 THR ILE | 79 THR VAL | 81 THR |
| ASN | 76 HIS VAL | 81 THR LEU | 82 PHE |
| ASN | 76 HIS VAL | 81 THR LEU | 82 HIS |
| ASN | 76 HIS ILE | 79 LEU LEU | 82 PHE |
| ASN | 76 HIS ILE | 79 LEU LEU | 82 HIS |
| ASN | 76 HIS ILE | 79 MET LEU | 82 PHE |
| ASN | 76 HIS ILE | 79 MET LEU | 82 HIS |
| ASN | 76 HIS ILE | 79 THR LEU | 82 PHE |
| ASN | 76 HIS ILE | 79 THR LEU | 82 HIS |
| ASN | 76 HIS ILE | 79 LEU VAL | 81 THR |
| ASN | 76 HIS ILE | 79 MET VAL | 81 THR |
| ASN | 76 HIS ILE | 79 THR VAL | 81 THR |
| ASN | 76 HIS SER | 78 ASN LEU | 82 PHE |
| ASN | 76 HIS SER | 78 ASN LEU | 82 HIS |
| ASN | 76 HIS SER | 78 THR LEU | 82 PHE |
| ASN | 76 HIS SER | 78 THR LEU | 82 HIS |
| ASN | 76 HIS SER | 78 ASN VAL | 81 THR |
| ASN | 76 HIS SER | 78 THR VAL | 81 THR |
| ASN | 76 HIS SER | 78 ASN ILE | 79 LEU |
| ASN | 76 HIS SER | 78 ASN ILE | 79 MET |
| ASN | 76 HIS SER | 78 ASN ILE | 79 THR |
| ASN | 76 HIS SER | 78 THR ILE | 79 LEU |
| ASN | 76 HIS SER | 78 THR ILE | 79 MET |
| ASN | 76 HIS SER | 78 THR ILE | 79 THR |
| LEU | 75 ILE VAL | 81 THR LEU | 82 PHE |
| LEU | 75 ILE VAL | 81 THR LEU | 82 HIS |
| LEU | 75 MET VAL | 81 THR LEU | 82 PHE |
| LEU | 75 MET VAL | 81 THR LEU | 82 HIS |
| LEU | 75 ILE ILE | 79 LEU LEU | 82 PHE |
| LEU | 75 ILE ILE | 79 LEU LEU | 82 HIS |
| LEU | 75 ILE ILE | 79 MET LEU | 82 PHE |
| LEU | 75 ILE ILE | 79 MET LEU | 82 HIS |
| LEU | 75 ILE ILE | 79 THR LEU | 82 PHE |
| LEU | 75 ILE ILE | 79 THR LEU | 82 HIS |
| LEU | 75 MET ILE | 79 LEU LEU | 82 PHE |
| LEU | 75 MET ILE | 79 LEU LEU | 82 HIS |
| LEU | 75 MET ILE | 79 MET LEU | 82 PHE |
| LEU | 75 MET ILE | 79 MET LEU | 82 HIS |
| LEU | 75 MET ILE | 79 THR LEU | 82 PHE |
| LEU | 75 MET ILE | 79 THR LEU | 82 HIS |
| LEU | 75 ILE ILE | 79 LEU VAL | 81 THR |
| LEU | 75 ILE ILE | 79 MET VAL | 81 THR |
| LEU | 75 ILE ILE | 79 THR VAL | 81 THR |
| LEU | 75 MET ILE | 79 LEU VAL | 81 THR |
| LEU | 75 MET ILE | 79 MET VAL | 81 THR |
| LEU | 75 MET ILE | 79 THR VAL | 81 THR |
| LEU | 75 ILE SER | 78 ASN LEU | 82 PHE |
| LEU | 75 ILE SER | 78 ASN LEU | 82 HIS |
| LEU | 75 ILE SER | 78 THR LEU | 82 PHE |
| LEU | 75 ILE SER | 78 THR LEU | 82 HIS |
| LEU | 75 MET SER | 78 ASN LEU | 82 PHE |
| LEU | 75 MET SER | 78 ASN LEU | 82 HIS |

TABLE 10-continued

Triple Substitution Variants

| | | | | |
|---|---|---|---|---|
| LEU | 75 MET SER | 78 THR LEU | 82 PHE | |
| LEU | 75 MET SER | 78 THR LEU | 82 HIS | |
| LEU | 75 ILE SER | 78 ASN VAL | 81 THR | |
| LEU | 75 ILE SER | 78 THR VAL | 81 THR | |
| LEU | 75 MET SER | 78 ASN VAL | 81 THR | |
| LEU | 75 MET SER | 78 THR VAL | 81 THR | |
| LEU | 75 ILE SER | 78 ASN ILE | 79 LEU | |
| LEU | 75 ILE SER | 78 ASN ILE | 79 MET | |
| LEU | 75 ILE SER | 78 ASN ILE | 79 THR | |
| LEU | 75 ILE SER | 78 THR ILE | 79 LEU | |
| LEU | 75 ILE SER | 78 THR ILE | 79 MET | |
| LEU | 75 ILE SER | 78 THR ILE | 79 THR | |
| LEU | 75 MET SER | 78 ASN ILE | 79 LEU | |
| LEU | 75 MET SER | 78 ASN ILE | 79 MET | |
| LEU | 75 MET SER | 78 ASN ILE | 79 THR | |
| LEU | 75 MET SER | 78 THR ILE | 79 LEU | |
| LEU | 75 MET SER | 78 THR ILE | 79 MET | |
| LEU | 75 MET SER | 78 THR ILE | 79 THR | |
| LEU | 75 ILE ASN | 76 HIS LEU | 82 PHE | |
| LEU | 75 ILE ASN | 76 HIS LEU | 82 HIS | |
| LEU | 75 MET ASN | 76 HIS LEU | 82 PHE | |
| LEU | 75 MET ASN | 76 HIS LEU | 82 HIS | |
| LEU | 75 ILE ASN | 76 HIS VAL | 81 THR | |
| LEU | 75 MET ASN | 76 HIS VAL | 81 THR | |
| LEU | 75 ILE ASN | 76 HIS ILE | 79 LEU | |
| LEU | 75 ILE ASN | 76 HIS ILE | 79 MET | |
| LEU | 75 ILE ASN | 76 HIS ILE | 79 THR | |
| LEU | 75 MET ASN | 76 HIS ILE | 79 LEU | |
| LEU | 75 MET ASN | 76 HIS ILE | 79 MET | |
| LEU | 75 MET ASN | 76 HIS ILE | 79 THR | |
| LEU | 75 ILE ASN | 76 HIS SER | 78 ASN | |
| LEU | 75 ILE ASN | 76 HIS SER | 78 THR | |
| LEU | 75 MET ASN | 76 HIS SER | 78 ASN | |
| LEU | 75 MET ASN | 76 HIS SER | 78 THR | |

TABLE 11

Quadruple Substitution Variants

| | | | | |
|---|---|---|---|---|
| SER | 78 ASN ILE | 79 LEU VAL | 81 THR LEU | 82 PHE |
| SER | 78 ASN ILE | 79 LEU VAL | 81 THR LEU | 82 HIS |
| SER | 78 ASN ILE | 79 MET VAL | 81 THR LEU | 82 PHE |
| SER | 78 ASN ILE | 79 MET VAL | 81 THR LEU | 82 HIS |
| SER | 78 ASN ILE | 79 THR VAL | 81 THR LEU | 82 PHE |
| SER | 78 ASN ILE | 79 THR VAL | 81 THR LEU | 82 HIS |
| SER | 78 THR ILE | 79 LEU VAL | 81 THR LEU | 82 PHE |
| SER | 78 THR ILE | 79 LEU VAL | 81 THR LEU | 82 HIS |
| SER | 78 THR ILE | 79 MET VAL | 81 THR LEU | 82 PHE |
| SER | 78 THR ILE | 79 MET VAL | 81 THR LEU | 82 HIS |
| SER | 78 THR ILE | 79 THR VAL | 81 THR LEU | 82 PHE |
| SER | 78 THR ILE | 79 THR VAL | 81 THR LEU | 82 HIS |
| ASN | 76 HIS ILE | 79 LEU VAL | 81 THR LEU | 82 PHE |
| ASN | 76 HIS ILE | 79 LEU VAL | 81 THR LEU | 82 HIS |
| ASN | 76 HIS ILE | 79 MET VAL | 81 THR LEU | 82 PHE |
| ASN | 76 HIS ILE | 79 MET VAL | 81 THR LEU | 82 HIS |
| ASN | 76 HIS ILE | 79 THR VAL | 81 THR LEU | 82 PHE |
| ASN | 76 HIS ILE | 79 THR VAL | 81 THR LEU | 82 HIS |
| ASN | 76 HIS SER | 78 ASN VAL | 81 THR LEU | 82 PHE |
| ASN | 76 HIS SER | 78 ASN VAL | 81 THR LEU | 82 HIS |
| ASN | 76 HIS SER | 78 THR VAL | 81 THR LEU | 82 PHE |
| ASN | 76 HIS SER | 78 THR VAL | 81 THR LEU | 82 HIS |
| ASN | 76 HIS SER | 78 ASN ILE | 79 LEU LEU | 82 PHE |
| ASN | 76 HIS SER | 78 ASN ILE | 79 LEU LEU | 82 HIS |
| ASN | 76 HIS SER | 78 ASN ILE | 79 MET LEU | 82 PHE |
| ASN | 76 HIS SER | 78 ASN ILE | 79 MET LEU | 82 HIS |
| ASN | 76 HIS SER | 78 ASN ILE | 79 THR LEU | 82 PHE |
| ASN | 76 HIS SER | 78 ASN ILE | 79 THR LEU | 82 HIS |
| ASN | 76 HIS SER | 78 THR ILE | 79 LEU LEU | 82 PHE |
| ASN | 76 HIS SER | 78 THR ILE | 79 LEU LEU | 82 HIS |
| ASN | 76 HIS SER | 78 THR ILE | 79 MET LEU | 82 PHE |
| ASN | 76 HIS SER | 78 THR ILE | 79 MET LEU | 82 HIS |
| ASN | 76 HIS SER | 78 THR ILE | 79 THR LEU | 82 PHE |
| ASN | 76 HIS SER | 78 THR ILE | 79 THR LEU | 82 HIS |
| ASN | 76 HIS SER | 78 ASN ILE | 79 LEU VAL | 81 THR |

TABLE 11-continued

Quadruple Substitution Variants

| | | | | |
|---|---|---|---|---|
| ASN | 76 HIS SER | 78 ASN ILE | 79 MET VAL | 81 THR |
| ASN | 76 HIS SER | 78 ASN ILE | 79 THR VAL | 81 THR |
| ASN | 76 HIS SER | 78 THR ILE | 79 LEU VAL | 81 THR |
| ASN | 76 HIS SER | 78 THR ILE | 79 MET VAL | 81 THR |
| ASN | 76 HIS SER | 78 THR ILE | 79 THR VAL | 81 THR |
| LEU | 75 ILE ILE | 79 LEU VAL | 81 THR LEU | 82 PHE |
| LEU | 75 ILE ILE | 79 LEU VAL | 81 THR LEU | 82 HIS |
| LEU | 75 ILE ILE | 79 MET VAL | 81 THR LEU | 82 PHE |
| LEU | 75 ILE ILE | 79 MET VAL | 81 THR LEU | 82 HIS |
| LEU | 75 ILE ILE | 79 THR VAL | 81 THR LEU | 82 PHE |
| LEU | 75 ILE ILE | 79 THR VAL | 81 THR LEU | 82 HIS |
| LEU | 75 MET ILE | 79 LEU VAL | 81 THR LEU | 82 PHE |
| LEU | 75 MET ILE | 79 LEU VAL | 81 THR LEU | 82 HIS |
| LEU | 75 MET ILE | 79 MET VAL | 81 THR LEU | 82 PHE |
| LEU | 75 MET ILE | 79 MET VAL | 81 THR LEU | 82 HIS |
| LEU | 75 MET ILE | 79 THR VAL | 81 THR LEU | 82 PHE |
| LEU | 75 MET ILE | 79 THR VAL | 81 THR LEU | 82 HIS |
| LEU | 75 ILE SER | 78 ASN VAL | 81 THR LEU | 82 PHE |
| LEU | 75 ILE SER | 78 ASN VAL | 81 THR LEU | 82 HIS |
| LEU | 75 ILE SER | 78 THR VAL | 81 THR LEU | 82 PHE |
| LEU | 75 ILE SER | 78 THR VAL | 81 THR LEU | 82 HIS |
| LEU | 75 MET SER | 78 ASN VAL | 81 THR LEU | 82 PHE |
| LEU | 75 MET SER | 78 ASN VAL | 81 THR LEU | 82 HIS |
| LEU | 75 MET SER | 78 THR VAL | 81 THR LEU | 82 PHE |
| LEU | 75 MET SER | 78 THR VAL | 81 THR LEU | 82 HIS |
| LEU | 75 ILE SER | 78 ASN ILE | 79 LEU LEU | 82 PHE |
| LEU | 75 ILE SER | 78 ASN ILE | 79 LEU LEU | 82 HIS |
| LEU | 75 ILE SER | 78 ASN ILE | 79 MET LEU | 82 PHE |
| LEU | 75 ILE SER | 78 ASN ILE | 79 MET LEU | 82 HIS |
| LEU | 75 ILE SER | 78 ASN ILE | 79 THR LEU | 82 PHE |
| LEU | 75 ILE SER | 78 ASN ILE | 79 THR LEU | 82 HIS |
| LEU | 75 ILE SER | 78 THR ILE | 79 LEU LEU | 82 PHE |
| LEU | 75 ILE SER | 78 THR ILE | 79 LEU LEU | 82 HIS |
| LEU | 75 ILE SER | 78 THR ILE | 79 MET LEU | 82 PHE |
| LEU | 75 ILE SER | 78 THR ILE | 79 MET LEU | 82 HIS |
| LEU | 75 ILE SER | 78 THR ILE | 79 THR LEU | 82 PHE |
| LEU | 75 ILE SER | 78 THR ILE | 79 THR LEU | 82 HIS |
| LEU | 75 MET SER | 78 ASN ILE | 79 LEU LEU | 82 PHE |
| LEU | 75 MET SER | 78 ASN ILE | 79 LEU LEU | 82 HIS |
| LEU | 75 MET SER | 78 ASN ILE | 79 MET LEU | 82 PHE |
| LEU | 75 MET SER | 78 ASN ILE | 79 MET LEU | 82 HIS |
| LEU | 75 MET SER | 78 ASN ILE | 79 THR LEU | 82 PHE |
| LEU | 75 MET SER | 78 ASN ILE | 79 THR LEU | 82 HIS |
| LEU | 75 MET SER | 78 THR ILE | 79 LEU LEU | 82 PHE |
| LEU | 75 MET SER | 78 THR ILE | 79 LEU LEU | 82 HIS |
| LEU | 75 MET SER | 78 THR ILE | 79 MET LEU | 82 PHE |
| LEU | 75 MET SER | 78 THR ILE | 79 MET LEU | 82 HIS |
| LEU | 75 MET SER | 78 THR ILE | 79 THR LEU | 82 PHE |
| LEU | 75 MET SER | 78 THR ILE | 79 THR LEU | 82 HIS |
| LEU | 75 ILE SER | 78 ASN ILE | 79 LEU VAL | 81 THR |
| LEU | 75 ILE SER | 78 ASN ILE | 79 MET VAL | 81 THR |
| LEU | 75 ILE SER | 78 ASN ILE | 79 THR VAL | 81 THR |
| LEU | 75 ILE SER | 78 THR ILE | 79 LEU VAL | 81 THR |
| LEU | 75 ILE SER | 78 THR ILE | 79 MET VAL | 81 THR |
| LEU | 75 ILE SER | 78 THR ILE | 79 THR VAL | 81 THR |
| LEU | 75 MET SER | 78 ASN ILE | 79 LEU VAL | 81 THR |
| LEU | 75 MET SER | 78 ASN ILE | 79 MET VAL | 81 THR |
| LEU | 75 MET SER | 78 ASN ILE | 79 THR VAL | 81 THR |
| LEU | 75 MET SER | 78 THR ILE | 79 LEU VAL | 81 THR |
| LEU | 75 MET SER | 78 THR ILE | 79 MET VAL | 81 THR |
| LEU | 75 MET SER | 78 THR ILE | 79 THR VAL | 81 THR |
| LEU | 75 ILE ASN | 76 HIS VAL | 81 THR LEU | 82 PHE |
| LEU | 75 ILE ASN | 76 HIS VAL | 81 THR LEU | 82 HIS |
| LEU | 75 MET ASN | 76 HIS VAL | 81 THR LEU | 82 PHE |
| LEU | 75 MET ASN | 76 HIS VAL | 81 THR LEU | 82 HIS |
| LEU | 75 ILE ASN | 76 HIS ILE | 79 LEU LEU | 82 PHE |
| LEU | 75 ILE ASN | 76 HIS ILE | 79 LEU LEU | 82 HIS |
| LEU | 75 ILE ASN | 76 HIS ILE | 79 MET LEU | 82 PHE |
| LEU | 75 ILE ASN | 76 HIS ILE | 79 MET LEU | 82 HIS |
| LEU | 75 ILE ASN | 76 HIS ILE | 79 THR LEU | 82 PHE |
| LEU | 75 ILE ASN | 76 HIS ILE | 79 THR LEU | 82 HIS |
| LEU | 75 MET ASN | 76 HIS ILE | 79 LEU LEU | 82 PHE |
| LEU | 75 MET ASN | 76 HIS ILE | 79 LEU LEU | 82 HIS |
| LEU | 75 MET ASN | 76 HIS ILE | 79 MET LEU | 82 PHE |
| LEU | 75 MET ASN | 76 HIS ILE | 79 MET LEU | 82 HIS |
| LEU | 75 MET ASN | 76 HIS ILE | 79 THR LEU | 82 PHE |
| LEU | 75 MET ASN | 76 HIS ILE | 79 THR LEU | 82 HIS |

TABLE 11-continued

| Quadruple Substitution Variants | | | | |
|---|---|---|---|---|
| LEU | 75 ILE ASN | 76 HIS ILE | 79 LEU VAL | 81 THR |
| LEU | 75 ILE ASN | 76 HIS ILE | 79 MET VAL | 81 THR |
| LEU | 75 ILE ASN | 76 HIS ILE | 79 THR VAL | 81 THR |
| LEU | 75 MET ASN | 76 HIS ILE | 79 LEU VAL | 81 THR |
| LEU | 75 MET ASN | 76 HIS ILE | 79 MET VAL | 81 THR |
| LEU | 75 MET ASN | 76 HIS ILE | 79 THR VAL | 81 THR |
| LEU | 75 ILE ASN | 76 HIS SER | 78 ASN LEU | 82 PHE |
| LEU | 75 ILE ASN | 76 HIS SER | 78 ASN LEU | 82 HIS |
| LEU | 75 ILE ASN | 76 HIS SER | 78 THR LEU | 82 PHE |
| LEU | 75 ILE ASN | 76 HIS SER | 78 THR LEU | 82 HIS |
| LEU | 75 MET ASN | 76 HIS SER | 78 ASN LEU | 82 PHE |
| LEU | 75 MET ASN | 76 HIS SER | 78 ASN LEU | 82 HIS |
| LEU | 75 MET ASN | 76 HIS SER | 78 THR LEU | 82 PHE |
| LEU | 75 MET ASN | 76 HIS SER | 78 THR LEU | 82 HIS |
| LEU | 75 ILE ASN | 76 HIS SER | 78 ASN VAL | 81 THR |
| LEU | 75 ILE ASN | 76 HIS SER | 78 THR VAL | 81 THR |
| LEU | 75 MET ASN | 76 HIS SER | 78 ASN VAL | 81 THR |
| LEU | 75 MET ASN | 76 HIS SER | 78 THR VAL | 81 THR |
| LEU | 75 ILE ASN | 76 HIS SER | 78 ASN ILE | 79 LEU |
| LEU | 75 ILE ASN | 76 HIS SER | 78 ASN ILE | 79 MET |
| LEU | 75 ILE ASN | 76 HIS SER | 78 ASN ILE | 79 THR |
| LEU | 75 ILE ASN | 76 HIS SER | 78 THR ILE | 79 LEU |
| LEU | 75 ILE ASN | 76 HIS SER | 78 THR ILE | 79 MET |
| LEU | 75 ILE ASN | 76 HIS SER | 78 THR ILE | 79 THR |
| LEU | 75 MET ASN | 76 HIS SER | 78 ASN ILE | 79 LEU |
| LEU | 75 MET ASN | 76 HIS SER | 78 ASN ILE | 79 MET |
| LEU | 75 MET ASN | 76 HIS SER | 78 ASN ILE | 79 THR |
| LEU | 75 MET ASN | 76 HIS SER | 78 THR ILE | 79 LEU |
| LEU | 75 MET ASN | 76 HIS SER | 78 THR ILE | 79 MET |
| LEU | 75 MET ASN | 76 HIS SER | 78 THR ILE | 79 THR |

TABLE 12

| Quintuple Substitution Variants | | | | | |
|---|---|---|---|---|---|
| ASN | 76 HIS SER | 78 ASN ILE | 79 LEU VAL | 81 THR LEU | 82 PHE |
| ASN | 76 HIS SER | 78 ASN ILE | 79 LEU VAL | 81 THR LEU | 82 HIS |
| ASN | 76 HIS SER | 78 ASN ILE | 79 MET VAL | 81 THR LEU | 82 PHE |
| ASN | 76 HIS SER | 78 ASN ILE | 79 MET VAL | 81 THR LEU | 82 HIS |
| ASN | 76 HIS SER | 78 ASN ILE | 79 THR VAL | 81 THR LEU | 82 PHE |
| ASN | 76 HIS SER | 78 ASN ILE | 79 THR VAL | 81 THR LEU | 82 HIS |
| ASN | 76 HIS SER | 78 THR ILE | 79 LEU VAL | 81 THR LEU | 82 PHE |
| ASN | 76 HIS SER | 78 THR ILE | 79 LEU VAL | 81 THR LEU | 82 HIS |
| ASN | 76 HIS SER | 78 THR ILE | 79 MET VAL | 81 THR LEU | 82 PHE |
| ASN | 76 HIS SER | 78 THR ILE | 79 MET VAL | 81 THR LEU | 82 HIS |
| ASN | 76 HIS SER | 78 THR ILE | 79 THR VAL | 81 THR LEU | 82 PHE |
| ASN | 76 HIS SER | 78 THR ILE | 79 THR VAL | 81 THR LEU | 82 HIS |
| LEU | 75 ILE SER | 78 ASN ILE | 79 LEU VAL | 81 THR LEU | 82 PHE |
| LEU | 75 ILE SER | 78 ASN ILE | 79 LEU VAL | 81 THR LEU | 82 HIS |
| LEU | 75 ILE SER | 78 ASN ILE | 79 MET VAL | 81 THR LEU | 82 PHE |
| LEU | 75 ILE SER | 78 ASN ILE | 79 MET VAL | 81 THR LEU | 82 HIS |
| LEU | 75 ILE SER | 78 ASN ILE | 79 THR VAL | 81 THR LEU | 82 PHE |
| LEU | 75 ILE SER | 78 ASN ILE | 79 THR VAL | 81 THR LEU | 82 HIS |
| LEU | 75 ILE SER | 78 THR ILE | 79 LEU VAL | 81 THR LEU | 82 PHE |
| LEU | 75 ILE SER | 78 THR ILE | 79 LEU VAL | 81 THR LEU | 82 HIS |
| LEU | 75 ILE SER | 78 THR ILE | 79 MET VAL | 81 THR LEU | 82 PHE |
| LEU | 75 ILE SER | 78 THR ILE | 79 MET VAL | 81 THR LEU | 82 HIS |
| LEU | 75 ILE SER | 78 THR ILE | 79 THR VAL | 81 THR LEU | 82 PHE |
| LEU | 75 ILE SER | 78 THR ILE | 79 THR VAL | 81 THR LEU | 82 HIS |
| LEU | 75 MET SER | 78 ASN ILE | 79 LEU VAL | 81 THR LEU | 82 PHE |
| LEU | 75 MET SER | 78 ASN ILE | 79 LEU VAL | 81 THR LEU | 82 HIS |
| LEU | 75 MET SER | 78 ASN ILE | 79 MET VAL | 81 THR LEU | 82 PHE |
| LEU | 75 MET SER | 78 ASN ILE | 79 MET VAL | 81 THR LEU | 82 HIS |
| LEU | 75 MET SER | 78 ASN ILE | 79 THR VAL | 81 THR LEU | 82 PHE |
| LEU | 75 MET SER | 78 ASN ILE | 79 THR VAL | 81 THR LEU | 82 HIS |
| LEU | 75 MET SER | 78 THR ILE | 79 LEU VAL | 81 THR LEU | 82 PHE |
| LEU | 75 MET SER | 78 THR ILE | 79 LEU VAL | 81 THR LEU | 82 HIS |
| LEU | 75 MET SER | 78 THR ILE | 79 MET VAL | 81 THR LEU | 82 PHE |
| LEU | 75 MET SER | 78 THR ILE | 79 MET VAL | 81 THR LEU | 82 HIS |
| LEU | 75 MET SER | 78 THR ILE | 79 THR VAL | 81 THR LEU | 82 PHE |
| LEU | 75 MET SER | 78 THR ILE | 79 THR VAL | 81 THR LEU | 82 HIS |
| LEU | 75 ILE ASN | 76 HIS ILE | 79 LEU VAL | 81 THR LEU | 82 PHE |
| LEU | 75 ILE ASN | 76 HIS ILE | 79 LEU VAL | 81 THR LEU | 82 HIS |
| LEU | 75 ILE ASN | 76 HIS ILE | 79 MET VAL | 81 THR LEU | 82 PHE |

TABLE 12-continued

| Quintuple Substitution Variants | | | | | |
|---|---|---|---|---|---|
| LEU | 75 ILE ASN | 76 HIS ILE | 79 MET VAL | 81 THR LEU | 82 HIS |
| LEU | 75 ILE ASN | 76 HIS ILE | 79 THR VAL | 81 THR LEU | 82 PHE |
| LEU | 75 ILE ASN | 76 HIS ILE | 79 THR VAL | 81 THR LEU | 82 HIS |
| LEU | 75 MET ASN | 76 HIS ILE | 79 LEU VAL | 81 THR LEU | 82 PHE |
| LEU | 75 MET ASN | 76 HIS ILE | 79 LEU VAL | 81 THR LEU | 82 HIS |
| LEU | 75 MET ASN | 76 HIS ILE | 79 MET VAL | 81 THR LEU | 82 PHE |
| LEU | 75 MET ASN | 76 HIS ILE | 79 MET VAL | 81 THR LEU | 82 HIS |
| LEU | 75 MET ASN | 76 HIS ILE | 79 THR VAL | 81 THR LEU | 82 PHE |
| LEU | 75 MET ASN | 76 HIS ILE | 79 THR VAL | 81 THR LEU | 82 HIS |
| LEU | 75 ILE ASN | 76 HIS SER | 78 ASN VAL | 81 THR LEU | 82 PHE |
| LEU | 75 ILE ASN | 76 HIS SER | 78 ASN VAL | 81 THR LEU | 82 HIS |
| LEU | 75 ILE ASN | 76 HIS SER | 78 THR VAL | 81 THR LEU | 82 PHE |
| LEU | 75 ILE ASN | 76 HIS SER | 78 THR VAL | 81 THR LEU | 82 HIS |
| LEU | 75 MET ASN | 76 HIS SER | 78 ASN VAL | 81 THR LEU | 82 PHE |
| LEU | 75 MET ASN | 76 HIS SER | 78 ASN VAL | 81 THR LEU | 82 HIS |
| LEU | 75 MET ASN | 76 HIS SER | 78 THR VAL | 81 THR LEU | 82 PHE |
| LEU | 75 MET ASN | 76 HIS SER | 78 THR VAL | 81 THR LEU | 82 HIS |
| LEU | 75 ILE ASN | 76 HIS SER | 78 ASN ILE | 79 LEU LEU | 82 PHE |
| LEU | 75 ILE ASN | 76 HIS SER | 78 ASN ILE | 79 LEU LEU | 82 HIS |
| LEU | 75 ILE ASN | 76 HIS SER | 78 ASN ILE | 79 MET LEU | 82 PHE |
| LEU | 75 ILE ASN | 76 HIS SER | 78 ASN ILE | 79 MET LEU | 82 HIS |
| LEU | 75 ILE ASN | 76 HIS SER | 78 ASN ILE | 79 THR LEU | 82 PHE |
| LEU | 75 ILE ASN | 76 HIS SER | 78 ASN ILE | 79 THR LEU | 82 HIS |
| LEU | 75 ILE ASN | 76 HIS SER | 78 THR ILE | 79 LEU LEU | 82 PHE |
| LEU | 75 ILE ASN | 76 HIS SER | 78 THR ILE | 79 LEU LEU | 82 HIS |
| LEU | 75 ILE ASN | 76 HIS SER | 78 THR ILE | 79 MET LEU | 82 PHE |
| LEU | 75 ILE ASN | 76 HIS SER | 78 THR ILE | 79 MET LEU | 82 HIS |
| LEU | 75 ILE ASN | 76 HIS SER | 78 THR ILE | 79 THR LEU | 82 PHE |
| LEU | 75 ILE ASN | 76 HIS SER | 78 THR ILE | 79 THR LEU | 82 HIS |
| LEU | 75 MET ASN | 76 HIS SER | 78 ASN ILE | 79 LEU LEU | 82 PHE |
| LEU | 75 MET ASN | 76 HIS SER | 78 ASN ILE | 79 LEU LEU | 82 HIS |
| LEU | 75 MET ASN | 76 HIS SER | 78 ASN ILE | 79 MET LEU | 82 PHE |
| LEU | 75 MET ASN | 76 HIS SER | 78 ASN ILE | 79 MET LEU | 82 HIS |
| LEU | 75 MET ASN | 76 HIS SER | 78 ASN ILE | 79 THR LEU | 82 PHE |
| LEU | 75 MET ASN | 76 HIS SER | 78 ASN ILE | 79 THR LEU | 82 HIS |
| LEU | 75 MET ASN | 76 HIS SER | 78 THR ILE | 79 LEU LEU | 82 PHE |
| LEU | 75 MET ASN | 76 HIS SER | 78 THR ILE | 79 LEU LEU | 82 HIS |
| LEU | 75 MET ASN | 76 HIS SER | 78 THR ILE | 79 MET LEU | 82 PHE |
| LEU | 75 MET ASN | 76 HIS SER | 78 THR ILE | 79 MET LEU | 82 HIS |
| LEU | 75 MET ASN | 76 HIS SER | 78 THR ILE | 79 THR LEU | 82 PHE |
| LEU | 75 MET ASN | 76 HIS SER | 78 THR ILE | 79 THR LEU | 82 HIS |
| LEU | 75 ILE ASN | 76 HIS SER | 78 ASN ILE | 79 LEU VAL | 81 THR |
| LEU | 75 ILE ASN | 76 HIS SER | 78 ASN ILE | 79 MET VAL | 81 THR |
| LEU | 75 ILE ASN | 76 HIS SER | 78 ASN ILE | 79 THR VAL | 81 THR |
| LEU | 75 ILE ASN | 76 HIS SER | 78 THR ILE | 79 LEU VAL | 81 THR |
| LEU | 75 ILE ASN | 76 HIS SER | 78 THR ILE | 79 MET VAL | 81 THR |
| LEU | 75 ILE ASN | 76 HIS SER | 78 THR ILE | 79 THR VAL | 81 THR |
| LEU | 75 MET ASN | 76 HIS SER | 78 ASN ILE | 79 LEU VAL | 81 THR |
| LEU | 75 MET ASN | 76 HIS SER | 78 ASN ILE | 79 MET VAL | 81 THR |
| LEU | 75 MET ASN | 76 HIS SER | 78 ASN ILE | 79 THR VAL | 81 THR |
| LEU | 75 MET ASN | 76 HIS SER | 78 THR ILE | 79 LEU VAL | 81 THR |
| LEU | 75 MET ASN | 76 HIS SER | 78 THR ILE | 79 MET VAL | 81 THR |
| LEU | 75 MET ASN | 76 HIS SER | 78 THR ILE | 79 THR VAL | 81 THR |

TABLE 13

Sextuple Substitution Variants

| | | | | | |
|---|---|---|---|---|---|
| LEU 75 ILE ASN | 76 HIS SER | 78 ASN ILE | 79 LEU VAL | 81 THR LEU | 82 PHE |
| LEU 75 ILE ASN | 76 HIS SER | 78 ASN ILE | 79 LEU VAL | 81 THR LEU | 82 HIS |
| LEU 75 ILE ASN | 76 HIS SER | 78 ASN ILE | 79 MET VAL | 81 THR LEU | 82 PHE |
| LEU 75 ILE ASN | 76 HIS SER | 78 ASN ILE | 79 MET VAL | 81 THR LEU | 82 HIS |
| LEU 75 ILE ASN | 76 HIS SER | 78 ASN ILE | 79 THR VAL | 81 THR LEU | 82 PHE |
| LEU 75 ILE ASN | 76 HIS SER | 78 ASN ILE | 79 THR VAL | 81 THR LEU | 82 HIS |
| LEU 75 ILE ASN | 76 HIS SER | 78 THR ILE | 79 LEU VAL | 81 THR LEU | 82 PHE |
| LEU 75 ILE ASN | 76 HIS SER | 78 THR ILE | 79 LEU VAL | 81 THR LEU | 82 HIS |
| LEU 75 ILE ASN | 76 HIS SER | 78 THR ILE | 79 MET VAL | 81 THR LEU | 82 PHE |
| LEU 75 ILE ASN | 76 HIS SER | 78 THR ILE | 79 MET VAL | 81 THR LEU | 82 HIS |
| LEU 75 ILE ASN | 76 HIS SER | 78 THR ILE | 79 THR VAL | 81 THR LEU | 82 PHE |
| LEU 75 ILE ASN | 76 HIS SER | 78 THR ILE | 79 THR VAL | 81 THR LEU | 82 HIS |
| LEU 75 MET ASN | 76 HIS SER | 78 ASN ILE | 79 LEU VAL | 81 THR LEU | 82 PHE |
| LEU 75 MET ASN | 76 HIS SER | 78 ASN ILE | 79 LEU VAL | 81 THR LEU | 82 HIS |
| LEU 75 MET ASN | 76 HIS SER | 78 ASN ILE | 79 MET VAL | 81 THR LEU | 82 PHE |
| LEU 75 MET ASN | 76 HIS SER | 78 ASN ILE | 79 MET VAL | 81 THR LEU | 82 HIS |
| LEU 75 MET ASN | 76 HIS SER | 78 ASN ILE | 79 THR VAL | 81 THR LEU | 82 PHE |
| LEU 75 MET ASN | 76 HIS SER | 78 ASN ILE | 79 THR VAL | 81 THR LEU | 82 HIS |
| LEU 75 MET ASN | 76 HIS SER | 78 THR ILE | 79 LEU VAL | 81 THR LEU | 82 PHE |
| LEU 75 MET ASN | 76 HIS SER | 78 THR ILE | 79 LEU VAL | 81 THR LEU | 82 HIS |
| LEU 75 MET ASN | 76 HIS SER | 78 THR ILE | 79 MET VAL | 81 THR LEU | 82 PHE |
| LEU 75 MET ASN | 76 HIS SER | 78 THR ILE | 79 MET VAL | 81 THR LEU | 82 HIS |
| LEU 75 MET ASN | 76 HIS SER | 78 THR ILE | 79 THR VAL | 81 THR LEU | 82 PHE |
| LEU 75 MET ASN | 76 HIS SER | 78 THR ILE | 79 THR VAL | 81 THR LEU | 82 HIS |

One or more additional substitution mutations ("stabilizing substitutions") outside the epitope region may additionally be made in order to, for example, restabilize the protease upon mutation of the epitope region or to enhance the proteolytic activity of the variant. Many such stabilizing mutations are well known in the art. Examples of such stabilizing mutations are disclosed in, for example, WO 95/10591, Baeck et al., published Apr. 20, 1995; U.S. Pat. No. 4,914,031, Zukowski et al., issued Apr. 3, 1990; U.S. Pat. No. 5,470,733, Bryan et al., issued Nov. 28, 1995; U.S. Pat. No. 5,567,601, Bryan et al., issued Oct. 22, 1996; WO 89/07642, U.S. Pat. No. 5,707,848, Bryan et al., issued Jan. 13, 1998; Van Eekelen et al., published Aug. 24, 1989; WO 87/04461, Stabinsky et al., published Jul. 30, 1987; U.S. Pat. No. 4,760,025, Estell et al., issued Jul. 26, 1988; WO 92/11348, Branner et al., published Jul. 9, 1992; EP 0,405, 901, Casteleijn et al., published Jan. 2, 1991; WO 91/00345, Branner et al., published Jan. 10, 1991; and WO 94/10020, Brode et al., published Mar. 23, 1995.

Preferred stabilizing mutations include one or more of: 1107V; K213R; Y217L; Y217K; N218S; G169A; M50F; Q19E; P5A; S9A; I31L; E156S; G169A; N212G; S188P; T254A; S3C+Q206C; and Q271E. The more preferred stabilizing mutations include one or more of P5A; S9A; I31L; E156S; G169A; N212G; S188P; T254A; S3C+Q206C; Q271E; Y217L; and Y217K. The most preferred stabilizing mutations include Y217L and Y217K.

A preferred variant for use in personal care compositions is Δ75–83, Y217L.

Method of Making

The variants are prepared by mutating the nucleotide sequences that code for a wild-type serine protease, thereby resulting in variants having modified amino acid sequences. Such methods are well-known in the art; one such method is set forth below:

A phagemid (pSS-5) containing the wild-type subtilisin BPN' gene (Mitchison, C. and J. A. Wells, "Protein Engineering of Disulfide Bonds in Subtilisin BPN'", *Biochemistry*, Vol. 28, pp. 4807–4815 (1989) is transformed into *Escherichia coli* dut-ung- strain CJ236 and a single stranded uracil-containing DNA template is produced using the VCSM13 helper phage (Kunkel et al., "Rapid and Efficient Site-Specific Mutagenesis Without Phenotypic Selection", *Methods in Enzymology*, Vol 154, pp. 367–382 (1987), as modified by Yuckenberg et al., "Site-Directed in vitro Mutagenesis Using Uracil-Containing DNA and Phagemid Vectors", Directed Mutagenesis—A Practical *Approach*, McPherson, M. J. ed., pp. 27–48 (1991). Primer site-directed mutagenesis modified from the method of Zoller and Smith (Zoller, M. J., and M. Smith, "Oligonucleotide—Directed Mutagenesis Using M13—Derived Vectors: An Efficient and General Procedure for the Production of Point Mutations in any Fragment of DNA", *Nucleic Acids Research*, Vol. 10, pp. 6487–6500 (1982) is used to produce all mutants (essentially as presented by Yuckenberg et al., supra).

Oligonucleotides are made using a 380B DNA synthesizer (Applied Biosystems Inc.). Mutagenesis reaction products are transformed into *Escherichia coli* strain MM294 (American Type Culture Collection *E. coli* 33625). All mutations are confirmed by DNA sequencing and the isolated DNA is transformed into the *Bacillus subtilis* expression strain PG632 (Saunders et al., "Optimization of the Signal-Sequence Cleavage Site for Secretion from *Bacillus subtilis* of a 34-amino acid Fragment of Human Parathyroid Hormone", *Gene*, Vol. 102, pp. 277–282 (1991) and Yang et al., "Cloning of the Neutral Protease Gene of *Bacillus subtilis* and the Use of the Cloned Gene to Create an in vitro-Derived Deletion Mutation", *Journal of Bacteriology*, Vol. 160, pp. 15–21 (1984). Preliminary assessment of variant activity is determined by the ability of PG632 cells transformed with mutant plasmids to hydrolyze casein.

Fermentation is as follows. *Bacillus subtilis* cells (PG632) containing the variant of interest are grown to mid-log phase in one liter of LB broth containing 10 g/L glucose, and inoculated into a Biostat C fermentor (Braun Biotech, Inc., Allentown, Pa.) in a total volume of 9 liters. The fermentation medium contains yeast extract, casein hydrosylate, soluble—partially hydrolyzed starch (Maltrin M-250), antifoam, buffers, and trace minerals (see "Biology of Bacilli: Applications to Industry", Doi, R. H. and M.

McGloughlin, eds. (1992)). The broth is kept at a constant pH of 7.5 during the fermentation run. Kanamycin (50 g/mL) is added for antibiotic selection of the mutagenized plasmid. The cells are grown for 18 hours at 37 °C. to an $A_{600}$ of about 60 and the product harvested.

The fermentation broth is taken through the following steps to obtain pure variant. The broth is cleared of *Bacillus subtilis* cells by tangential flow against a 0.16 μm membrane. The cell-free broth is then concentrated by ultrafiltration with a 8000 molecular weight cut-off membrane. The pH is adjusted to 5.5 with concentrated MES buffer (2-(N-morpholino)ethanesulfonic acid). The variant is further purified by cation exchange chromatography with S-sepharose and elution with NaCl gradients. (see Scopes, R. K., "Protein Purification Principles and Practice", Springer-Verlag, New York (1984).

A pNA assay (DelMar et al., *Analytical Biochemistry*, Vol. 99, pp. 316–320 (1979)) is used to determine the active variant concentration for fractions collected during gradient elution. This assay measures the rate at which p-nitroaniline is released as the variant hydrolyzes the soluble synthetic substrate, succinyl-alanine-alanine-proline-phenylalanine-p-nitroaniline (sAAPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the variant purity, and is used to identify fractions to be pooled for the stock solution.

To avoid autolysis of the variant during storage, an equal weight of propylene glycol is added to the pooled fractions obtained from the chromatography column. Upon completion of the purification procedure the purity of the stock variant solution is checked with SDS-PAGE (sodium dodecyl sulfate polyacrylamide gel electrophoresis) and the absolute enzyme concentration is determined via an active site titration method using trypsin inhibitor type II-T: turkey egg white (Sigma Chemical Company, St. Louis, Mo.).

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M tris buffer (tris (hydroxymethyl-aminomethane) containing 0.0M $CaCl_2$ and pH adjusted to 8.6 with HCl. All experiments are carried out at pH 8.6 in tris buffer thermostated at 25 °C.

Analytical Methods

The present variants may be tested for enzymatic activity and immune and/or allergenic response using the following methods, both of which are known to one skilled in the art. Alternatively, other methods well-known in the art may be used.

Variant Activity

The protease activity of a variant of the present invention may be assayed by methods which are well-known in the art. Two such methods are set forth herein below:

Skin Flake Activity Method

Using Scotch® #3750G tape, human skin flakes are stripped from the legs of a subject repeatedly until the tape is substantially opaque with flakes. The tape is then cut into 1 inch by 1 inch squares and set aside. In a 10 mm by 35 mm petri dish, 2 mL of 0.75 mg/mL of a control enzyme (for example, subtilisin BPN') or the variant to be tested is added in 0.01 M $KH_2PO_4$ pH 5.5 buffer. To this solution 1 mL of 2.5% sodium laurate pH 8.6 solution is added. The solution is gently mixed on a platform shaker. The previously prepared tape square is soaked in the solution (flake side up) for ten minutes continuing gentle mixing. The tape square is then rinsed gently in tap water for fifteen seconds. Stevenel Blue Stain (3 mL, commercially available from Sigma Chemical Co., St. Louis, Mo.) is pipetted into a clean petri dish. The rinsed tape square is placed into the stain for three minutes (flake side up) with gentle mixing. The tape square is removed from the stain and rinsed consecutively in two beakers of 300 mL distilled water, for fifteen seconds per rinse. The tape square is allowed to air-dry. The color intensity between the tape square obtained from the control enzyme and the tape square obtained from the variant is compared visually or by using a chromameter. Relative to the control enzyme tape square, a variant tape square showing less color intensity is indicative of a variant having higher activity.

Dyed Collagen Activity Method

Combine 50 mL of 0.1 M tris buffer (tris-hydroxymethyl-aminomethane) containing 0.01 M $CaCl_2$ to give pH 8.6, and 0.5 g azocoll (azo dye impregnated collagen, commercially available from Sigma Chemical Co., St. Louis, Mo.). Incubate this mixture at 25 °C. while gently mixing with a platform shaker. Filter 2 mL of the mixture through a 0.2 micron syringe filter and read absorbance of the mixture at 520 nm to zero a spectrophotometer. Add 1 ppm of a control enzyme (for example, subtilisin BPN') or the variant to be tested to the remaining 48 mL of tris/azocoll mixture. Filter 2 mL of the control/variant containing solution through a 0.2 micron syringe filter every two minutes for a total of ten minutes. For each filtered sample, read the absorbance immediately at 520 run. Plot the results against time. The slopes of the control and the test conjugate are indicative of relative activities of the samples. A higher slope is indicative of a higher activity. The test variant activity (slope) may be expressed as a percent of the control activity (slope).

T-Cell Proliferation Assay

The immune and/or allergenic potential of the variants of the present invention may be determined using a T-cell proliferation assay such as the assay presented hereinbelow. This assay is a variation of the assay disclosed in Bungy Poor Fard et al., "T Cell Epitopes of the Major Fraction of Rye Grass *Lolium perenne* (Lol p I) Defined Using Overlapping Peptides in vitro and in vivo", *Clinical Experimental Immunology*, Vol. 94, pp. 111–116(1993).

The blood of subjects allergic to subtilisin BPN'(prick test positive) and control subjects (prick test negative) are used in this assay. Blood (~60 mL) from each subject is collected and mononuclear cells are harvested using ficoll-hypaque (which may be obtained from Pharmacia, Piscataway, N.J.). The cells are washed twice in RPMI 1640 (which may be obtained from Gibco, Grand Island, N.Y.) and then resuspended in complete medium RPMI supplemented with 10% human AB-serumn, 2 mM L-glutamine, and 25 μg/mL gentamicin (which may be obtained from Gibco). Cells are cultured at a concentration of $2 \times 10^5$ cells/well in 0.2 mL of complete medium in U-bottomed 96-well microtiter plates. The potential antigen to be tested (either inactivated BPN' as positive control or a variant of the present invention is added at a final concentration up to about 40 μg/mL. Cultures are incubated at 37° C. in 5% $CO_2$. After five days, 1 μCi/well of methyl-$^3$H-thymidine is added and 18 hours later the cells are harvested. $^3$H-thymidine incorporation by the cell is assessed as a measure of T-cell proliferation by liquid scintillation counting.

Compositions of the Present Invention

The variants herein can be used in any application which is suitable for the respective wild-type protease. One such example includes cleaning compositions. Because of the desirable reduced allergenicity and/or immunogenicity properties of the present variants, the variants may further be used in applications which have minimally benefitted from the use of proteases. Examples of such applications include those in which the variant necessarily comes in close contact with human skin, such as with the use of personal care compositions.

Cleaning Compositions

The variants may be utilized in cleaning compositions including, but not limited to, laundry compositions, hard surface cleansing compositions, light duty cleaning compositions including dish cleansing compositions, and automatic dishwasher detergent compositions.

The cleaning compositions herein comprise an effective amount of one or more variants of the present invention and a cleaning composition carrier.

As used herein, "effective amount of variant", or the like, refers to the quantity of variant necessary to achieve the proteolytic activity necessary in the specific cleaning composition. Such effective amounts are readily ascertained by one of ordinary skill in the art and is based on many factors, such as the particular variant used, the cleaning application, the specific composition of the cleaning composition, and whether a liquid or dry (e.g., granular, bar) composition is desired, and the like. Preferably, the cleaning compositions comprise from about 0.0001% to about 10%, more preferably from about 0.001% to about 1%, and most preferably from about 0.01% to about 0.1% of one or more variants of the present invention. Several examples of various cleaning compositions wherein the variants may be employed are discussed in further detail below.

In addition to the present variants, the present cleaning compositions further comprise a cleaning composition carrier comprising one or more cleaning composition materials compatible with the variant. The term "cleaning composition material", as used herein, means any material selected for the particular type of cleaning composition desired and the form of the product (e.g., liquid, granule, bar, spray, stick, paste, gel), which materials are also compatible with the variant used in the composition. The specific selection of cleaning composition materials is readily made by considering the material to be cleaned, the desired form of the composition for the cleaning condition during use. The term "compatible", as used herein, means the cleaning composition materials do not reduce the proteolytic activity of the variant to such an extent that the variant is not effective as desired during normal use situations. Specific cleaning composition materials are exemplified in detail hereinafter.

The variants of the present invention may be used in a variety of detergent compositions where high sudsing and good cleansing activity is desired. Thus, the variants can be used with various conventional ingredients to provide fully-formulated hard-surface cleaners, dishwashing compositions, fabric laundering compositions, and the like. Such compositions can be in the form of liquids, granules, bars, and the like. Such compositions can be formulated as "concentrated" detergents which contain as much as from about 30% to about 60% by weight of surfactants.

The cleaning compositions herein may optionally, and preferably, contain various surfactants (e.g., anionic, nonionic, or zwitterionic surfactants). Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)_x(CHOSO_3)^- M^{(+)CH}_3$ and $CH_3(CH_2)_y(CHOSO_3^-M+) CH_2CH_3$ wherein x and (y+1) are integers of at least about 7, preferably at least about 9, and M is a water-solubilizing cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ α-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. The use of such surfactants in combination with the amine oxide and/or betaine or sultaine surfactants is also preferred, depending on the desires of the formulator. Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993.

A wide variety of other ingredients useful in detergent cleaning compositions can be included in the compositions herein including, for example, other active ingredients, carriers, hydrotropes, processing aids, dyes or pigments, and solvents for liquid formulations. If an additional increment of sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additional sudsing.

The liquid detergent compositions herein may contain water and other solvents as carriers. Low molecular weight primary or secondary alcohols exemplified by methanol, ethanol, propanol, and iso-propanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11. Finished products are typically formulated at this range. Techniques for controlling pH at recommended usage levels include the use of, for example, buffers, alkalis, and acids. Such techniques are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Soil release agents, especially of the anionic oligoester type, chelating agents, especially the aminophosphonates and ethylenediaminedisuccinates, clay soil removal agents, especially ethoxylated tetraethylene pentamine, dispersing agents, especially polyacrylates and polyasparatates, brighteners, especially anionic brighteners, suds suppressors, especially silicones and secondary alcohols, fabric softeners, especially smectite clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions. Such enzyme stabilizers include propylene glycol (preferably from about 1% to about 10%), sodium formate (preferably from about 0.1% to about 1%) and calcium formate (preferably from about 0.1% to about 1%).

The present variants are useful in hard surface cleaning compositions. As used herein "hard surface cleaning composition" refers to liquid and granular detergent compositions for cleaning hard surfaces such as floors, walls, bathroom tile, and the like. Hard surface cleaning compositions of the present invention comprise an effective amount of one or more variants of the present invention, preferably from about 0.001% to about 10%, more preferably from about 0.01% to about 5%, more preferably still from about 0.05% to about 1% by weight of variant of the composition. In addition to comprising one or more of the variants, such hard surface cleaning compositions typically comprise a surfactant and a water-soluble sequestering builder. In certain specialized products such as spray window cleaners, however, the surfactants are sometimes not used since they may produce a filmy and/or streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%.

Preferably the pH should be in the range of from about 7 to about 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropyleneglycol monobutyl ether, and diols such as 2,2,4-trimethyl-1,3-pentanediol and 2-ethyl-1,3-hexanediol. When used, such solvents are typically present at levels of from about 0.5% to about 15%, more preferably from about 3% to about 11%.

Additionally, highly volatile solvents such as iso-propanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

Hard surface cleaning compositions of the present invention are illustrated by the following examples.

EXAMPLES 1—6

| | Liquid Hard Surface Cleaning Compositions | | | | | |
|---|---|---|---|---|---|---|
| | Ex. 1 | Ex. 2 | Ex. 3 | Ex. 4 | Ex. 5 | Ex. 6 |
| G70* + S78* + I79* | 0.05% | 0.50% | 0.02% | 0.03% | 0.30% | 0.05% |
| EDTA | — | — | 2.90% | 2.90% | — | — |
| Sodium Citrate | — | — | — | — | 2.90% | 2.90% |
| NaC$_{12}$ Alkyl-benzene sulfonate | 1.95% | — | 1.95% | — | 1.95% | — |
| NaC$_{12}$ Alkylsulfate | — | 2.20% | — | 2.20% | — | 2.20% |
| NaC$_{12}$ (ethoxy) sulfate | — | 2.20% | — | 2.20% | — | 2.20% |
| C$_{12}$ Dimethylamine oxide | — | 0.50% | — | 0.50% | — | 0.50% |
| Sodium cumene sulfonate | 1.30% | — | 1.30% | — | 1.30% | — |
| Hexyl Carbitol | 6.30% | 6.30% | 6.30% | 6.30% | 6.30% | 6.30% |
| Water | 90.4% | 88.3% | 87.53% | 85.87% | 87.25% | 85.85% |

All formulas are adjusted to pH 7.

In Examples 1–6, the variants recited in Tables 2–10, and the preferred variants cited herein, among others, are substituted for G70*+S78*+I79*, with substantially similar results.

In another embodiment of the present invention, dishwashing compositions comprise one or more variants of the present invention. As used herein, "dishwashing composition" refers to all forms of compositions for cleaning dishes including, but not limited to, granular and liquid forms. Dishwashing compositions of the present invention are illustrated by the following examples.

EXAMPLES 7–10

| Liquid Dish Detergent | | | | |
|---|---|---|---|---|
| | Ex. 7 | Ex. 8 | Ex. 9 | Ex. 10 |
| G70* + L75* + N76* + N77* + S78* + I79* + G80* + V81* + L82* | 0.05% | 0.50% | 0.02% | 0.40% |
| $C_{12}$—$C_{14}$ N-methyl glucamide | 0.90% | 0.90% | 0.90% | 0.90% |
| $C_{12}$ ethoxy (1) sulfate | 12.0% | 12.0% | 12.0% | 12.0% |
| 2-Methyl undecanoic acid | 4.50% | 4.50% | 4.50% | 4.50% |
| $C_{12}$ ethoxy (2) carboxylate | 4.50% | 4.50% | 4.50% | 4.50% |
| $C_{12}$ alcohol ethoxylate (4) | 3.00% | 3.00% | 3.00% | 3.00% |
| $C_{12}$ amine oxide | 3.00% | 3.00% | 3.00% | 3.00% |
| Sodium cumene sulfonate | 2.00% | 2.00% | 2.00% | 2.00% |
| Ethanol | 4.00% | 4.00% | 4.00% | 4.00% |
| $Mg^{2+}$ (as $MgCl_2$) | 0.20% | 0.20% | 0.20% | 0.20% |
| $Ca^{2+}$ (as $CaCl_2$) | 0.40% | 0.40% | 0.40% | 0.40% |
| Water | 65.45% | 65% | 65.48% | 65.1% |

All formulas are adjusted to pH 7.

In Examples 7–10, the variants recited in Tables 2–10, and the preferred variants cited herein, among others, are substituted for G70*+L75*+N76*+N77*+S78*+I79*+G80*+V81*+L82*, with substantially similar results.

Liquid fabric cleaning compositions of the present invention are illustrated by the following examples.

EXAMPLES 11–13

| Liquid Fabric Cleaning Compositions | | | |
|---|---|---|---|
| | Ex. 11 | Ex. 12 | Ex. 13 |
| G70* | 0.05% | 0.03% | 0.30% |
| Sodiuam $C_{12}$—$C_{14}$ alkyl sulfate | 20.0% | 20.0% | 20.0% |
| 2-Butyl octanoic acid | 5.0% | 5.0% | 5.0% |
| Sodium citrate | 1.0% | 1.0% | 1.0% |
| $C_{10}$ Alcohol ethoxylate (3) | 13.0% | 13.0% | 13.0% |
| Monoethanolamine | 2.50% | 2.50% | 2.50% |
| Water/propylene glycol/ethanol (100:1:1) | 58.45% | 53.47% | 58.20% |

In Examples 11–13, the variants recited in Tables 2–10, and the preferred variants cited herein, among others, are substituted for G70*, with substantially similar results.

Personal Care Compositions

The present variants are particularly suited for use in personal care compositions such as, for example, leave-on and rinse-off hair conditioners, shampoos, leave-on and rinse-off acne compositions, facial milks and conditioners, shower gels, soaps, foaming and non-foaming facial cleansers, cosmetics, hand, facial, and body lotions and moisturizers, leave-on facial moisturizers, cosmetic and cleansing wipes, oral care compositions, and contact lens care compositions. The present personal care compositions comprise one or more variants of the present invention and a personal care carrier.

To illustrate, the present variants are suitable for inclusion in the compositions described in the following references: U.S. Pat. No. 5,641,479, Linares et al., issued Jun. 24, 1997 (skin cleansers); U.S. Pat. No. 5,599,549, Wivell et al., issued Feb. 4, 1997 (skin cleansers); U.S. Pat. No. 5,585,104, Ha et al., issued Dec. 17, 1996 (skin cleansers); U.S. Pat. No. 5,540,852, Kefauver et al., issued Jul. 30, 1996 (skin cleansers); U.S. Pat. No. 5,510,050, Dunbar et al., issued Apr. 23, 1996 (skin cleansers); U.S. Pat. No. 5,612,324, Guang Lin et al., issued Mar. 18, 1997 (anti-acne preparations); U.S. Pat. No. 5,587,176, Warren et al., issued Dec. 24, 1996 (anti-acne preparation; U.S. Pat. No. 5,549,888, Venkateswaran, issued Aug. 27, 1996 (anti-acne preparations); U.S. Pat. No. 5,470,884, Corless et al., issued Nov. 28, 1995 (anti-acne preparations); U.S. Pat. No. 5,650,384, Gordon et al., issued Jul. 22, 1997 (shower gels); U.S. Pat. No. 5,607,678, Moore et al., issued Mar. 4, 1997 (shower gels); U.S. Pat. No. 5,624,666, Coffindaffer et al., issued Apr. 29, 1997 (hair conditioners and/or shampoos); U.S. Pat. No. 5,618,524, Bolich et al., issued Apr. 8, 1997 (hair conditioners and/or shampoos); U.S. Pat. No. 5,612,301, Inman, issued Mar. 18, 1997 (hair conditioners and/or shampoos); U.S. Pat. No. 5,573,709, Wells, issued Nov. 12, 1996 (hair conditioners and/or shampoos); U.S. Pat. No. 5,482,703, Pings, issued Jan. 9, 1996 (hair conditioners and/or shampoos); U.S. Pat. No. Re. 34,584, Grote et al., Reissued Apr. 12, 1994 (hair conditioners and/or shampoos); U.S. Pat. No. 5,641,493, Date et al., issued Jun. 24, 1997 (cosmetics); U.S. Pat. No. 5,605,894, Blank et al., issued Feb. 25, 1997 (cosmetics); U.S. Pat. No. 5,585,090, Yoshioka et al., issued Dec. 17, 1996 (cosmetics); U.S. Pat. No. 4,939,179, Cheney et al., issued Jul. 3, 1990 (hand, face, and/or body lotions); U.S. Pat. No. 5,607,980, McAtee et al., issued Mar. 4, 1997 (hand, face, and/or body lotions); U.S. Pat. No. 4,045,364, Richter et al., issued Aug. 30, 1977 (cosmetic and cleansing wipes); European Patent Application, EP 0 619 074, Touchet et al., published Oct. 12, 1994 (cosmetic and cleansing wipes); U.S. Pat. No. 4,975,217, Brown-Skrobot et al., issued Dec. 4, 1990 (cosmetic and cleansing wipes); U.S. Pat. No. 5,096,700, Seibel, issued Mar. 17, 1992 (oral cleaning compositions); U.S. Pat. No. 5,028,414, Sampathkumar, issued Jul. 2, 1991 (oral cleaning compositions); U.S. Pat. No. 5,028,415, Benedict et al., issued Jul. 2, 1991 (oral cleaning compositions); U.S. Pat. No. 5,028,415, Benedict et al., issued Jul. 2, 1991 (oral cleaning compositions); U.S. Pat. No. 4,863,627, Davies et al., Sep. 5, 1989 (contact lens cleaning solutions); U.S. Pat. No. Re. 32,672, Huth et al, reissued May 24, 1988 (contact lens cleaning solutions); and U.S. Pat. No. 4,609,493, Schafer, issued Sep. 2, 1986 (contact lens cleaning solutions).

To further illustrate oral cleaning compositions of the present invention, a pharmaceutically-acceptable amount of one or more variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatibility, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in the references cited hereinabove.

In another embodiment of the present invention, denture cleaning compositions for cleaning dentures outside of the oral cavity comprise one or more variants of the present invention. Such denture cleaning compositions comprise an effective amount of one or more of the variants, preferably from about 0.0001% to about 50% of one or more of the variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see, e.g., U.S. Pat. No. 5,055,305, Young), and are generally appropriate for incorporation of one or more of the variants for removing proteinaceous stains from dentures.

In another embodiment of the present invention, contact lens cleaning compositions comprise one or more variants of the present invention. Such contact lens cleaning compositions comprise an effective amount of one or more of the variants, preferably from about 0.01% to about 50% of one or more of the variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art and are generally appropriate for incorporation of one or more variants of the present invention for removing proteinaceous stains from contact lenses.

The contact lens cleaning composition embodiment of the present invention is illustrated by Examples 14–17.

EXAMPLES 14–17

| Contact Lens Cleaning Solution | | | | |
|---|---|---|---|---|
| | Ex. 14 | Ex. 15 | Ex. 16 | Ex. 17 |
| N76* | 0.01% | 0.5% | 0.1% | 2.0% |
| Glucose | 50.0% | 50.0% | 50.0% | 50.0% |
| Nonionic surfactant (polyoxyethlene-polyoxypropylene copolymer) | 2.0% | 2.0% | 2.0% | 2.0% |
| Anionic surfactant (polyoxyethylene-alkylphenylether sodium sulfricester) | 1.0% | 1.0% | 1.0% | 1.0% |
| Sodium Chloride | 1.0% | 1.0% | 1.0% | 1.0% |
| Borax | 0.30% | 0.30% | 0.30% | 0.30% |
| Water | 45.69% | 45.20% | 45.60% | 43.70% |

In Examples 14–17, the variants recited in Tables 2–10, and the preferred variants cited herein, among others, are substituted for N76*, with substantially similar results.

Examples 18–21 illustrate the use of the present variants in bodywash products:

EXAMPLES 18–21

| Bodywash Products | | | | |
|---|---|---|---|---|
| | Ex. 18 | Ex. 19 | Ex. 20 | Ex. 21 |
| Water | 62.62% | 65.72% | 57.72% | 60.72% |
| Disodium EDTA | 0.2% | 0.2% | 0.2% | 0.2% |
| Glycerine | 3.0% | 3.0% | 3.0% | 3.0% |
| Polyquaternium 10 | 0.4% | 0.4% | 0.4% | 0.4% |
| Sodium laureth sulphate | 12.0% | 12.0% | 12.0% | 12.0% |
| Cocamide MEA | 2.8% | 2.8% | 2.8% | 2.8% |
| Sodium lauraphoacetate | 6.0% | 6.0% | 6.0% | 6.0% |
| Myristic Acid | 1.6% | 1.6% | 1.6% | 1.6% |
| Magnesium sulphate heptahydrate | 0.3% | 0.3% | 0.3% | 0.3% |
| Trihydroxystearin | 0.5% | 0.5% | 0.5% | 0.5% |
| PEG-6 caprylic/capric triglycerides | 3.0% | — | — | — |
| Sucrose polyesters of cottonate fatty acid | 3.0% | — | — | — |
| Sucrose polyesters of behenate fatty acid | 3.0% | — | 4.0% | — |
| Petrolatum | — | 4.0% | 8.0% | — |
| Mineral Oil | — | — | — | 6.0% |
| DMDM Hydantoin | 0.08% | 0.08% | 0.08% | 0.08% |
| L75* + N76* + N77* + S78* + I79* + G80* + V81* + L82* | 0.1% | 2.0% | 2.0% | 5.0% |
| Citric Acid | 1.40% | 1.40% | 1.40% | 1.40% |

In Examples 18–21, the variants recited in Tables 2–10, and the preferred variants cited herein, among others, are substituted for L75*+N76*+N77*+S78*+I79*+G80*+V81*+L82*, with substantially similar results.

Examples 18–21 illustrate the use of the present variants in facewash products:

EXAMPLES 22–25

| Facewash Products | | | | |
|---|---|---|---|---|
| | Ex. 22 | Ex. 23 | Ex. 24 | Ex. 25 |
| Water | 66.52% | 65.17% | 68.47% | 68.72% |
| Disodium EDTA | 0.1% | 0.1% | 0.2% | 0.2% |
| Citric Acid | — | — | 1.4% | 1.4% |
| Sodium Laureth-3 Sulfate | 3.0% | 3.5% | — | — |
| Sodium Laureth-4 Carboxylate | 3.0% | 3.5% | — | — |
| Laureth-12 | 1.0% | 1.2% | — | — |
| Polyquaternium 10 | — | — | 0.4% | 0.4% |
| Polyquaternium 25 | 0.3% | 0.3% | — | — |
| Glycerine | 3.0% | 3.0% | 3.0% | 3.0% |
| Sodium Lauroamphoacetate | — | — | 6.0% | 6.0% |
| Lauric Acid | 6.0% | 6.0% | 3.0% | 3.0% |
| Myristic Acid | — | — | 3.0% | 3.0% |
| Magnesium sulphate heptahydrate | 2.3% | 2.0% | 2.0% | 2.0% |
| Triethanol amine | 4.0% | 4.0% | 4.0% | 4.0% |
| Trihydroxystearin | 0.5% | 0.5% | 0.5% | 0.5% |
| Sucrose polyesters of behenate fatty acid | 2.0% | 2.0% | — | — |
| Sucrose polyesters of cottonate fatty acid | 3.0% | 2.0% | — | — |
| PEG-6 caprylic/capric triglycerides | — | — | — | 2.0% |
| Petrolatum | — | — | 4.0% | — |
| Mineral Oil | — | — | — | 2.0% |
| Cocamidopropyl betaine | 2.0% | 3.0% | 1.8% | 1.8% |
| Lauryl dimethylamine oxide | 1.0% | 1.2% | 1.2% | 1.2% |
| Dex Panthenol | 1.0% | 0.25% | 0.25% | — |
| DMDM Hydantoin | 0.08% | 0.08% | 0.08% | 0.08% |
| L75* | 1.0% | 2.0% | 0.5% | 0.5% |
| Fragrance | 0.2% | 0.2% | 0.2% | 0.2% |

In Examples 22–25, the variants recited in Tables 2–10, and the preferred variants cited herein, among others, are substituted for L75*, with substantially similar results. Examples 26–27 illustrate the use of the present variants in leave-on skin moisturizing compositions:

EXAMPLES 26–27

Leave-on Skin Moisturizing Composition

| | Ex. 26 | Ex. 27 |
|---|---|---|
| Glycerine | 5.0% | — |
| Stearic acid | 3.0% | — |
| $C_{11-13}$ Isoparaffin | 2.0% | — |
| Glycol stearate | 1.5% | — |
| Propylene glycol | — | 3.0% |
| Mineral oil | 1.0% | 10.0% |
| Sesame oil | — | 7.0% |
| Petrolatum | — | 1.8% |
| Triethanolamine | 0.7% | — |
| Cetyl acetate | 0.65% | — |
| Glyceryl stearate | 0.48% | 2.0% |
| TEA stearate | — | 2.5% |
| Cetyl alcohol | 0.47% | — |
| Lanolin alcohol | — | 1.8% |
| DEA - cetyl phosphate | 0.25% | — |
| Methylparaben | 0.2% | 0.2% |
| Propylparaben | 0.12% | 0.1% |
| Carbomer 934 | 0.11% | — |
| Disodium EDTA | 0.1% | — |
| L82* | 0.1% | 0.5% |
| Water | 84.32% | 71.1% |

In Examples 26–27, the variants recited in Tables 2–10, and the preferred variants cited herein, among others, are substituted for L82*, with substantially similar results.

Example 28 illustrates the use of the present variants in cleansing wipe compositions:

EXAMPLE 28

Cleansing Wipe Composition

| | |
|---|---|
| Propylene Glycol | 1.0% |
| Ammonium lauryl sulfate | 0.6% |
| Succinic acid | 4.0% |
| Sodium succinate | 3.2% |
| Triclosan ® | 0.15% |
| S78* | 0.05% |
| Water | 91.0% |

The above composition is impregnated onto a woven absorbent sheet comprised of cellulose and/or polyester at about 250 %, by weight of the absorbent sheet.

In Example 28, the variants recited in Tables 2–10, and the preferred variants cited herein, among others, are substituted for S78*, with substantially similar results.

What is claimed is:

1. A serine protease variant having a modified amino acid sequence of a wild-type amino acid sequence comprising a substitution by a substituting amino acid in at least one position corresponding to positions 75–76 and 78–81 of subtilisin BPN' wherein:
   (a) when the substitution occurs at position 75, the substituting amino acid is selected from the group consisting of Ala, Arg, Asn, Cys, Gly, Phe, His, Ile, Lys, Met, Gln, Ser, Thr, Trp, Tyr, and Val;
   (b) when the substitution occurs at position 76, the substituting amino acid is selected from the group consisting of Ala, Arg, Cys, Ile, Leu, Met, Gln Ser, Thr, Trp, Tyr, and Val;
   (c) when the substitution occurs at position 78, the substituting amino acid is selected from the group consisting of Ala, Arg, Asn, Cys, Gly, Phe, His, Ile, Lys, Leu, Met, Pro, Gln, Thr, Trp, Tyr, and Val;
   (d) when the substitution occurs at position 79, the substituting amino acid is selected from the group consisting of Ala, Arg, Asn, Cys, Gly, Phe, His, Lys, Leu, Met, Pro, Gln, Ser, Thr, Trp, Tyr, and Val;
   (e) when the substitution occurs at position 80, the substituting amino acid is selected from the group consisting of Ala, Arg, Asn, Cys, Phe, His, Ile, Lys, Leu, Met, Pro, Gln, Ser, Thr, Trp, Tyr, and Val; and,
   (f) when the substitution occurs at position 81, the substituting amino acid is selected from the group consisting of Ala, Arg, Asn, Cys, Gly, Phe, His, Ile, Lys, Leu, Met, Pro, Gln Ser, Thr, Trp, and Tyr.

2. A variant according to claim 1 wherein the serine protease is selected from the group consisting of subtilisin BPN', subtilisin Carlsberg, subtilisin DY, subtilisin 309, proteinase K, and thermitase.

3. A variant according to claim 2 wherein the serine protease is subtilisin BPN'.

4. A variant of claim 3 wherein the substitution is of one or more of positions 75, 76 and 78–81.

5. A variant according to claim 1 further comprising one or more stabilizing mutations.

6. A variant according to claim 5 wherein the stabilizing mutations are selected from the group consisting of 107V, K213R, Y217L, Y217K, N218S, G169A, M50F, Q19E, P5A, S9A, I31L, E156S, G169A, N212G, S188P, T254A, S3C+Q206C, and Q271E.

7. A variant according to claim 6 wherein the stabilizing mutation is Y217L.

8. A mutant serine protease gene encoding the variant according to claim 1.

9. A cleaning composition comprising a variant according to claim 1 and a cleaning composition carrier.

10. A personal care composition comprising a variant according to claim 1 and a personal care carrier.

11. A personal care composition according to claim 10 which is selected from the group consisting of oral cleaning compositions, contact lens cleaning compositions, hair care compositions, beauty care compositions, and skin care compositions.

* * * * *

UNITED STATES PATENT AND TRADEMARK OFFICE
CERTIFICATE OF CORRECTION

PATENT NO. : 6,569,663 B1
DATED : May 27, 2003
INVENTOR(S) : Rubingh et al.

It is certified that error appears in the above-identified patent and that said Letters Patent is hereby corrected as shown below:

Column 3,
Line 40, omit "E. J.".

Column 4,
Lines 63 and 67, "Gin" should read -- Gln --.

Column 5,
Lines 4, 8, 12, 16, 20, 26, 33 and 41, "Gin" should read -- Gln --.
Line 7, after "His," insert -- Ile, --.
Line 66, "Gln" should read -- Gln, --.

Column 6,
Lines 3, 7, 11, 15, 19 and 23, "Gln" should read -- Gln, --.

Column 10,
Lines 30, 54, 57 and 63, "PRE" should read -- PHE --.

Column 11,
Line 11, delete lines 11-55, starting with "SER 78 GLN ILE 79 LEU LEU 82 PHE" and ending with "SER 78 THR ILE 79 VAL VAL 81 THR".

Column 53,
Line 7, under Table 7, "LEU 75 ILE ASN 76 HIS SER 78 ASN ILE 79 THR VAL 81 THR LEU 82 PRE" should read -- LEU 75 ILE ASN 76 HIS SER 78 ASN ILE 79 THR VAL 81 THR LEU 82 PHE --

Column 59,
Line 70, line under Table 7 - continued, "LEU 75 VAL ASN 76 HIS SER 73 TYR ILE 79 MET VAL 81 THR LEU 82 TYR" should read -- LEU 75 VAL ASN 76 HIS SER 78 TYR ILE 79 MET VAL 81 THR LEU 82 TYR --.
Line 76, under Table 7 - continued, at the end of the table, insert the line
-- LEU 75 VAL ASN 76 HIS SER 78 TYR ILE 79 VAL VAL 81 THR LEU 82 TYR --.

Column 67,
Line 47, "1107V" should read -- I107V --.

Column 68,
Line 66, "antifoarm" should read -- antifoam --.

UNITED STATES PATENT AND TRADEMARK OFFICE
CERTIFICATE OF CORRECTION

PATENT NO. : 6,569,663 B1
DATED : May 27, 2003
INVENTOR(S) : Rubingh et al.

It is certified that error appears in the above-identified patent and that said Letters Patent is hereby corrected as shown below:

Column 70,
Line 33, "520 run" should read -- 520 nm --.
Line 56, "AB-serumn" should read -- AB-serum --.

Column 75,
Line 41, "53.47%" should read -- 58.47% --.

Column 76,
Line 4, "preparation" should read -- preparations --.

Column 81,
Line 38, "Gln" should read -- Gln, --.

Column 82,
Line 37, "107V" should read -- I107V --.

Signed and Sealed this

Seventh Day of October, 2003

JAMES E. ROGAN
*Director of the United States Patent and Trademark Office*